US012636345B2

(12) United States Patent
Lim et al.

(10) Patent No.: US 12,636,345 B2
(45) Date of Patent: *May 26, 2026

(54) METHODS OF TREATING GLIOBLASTOMAS

(71) Applicant: The Regents of the University of California, Oakland, CA (US)

(72) Inventors: Wendell A. Lim, San Francisco, CA (US); Hideho Okada, San Francisco, CA (US); Kole T. Roybal, San Francisco, CA (US); Joseph H. Choe, San Francisco, CA (US); Payal B. Watchmaker, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/737,881

(22) Filed: Jun. 7, 2024

(65) Prior Publication Data

US 2024/0325449 A1 Oct. 3, 2024

Related U.S. Application Data

(63) Continuation of application No. 17/042,032, filed as application No. PCT/US2019/025860 on Apr. 4, 2019, now Pat. No. 12,090,170.

(60) Provisional application No. 62/653,929, filed on Apr. 6, 2018.

(51) Int. Cl.
| | |
|---|---|
| *A61K 38/17* | (2006.01) |
| *A61K 35/17* | (2015.01) |
| *A61K 40/11* | (2025.01) |
| *A61K 40/31* | (2025.01) |
| *A61K 40/42* | (2025.01) |

(52) U.S. Cl.
CPC .......... *A61K 38/1793* (2013.01); *A61K 35/17* (2013.01); *A61K 40/11* (2025.01); *A61K 40/31* (2025.01); *A61K 40/4217* (2025.01); *A61K 40/422* (2025.01); *A61K 2239/47* (2023.05)

(58) Field of Classification Search
CPC .... A61K 38/1793; A61K 35/17; A61K 40/11; A61K 40/31; A61K 40/4217; A61K 40/422; A61K 2239/47; A61P 35/00; C07K 14/7051; C07K 2319/03; C07K 16/28
See application file for complete search history.

(56) References Cited

U.S. PATENT DOCUMENTS

| | | | |
|---|---|---|---|
| 9,493,568 B2 | 11/2016 | Reilly et al. | |
| 2012/0252875 A1* | 10/2012 | Feinstein | A61P 27/06 |
| | | | 536/24.5 |
| 2016/0264665 A1* | 9/2016 | Lim | C07K 14/71 |
| 2017/0029512 A1 | 2/2017 | Raum et al. | |
| 2017/0210811 A1 | 7/2017 | Wong et al. | |
| 2017/0309025 A1 | 10/2017 | O'Rourke et al. | |
| 2018/0079812 A1 | 3/2018 | Lim et al. | |
| 2018/0085401 A1 | 3/2018 | Wu et al. | |
| 2021/0023136 A1 | 1/2021 | Lim et al. | |
| 2021/0023138 A1 | 1/2021 | Lim et al. | |

FOREIGN PATENT DOCUMENTS

| | | |
|---|---|---|
| WO | WO 2014/130657 A1 | 8/2014 |
| WO | WO 2016/138034 A1 | 9/2016 |
| WO | WO 2017/025038 A1 | 2/2017 |
| WO | WO 2017/087723 A1 | 5/2017 |
| WO | WO 2017/193059 A1 | 11/2017 |
| WO | WO 2018/039247 A1 | 3/2018 |
| WO | WO 2019/195576 A1 | 10/2019 |
| WO | WO 2019/195586 A1 | 10/2019 |

OTHER PUBLICATIONS

Hegde, M et. al. "Tandem CAR T cells targeting HER2 and IL13Rα2 mitigate tumor antigen escape", 2016, The Journal of Clinical Investigation, 126(8), 3036-3052. (Year: 2016).*
Cajal et al., "Beyond molecular tumor heterogeneity: protein synthesis takes control", Oncogene, 2018, 37(19): 2490-2501.
Ding et al., "Clonal evolution in relapsed acute myeloid leukemia revealed by whole genome sequencing", Nature, 2012, 481(7382): 506-510.
Gerlinger et al., "Genomic architecture and evolution of clear cell renal cell carcinomas defined by multiregion sequencing", Nat Genet., 2014, 46(3): 225-233.
Kortum et al., "Targeted sequencing of refractory myeloma reveals a high incidence of mutations in CRBN and Ras pathway genes", Blood, 2016, 128(9): 1226-1233.
Landau et al., "Evolution and Impact of Subclonal Mutations in Chronic Lymphocytic Leukemia", Cell, 2013, 152: 714-726.

(Continued)

*Primary Examiner* — Nelson B Moseley, II
*Assistant Examiner* — Alyssa Rae Stonebraker
(74) *Attorney, Agent, or Firm* — James S. Keddie; Bozicevic, Field & Francis LLP

(57) ABSTRACT

Provided herein is a method of treating a subject for a glioblastoma, the method comprising: administering to the subject an immune cell genetically modified with: (a) a nucleic acid sequence encoding a binding triggered transcriptional switch (BTTS) that binds to a priming antigen that is tissue-specifically expressed in the central nervous system; (b) a nucleic acid sequence encoding a tandem chimeric antigen receptor (CAR) or T cell receptor (TCR) that has a first binding domain that recognizes Ephrin type-A receptor 2 (EphA2) and a second binding domain that recognizes Interleukin-13 receptor subunit alpha-2 (IL13RA2); and (c) a regulatory sequence operably linked to (b) that is responsive to the BTTS, wherein binding of the BTTS to the priming antigen activates expression of the tandem CAR or TCR, which binds EphA2 and/or IL13RA2 in the glioblastoma and induces killing of glioblastoma cells.

8 Claims, 5 Drawing Sheets

Specification includes a Sequence Listing.

(56)            References Cited

OTHER PUBLICATIONS

Liang et al., "Complex roles of the stroma in the intrinsic resistance to gemcitabine in pancreatic cancer: where we are and where we are going", Experimental & Molecular Medicine, 2017, 49: e406.

Lim et al., "The Principles of Engineering Immune Cells to Treat Cancer", Cell, 2017, 168(4): 724-740.

Rathore et al., "Radiomic MRI signature reveals three distinct subtypes of glioblastoma with different clinical and molecular characteristics, offering prognostic value beyond IDH1", Scientific Reports, 2018, 8: 5087.

Roybal et al., "Synthetic Immunology: Hacking Immune Cells to Expand Their Therapeutic Capabilities", Annu Rev Immunol, 2017, 35: 229-253.

Wang et al., "Clonal Evolution in Breast Cancer Revealed by Single Nucleus Genome Sequencing", Nature, 2014, 512(7513): 155-160.

Akhavan et al., "CAR T cells for brain tumors: Lessons learned and road ahead", Immunol Rev. Jul. 2019, 290(1): 60-84.

Choe et al., "SynNotch-CAR T cells overcome challenges of specificity, heterogeneity, and persistence in treating glioblastoma", Science Translational Medicine, Apr. 28, 2021, 13, eabe7378, 15 pages.

Choi et al., "Engineering Chimeric Antigen Receptor T cells to Treat Glioblastoma", J Target Ther Cancer., Aug. 2017, 6(4): 22-25.

Dauth et al., "Extracellular Matrix Protein Expression is Brain Region Dependent", The Journal of Comparative Neurology, 2016, 524:1309-1336.

Ferrerosa et al., "IMMU-14. Synnotch Chimeric Antigen Receptor (CAR) T-Cells as a Potential Treatment for Diffuse Intrinsic Pontine Glioma (DIPG)/Diffuse Midline Glioma (DMG)", Jun. 2022, 24(Suppl 1): i84, doi: 10.1093/neuonc/noac079.307.

Mao et al., "Updates on Chimeric Antigen Receptor-Mediated Glioblastoma Immunotherapy", Rhode Island Medical Journal, 2017, 100(6): 39-42.

Nakagawa et al., "Identification of glioblastoma-specific antigens expressed in patient-derived tumor cells as candidate targets for chimeric antigen receptor T cell therapy", Neuro-Oncology Advances, Nov. 15, 2022, 5(1): 1-9.

Nehama et al., "B7-H3-redirected chimeric antigen receptor T cells target glioblastoma and neurospheres", EBioMedicine, 2019, 47: 33-43.

Razpotnik et al., "Targeting Malignant Brain Tumors with Antibodies", Frontiers in Immunology, 2017, 8(1181), pp. 1-14.

Shraibman et al., "Identification of Tumor Antigens Among the HLA Peptidomes of Glioblastoma Tumors and Plasma", Molecular & Cellular Proteomics, Jun. 2019, 18(6): 1255-1268.

Szeto et al., "TCR Recognition of Peptide-MHC-I: Rule Makers and Breakers", International Journal of Molecular Sciences, Dec. 2020, 22(1):68, 26 pages.

Wang et al., "Identification of tumor-associated antigens and immune subtypes of lower-grade glioma and glioblastoma for mRNA vaccine development", Chinese Neurosurgical Journal, Oct. 28, 2022, 8:34, 14 pages.

Watchmaker et al., "EXTH-33. Priming of Synnotch CAR T Cells Via CNS-Specific Antigen Allows Spatial and Temporal Regulation of Car Expression, Effective Homing and Persistence of T Cells in the CNS", Neuro-Oncology, Nov. 2022, vol. 24, Issue Supplement_7, Nov. 2022, p. vii216, https://doi.org/10.1093/neuonc/noac209.831.

Wu et al., "Tumor antigens and immune subtypes of glioblastoma: the fundamentals of mRNA vaccine and individualized immunotherapy development", Journal of Big Data, Jul. 14, 2022, 9:92, 25 pages.

Yamada et al., "Molecular Cloning of Brevican, a Novel Brain Proteoglycan of the Aggrecan/versican Family", The Journal of Biological Chemistry, 1994, 269(13): 10119-10126.

Yang et al., "Targeting EGFRvIII for glioblastoma multiforme", Cancer Letters, 2017, 403: 224-230.

Yang et al., "T cells expressing NKG2D chimeric antigen receptors efficiently eliminate glioblastoma and cancer stem cells", Journal for ImmunoTherapy of Cancer, 2019, 7:171, 13 pages.

Montano et al., "Expression of EGFRvIII in Glioblastoma: Prognostic Significance Revisited", Neoplasia, 2011, 13(12): 1113-1121.

Sattiraju et al., "IL13RA2 targeted alpha particle therapy against glioblastomas", Oncotarget, 2017, 8(26): 42997-43007.

Chow et al., "T Cells Redirected to EphA2 for the Immunotherapy of Glioblastoma", Molecular Therapy, 2013, 21(3): 629-637.

Migliorini et al. (2018) "CART-Cell Therapies in Glioblastoma: A First Look" Clinical Cancer Research, 24(3): 535-540.

O'Rourke et al. (2017) "A single dose of peripherally infused EGFRvIII-directed CART cells mediates antigen loss and induces adaptive resistance in patients with recurrent glioblastoma" Science Translational Medicine, 9(399):1-15.

Johnson et al., "Rational development and characterization of humanized anti-EGFR variant III chimeric antigen receptor T cells for glioblastoma", Science Translational Medicine, 2015, 7(275): 1-16.

Bielamowicz et al., "Trivalent CAR T cells overcome interpatient antigenic variability in glioblastoma", Neuro-Oncology, 2017, 20(4): 506-518.

Bielamowicz et al., "Trivalent CAR T cells overcome interpatient antigenic variability in glioblastoma", Neuro-Oncology, 2017, 20(4), Supplemental Tables 1-3.

Dutoit et al., "Exploiting the glioblastoma peptidome to discover novel tumour-associated antigens for immunotherapy", Brain, 2012, 135: 1042-1054.

Genbler et al., "Dual targeting of glioblastoma with chimeric antigen receptor-engineered natural killer cells overcomes heterogeneity of target antigen expression and enhances antitumor activity and survival", Oncoimmunology, 2016, 5(4): e1119354, 12 pages.

Hegde et al., "Combinational Targeting Offsets Antigen Escape and Enhances Effector Functions of Adoptively Transferred T Cells in Glioglastoma", Molecular Therapy, 2013, 21(11): 2087-2101.

Suryadevara et al., "Are BiTEs the "missing link" in cancer therapy?", Oncoimmunology, 2015, 4(6): e1008339, 10 pages.

Inda et al., "Tumor hetergeneity is an active process maintained by a mutant EGFR-induced cytokine circuit in glioblastoma", Genes & Development, 2010, 24: 1731-1745.

Jeuken et al., "Robust Detection of EGFR Copy Number Changes and EGFR Variant III: Technical Aspects and Relevance for Glioma Diagnostics", Brain Pathology, 2009, 19: 661-671.

Simic et al., "Programming tissue-sensing T cells that deliver therapies to the brain", Science, Dec. 6, 2024, 386: 1109, eadl4237, 14 pages.

Allen et al., "Expression of epidermal-growth-factor receptor in the K562 cell line by transfection", Biochem. J., 1990, 271: 785-790.

Oh et al., "Targeting EGFR and uPAR on human rhabdomyosarcoma, osteosarcoma, and ovarian adenocarcinoma with a bispecific ligand-directed toxin", Clinical Pharmacology: Advances and Applications, 2018, 10: 113-121.

Lohmueller et al., "Current modalities in cancer immunotherapy: immunomodulatory antibodies, CARs and vaccines", Pharmacol Ther., Oct. 2017, 178: 31-47.

Morello et al., "Mesothelin-Targeted CARs: Driving T cells to Solid Tumors", Cancer Discov., Feb. 2016, 6(2): 133-146.

Watanabe et al., "Expanding the Therapeutic Window for CAR T Cell Therapy in Solid Tumors: The Knowns and Unknowns of CAR T Cell Biology", Frontiers in Immunology, Oct. 2018, 9:2486.

Jarboe et al., "Expression of Interleukin-13 Receptor α2 in Glioblastoma Multiforme: Implications for Targeted Therapies", Cancer Res, Sep. 2007; 67(17): 7983-7986.

Roybal et al., "Precision Tumor Recognition by T Cells With Combinatorial Antigen-Sensing Circuits", Cell, Feb. 2016, 164: 770-779.

Wykosky et al., "Interleukin-13 Receptor α2, EphA2, and Fos-Related Antigen 1as Molecular Denominators of High-Grade Astrocytomas and Specific Targets for Combinatorial Therapy", Clin Cancer Res, Jan. 2008, 14(1): 199-208.

* cited by examiner

FIG. 1A

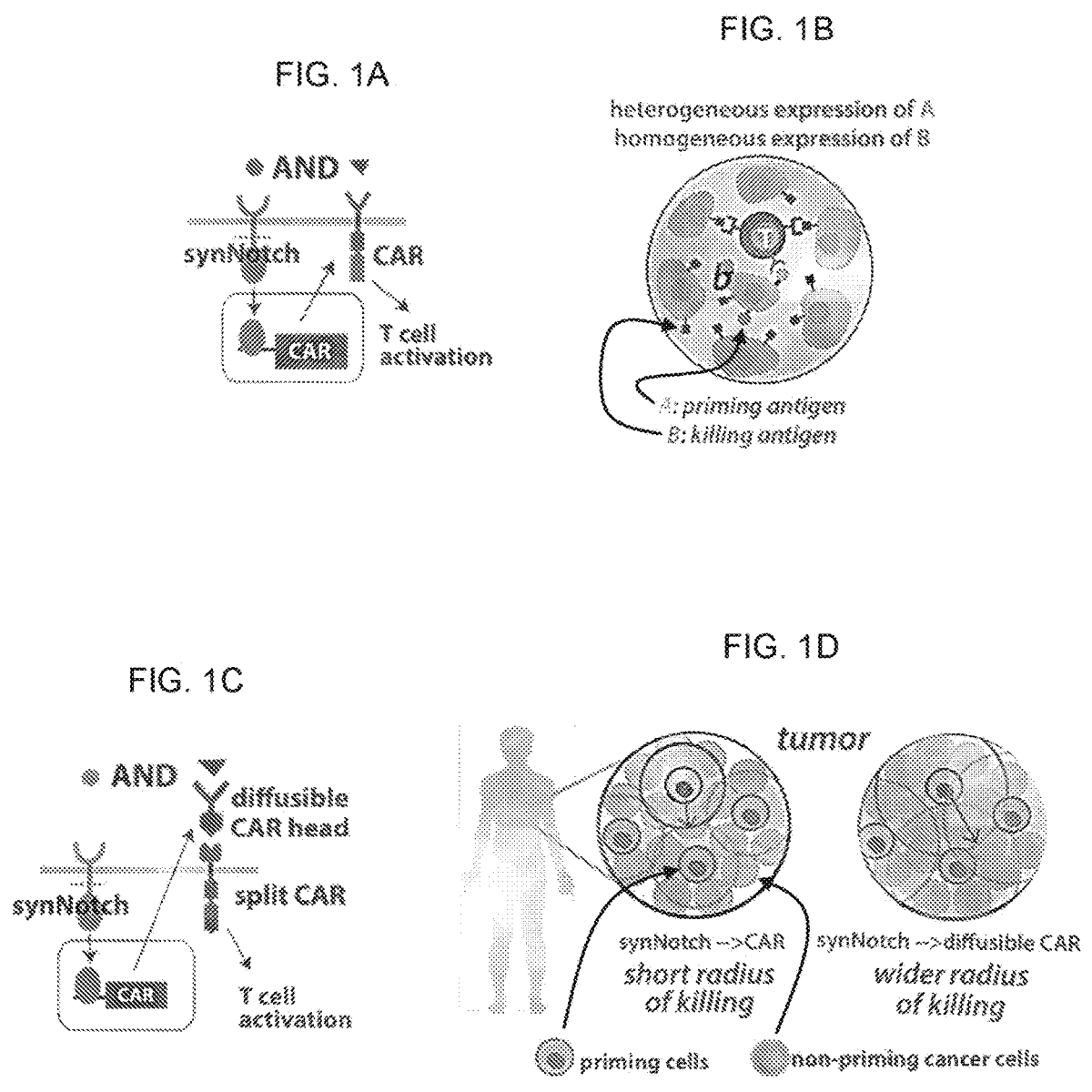

● AND ▼ synNotch | CAR

CAR

T cell activation

FIG. 1B heterogeneous expression of A
homogeneous expression of B

A: priming antigen
B: killing antigen

FIG. 1C

● AND ▼ diffusible CAR head synNotch | split CAR

CAR

T cell activation

FIG. 1D tumor synNotch –>CAR
short radius
of killing synNotch –>diffusible CAR
wider radius
of killing priming cells   non-priming cancer cells

FIG. 2A

48 Hours

T cell positive for synNotch Activation
SynNotch -> CAR T cells co-cultured with GBM6

Glioblastoma SynNotch --> CAR Killing (GBM synNotch --> Gal4UAS IL13Ra2/EphA2 CAR GFP PGK BFP)

CAR Expression (GFP)

METHODS OF TREATING GLIOBLASTOMAS

CROSS-REFERENCE TO RELATED APPLICATIONS

This application is a continuation of U.S. application Ser. No. 17/042,032, filed on Sep. 25, 2020, which is a § 371 national phase of International Application No. PCT/US2019/025860, filed on Apr. 4, 2019, which claims the benefit of United States Provisional Patent Application Ser. Nos. 62/653,929 filed Apr. 6, 2018; the disclosure of which applications are herein incorporated by reference.

STATEMENT REGARDING FEDERALLY SPONSORED RESEARCH

This invention was made with government support under grant nos. R01 CA196277, P50 GM081879 and R35 NS105068 awarded by the National Institutes of Health. The government has certain rights in the invention.

INCORPORATION BY REFERENCE OF SEQUENCE LISTING PROVIDED AS A SEQUENCE LISTING XML TEXT FILE

A Sequence Listing is provided herewith as a Sequence Listing XML, "UCSF-565CON_SEQLIST.xml" created on Jun. 7, 2024, and having a size of 121,552 bytes. The contents of the Sequence Listing XML are incorporated by reference herein in their entirety.

INTRODUCTION

Among neuroepithelial tumors, the most frequent (50-60%) is glioblastoma. Glioblastoma multiforme (GBM) is highly anaplastic and develops from a diffuse astrocytoma or de novo. GBM is often found in the cerebral hemispheres and its peak incidence occurs at an age of 45-70 years. The median survival of patients with GBM is typically less than 2 years. GBM tumors commonly appear as a heterogeneous mixture containing cells of various phenotypes and polymorphisms. Heterogeneity in GBM tumors at the cellular level undoubtedly contributes to the aggressive pathology of the disease and may play a role in tumor recurrences following treatment (see e.g., Soeda et al., Scientific Reports (2015) 5:7979). Epidermal growth factor receptor (EGFR) is over expressed in approximately 50-60% of glioblastoma (GBM) tumors. Moreover, mutation of EGFR giving rise to detrimental EGFR variants, e.g., such as EGFR variant III (EGFRvIII), is common and, when present, appears to occur in the early stages of cancer progression consistent with a cancer stem cell model for GBM. In some subjects, EGFRvIII may not arise at all during GBM disease progression, meaning therapies specifically directed to this variant would not be indicated in certain patients.

SUMMARY

Methods are provided for treating a subject for glioblastoma, including e.g., an EGFRvIII negative glioblastoma. The methods of the present disclosure involve administering to a subject a molecular circuit that includes a binding triggered transcriptional switch (BTTS) that binds to a priming antigen expressed by the subject's glioblastoma multiforme (GBM) that, when bound to the priming antigen, induces one or more encoded therapeutics specific for one or more antigens expressed by the GBM. Nucleic acids containing sequences encoding all or portions of such circuits are also provided, as well as cells, expression cassettes and vectors that contain such nucleic acids. Also provided are kits for practicing the described methods.

BRIEF DESCRIPTION OF THE DRAWINGS

FIG. 1A-1D depict examples of prime/kill circuits, with or without diffusible components, and employing antigen recognition and therapeutic targeting using priming antigen and targeting antigen expressed on EGFRvIII(−) GBM cells.

Figure 2A:
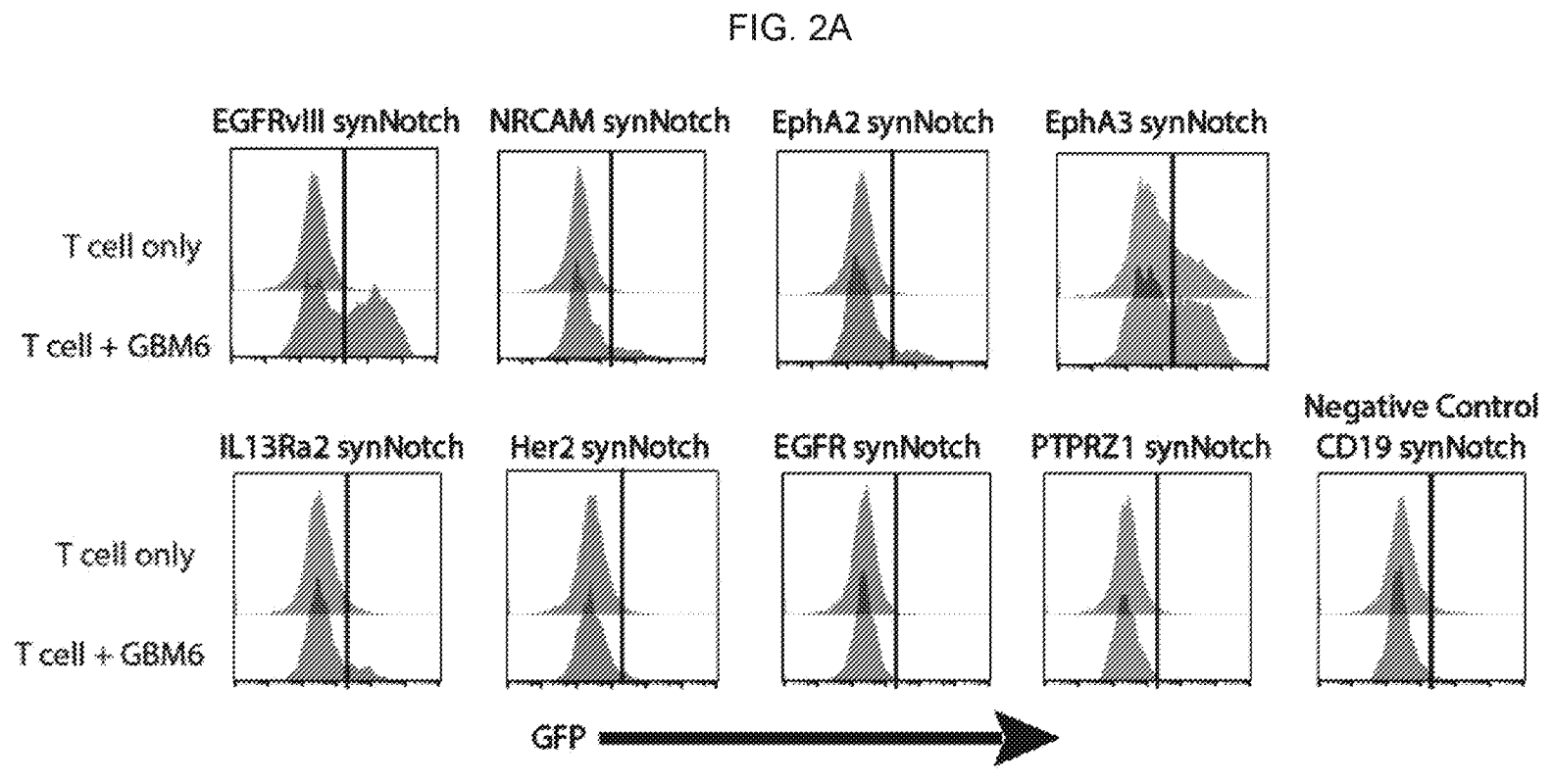

FIG. 2A-2B demonstrate the activation, selectively in the presence of targeted GBM cells, of synNotch receptors targeted to various antigens in synNotch→CAR T cell GBM circuits as described herein.

FIG. 3A-3D demonstrate selective synNotch activation and cell killing in the presence of targeted GBM cells with synNotch→CAR T circuits as described herein.

DEFINITIONS

Figures 2B, 3A, 3B:
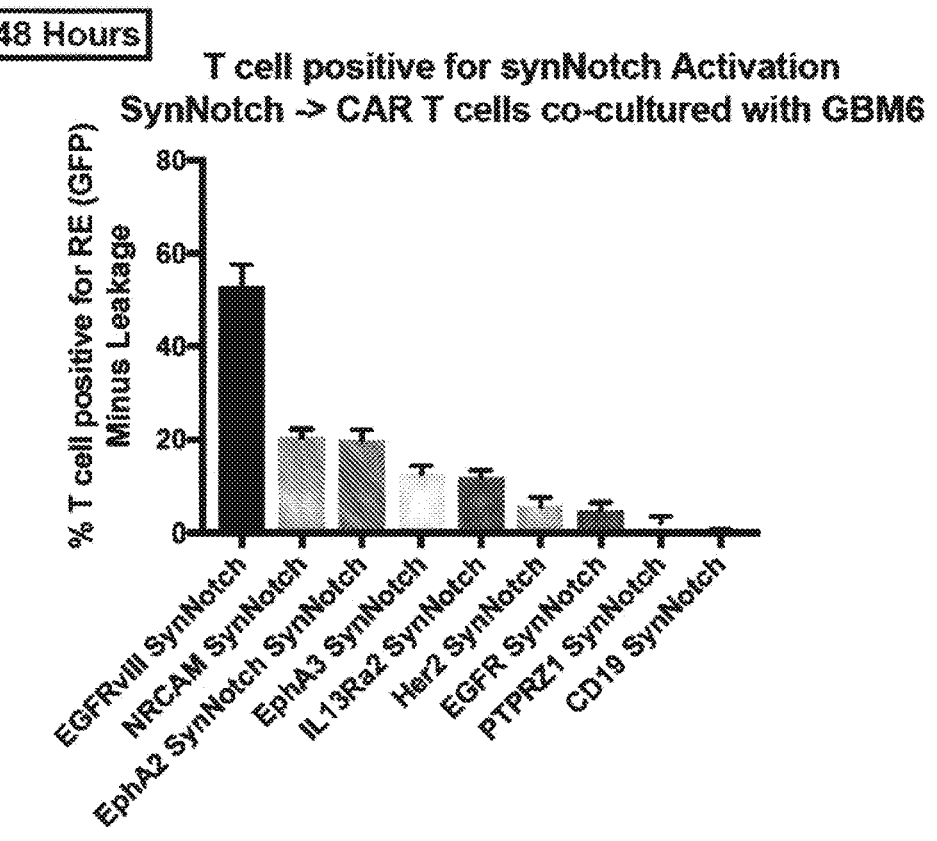

As used herein, the term "heterogeneous", when used in reference to cancer, generally refers to a cancer displaying some level of intracancer or intratumor heterogeneity, e.g., at the molecular, cellular, tissue or organ level. A heterogeneous cancer is composed of at least two different cell types, where different cell types may be defined in variety of ways. For example, different cell types may differ genomically (e.g., through the presence of a mutation in one cell type that is absent in another), transcriptionally (e.g., through expression of a gene in one cell type that is not expressed in another, through enhanced or reduced expression of a gene in one cell type as compared to another, etc.), or proteomically (e.g., through expression of a protein in one cell type that is not expressed in another, through enhanced or reduced expression of a protein in one cell type as compared to another, etc.). In some instances, cancer heterogeneity may be identified based on the presence of two or more phenotypically different cells present in a cancer, including e.g., where such phenotypically different cells are identified through clinical testing (e.g., histology, immunohistochemistry, in situ hybridization, cytometry, transcriptomics, mutational analysis, whole genome sequencing, proteomics, etc.).

As such, a heterogeneous cancer, as defined herein, will generally include at least one cancerous cell type and at least one other cell type, where the one other cell type may be a second cancerous cell type or a non-cancerous cell type. For example, a heterogeneous cancer may include a first cancerous cell type and a second cancerous cell type. Alternatively, a heterogeneous cancer may include a cancerous cell type and a non-cancerous cell type. Although a heterogeneous cancer will include at least two different cell types, such cancers are not so limited and may include e.g., more than two different cell types, three or more different cell types, four or more different cell types, five or more different cell types, etc., where at least one cell type is cancerous and the additional cell types may each be cancerous or non-cancerous.

As summarized above, heterogeneity of a cancer may be defined by differing gene or protein expression by different subpopulations of cells of the cancer. For example, in some instances, a first subpopulation of cells may express a first gene product from a first gene that is not expressed by a second subpopulation of cells, where such a second cell population may or may not express a second gene product from a second gene that defines the second population. Put another way, subpopulations of cells within a heterogeneous cancer may, in some instances, each be defined by the presence or absence (or relative levels) of one or more expressed gene products, where useful expressed gene products for defining cell types may include but are not limited to biomarkers, antigens, wild-type proteins, mutated proteins, wild-type transcripts, mutated transcripts, etc.

Cancer heterogeneity, in some instances, may include or exclude heterogeneity at the subject level, i.e., intrapatient heterogeneity. As used herein, the term "intrapatient heterogeneity" generally refers to heterogeneity observed between multiple cancers, e.g., multiple tumors, present in a single subject. For example, a primary tumor and a metastasis with a subject may be heterogeneous, e.g., differentially expressing a particular gene product, such as a biomarker, an antigen or a mutated protein. Multiple heterogeneous cancers may arise in a subject through various mechanisms including but not limited to mutation, clonal expansion, metastasis, selection, and combinations thereof. For example, two different intrapatient heterogeneous cancers arising by metastasis of a primary tumor may be heterogeneous with respect to the tissues in which they reside. Alternatively, two different intrapatient heterogeneous cancers derived from the same primary tumor may arise due to mutation and clonal expansion, where one cancer is a subclone of the other. Various other mechanism by which different intrapatient heterogeneous cancers may arise are possible and fall within the scope of the term as used herein.

Cancer heterogeneity, in some instances as used herein, may exclude heterogeneity at the population level, i.e., interpatient heterogeneity. As used herein, the term "interpatient heterogeneity" generally refers to differences observed between two cancers or two tumors present in separate subjects or patients.

As used herein, the terms "treatment." "treating," "treat" and the like, refer to obtaining a desired pharmacologic and/or physiologic effect and/or a response related to the treatment. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of an agent (including biologic agents, such as cells), or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "individual," "subject." "host," and "patient," used interchangeably herein, refer to a mammal, including, but not limited to, murines (e.g., rats, mice), non-human primates, humans, canines, felines, ungulates (e.g., equines, bovines, ovines, porcines, caprines), lagomorphs, etc. In some cases, the individual is a human. In some cases, the individual is a non-human primate. In some cases, the individual is a rodent, e.g., a rat or a mouse. In some cases, the individual is a lagomorph, e.g., a rabbit.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also called resistant cancer.

The term "histology" and "histological" as used herein generally refers to microscopic analysis of the cellular anatomy and/or morphology of cells obtained from a multicellular organism including but not limited to plants and animals.

The term "cytology" and "cytological" as used herein generally refers to a subclass of histology that includes the microscopic analysis of individual cells, dissociated cells, loose cells, clusters of cells, etc. Cells of a cytological sample may be cells in or obtained from one or more bodily fluids or cells obtained from a tissue that have been dissociated into a liquid cellular sample.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional heterodimerization of the two portions of the split CAR is pharmacologically controlled (e.g., as described in PCT publication no. WO 2014/127261 A1 and US Patent Application No. 2015/0368342 A1, the disclosures of which are incorporated herein by reference in their entirety). CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety. Useful CARs also include the anti-CD19-4-1BB-CD3ζ CAR expressed by lentivirus loaded CTL019 (Tisagenlecleucel-T) CAR-T cells as commercialized by Novartis (Basel. Switzerland).

The terms "T cell receptor" and "TCR" are used interchangeably and will generally refer to a molecule found on the surface of T cells, or T lymphocytes, that is responsible for recognizing fragments of antigen as peptides bound to major histocompatibility complex (MHC) molecules. The TCR complex is a disulfide-linked membrane-anchored heterodimeric protein normally consisting of the highly variable alpha (α) and beta (β) chains expressed as part of a complex with CD3 chain molecules. Many native TCRs exist in heterodimeric αβ or γδ forms. The complete endogenous TCR complex in heterodimeric αβ form includes eight chains, namely an alpha chain (referred to herein as TCRα or TCR alpha), beta chain (referred to herein as TCRβ or TCR beta), delta chain, gamma chain, two epsilon chains and two zeta chains. In some instance, a TCR is generally referred to by reference to only the TCRα and TCRβ chains, however, as the assembled TCR complex may associate with endogenous delta, gamma, epsilon and/or zeta chains an ordinary skilled artisan will readily understand that reference to a TCR as present in a cell membrane may include reference to the fully or partially assembled TCR complex as appropriate.

Recombinant or engineered individual TCR chains and TCR complexes have been developed. References to the use of a TCR in a therapeutic context may refer to individual recombinant TCR chains. As such, engineered TCRs may include individual modified TCRα or modified TCRβ chains as well as single chain TCRs that include modified and/or unmodified TCRα and TCRβ chains that are joined into a single polypeptide by way of a linking polypeptide.

As used herein, by "chimeric bispecific binding member" is meant a chimeric polypeptide having dual specificity to two different binding partners (e.g., two different antigens). Non-limiting examples of chimeric bispecific binding members include bispecific antibodies, bispecific conjugated monoclonal antibodies (mab)$_2$, bispecific antibody fragments (e.g., F(ab)$_2$, bispecific scFv, bispecific diabodies, single chain bispecific diabodies, etc.), bispecific T cell engagers (BiTE), bispecific conjugated single domain antibodies, micabodies and mutants thereof, and the like. Non-limiting examples of chimeric bispecific binding members also include those chimeric bispecific agents described in Kontermann. MAbs. (2012) 4(2): 182-197; Stamova et al. *Antibodies* 2012, 1(2), 172-198; Farhadfar et al. *Leuk Res*. (2016) 49:13-21; Benjamin et al. *Ther Adv Hematol*. (2016) 7(3):142-56; Kiefer et al. *Immunol Rev*. (2016) 270(1):178-92; Fan et al. *J Hematol Oncol*. (2015) 8:130; May et al. *Am J Health Syst Pharm*. (2016) 73(1):e6-e13; the disclosures of which are incorporated herein by reference in their entirety.

A "biological sample" encompasses a variety of sample types obtained from an individual or a population of individuals and can be used in various ways, including e.g., the isolation of cells or biological molecules, diagnostic assays, etc. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by mixing or pooling of individual samples, treatment with reagents, solubilization, or enrichment for certain components, such as cells, polynucleotides, polypeptides, etc. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples (e.g., biopsy samples), and cellular samples. Accordingly, biological samples may be cellular samples or acellular samples.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, nanobodies, single-domain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag. New York, pp. 269-315 (1994).

The term "nanobody" (Nb), as used herein, refers to the smallest antigen binding fragment or single variable domain (V$_{HH}$) derived from naturally occurring heavy chain antibody and is known to the person skilled in the art. They are derived from heavy chain only antibodies, seen in camelids (Hamers-Casterman et al. (1993) *Nature* 363:446; Desmyter et al. (2015) *Curr. Opin. Struct. Biol.* 32:1). In the family of "camelids" immunoglobulins devoid of light polypeptide chains are found. "Camelids" comprise old world camelids (*Camelus bactrianus* and *Camelus dromedarius*) and new world camelids (for example, *Llama paccos. Llama glama, Llama guanicoe* and *Llama vicugna*). A single variable domain heavy chain antibody is referred to herein as a nanobody or a V$_{HH}$ antibody.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

A "orthogonal" or "orthogonalized" member or members of a binding pair are modified from their original or wild-type forms such that the orthogonal pair specifically bind one another but do not specifically or substantially bind the non-modified or wild-type components of the pair. Any binding partner/specific binding pair may be orthogonalized, including but not limited to e.g., those binding partner/specific binding pairs described herein.

The terms "domain" and "motif", used interchangeably herein, refer to both structured domains having one or more particular functions and unstructured segments of a poly-peptide that, although unstructured, retain one or more particular functions. For example, a structured domain may encompass but is not limited to a continuous or discontinu-ous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disor-dered. Also encompassed within this definition are domains that may be disordered or unstructured but become struc-tured or ordered upon association with a target or binding partner. Non-limiting examples of intrinsically unstructured domains and domains of intrinsically unstructured proteins are described, e.g., in Dyson & Wright. *Nature Reviews Molecular Cell Biology* 6:197-208.

The terms "synthetic", "chimeric" and "engineered" as used herein generally refer to artificially derived polypep-tides or polypeptide encoding nucleic acids that are not naturally occurring. Synthetic polypeptides and/or nucleic acids may be assembled de novo from basic subunits includ-ing, e.g., single amino acids, single nucleotides, etc., or may be derived from pre-existing polypeptides or polynucle-otides, whether naturally or artificially derived, e.g., as through recombinant methods. Chimeric and engineered polypeptides or polypeptide encoding nucleic acids will generally be constructed by the combination, joining or fusing of two or more different polypeptides or polypeptide encoding nucleic acids or polypeptide domains or polypep-tide domain encoding nucleic acids. Chimeric and engi-neered polypeptides or polypeptide encoding nucleic acids include where two or more polypeptide or nucleic acid "parts" that are joined are derived from different proteins (or nucleic acids that encode different proteins) as well as where the joined parts include different regions of the same protein (or nucleic acid encoding a protein) but the parts are joined in a way that does not occur naturally.

The term "recombinant", as used herein describes a nucleic acid molecule, e.g., a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "operably linked" refers to a juxtaposition wherein the components so described are in a relationship permitting them to function in their intended manner. For instance, a promoter is operably linked to a coding sequence if the promoter affects its transcription or expression. Oper-ably linked nucleic acid sequences may but need not nec-essarily be adjacent. For example, in some instances a coding sequence operably linked to a promoter may be adjacent to the promoter. In some instances, a coding sequence operably linked to a promoter may be separated by one or more intervening sequences, including coding and non-coding sequences. Also, in some instances, more than two sequences may be operably linked including but not limited to e.g., where two or more coding sequences are operably linked to a single promoter.

The terms "polynucleotide" and "nucleic acid," used interchangeably herein, refer to a polymeric form of nucleo-tides of any length, either ribonucleotides or deoxyribo-nucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleo-tide bases.

The terms "polypeptide," "peptide." and "protein", used interchangeably herein, refer to a polymeric form of amino acids of any length, which can include genetically coded and non-genetically coded amino acids, chemically or biochemi-cally modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "vector" or "expression vector" is a replicon, such as plasmid, phage, virus, or cosmid, to which another DNA segment, i.e, an "insert", may be attached so as to bring about the replication of the attached segment in a cell.

The term "Heterologous", as used herein, means a nucleo-tide or polypeptide sequence that is not found in the native (e.g., naturally-occurring) nucleic acid or protein, respec-tively. Heterologous nucleic acids or polypeptide may be derived from a different species as the organism or cell within which the nucleic acid or polypeptide is present or is expressed. Accordingly, a heterologous nucleic acids or polypeptide is generally of unlike evolutionary origin as compared to the cell or organism in which it resides.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides methods of treating a subject for a glioblastoma, including an EGFRvIII negative glioblastoma. The methods of the present disclosure involve administering to the subject a molecular circuit that is primed by priming antigen to induce one or more encoded therapeutics specific for one or more antigens expressed by the glioblastoma. The circuit may be administered in the form of cells encoding the molecular circuit, vector(s) that deliver nucleic acids encoding the circuit to cells of the subject, or the like. Accordingly, nucleic acids containing sequences encoding all or portions of such circuits are also provided, as well as cells, expression cassettes and vectors that contain such nucleic acids. Also provided are kits for practicing the described methods.

The subject circuits may integrate the expression of a priming antigen on a glioblastoma multiforme (GBM) cell and at least a second antigen expressed on a second cell of the GBM to produce a desired outcome with respect to the second cell. In some instances, the subject circuits may integrate the expression of a priming antigen on an EGFRvIII-negative ("EGFRvIII(–)") glioblastoma multiforme (GBM) cell and at least a second antigen expressed on a second cell of the EGFRvIII(–) GBM to produce a desired outcome with respect to the second cell. The integration of two antigens expressed by different cells of a heterogeneous cell population to result in a desired targeting event may be referred to herein as "trans-targeting".

For example, an employed circuit may integrate "priming antigen" expressed by a first GBM cell (e.g., an EGFRvIII(–) GBM cell), referred to as a "priming cell", and a second antigen (e.g., a "targeting antigen" or "targeted antigen" or "killing antigen") expressed by a second cell, e.g., a nearby cell, of the GBM (e.g., EGFRvIII(–) GBM), referred to as a "targeted cell", to target the second cell type in trans. A therapeutic cell modified with such a circuit is primed by the presence of the priming antigen on the first cell to then target the targeted cell.

For comparison, in this context cis-targeting refers to integrating of two antigens to target a single cell which expresses both a priming antigen and a targeting antigen to produce a desired outcome with respect to the single cell. Thus, in cis-targeting, the targeted cell expresses both the priming antigen and the targeting antigen such that the two antigens are expressed in cis with respect to the cell. In trans-targeting, the targeted cell expresses only the targeting antigen and not the priming antigen such that the two antigens are expressed in trans with respect to the two cells. As such, trans targeting may be employed to target a cell that does not express a priming antigen. In some instances, a circuit of the present disclosure may employ both trans-targeting and cis-targeting, i.e., cis- and trans-targeting may be combined in a single circuit. In some instances, a circuit of the present disclosure may employ only trans-targeting and may e.g., exclude cis-targeting.

The circuits of the present disclosure will generally employ at least one binding triggered transcriptional switch (BTTS) as described in more detail below. A therapeutic cell may be modified to express a BTTS responsive to a priming antigen. The BTFS may be expressed in the plasma membrane of the cell. Binding of the BTTS to priming antigen may induce expression of a protein in the BTTS expressing cell. The induced protein may be a heterologous antigen-specific protein, such as a second BTTS or a heterologous antigen-specific therapeutic, as described in more detail below. In the context of cis-targeting, binding of the BTTS to priming antigen expressed on a GBM priming cell (e.g., an EGFRvIII(–) GBM priming cell) induces expression of an antigen specific protein that is specific for a targeting antigen that is also expressed by the GBM priming cell (e.g., EGFRvIII(–) GBM priming cell) (i.e., the GBM cell is both the priming cell and the targeted cell). In the context of trans-targeting, binding of the BTTS to priming antigen expressed on a GBM priming cell (e.g., EGFRvIII(–) GBM priming cell) induces expression of an antigen specific protein that is specific for a targeting antigen that is expressed on a GBM cell (e.g., an EGFRvIII(–) GBM cell) that does not express the priming antigen (i.e., a GBM cell (e.g., EGFRvIII(–) GBM cell) other than the priming cell).

In this manner, trans-targeting allows for targeting of cells by an antigen specific protein, such as an antigen-specific therapeutic, only in the presence of priming cells. Correspondingly, trans-targeting allows for targeting of cells with an antigen specific protein, such as an antigen-specific therapeutic, in a heterogeneous cell population, such as a heterogeneous cancer, where the targeted cells do not express priming antigen, i.e., are priming-antigen(−) cells. Accordingly, such targeted priming antigen(−) GBM cells (e.g., priming-antigen(−)/EGFRvIII(−) GBM cells) may be spatially associated with priming-antigen-positive ("priming-antigen(+)") GBM cells (e.g., priming-antigen(+)/EG-FRvIII(−) GBM cells), i.e., cells that that do express priming antigen.

While the subject methods are described primarily herein with respect to EGFRvIII(−) GBM cells (i.e., EGFRvIII(−) GBM priming cells and EGFRvIII(−) GBM targeted cells), in some instances the described circuits may be employed in methods of trans-targeting of a GBM cell in a subject that is a EGFRvIII(+) cell and/or a cell present in an EGFRvIII-positive ("EGFRvIII(+)") GBM. In such instances, the priming antigen employed will generally not be EGFRvIII (i.e., the priming antigen may be a non-EGFRvIII priming antigen). Accordingly, the present disclosure includes methods of treating a subject, as described in more detail below, for a GBM, which may be EGFRvIII(+) or EGFRvIII(−), that include administering to the subject an immune cell genetically modified with: (a) a nucleic acid sequence encoding a binding triggered transcriptional switch (BTTS) that binds to a priming antigen other than EGFRvIII (i.e., a non-EG-FRvIII priming antigen); (b) a nucleic acid sequence encoding an antigen-specific therapeutic that binds to a killing antigen expressed by the GBM; (c) a regulatory sequence operably linked to (b) that is responsive to the BTTS; wherein binding of the BTTS to the priming antigen activates expression of the antigen-specific therapeutic which binds the killing antigen thereby inducing killing of GBM cells expressing the killing antigen.

Useful non-EGFRvIII priming antigens for cis- or trans-targeting of EGFRvIII(+) GBM cells include but are not limited to those priming antigens described below for targeting EGFRvIII(−) GBM cells. Moreover, the use of a non-EGFRvIII priming antigen in a method of the present disclosure does not necessarily preclude the use of EGFRvIII as a targeting antigen; however, in some instances, the subject methods may specifically exclude the use of EGFRvIII as a targeting/killing antigen. As will be readily recognized, wherein methods and/or components of methods are described below with respect to targeting EGFRvIII(−) GBM cells and/or treating a subject for a EGFRvIII(−) GBM, such methods may be equally applied or adapted in many cases to targeting EGFRvIII(+) GBM cells using a non-EGFRvIII priming antigen and/or treating a subject for a EGFRvIII(−) GBM using a non-EGFRvIII priming antigen.

Methods

As summarized above, the present disclosure provides methods of targeting priming-antigen(−) cells in a heterogeneous EGFRvIII(−) GBM, including where such cells are targeted in trans. Such methods may include administering, to a subject in need thereof, a circuit encoding a BTTS responsive to priming antigen that induces expression of an antigen-specific therapeutic, where the antigen-specific therapeutic may be responsive to one or more antigens other than the priming antigen. Such circuits, when expressed on a therapeutic immune cell, may activate the immune cell to mediate the targeted killing of priming-antigen(−)/EG-FRvIII(−) GBM cells in a EGFR(−) GBM tumor where at least some of the cells heterogeneously express the priming antigen.

Methods of Treatment

As summarized above, the methods of the present disclosure find use in treating a subject for an EGFRvIII(−) GBM.

Such treatments may include obtaining a desired effect with respect to at least one EGFRvIII(−) GBM cell type (or subpopulation thereof) of a GMB tumor heterogeneously positive for priming antigen. The term "heterogeneously positive", as used herein, is generally meant a GBM tumor containing at least some cells that express the priming antigen and at least some cells that do not express the priming antigen. Such tumors may, in some instances, include a subpopulation of cells that does not express the priming antigen that was derived from a parent population expressing the priming antigen. In some instances, a subpopulation of a tumor may begin expressing a priming antigen de novo from a parent population that does not express the priming antigen. In some instances, antigen expression of GBM cells may change or evolve over the course of tumor progression.

In some instances, treatments may include obtaining a desired effect with respect to one cell type or more than one cell type (or subpopulation of cells) of the heterogeneous EGFRvIII(−) GBM, including two or more, three or more, four or more, five or more, etc., cell types or subpopulations of cells of the heterogeneous EGFRvIII(−) GBM. Desired effects of the treatments, as described in more detail below, will vary. For example, with respect to one or more targeted cell types, desired effects will vary and may include but are not limited to e.g., killing of the one or more targeted cell types, reducing the proliferation of the one or more targeted cell types, and the like.

The subject methods may include introducing into a subject in need thereof, cells that contain nucleic acid sequences encoding a circuit for trans-targeting of a cell of a heterogeneous EGFRvIII(−) GBM. The introduced cells may be immune cells, including e.g., myeloid cells or lymphoid cells.

In some instances, the instant methods may include contacting a cell with one or more nucleic acids encoding a circuit wherein such contacting is sufficient to introduce the nucleic acid(s) into the cell. Any convenient method of introducing nucleic acids into a cell may find use herein including but not limited viral transfection, electroporation, lipofection, bombardment, chemical transformation, use of a transducible carrier (e.g., a transducible carrier protein), and the like. Nucleic acids may be introduced into cells maintained or cultured in vitro or ex vivo. Nucleic acids may also be introduced into a cell in a living subject in vivo, e.g., through the use of one or more vectors (e.g., viral vectors) that deliver the nucleic acids into the cell without the need to isolate, culture or maintain the cells outside of the subject.

Introduced nucleic acids may be maintained within the cell or transiently present. As such, in some instance, an introduced nucleic acid may be maintained within the cell, e.g., integrated into the genome. Any convenient method of nucleic acid integration may find use in the subject methods, including but not limited to e.g., viral-based integration, transposon-based integration, homologous recombination-based integration, and the like. In some instance, an introduced nucleic acid may be transiently present, e.g., extra-chromosomally present within the cell. Transiently present nucleic acids may persist, e.g., as part of any convenient transiently transfected vector.

An introduced nucleic acid encoding a circuit may be introduced in such a manner as to be operably linked to a regulatory sequence, such as a promoter, that drives the expression of one or more components of the circuit. The source of such regulatory sequences may vary and may include e.g., where the regulatory sequence is introduced with the nucleic acid, e.g., as part of an expression construct or where the regulatory sequence is present in the cell prior to introducing the nucleic acid or introduced after the nucleic acid. As described in more detail herein, useful regulatory sequence can include e.g., endogenous promoters and heterologous promoters. For example, in some instances, a nucleic acid may be introduced as part of an expression construct containing a heterologous promoter operably linked to a nucleic acid sequence. In some instances, a nucleic acid may be introduced as part of an expression construct containing a copy of a promoter that is endogenous to the cell into which the nucleic acid is introduced. In some instances, a nucleic acid may be introduced without a regulatory sequence and, upon integration into the genome of the cell, the nucleic acid may be operably linked to an endogenous regulatory sequence already present in the cell. Depending on the confirmation and/or the regulatory sequence utilized, expression of each component of the circuit from the nucleic acid may be configured to be constitutive, inducible, tissue-specific, cell-type specific, etc., including combinations thereof.

Any convenient method of delivering the circuit encoding components may find use in the subject methods. In some instances, the subject circuit may be delivered by administering to the subject a cell expressing the circuit. In some instances, the subject circuit may be delivered by administering to the subject a nucleic acid comprising one or more nucleotide sequences encoding the circuit. Administering to a subject a nucleic acid encoding the circuit may include administering to the subject a cell containing the nucleic acid where the nucleic acid may or may not yet be expressed. In some instances, administering to a subject a nucleic acid encoding the circuit may include administering to the subject a vector designed to deliver the nucleic acid to a cell.

Accordingly, in the subject methods of treatment, nucleic acids encoding a circuit or components thereof may be administered in vitro, ex vivo or in vivo. In some instances, cells may be collected from a subject and transfected with nucleic acid and the transfected cells may be administered to the subject, with or without further manipulation including but not limited to e.g., in vitro expansion. In some instances, the nucleic acid, e.g., with or without a delivery vector, may be administered directly to the subject.

Priming cells and targeted cells of a subject circuit will generally differ in at least the expression of priming antigen and targeting antigen. In some instances, priming cells and targeted cells may differ in the expression of at least one surface expressed epitope, e.g., a surfaced expressed protein, an antigen presented in the context of MHC, etc., including e.g., where the surface expressed epitope is a molecule other than the priming antigen and/or the targeting antigen. In some instances, two different targeted cells may differ in the expression of at least one surface expressed epitope, e.g., a surfaced expressed protein, an antigen presented in the context of MHC, etc.

Differential expression between two cells or two cell types of a EGFRvIII(−) GBM will vary. For example, in some instances, a cell expresses one surface epitope not expressed by the other. In some instances, a cell expresses one surface epitope more highly than the surface epitope is expressed by the other cell. Where cells differ in the level, e.g., as compared to the presence/absence, of expression of a surface epitope the difference in level may vary but will generally be substantially different, e.g., sufficiently different to allow for practical targeting of one cell versus the other. Differences in expression between cells may range from less than one order of magnitude of expression to ten orders of magnitude of expression or more, including but not limited to e.g., 1 order of magnitude, 2 orders of magnitude, 3 orders of magnitude, 4 orders of magnitude, 5 orders of magnitude, 6 orders of magnitude, 7 orders of magnitude, 8 orders of magnitude, 9 orders of magnitude, 10 orders of magnitude, etc. In some instances, two cell types differing in level of expression of a particular epitope may be said to be "high" and "low" for the epitope, respectively, where high versus low expression may be differentiated using conventional methods known to the relevant artisan.

In some instances, the presence or absence of a particular epitope will be defined by the limit of detection of the method employed to detect the epitope, including e.g., where such limit of detection may or may not be based on an appropriate reference standard or positive or negative control. For example, where the epitope is present below the limit of detection the cell may be said to be "negative" for the epitope. Correspondingly, where the epitope is present below the level detected in a reference standard or appropriate control the cell may be said to be negative for the epitope. Where the epitope is present above the limit of detection the cell may be said to be "positive" for the epitope. Correspondingly, where the epitope is present above the level detected in a reference standard or appropriate control the cell may be said to be positive for the epitope.

As summarized above, priming cells and targeted cells in a heterogeneous GBM will generally be in sufficient proximity to allow for recognition of a targeted cell expressing a targeting antigen, but not the priming antigen, by a primed immune cell. Relative proximity between a priming cell and a targeted cell sufficient for trans-targeting of the targeted cell will vary and, as described herein, may be modified as desired depending on how the subject circuit is designed (e.g., through the use of a more or less stable antigen-specific therapeutic, through the use of a diffusible payload, etc.). In some instances, the priming cell and the targeted cell may be adjacent. In some instances, the priming cell and the targeted cell may be non-adjacent. As such, the proximity, expressed in this context as the distance between, a priming cell and a targeted cell may range from about 1 cell diameter to 100 cell diameters or more, including but not limited to e.g., 1 to 100 cell diameters, 2 to 100 cell diameters, 5 to 100 cell diameters, 10 to 100 cell diameters, 1 to 50 cell diameters, 2 to 50 cell diameters, 5 to 50 cell diameters, 10 to 50 cell diameters, 1 to 25 cell diameters, 2 to 25 cell diameters, 5 to 25 cell diameters, 10 to 25 cell diameters, etc.

Heterogeneity of EGFRvIII(−) GBM tumors treated using the methods described herein will vary. For example, in some instances, the degree of heterogeneity in a heterogeneous EGFRvIII(−) GBM will vary. For example, with respect to each individual cell type present in a heterogeneous GBM, a subject cell type (e.g., a priming cell, a first targeted cell type, a second targeted cell type, or another cell type) will represent less than 100% of the cells of the EGFRvIII(−) GBM including but not limited to e.g., less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than 3%, less than 2%, or less than 1% of the cells of the heterogeneous EGFRvIII(−) GBM.

In some instances, 75% or less of the cells of a heterogeneous EGFRvIII(−) GBM express the relevant priming antigen, including but not limited to e.g., 70% or less, 65% or less, 60% or less, 55% or less, 50% or less, 45% or less, 40% or less, 35% or less, 30% or less, 25% or less, or 20% or less. In some instances, methods of the present disclosure find use in treating a heterogeneous EGFRvIII(−) GBM in a subject where the percentage of cells of the EGFRvIII(−) GBM that express the relevant priming antigen ranges from 1% or more than 1% to 99% or less than 99%, including but not limited to e.g., from 1% to 99%, from 5% to 90%, from 10% to 85%, from 20% to 80%, from 25% to 75% and the like.

In some instances, a targeted cell (e.g., a targeting antigen-positive, EGFR(−) cell of the tumor) of a herein disclosed methods may represent less than 50% of the cells of the heterogeneous cancer or heterogeneous tumor, including but not limited to e.g., less than 45%, less than 40%, less than 35%, less than 30%, less than 25%, less than 20%, less than 15%, less than 10%, less than 5%, less than 4%, less than 3%, less than 2%, or less than 1% of the cells of the heterogeneous cancer or a heterogeneous tumor.

In some instances, a particular cell type present in a heterogeneous EGFR(−) GBM (e.g., a priming cell type, a targeted cell type or another cell type) may be a majority cell type of the heterogeneous cancer, including e.g., where the particular cell type represents 50% or greater, including e.g., 60% or greater, 70% or greater, 80% or greater, 90% or greater, 95% or greater, of the cells of the heterogeneous GBM. In some instances, a priming cell of a herein disclosed method may represent 50% or greater of the cells of the heterogeneous GBM, including but not limited to e.g., 60% or greater, 70% or greater, 80% or greater, 90% or greater, 95% or greater, of the cells of the heterogeneous GBM. In some instances, a EGFRvIII(−) targeted cell expressing targeting antigen of a herein disclosed method may represent 50% or greater of the cells of the heterogeneous GBM, including but not limited to e.g., 60% or greater, 70% or greater, 80% or greater, 90% or greater, 95% or greater, of the cells of the heterogeneous GBM.

The methods of the present disclosure may be employed to target and treat a variety of GBM tumors, including e.g., primary GBM, secondary GBM tumors, re-growing GBM tumors, recurrent GBM tumors, refractory GBM tumors and the like. For example, in some instances, the methods of the present disclosure may be employed as an initial treatment of a primary GBM identified in a subject, including where the primary GBM is identified as EGFRvIII(−). In some instances, the methods of the present disclosure may be employed as a non-primary (e.g., secondary or later) treatment, e.g., in a subject with a GBM that is refractory to at least one prior treatment, in a subject with a GBM that is re-growing following at least one prior treatment, in a subject with a mixed response to at least one prior treatment (e.g., a positive response in at least one tumor in the subject and a negative or neutral response in at least a second tumor in the subject, including e.g., a mixed response to a treatment for multiple GBM), and the like.

In some instances, the method of the present disclosure may be employed to target, treat or clear a subject for minimal residual disease (MRD) remaining after a prior GBM therapy. Targeting, treating and/or clearance of EGFRvIII(−) GBM MRD may be pursued using the instant methods whether or not the MRD is or has been determined to be refractory to the prior treatment. In some instances, a method of the present disclosure may be employed to target, treat and/or clear a subject of MRD following a determination that the MRD is refractory to a prior treatment or one or more available treatment options other than those employing the herein described circuits.

In some instances, the instant methods may be employed prophylactically for surveillance. For example, a subject in need thereof may be administered a treatment involving one or more of the herein described circuits when the subject does not have detectable disease but is at risk of developing a GBM or a recurrent GBM. In some instances, a prophylactic approach may be employed when a subject is at particularly high risk of developing a primary GBM that would be predicted to be a heterogeneous GBM and may, e.g., be predicted to be EGFRvIII(−). In some instances, a prophylactic approach may be employed when a subject has been previously treated for a GBM and is at risk of reoccurrence. Essentially any combination of priming antigen and targeting antigen may be employed in prophylactic treatments, including those described herein.

In some instances, the herein described methods may be used to prophylactically surveil a subject for GBM cells expressing one or more mutations commonly present in GBM tumors, including mutations found in recurrent and/or refractory GBM or that occur in primary GBM. Mutations found in primary, recurrent and/or refractory GBM (and subtypes thereof) include but are not limited to e.g., IDH1 mutation, TP53 mutation, ALK mutation, RRM1 mutation, TUBB3 mutation. ATRX mutation, BRAF mutation. PTEN mutation, PDGFRA mutation, PTPN11 mutation, and SMARCA4 mutation. In some instances, methods may employ an antigen-specific therapeutic specific for one or more killing antigens, where the one or more killing antigens include one or more commonly mutated proteins, including surface expressed proteins.

In some instances, methods of the present disclosure may be employed to treat subjects that do not necessarily present with a heterogeneous GBM, including primary and non-primary GBMs, but are at an increased risk of developing such a heterogeneous GBM. For example, a subject having an apparently homogeneous EGFRvIII(−) GBM may be treated with a circuit to prophylactically surveil a subject for GBM cells expressing one or more mutations that occur in GBM (where such mutations may exclude, in some instances, mutations resulting in production of a EGFRvIII variant).

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy.

With respect to the GBM as a whole, desired effects of the described treatments may result in a reduction in the number of cells in the GBM, a reduction in the size of a GBM tumor, a reduction in the overall proliferation of the GBM, a reduction in the overall growth rate of a GBM tumor, etc. For example, an effective treatment is in some cases a treatment that, when administered in one or more doses to an individual in need thereof, reduces the number of cancer cells in the individual and/or reduces tumor mass in the individual, by at least about 10%, at least about 15%, at least about 20%, at least about 25%, at least about 30%, at least about 40%, at least about 50%, at least about 75%, or more than 75%, compared to the number of cancer cells and/or tumor mass in the absence of the treatment. Reductions in the number of cancer cells or the size of the tumor mass may be defined with respect to the heterogeneous tumor as a whole or with respect to the targeted cells of the GBM.

In some embodiments, an effective treatment is a treatment that, when administered alone (e.g., in monotherapy) or in combination (e.g., in combination therapy) with one or more additional therapeutic agents, in one or more doses, is effective to reduce one or more of tumor growth rate, GBM cell number, and tumor mass, by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the tumor growth rate, GBM cell number, or tumor mass in the absence of the treatment. Reductions in the tumor growth rate, GBM cell number, or tumor mass may be defined with respect to the heterogeneous tumor as a whole or with respect to the targeted cells of the GBM.

In some instances, treatment may involve activation of an immune cell containing nucleic acid sequences encoding a circuit as described herein. Accordingly, the present disclosure correspondingly presents methods of activating an immune cell, e.g., where the immune cell expresses a priming/targeting circuit as described herein and is contacted with a first cell of a EGFRvIII(−) GBM expressing a priming antigen and a second cell of the GBM expressing a targeting antigen.

Immune cell activation, as a result of the methods described herein, may be measured in a variety of ways, including but not limited to e.g., measuring the expression level of one or more markers of immune cell activation. Useful markers of immune cell activation include but are not limited to e.g., CD25, CD38, CD40L (CD154), CD69, CD71, CD95. HLA-DR, CD137 and the like. For example, in some instances, upon antigen binding by an immune cell receptor an immune cell may become activated and may express a marker of immune cell activation (e.g., CD69) at an elevated level (e.g., a level higher than a corresponding cell not bound to antigen). Levels of elevated expression of activated immune cells of the present disclosure will vary and may include an increase, such as a 1-fold or greater increase in marker expression as compared to un-activated control, including but not limited to e.g., a 1-fold increase, a 2-fold increase, a 3-fold increase, a 4-fold increase, etc.

In some instances, an immune cell modified to encode a circuit of the present disclosure, when bound to a targeted antigen, may have increased cytotoxic activity, e.g., as compared to an un-activated control cell. In some instances, activated immune cells encoding a subject circuit may show 10% or greater cell killing of antigen expressing target cells as compared to un-activated control cells. In some instances, the level of elevated cell killing of activated immune cells will vary and may range from 10% or greater, including but not limited to e.g., 20% or greater, 30% or greater, 40% or greater, 50% or greater, 60% or greater, 70% or greater, 80% or greater, 90% or greater, etc., as compared to an appropriate control.

In some instances, treatment may involve modulation, including induction, of the expression and/or secretion of a cytokine by an immune cell containing nucleic acid sequences encoding a circuit as described herein. Non-limiting examples of cytokines, the expression/secretion of which may be modulated, include but are not limited to e.g., Interleukins and related (e.g., IL-1-like, IL-1α, IL-1β, IL-1RA, IL-18, IL-2, IL-4, IL-7, IL-9, IL-13, IL-15, IL-3, IL-5, GM-CSF, IL-6-like, IL-6, IL-11, G-CSF, IL-12, LIF, OSM, IL-10-like, IL-10, IL-20, IL-14, IL-16, IL-17, etc.), Interferons (e.g., IFN-α, IFN-β, IFN-γ, etc.), TNF family (e.g., CD154, LT-β, TNF-α, TNF-β, 4-1BBL, APRIL, CD70, CD153, CD178. GITRL, LIGHT, OX40L, TALL-1, TRAIL. TWEAK, TRANCE, etc.), TGF-β family (e.g., TGF-β1, TGF-β2, TGF-β3, etc.) and the like.

In some instances, activation of an immune cell through a circuit of the present disclosure may induce an increase in cytokine expression and/or secretion relative to that of a comparable cell where the circuit is not present or otherwise inactive. The amount of the increase may vary and may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

Conventional Treatments and Combination Therapy

As will be readily understood, the methods of treating described herein may, in some instances, be combined with one or more conventional treatments. For example, in the case of oncology for GBM, the methods described herein may, in some instances, be combined with a conventional GBM therapy including but not limited to e.g., conventional chemotherapy, conventional radiation therapy, conventional immunotherapy, surgery, etc. Also as described above, in some instances, the methods of treating described herein may be employed following conventional therapy, e.g., to treat a heterogeneous EGFRvIII(−) GBM that is refractory to a conventional therapy, to treat a heterogeneous EGFRvIII (−) GBM that is recurrent after a conventional therapy, to treat a subject for MRD following conventional therapy, and the like.

In some instances, the methods described herein may be used before or after a conventional therapy. For example, the methods described herein may be used as an adjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Standard GBM therapies include surgery (e.g., surgical removal of cancerous tissue), radiation therapy, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Antibodies suitable for use in, or under investigation for, GBM treatment include, but are not limited to, naked antibodies, e.g., trastuzumab (Herceptin), bevacizumab (AVASTIN™), cetuximab (ERBITUX™), panitumumab (VECTIBIX™), Ipilimumab (YERVOY™), rituximab (Rituxan), alemtuzumab (LEMTRADA™), Oregovomab (OVAREX™), Lambrolizumab (pembrolizumab, MK-3475, KEYTRUDA™), ranibizumab (LUCENTIS™) etc., and conjugated antibodies, e.g., conjugated antibodies of those listed above and the like.

Conventional cancer therapies also include targeted therapies for cancer including but not limited to e.g., Bevacizumab (Avastin) targeting VEGF ligand (approved for use in Glioblastoma) and the like.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α.; (7) interferon- γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, epothilone A, epothilone B, discodermolide; estramustine, nocodazole, and the like.

Hormone modulators and steroids (including synthetic analogs) that are suitable for use include, but are not limited to, adrenocorticosteroids, e.g, prednisone, dexamethasone, etc.; estrogens and pregestins, e.g, hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl) propoxy) quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™. TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example. Sigma Chemical Co., St. Louis, Mo. (T7402 from *Taxus brevifolia*; or T-1912 from *Taxus yunnanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113: piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some instances, methods of treating a subject for cancer may further include administering an agent which enhances the activity of the treatment. Such agents that enhance the activity of the treatment will vary widely and may include but are not limited to e.g., agents that inhibit an inhibitor molecule. Suitable inhibitory molecules that may be targeted include but are not limited to e.g., PD1, PD-L1, CTLA4, TIM3, LAG3, VISTA, BTLA, TIGIT, LAIR1, CD160, 2B4 and TGFR beta.

Inhibiting of inhibitory molecules may be achieved by any convenient method including but not limited to e.g., the administration of a direct inhibitor of the inhibitory molecule (e.g., an antibody that binds the inhibitory molecule, a small molecule antagonist of the inhibitory molecule, etc.), administration of an agent that inhibits expression of the inhibitory molecule (e.g., an inhibitory nucleic acid, e.g., a dsRNA, e.g., an siRNA or shRNA targeting a nucleic acid encoding the inhibitory molecule), an indirect inhibitor of the inhibitory signaling, and the like. In some instances, an agent that may be administered may be an antibody or antibody fragment that binds to an inhibitory molecule. For example, the agent can be an antibody or antibody fragment that binds to PD1, PD-L1. PD-L2 or CTLA4 (e.g., ipilim- umab (also referred to as MDX-010 and MDX-101, and marketed as Yervoy (Bristol-Myers Squibb)), Tremelim- umab (Pfizer, formerly known as ticilimumab, CP-675, 206)), TIM3, LAG3, or the like.

In some instances, the methods of the instant disclosure may be used without any additional conventional therapy including e.g., where the method described herein is the sole method used to treat the subject. For example, in the case of oncology, the methods described herein may, in some instances, be the sole method used to treat the subject for a GBM, including e.g., a primary GBM, a recurrent GBM, and the like.

Determining when combination therapies, e.g., involving the administration of one or more agents that ameliorates one or more side effects of a therapy described herein or involving the administration of one or more agents that enhances a therapy described herein, are indicated and the specifics of the administration of such combination therapies are within the skill of the relevant medical practitioner. In some instances, dosage regimens and treatment schedules of combination therapies may be determined through clinical trials.

Testing

As summarized above, the methods of the present disclo- sure may, in some instances, include testing, where such testing may include but is not limited to e.g., testing of the subject, testing of a biological sample obtained from the subject, and the like. In some instances, methods of the present disclosure may include testing and/or evaluating a subject for a heterogeneous GBM. In some instances, meth- ods of the present disclosure may include testing and/or evaluating a subject for a heterogeneous EGFRvIII(–) GBM. Testing may be employed, in some instances, to determine or identify whether a subject has a heterogeneous GBM or whether a GBM (e.g., an EGFRvIII(–) GBM), in a subject known to have such, is a heterogeneous GBM.

In some instances, a GBM of a subject may be tested or evaluated to determine, detect or identify whether the GBM expresses one or more particular antigens, including but not limited to e.g., an EGFRvIII antigen, a priming antigen (including but not limited to e.g., Interleukin-13 receptor subunit alpha-2 (IL13RA2). Interleukin-13 receptor subunit alpha-1 (IL13RA1). Neuroligin(s), Neurexin-1-beta (NRXN1), Receptor-type tyrosine-protein phosphatase zeta (PTPRZ1), Neuronal cell adhesion molecule (NRCAM), Cadherin-10 (CDH10) and Protocadherin gamma-C5 (PCDHGC5), CD70 antigen (CD70), Chondroitin sulfate proteoglycan 5 (CSPG5), Brevican core protein (BCAN), Metabotropic glutamate receptor 3 (GRM3), Protein crumbs homolog 1 (CRB1). Neuromodulin (GAP43), Sodium/po- tassium-transporting ATPase subunit beta-2 (ATP1B2). Ran- binding protein MOG1 (MOG1), and a Receptor-type tyro- sine-protein phosphatase zeta-Hepatocyte growth factor receptor fusion (PTPRZ1-MET), combinations thereof and the like) and/or a targeting antigen (including but not limited to e.g., Ephrin type-A receptor 2 (EphA2), Ephrin type-A receptor 3 (EphA3), Interleukin-13 receptor (IL13R) (e.g., IL13RA1 or IL13RA2), Epidermal growth factor receptor (EGFR), erb-b2 receptor tyrosine kinase 2 (ERBB2), com- binations thereof and the like). In some instances, whether a method of the present disclosure is employed and/or the particular combination of priming antigen(s) and targeting antigen(s) employed in a subject circuit may be determined based on testing the subject for particular antigen expression in the cells of the subject's GBM.

Subjects suitable for testing will include those that have or have not been previously treated for a GBM including a heterogeneous GBM and/or a EGFRvIII(–) GBM. For example, in some instances, a subject may have been recently diagnosed with a GBM and the subject may be tested, e.g., to evaluate the presence of EGFRvIII, one or more priming antigens and/or one or more targeting anti- gens, before any treatment of the diagnosed GBM. In some instances, the subject may have been previously treated for a GBM and the subject may be tested, e.g., to evaluate the presence of EGFRvIII, one or more priming antigens and/or one or more targeting antigens, after treatment of the diag- nosed GBM, including e.g., where the subject's GBM is responsive or refractory to the prior treatment. In some instances, the subject may be undergoing treatment for a GBM and the subject may be tested, e.g., to evaluate the presence of EGFRvIII, one or more priming antigens and/or one or more targeting antigens, during the treatment of the diagnosed GBM, including e.g., where the subject's GBM is responsive or refractory to the ongoing treatment or where the subject's response is as yet unknown.

Testing of a subject may include assaying a biological sample obtained from the subject. Useful biological samples may include but are not limited to e.g., biopsy (e.g., a GBM tumor biopsy, etc.), blood samples, and the like. Any con- venient method of collecting a biological sample may find use in the herein described methods including but not limited to e.g., needle biopsy, stereotactic biopsy, open biopsy, and the like.

In a brain tumor needle biopsy, a small cut may be made and a small hole, called a burr hole, may be drilled in the skull. A narrow, hollow needle may be inserted through the hole, and tumor tissue may be removed from the core of the needle. In a stereotactic biopsy (a.k.a, a "closed" biopsy) of a brain tumor, the same general procedure may be employed as described for a needle biopsy; however, a computer- assisted guidance system that aids in the location and diagnosis of the tumor may be employed. A computer, using information from a CT or MRI scan, may provide precise information about a tumor's location and its position relative to other structures in the brain. Stereotactically guided equipment might be moved into the burr hole to remove a sample of the tumor. In an open biopsy of a brain tumor a tissue sample is taken during an operation while the tumor is exposed. The sample, regardless of the biopsy method employed for collection, may then be sent for study and review, e.g., by a pathologist.

Any convenient method of assaying a biological sample may find use in the herein described methods including but not limited to e.g., a blood chemistry test, cancer gene mutation testing, complete blood count (CBC), cytogenetic analysis, immunophenotyping, tumor marker tests, histol- ogy, cytology (including e.g., flow cytometry, including FACS), immunohistochemistry, gene expression analysis, proteomics, in situ hybridization, and the like. For example, in some instances, immunohistochemistry and/or in situ hybridization may be performed on a biopsy sample obtained from the subject, e.g., to detect the expression of one or more antigens. In some instances, cytology may be performed on a blood sample from the subject, e.g., to detect circulating tumor cells (CTCs).

In some instances, antigen detection in a biological sample may include molecular detection of antigen transcript. Any convenient method of transcript detection may be employed including but not limited to PCR-based assays. Antigen transcript detection may find use in various embodiments of the herein described methods, including but not limited to e.g., where the methods include determining whether one of more cells from a sample of a subject express EGFRvIII. EGFR or both EGFRvIII and EGFR and/or performing quantification of the level(s) of expression thereof.

In some instances, immunohistochemistry methods (including e.g., colorimetric or immunofluorescence assays thereof) may be employed to evaluate the presence or absence of EGFRvIII, EGFR or both EGFRvIII and EGFR and/or quantify of the level(s) of expression thereof. Essentially any convenient and appropriate method for detecting and/or quantifying EGFRvIII, EGFR or both EGFRvIII and EGFR may be employed in the methods described herein, e.g., methods employing a specific binding member for EGFRvIII, a specific binding member for EGFR or both. Specific binding members that specifically bind EGFRvIII or EGFR for use in the present methods may, in some instances, specifically bind to an EGFRvIII or an EGFR represented, respectively, by a human amino acid sequence of the subject protein provided or described herein.

The amino acid sequence of EGFRvIII may vary, e.g., depending on the particular mutation and/or rearrangement from which a particular EGFRvIII is derived. A non-limiting example of an EGFRvIII amino acid sequence is as follows:

```
                                        (SEQ ID NO: 1)
MRPSGTAGAAFLALLAALCPASRALEEKKGNYVVTDHGSCVRACGADSY

EMEEDGVRKCKKCEGPCRKVCNGIGIGEFKDSLSINATNIKHFKNCTSI

SGDLHILPVAFRGDSFTHTPPLDPQELDILKTVKEITGFLLIQAWPENR

TDLHAFENLEIIRGRTKQHGQFSLAVVSLNITSLGLRSLKEISDGDVII

SGNKNLCYANTINWKKLFGTSGQKTKIISNRGENSCKATGQVCHALCSP

EGCWGPEPRDCVSCRNVSRGRECVDKCNLLEGEPREFVENSECIQCHPE

CLPQAMNITCTGRGPDNYIQCAHYIDGPHCVKTCPAGVMGENNTLVWKY

ADAGHVCHLCHPNCTYGCTGPGLEGCPTNGPKIPSIATGMVGALLLLLV

VALGIGLFMRRRHIVRKRTLRRLLQERELVEPLTPSGEAPNQALLRILK

ETEFKKIKVLGSGAFGTVYKGLWIPEGEKVKIPVAIKELREATSPKANK

EILDEAYVMASVDNPHVCRLLGICLTSTVQLITQLMPFGCLLDYVREHK

DNIGSQYLLNWCVQIAKGMNYLEDRRLVHRDLAARNVLVKTPQHVKITD

FGLAKLLGAEEKEYHAEGGKVPIKWMALESILHRIYTHQSDVWSYGVTV

WELMTFGSKPYDGIPASEISSILEKGERLPQPPICTIDVYMIMVKCWMI

DADSRPKFRELIIEFSKMARDPQRYLVIQGDERMHLPSPTDSNFYRALM

DEEDMDDVVDADEYLIPQQGFFSSPSTSRTPLLSSLSATSNNSTVACID

RNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNS

TFDSPAHWAQKGSHQISLDNPDYQQDFFPKEAKPNGIFKGSTAENAEYL

RVAPQSSEFIGA.
```

EGFRvIII proteins, and the amino acid sequences thereof, may vary from that provided above. For example, in some instances, a subject EGFRvIII variant may include one or more mutations relative to the sequence provided above, including but not limited to e.g., 1 mutation, 2 or less, 3 or less, 4 or less, 5 or less mutations, etc. In some instances, a subject EGFRvIII variant may share 80% or greater sequence identity with the amino acid sequence provided above, including but not limited to e.g., 85% or greater, 90% or greater, 95% or greater, 96% or greater, 97% or greater, 98% or greater, 99% or greater, or 100% sequence identity with the above EGFRvIII sequence.

EGFR proteins, and the amino acid sequences thereof, may vary, including from those provided herein. For example, in some instances, a subject EGFR variant may include one or more mutations relative to the sequence provided herein, including but not limited to e.g., 1 mutation, 2 or less, 3 or less, 4 or less, 5 or less mutations, etc. In some instances, a subject EGFR variant may share 80% or greater sequence identity with the amino acid sequence provided herein, including but not limited to e.g., 85% or greater, 90% or greater, 95% or greater, 96% or greater, 97% or greater, 98% or greater, 99% or greater, or 100% sequence identity with a herein provided EGFR sequence.

In some instances, testing of a subject may include multi-sampling. Multi-sampling, as used herein, generally refers to the process of taking multiple samples of a suspected tumor and/or multiple samples of multiple tumors present in a subject. Multi-sampling may be performed at one instance, e.g., where multiple samples are collected from various locations during one period of collection, or over multiple instances, e.g., were one or more sites are sampled over at multiple instances over a period of time. Multi-sampling may find use in subject with heterogeneous cancers, e.g., to ensure that the heterogeneity of a cancer or tumor is sufficiently sampled, e.g., to detect the cellular distribution and/or antigen distribution of a particular cancer or tumor.

In some instances, a subject may be evaluated, in certain contexts, through one or more of the following diagnostics procedures: 3D CT angiography, Angiography, Anoscopy, Autofluorescence bronchoscopy/fluorescence bronchoscopy, Barium swallow or enema, Biopsy, Bone Marrow Aspiration and Biopsy, Bone Scan, Bronchoscopy, CA-125 test, CAD for mammography, CTC Test, Chest x-ray, Colonoscopy, Complete Blood Count Test, Computed Tomography Scan, CT-guided biopsy, DEXA scan, Digital Breast Tomosynthesis, Electrocardiogram, Endobronchial ultrasound, Endoscopic ultrasound, ERCP, Flow cytometry, Full-field digital mammography, Genetic testing, Large bore CT scanner/RT with simulation. Lumbar puncture, Magnetic Resonance Imaging, Mammography, Miraluma breast imaging, MRI-Guided Breast Biopsy, Multi-detector CT scanner, Multiple-gated acquisition (MUGA) scan, Navigational Bronchoscopy, Nuclear Medicine Imaging, Oncotype DX Test, Pap test, Pelvic exam, PET Scan, PET-CT Scan, Radiofrequency ablation, Sentinel lymph node biopsy, Spiral CT, Tumor marker testing, Tumor molecular profiling, Ultrasound, Video Capsule Endoscopy, X-ray, and the like.

Diagnostic procedures may be performed for a variety of reasons including but not limited to e.g., to screen for GBM or precancerous conditions indicative of increased risk of GBM (e.g., CMV infection) before a person has any symptoms of disease; to help diagnose GBM; to provide information about the stage of a GBM; to provide information about the malignancy of a GBM; to provide information about the size and/or extent of a primary GBM; to provide information about whether or not a GBM has metastasized; to plan treatment; to monitor a patient's general health during treatment; to check for potential side effects of the treatment; to determine whether a GBM is responding to treatment; to find out whether a GBM has recurred; etc.

Antigens

Antigens employed in the present methods include, as described above, a priming antigen and one or more targeting antigens and others in some instances. In instances where the targeted cell is targeted for killing, the subject targeting antigen may be referred to herein as a "killing antigen". Such terms may, but need not necessarily, be used interchangeably where appropriate.

As described herein with regards to cancer heterogeneity, the relative presence of an antigen and/or the relative presence of cells expressing an antigen will vary. In general, less than 100% of the cells of a heterogeneous cancer treated with the described methods will express a priming antigen, including but not limited to e.g., where less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20% of cells of the heterogeneous cancer express the priming antigen.

Useful priming antigens will vary and may include but are not limited to e.g., Interleukin-13 receptor subunit alpha-2 (IL13RA2), Interleukin-13 receptor subunit alpha-1 (IL13RA1), Neuroligin(s), Neurexin-1-beta (NRXN1), Receptor-type tyrosine-protein phosphatase zeta (PTPRZ1), Neuronal cell adhesion molecule (NRCAM), Cadherin-10 (CDH10) and Protocadherin gamma-C5 (PCDHGC5). Useful priming antigens may also include but are not limited to e.g., CD70 antigen (CD70). Chondroitin sulfate proteoglycan 5 (CSPG5), Brevican core protein (BCAN). Metabotropic glutamate receptor 3 (GRM3), Protein crumbs homolog 1 (CRB1). Neuromodulin (GAP43), Sodium/potassium-transporting ATPase subunit beta-2 (ATP1B2), Ran-binding protein MOG1 (MOG1), and a Receptor-type tyrosine-protein phosphatase zeta-Hepatocyte growth factor receptor fusion (PTPRZ1-MET).

In some instances, useful priming antigens may include Interleukin-13 receptor subunit alpha-2 (IL13RA2), IL13RA2 is encoded by the interleukin 13 receptor subunit alpha 2 gene, located in humans at Xq23, and is a subunit of the interleukin 13 receptor complex, IL13RA2 binds IL13 with high affinity, but lacks cytoplasmic domain, IL13RA2 protein may be found in at least one isoform in humans, including IL13RA2 having the following amino acid sequence:

```
                                        (SEQ ID NO: 2)
MAFVCLAIGCLYTFLISTTFGCTSSSDTEIKVNPPQDFEIVDPGYLGYL

YLQWQPPLSLDHFKECTVEYELKYRNIGSETWKTIITKNLHYKDGFDLN

KGIEAKIHTLLPWQCTNGSEVQSSWAETTYWISPQGIPETKVQDMDCVY

YNWQYLLCSWKPGIGVLLDTNYNLFYWYEGLDHALQCVDYIKADGQNIG

CRFPYLEASDYKDFYICVNGSSENKPIRSSYFTFQLQNIVKPLPPVYLT

FTRESSCEIKLKWSIPLGPIPARCFDYEIEIREDDTTLVTATVENETYT

LKTTNETRQLCFVVRSKVNIYCSDDGIWSEWSDKQCWEGEDLSKKTLLR

FWLPFGFILILVIFVTGLLLRKPNTYPKMIPEFFCDT.
```

In some instances, the methods described herein may employ a BTTS that specifically binds IL13RA2, including e.g., human IL13RA2.

In some instances, useful priming antigens may include Interleukin-13 receptor subunit alpha-1 (IL13RA1), IL13RA1 is encoded by the interleukin 13 receptor subunit alpha 1 gene, located in humans at Xq24, and is a subunit of the interleukin 13 receptor which forms a receptor complex with IL4 receptor alpha, a subunit shared by IL13 and IL4 receptors. IL13RA1 is a primary IL13-binding subunit of the IL13 receptor, IL13RA1 protein may be found in at least one isoform in humans, including IL13RA1 Isoform 1 having the following amino acid sequence:

```
                                        (SEQ ID NO: 3)
MEWPARLCGLWALLLCAGGGGGGGGAAPTETQPPVTNLSVSVENLCTVI

WTWNPPEGASSNCSLWYFSHFGDKQDKKIAPETRRSIEVPLNERICLQV

GSQCSTNESEKPSILVEKCISPPEGDPESAVTELQCIWHNLSYMKCSWL

PGRNTSPDTNYTLYYWHRSLEKIHQCENIFREGQYFGCSFDLTKVKDSS

FEQHSVQIMVKDNAGKIKPSFNIVPLTSRVKPDPPHIKNLSFHNDDLYV

QWENPQNFISRCLFYEVEVNNSQTETHNVFYVQEAKCENPEFERNVENT

SCFMVPGVLPDTLNTVRIRVKTNKLCYEDDKLWSNWSOEMSIGKKRNST

LYITMLLIVPVIVAGAIIVLLLYLKRLKIIIFPPIPDPGKIFKEMFGDq

NDDTLHWKKYDIYEKOTKEETDSVVLIENLKKASQ;
``` and IL13RA1 Isoform 2 having the following amino acid sequence:

```
                                        (SEQ ID NO: 4)
MEWPARLCGLWALLLCAGGGGGGGGAAPTETQPPVTNLSVSVENLCTVI

WTWNPPEGASSNCSLWYFSHFGDKQDKKIAPETRRSIEVPLNERICLQV

GSQCSTNESEKPSILVEKCISPPEGDPESAVTELQCIWHNLSYMKCSWL

PGRNTSPDTNYTLYYWHRSLEKIHQCENIFREGQYFGCSFDLTKVKDSS

FEQHSVQIMVKDNAGKIKPSFNIVPLTSRVKPDPPHIKNLSFHNDDLYV

QWENPQNFISRCLFYEVEVNNSQTETHNVFYVRF.
```

In some instances, the methods described herein may employ a BTTS that specifically binds IL13RA1, including e.g., human IL13RA1 Isoform 1, human IL13RA1 Isoform 2, or both human IL13RA1 Isoform 1 and human IL13RA1 Isoform 2.

In some instances, useful priming antigens may include neuroligins. Neuroligins include e.g., Neuroligin-4, X-linked (NLGN4X) encoded by the neuroligin 4. X-linked gene at Xp22.32-p22.31 in humans. The NLGN4X protein may be found in at least one isoform in humans, including but not limited to e.g., NLGN4X Isoform 1 having the following amino acid sequence:

```
                                        (SEQ ID NO: 5)
MSRPQGLLWLPLLFTPVCVMLNSNVLLWLTALAIKFTLIDSQAQYPVVNT

NYGKIRGLRTPLPNEILGPVEQYLGVPYASPPTGERRFQPPEPPSSWTGI

RNTTQFAAVCPQHLDERSLLHDMLPIWFTANLDTLMTYVQDQNEDCLYLN

IYVPTEDDIHDQNSKKPVMVYIHGGSYMEGTGNMIDGSILASYGNVIVIT
```

-continued
INYRLGILGFLSTGDQAAKGNYGLLDQIQALRWIEENVGAFGGDPKRVTI

FGSGAGASCVSLLTLSHYSEGLFQKAIIQSGTALSSWAVNYQPAKYTRIL

ADKVGCNMLDTTDMVECLRNKNYKELIQQTITPATYHIAFGPVIDGDVIP

DDPQILMEQGEFLNYDIMLGVNQGEGLKFVDGIVDNEDGVTPNDFDFSVS

NFVDNLYGYPEGKDTLRETIKFMYTDWADKENPETRRKTLVALFTDHQWV

APAVATADLHAQYGSPTYFYAFYHHCQSEMKPSWADSAHGDEVPYVFGIP

MIGPTELFSCNFSKNDVMLSAVVMTYWTNFAKTGDPNQPVPQDTKFIHTK

PNRFEEVAWSKYNPKDQLYLHIGLKPRVRDHYRATKVAFWLELVPHLHNL

NEIFQYVSTTTKVPPPDMTSFPYGTRRSPAKIWPTTKRPAITPANNPKHS

KDPHKTGPEDTTVLIETKRDYSTELSVTIAVGASLLFLNILAFAALYYKK

DKRRHETHRRPSPQRNTTNDIAHIQNEEIMSLQMKQLEHDHECESLQAHD

TLRLTCPPDYTLTLRRSPDDIPLMTPNTITMIPNTLTGMQPLHTFNTFSG

GQNSTNLPHGHSTTRV, and NLGN4X Isoform 2 having the following amino acid
sequence:

(SEQ ID NO: 6)
MSRPQGLLWLPLLFTPVCVMLNSNVLLWLTALAIKFTLIDSQAYPVVNT

NYGKIRGLRTPLPNEILGPVEQYLGVPYASPPTGERRFQPPEPPSSWTGI

RNTTQFAAVCPQHLDERSLLHDMLPIWFTANLDTLMTYVQDQNEDCLYLN

IYVPTEDGANTKKNADDITSNDRGEDEDIHDQNSKKPVMVYIHGGSYMEG

TGNMIDGSILASYGNVIVITINYRLGILGFLSTGDQAAKGNYGLLDQIQA

LRWIEENVGAFGGDPKRVTIFGSGAGASCVSLLTLSHYSEGLFQKAIIQS

GTALSSWAVNYQPAKYTRILADKVGCNMLDTTDMVECLRNKNYKELIQQT

ITPATYHIAFGPVIDGDVIPDDPQILMEQGEFLNYDIMLGVNQGEGLKFV

DGIVDNEDGVTPNDFDFSVSNFVDNLYGYPEGKDTLRETIKFMYTDWADK

ENPETRRKTLVALFTDHQWVAPAVATADLHAQYGSPTYFYAFYHHCQSEM

KPSWADSAHGDEVPYVFGIPMIGPTELFSCNFSKNDVMLSAVVMTYWTNF

AKTGDPNQPVPQDTKFIHTKPNRFEEVAWSKYNPKDQLYLHIGLKPRVRD

HYRATKVAFWLELVPHLHNLNEIFQYVSTTTKVPPPDMTSFPYGTRRSPA

KIWPTTKRPAITPANNPKHSKDPHKTGPEDTTVLIETKRDYSTELSVTIA

VGASLLFLNILAFAALYYKKDKRRHETHRRPSPQRNTTNDIAHIQNEEIM

SLQMKQLEHDHECESLQAHDTLRLTCPPDYTLTLRRSPDDIPLMTPNTIT

MIPNTLTGMQPLHTFNTFSGGQNSTNLPHGHSTTRV.

In some instances, the methods described herein may
employ a BTTS that specifically binds NLGN4X, including
e.g., human NLGN4X Isoform 1, human NLGN4X Isoform
2, or both human NLGN4X Isoform 1 and human NLGN4X
Isoform 2.

Neuroligins also include e.g., Neuroligin-4, Y-linked
(NLGN4Y) encoded by the neuroligin 4, Y-linked gene at
Yq11,221 in humans. The NLGN4Y protein may be found in
at least one isoform in humans, including but not limited to
e.g., NLGN4Y Isoform 1 having the following amino acid
sequence:

(SEQ ID NO: 7)
MLRPQGLLWLPLLFTSVCVMLNSNVLLWITALAIKFTLIDSQAQYPVVN

TNYGKIQGLRTPLPSEILGPVEQYLGVPYASPPTGERRFQPPESPSSWT

GIRNATQFSAVCPQHLDERFLLHDMLPIWFTTSLDTLMTYVQDQNEDCL

YLNIYVPMEDDIHEQNSKKPVMVYIHGGSYMEGTGNMIDGSILASYGNV

IVITINYRLGILGFLSTGDQAAKGNYGLLDQIQALRWIEENVGAFGGDP

KRVTIFGSGAGASCVSLLTLSHYSEGLFQKAIIQSGTALSSWAVNYQPA

KYTRILADKVGCNMLDTTDMVECLKNKNYKELIQQTITPATYHIAFGPV

IDGDVIPDDPQILMEQGEFLNYDIMLGVNQGEGLKFVDGIVDNEDGVTP

NDFDFSVSNFVDNLYGYPEGKDTLRETIKFMYTDWADKENPETRRKTLV

ALFTDHQWVAPAVATADLHAQYGSPTYFYAFYHHCQSEMKPSWADSAHG

DEVPYVFGIPMIGPTELFSCNFSKNDVMLSAVVMTYWTNFAKTGDPNQP

VPQDTKFIHTKPNRFEEVAWSKYNPKDQLYLHIGLKPRVRDHYRATKVA

FWLELVPHLHNLNEIFQYVSTTTKVPPPDMTSFPYGTRRSPAKIWPTTK

RPAITPANNPKHSKDPHKTGPEDTTVLIETKRDYSTELSVTIAVGASLL

FLNILAFAALYYKKDKRRHETHRHPSPQRNTTNDITHIQNEEIMSLQMK

QLEHDHECESLQAHDTLRLTCPPDYTLTLRRSPDDIPFMTPNTITMIPN

TLMGMQPLHTFKTFSGGQNSTNLPHGHSTTRV,

NLGN4Y Isoform 2 having the following amino acid
sequence:

(SEQ ID NO: 8)
MVYIHGGSYMEGTGNMIDGSILASYGNVIVITINYRLGILGFLSTGDQA

AKGNYGLLDQIQALRWIEENVGAFGGDPKRVTIFGSGAGASCVSLLTLS

HYSEGLFQKAIIQSGTALSSWAVNYQPAKYTRILADKVGCNMLDTTDMV

ECLKNKNYKELIQQTITPATYHIAFGPVIDGDVIPDDPQILMEQGEFLN

YDIMLGVNQGEGLKFVDGIVDNEDGVTPNDFDFSVSNFVDNLYGYPEGK

DTLRETIKFMYTDWADKENPETRRKTLVALFTDHQWVAPAVATADLHAQ

YGSPTYFYAFYHHCQSEMKPSWADSAHGDEVPYVFGIPMIGPTELFSCN

FSKNDVMLSAVVMTYWTNFAKTGDPNQPVPQDTKFIHTKPNRFEEVAWS

KYNPKDQLYLHIGLKPRVRDHYRATKVAFWLELVPHLHNLNEIFQYVST

TTKVPPPDMTSFPYGTRRSPAKIWPTTKRPAITPANNPKHSKDPHKTGP

EDTTVLIETKRDYSTELSVTIAVGASLLFLNILAFAALYYKKDKRRHET

HRHPSPQRNTTNDITHIQNEEIMSLQMKQLEHDHECESLQAHDTLRLTC

PPDYTLTLRRSPDDIPFMTPNTITMIPNTLMGMQPLHTFKTFSGGQNST

NLPHGHSTTRV,

NLGN4Y Isoform 3 having the following amino acid
sequence:

(SEQ ID NO: 9)
MLPIWFTTSLDTLMTYVQDQNEDCLYLNIYVPMEDGTNIKRNADDITSN

DHGEDKDIHEQNSKKPVMVYIHGGSYMEGTGNMIDGSILASYGNVIVIT

INYRLGILGMQEARLCGSSKMFNYFKSPFTNLINFF, and NLGN4Y Isoform 4 having the following amino acid
sequence:

(SEQ ID NO: 10)
MLRPQGLLWLPLLFTSVCVMLNSNVLLWITALAIKFTLIDSQAQYPVVN

TNYGKIQGLRTPLPSEILGPVEQYLGVPYASPPTGERRFQPPESPSSWT

GIRNATQFSAVCPQHLDERFLLHDMLPIWFTTSLDTLMTYVQDQNEDCL

YLNIYVPMEDGTNIKRNADDITSNDHGEDKDIHEQNSKKPVMVYIHGGS

YMEGTGNMIDGSILASYGNVIVITINYRLGILGMQEARLCGSSKMFNYF

KSPFTNLINFF.

In some instances, the methods described herein may employ a BTTS that specifically binds NLGN4Y, including e.g., human NLGN4Y Isoform 1, human NLGN4Y Isoform 2, human NLGN4Y Isoform 3, human NLGN4Y Isoform 4, or any combination thereof.

Neuroligins also include e.g., Neuroligin-3 (NLGN3) encoded by the neuroligin 3 gene at Xq13.1 in humans. The NLGN3 protein may be present in at least one isoform in humans, including but not limited to e.g., NLGN3 Isoform 1 having the following amino acid sequence:

(SEQ ID NO: 11)
MWLRLGPPSLSLSPKPTVGRSLCLTLWFLSLALRASTQAPAPTVNTHFG

KLRGARVPLPSEILGPVDQYLGVPYAAPPIGEKRFLPPEPPPSWSGIRN

ATHFPPVCPQNIHTAVPEVMLPVWFTANLDIVATYIQEPNEDCLYLNVY

VPTEDVKRISKECARKPNKKICRKGGSGAKKQGEDLADNDGDEDEDIRD

SGAKPVMVYIHGGSYMEGTGNMIDGSILASYGNVIVITLNYRVGVLGFL

STGDQAAKGNYGLLDQIQALRWVSENIAFFGGDPRRITVFGSGIGASCV

SLLTLSHHSEGLFQRAIIQSGSALSSWAVNYQPVKYTSLLADKVGCNVL

DTVDMVDCLRQKSAKELVEQDIQPARYHVAFGPVIDGDVIPDDPEILME

QGEFLNYDIMLGVNQGEGLKFVEGVVDPEDGVSGTDFDYSVSNFVDNLY

GYPEGKDTLRETIKFMYTDWADRDNPETRRKTLVALFTDHQWVEPSVVT

ADLHARYGSPTYFYAFYHHCQSLMKPAWSDAAHGDEVPYVFGVPMVGPT

DLFPCNFSKNDVMLSAVVMTYWTNFAKTGDPNKPVPQDTKFIHTKANRF

EEVAWSKYNPRDQLYLHIGLKPRVRDHYRATKVAFWKHLVPHLYNLHDM

FHYTSTTTKVPPPDTTHSSHITRRPNGKTWSTKRPAISPAYSNENAQGS

WNGDQDAGPLLVENPRDYSTELSVTIAVGASLLFLNVLAFAALYYRKDK

RRQEPLRQPSPQRGAGAPELGAAPEEELAALQLGPTHHECEAGPPHDTL

RLTALPDYTLTLRRSPDDIPLMTPNTITMIPNSLVGLQTLHPYNTFAAG

FNSTGLPHSHSTTRV,

NLGN3 Isoform 2 having the following amino acid sequence:

(SEQ ID NO: 12)
MWLRLGPPSLSLSPKPTVGRSLCLTLWFLSLALRASTQAPAPTVNTHFG

KLRGARVPLPSEILGPVDQYLGVPYAAPPIGEKRFLPPEPPPSWSGIRN

ATHFPPVCPQNIHTAVPEVMLPVWFTANLDIVATYIQEPNEDCLYLNVY

VPTEDGSGAKKQGEDLADNDGDEDEDIRDSGAKPVMVYIHGGSYMEGTG

NMIDGSILASYGNVIVITLNYRVGVLGFLSTGDQAAKGNYGLLDQIQAL

-continued
RWVSENIAFFGGDPRRITVFGSGIGASCVSLLTLSHHSEGLFQRAIIQS

GSALSSWAVNYQPVKYTSLLADKVGCNVLDTVDMVDCLRQKSAKELVEQ

DIQPARYHVAFGPVIDGDVIPDDPEILMEQGEFLNYDIMLGVNQGEGLK

FVEGVVDPEDGVSGTDFDYSVSNFVDNLYGYPEGKDTLRETIKFMYTDW

ADRDNPETRRKTLVALFTDHQWVEPSVVTADLHARYGSPTYFYAFYHHC

QSLMKPAWSDAAHGDEVPYVFGVPMVGPTDLFPCNFSKNDVMLSAVVMT

YWTNFAKTGDPNKPVPQDTKFIHTKANRFEEVAWSKYNPRDQLYLHIGL

KPRVRDHYRATKVAFWKHLVPHLYNLHDMFHYTSTTTKVPPPDTTHSSH

ITRRPNGKTWSTKRPAISPAYSNENAQGSWNGDQDAGPLLVENPRDYST

ELSVTIAVGASLLFLNVLAFAALYYRKDKRRQEPLRQPSPQRGAGAPEL

GAAPEEELAALQLGPTHHECEAGPPHDTLRLTALPDYTLTLRRSPDDIP

LMTPNTITMIPNSLVGLQTLHPYNTFAAGFNSTGLPHSHSTTRV, and NLGN3 Isoform 3 having the following amino acid sequence:

(SEQ ID NO: 13)
MWLRLGPPSLSLSPKPTVGRSLCLTLWFLSLALRASTQAPAPTVNTHF

GKLRGARVPLPSEILGPVDQYLGVPYAAPPIGEKRFLPPEPPPSWSGI

RNATHFPPVCPQNIHTAVPEVMLPVWFTANLDIVATYIQEPNEDCLYL

NVYVPTEDDIRDSGAKPVMVYIHGGSYMEGTGNMIDGSILASYGNVIV

ITLNYRVGVLGFLSTGDQAAKGNYGLLDQIQALRWVSENIAFFGGDPR

RITVFGSGIGASCVSLLTLSHHSEGLFQRAIIQSGSALSSWAVNYQPV

KYTSLLADKVGCNVLDTVDMVDCLRQKSAKELVEQDIQPARYHVAFGP

VIDGDVIPDDPEILMEQGEFLNYDIMLGVNQGEGLKFVEGVVDPEDGV

SGTDFDYSVSNFVDNLYGYPEGKDTLRETIKFMYTDWADRDNPETRRK

TLVALFTDHQWVEPSVVTADLHARYGSPTYFYAFYHHCQSLMKPAWSD

AAHGDEVPYVFGVPMVGPTDLFPCNFSKNDVMLSAVVMTYWTNFAKTG

DPNKPVPQDTKFIHTKANRFEEVAWSKYNPRDQLYLHIGLKPRVRDHY

RATKVAFWKHLVPHLYNLHDMFHYTSTTTKVPPPDTTHSSHITRRPNG

KTWSTKRPAISPAYSNENAQGSWNGDQDAGPLLVENPRDYSTELSVTI

AVGASLLFLNVLAFAALYYRKDKRRQEPLRQPSPQRGAGAPELGAAPE

EELAALQLGPTHHECEAGPPHDTLRLTALPDYTLTLRRSPDDIPLMTP

NTITMIPNSLVGLQTLHPYNTFAAGFNSTGLPHSHSTTRV.

In some instances, the methods described herein may employ a BTTS that specifically binds NLGN3, including e.g., human NLGN3 Isoform 1, human NLGN3 Isoform 2, human NLGN3 Isoform 3, or any combination thereof.

In some instances, useful priming antigens may include Neurexin-1-beta (NRXN1). NRXN1 is a single-pass type I membrane protein involved in cell-cell-interactions, exocytosis of secretory granules and regulation of signal transmission encoded by the neurexin 1 gene located at 2p16.3 in humans. Various variants of Neurexin family members are produced through the use of multiple alternative promoters (e.g., at least alpha and beta promoters) and extensive alternative splicing. NRXN1 protein may be found in at least one isoform in humans, including NRXN1 Isoform 1b having the following amino acid sequence:

(SEQ ID NO: 14)

MYQRMLRCGAELGSPGGGGGGGGGGGGAGGRLALLWIVPLTLSGLLGVAW

GASSLGAHHIHHFHGSSKHHSVPIAIYRSPASLRGGHAGTTYIFSKGGG

QITYKWPPNDRPSTRADRLAIGFSTVQKEAVLVRVDSSSGLGDYLELHI

HQGKIGVKFNVGTDDIAIEESNAIINDGKYHVVRFTRSGGNATLQVDSW

PVIERYPAGNNDNERLAIARQRIPYRLGRVVDEWLLDKGRQLTIFNSQA

TIIIGGKEQGQPFQGQLSGLYYNGLKVLNMAAENDANIAIVGNVRLVGE

VPSSMTTESTATAMQSEMSTSIMETTTTLATSTARRGKPPTKEPISQTT

DDILVASAECPSDDEDIDPCEPSSGGLANPTRAGGREPYPGSAEVIRES

SSTTGMVVGIVAAAALCILILLYAMYKYRNRDEGSYHVDESRNYISNSA

QSNGAVVKEKQPSSAKSSNKNKKNKDKEYYV,

NRXN1 Isoform 3b having the following amino acid sequence:

(SEQ ID NO: 15)

MYQRMLRCGAELGSPGGGGGGGGGGGGAGGRLALLWIVPLTLSGLLGVAW

GASSLGAHHIHHFHGSSKHHSVPIAIYRSPASLRGGHAGTTYIFSKGGG

QITYKWPPNDRPSTRADRLAIGFSTVQKEAVLVRVDSSSGLGDYLELHI

HQGKIGVKFNVGTDDIAIEESNAIINDGKYHVVRFTRSGGNATLQVDSW

PVIERYPAGRQLTIFNSQATIIIGGKEQGQPFQGQLSGLYYNGLKVLNM

AAENDANIAIVGNVRLVGEVPSSMTTESTATAMQSEMSTSIMETTTTLA

TSTARRGKPPTKEPISQTTDDILVASAECPSDDEDIDPCEPSSGGLANP

TRAGGREPYPGSAEVIRESSSTTGMVVGIVAAAALCILILLYAMYKYRN

RDEGSYHVDESRNYISNSAQSNGAVVKEKQPSSAKSSNKNKKNKDKEYY

V,

NRXN1 Isoform 1a having the following amino acid sequence:

(SEQ ID NO: 16)

MGTALLQRGGCFLLCLSLLLLGCWAELGSGLEFPGAEGQWTRFPKWNAC

CESEMSFQLKTRSARGLVLYFDDEGFCDFLELILTRGGRLQLSFSIFCA

EPATLLADTPVNDGAWHSVRIRRQFRNTTLFIDQVEAKWVEVKSKRRDM

TVFSGLFVGGLPPELRAAALKLTLASVREREPFKGWIRDVRVNSSQVLP

VDSGEVKLDDEPPNSGGGSPCEAGEEGEGGVCLNGGVCSVVDDQAVCDC

SRTGFRGKDCSQEDNNVEGLAHLMMGDQGKSKGKEEYIATFKGSEYFCY

DLSQNPIQSSSDEITLSFKTLQRNGLMLHTGKSADYVNLALKNGAVSLV

INLGSGAFEALVEPVNGKFNDNAWHDVKVTRNLRQHSGIGHAMVTISVD

GILTTTGYTQEDYTMLGSDDFFYVGGSPSTADLPGSPVSNNFMGCLKEV

VYKNNDVRLELSRLAKQGDPKMKIHGVVAFKCENVATLDPITFETPESF

ISLPKWNAKKTGSISFDFRTTEPNGLILFSHGKPRHQKDAKHPQMIKVD

FFAIEMLDGHLYLLLDMGSGTIKIKALLKKVNDGEWYHVDFQRDGRSGT

ISVNTLRTPYTAPGESEILDLDDELYLGGLPENKAGLVFPTEVWTALLN

YGYVGCIRDLFIDGQSKDIRQMAEVQSTAGVKPSCSKETAKPCLSNPCK

-continued

NNGMCRDGWNRYVCDCSGTGYLGRSCEREATVLSYDGSMFMKIQLPVVM

HTEAEDVSLRFRSQRAYGILMATTSRDSADTLRLELDAGRVKLTVNLDC

IRINCNSSKGPETLFAGYNLNDNEWHTVRVVRRGKSLKLTVDDQQAMTG

QMAGDHTRLEFHNIETGIITERRYLSSVPSNFIGHLQSLTFNGMAYIDL

CKNGDIDYCELNARFGFRNIIADPVTFKTKSSYVALATLQAYTSMHLFF

QFKTTSLDGLILYNSGDGNDFIVVELVKGYLHYVFDLGNGANLIKGSSN

KPLNDNQWHNVMISRDTSNLHTVKIDTKITTQITAGARNLDLKSDLYIG

GVAKETYKSLPKLVHAKEGFQGCLASVDLNGRLPDLISDALFCNGQIER

GCEGPSTTCQEDSCSNQGVCLQQWDGFSCDCSMTSFSGPLCNDPGTTYI

FSKGGGQITYKWPPNDRPSTRADRLAIGFSTVQKEAVLVRVDSSSGLGD

YLELHIHQGKIGVKFNVGTDDIAIEESNAIINDGKYHVVRFTRSGGNAT

LQVDSWPVIERYPAGRQLTIFNSQATIIIGGKEQGQPFQGQLSGLYYNG

LKVLNMAAENDANIAIVGNVRLVGEVPSSMTTESTATAMQSEMSTSIME

TTTTLATSTARRGKPPTKEPISQTTDDILVASAECPSDDEDIDPCEPSS

GGLANPTRAGGREPYPGSAEVIRESSSTTGMVVGIVAAAALCILILLYA

MYKYRNRDEGSYHVDESRNYISNSAQSNGAVVKEKQPSSAKSSNKNKKN

KDKEYYV,

NRXN1 Isoform 2a having the following amino acid sequence:

(SEQ ID NO: 17)

MGTALLQRGGCFLLCLSLLLLGCWAELGSGLEFPGAEGQWTRFPKWNAC

CESEMSFQLKTRSARGLVLYFDDEGFCDFLELILTRGGRLQLSFSIFCA

EPATLLADTPVNDGAWHSVRIRRQFRNTTLFIDQVEAKWVEVKSKRRDM

TVFSGLFVGGLPPELRAAALKLTLASVREREPFKGWIRDVRVNSSQVLP

VDSGEVKLDDEPPNSGGGSPCEAGEEGEGGVCLNGGVCSVVDDQAVCDC

SRTGFRGKDCSQEDNNVEGLAHLMMGDQGKSKGKEEYIATFKGSEYFCY

DLSQNPIQSSSDEITLSFKTLQRNGLMLHTGKSADYVNLALKNGAVSLV

INLGSGAFEALVEPVNGKFNDNAWHDVKVTRNLRQVTISVDGILTTTGY

TQEDYTMLGSDDFFYVGGSPSTADLPGSPVSNNFMGCLKEVVYKNNDVR

LELSRLAKQGDPKMKIHGVVAFKCENVATLDPITFETPESFISLPKWNA

KKTGSISFDFRTTEPNGLILFSHGKPRHQKDAKHPQMIKVDFFAIEMLD

GHLYLLLDMGSGTIKIKALLKKVNDGEWYHVDFQRDGRSGTISVNTLRT

PYTAPGESEILDLDDELYLGGLPENKAGLVFPTEVWTALLNYGYVGCIR

DLFIDGQSKDIRQMAEVQSTAGVKPSCSKETAKPCLSNPCKNNGMCRDG

WNRYVCDCSGTGYLGRSCEREATVLSYDGSMFMKIQLPVVMHTEAEDVS

LRFRSQRAYGILMATTSRDSADTLRLELDAGRVKLTVNLDCIRINCNSS

KGPETLFAGYNLNDNEWHTVRVVRRGKSLKLTVDDQQAMTGQMAGDHTR

LEFHNIETGIITERRYLSSVPSNFIGHLQSLTFNGMAYIDLCKNGDIDY

CELNARFGFRNIIADPVTFKTKSSYVALATLQAYTSMHLFFQFKTTSLD

GLILYNSGDGNDFIVVELVKGYLHYVFDLGNGANLIKGSSNKPLNDNQW

HNVMISRDTSNLHTVKIDTKITTQITAGARNLDLKSDLYIGGVAKETYK

-continued

SLPKLVHAKEGFQGCLASVDLNGRLPDLISDALFCNGQIERGCEGPSTT

CQEDSCSNQGVCLQQWDGFSCDCSMTSFSGPLCNDPGTTYIFSKGGGQI

TYKWPPNDRPSTRADRLAIGFSTVQKEAVLVRVDSSSGLGDYLELHIHQ

GKIGVKFNVGTDDIAIEESNAIINDGKYHVVRFTRSGGNATLQVDSWPV

IERYPAGNNDNERLAIARQRIPYRLGRVVDEWLLDKGRQLTIFNSQATI

IIGGKEQGQPFQGQLSGLYYNGLKVLNMAAENDANIAIVGNVRLVGEVP

SSMTTESTATAMQSEMSTSIMETTTTLATSTARRGKPPTKEPISQTTDD

ILVASAECPSDDEDIDPCEPSSANPTRAGGREPYPGSAEVIRESSSTTG

MVVGIVAAAALCILILLYAMYKYRNRDEGSYHVDESRNYISNSAQSNGA

VVKEKQPSSAKSSNKNKKNKDKEYYV,

NRXN1 Isoform 3a having the following amino acid
sequence:

(SEQ ID NO: 18)
MGTALLQRGGCFLLCLSLLLLGCWAELGSGLEFPGAEGQWTRFPKWNAC

CESEMSFQLKTRSARGLVLYFDDEGFCDFLELILTRGGRLQLSFSIFCA

EPATLLADTPVNDGAWHSVRIRRQFRNTTLFIDQVEAKWVEVKSKRRDM

TVFSGLFVGGLPPELRAAALKLTLASVREREPFKGWIRDVRVNSSQVLP

VDSGEVKLDDEPPNSGGGSPCEAGEEGEGGVCLNGGVCSVVDDQAVCDC

SRTGFRGKDCSQEIKFGLQCVLPVLLHDNDQGKYCCINTAKPLTEKDNN

VEGLAHLMMGDQGKSKGKEEYIATFKGSEYFCYDLSQNPIQSSSDEITL

SFKTLQRNGLMLHTGKSADYVNLALKNGAVSLVINLGSGAFEALVEPVN

GKFNDNAWHDVKVTRNLRQHSGIGHAMVNKLHCSVTISVDGILTTTGYT

QEDYTMLGSDDFFYVGGSPSTADLPGSPVSNNFMGCLKEVVYKNNDVRL

ELSRLAKQGDPKMKIHGVVAFKCENVATLDPITFETPESFISLPKWNAK

KTGSISFDFRTTEPNGLILFSHGKPRHQKDAKHPQMIKVDFFAIEMLDG

HLYLLLDMGSGTIKIKALLKKVNDGEWYHVDFQRDGRSGTISVNTLRTP

YTAPGESEILDLDDELYLGGLPENKAGLVFPTEVWTALLNYGYVGCIRD

LFIDGQSKDIRQMAEVQSTAGVKPSCSKETAKPCLSNPCKNNGMCRDGW

NRYVCDCSGTGYLGRSCEREATVLSYDGSMFMKIQLPVVMHTEAEDVSL

RFRSQRAYGILMATTSRDSADTLRLELDAGRVKLTVNLDCIRINCNSSK

GPETLFAGYNLNDNEWHTVRVVRRGKSLKLTVDDQQAMTGQMAGDHTRL

EFHNIETGIITERRYLSSVPSNFIGHLQSLTFNGMAYIDLCKNGDIDYC

ELNARFGFRNIIADPVTFKTKSSYVALATLQAYTSMHLFFQFKTTSLDG

LILYNSGDGNDFIVVELVKGYLHYVFDLGNGANLIKGSSNKPLNDNQWH

NVMISRDTSNLHTVKIDTKITTQITAGARNLDLKSDLYIGGVAKETYKS

LPKLVHAKEGFQGCLASVDLNGRLPDLISDALFCNGQIERGCEGPSTTC

QEDSCSNQGVCLQQWDGFSCDCSMTSFSGPLCNDPGTTYIFSKGGGQIT

YKWPPNDRPSTRADRLAIGFSTVQKEAVLVRVDSSSGLGDYLELHIHQG

KIGVKFNVGTDDIAIEESNAIINDGKYHVVRFTRSGGNATLQVDSWPVI

ERYPAGNNDNERLAIARQRIPYRLGRVVDEWLLDKGRQLTIFNSQATII

-continued
IGGKEQGQPFQGQLSGLYYNGLKVLNMAAENDANIAIVGNVRLVGEVPS

SMTTESTATAMQSEMSTSIMETTTTLATSTARRGKPPTKEPISQTTDDI

LVASAECPSDDEDIDPCEPSSGGLANPTRAGGREPYPGSAEVIRESSST

TGMVVGIVAAAALCILILLYAMYKYRNRDEGSYHVDESRNYISNSAQSN

GAVVKEKQPSSAKSSNKNKKNKDKEYYV, and NRXN1 Isoform 4 having the following amino acid
sequence:

(SEQ ID NO: 19)
MDMRWHCENSQTTDDILVASAECPSDDEDIDPCEPSSANPTRAGGREPY

PGSAEVIRESSSTTGMVVGIVAAAALCILILLYAMYKYRNRDEGSYHVD

ESRNYISNSAQSNGAVVKEKQPSSAKSSNKNKKNKDKEYYV.

In some instances, the methods described herein may
employ a BTTS that specifically binds NRXN1, including
e.g., human NRXN1 Isoform 1b, human NRXN1 Isoform
3b, human NRXN1 Isoform 1a, human NRXN1 Isoform 2a,
human NRXN1 Isoform 3a, human NRXN1 Isoform 4, or
any combination thereof.

In some instances, useful priming antigens may include
receptor-type tyrosine-protein phosphatase zeta (PTPRZ1),
also known as Protein-tyrosine phosphatase receptor type Z
polypeptide 1, R-PTP-zeta HTPZP2, PTPRZ, PTPRZ2, and
PTPZ. PTPRZ1 is a receptor protein tyrosine phosphatase
encoded by the protein tyrosine phosphatase, receptor type
Z1 gene in humans, located in humans at 7q31.32, PTPRZ1
protein may be found in at least one isoform in humans,
including PTPRZ1 Isoform 1 having the following amino
acid sequence:

(SEQ ID NO: 20)
MRILKRFLACIQLLCVCRLDWANGYYRQQRKLVEEIGWSYTGALNQKNWG

KKYPTCNSPKQSPINIDEDLTQVNVNLKKLKFQGWDKTSLENTFIHNTGK

TVEINLTNDYRVSGGVSEMVFKASKITFHWGKCNMSSDGSEHSLEGQKFP

LEMQIYCFDADRFSSFEEAVKGKGKLRALSILFEVGTEENLDFKAIIDGV

ESVSRFGKQAALDPFILLNLLPNSTDKYYIYNGSLTSPPCTDTVDWIVFK

DTVSISESQLAVFCEVLTMQQSGYVMLMDYLQNNFREQQYKFSRQVFSSY

TGKEEIHEAVCSSEPENVQADPENYTSLLVTWERPRVVYDTMIEKFAVLY

QQLDGEDQTKHEFLTDGYQDLGAILNNLLPNMSYVLQIVAICTNGLYGKY

SDQLIVDMPTDNPELDLFPELIGTEEIIKEEEEGKDIEEGAIVNPGRDSA

TNQIRKKEPQISTTTHYNRIGTKYNEAKTNRSPTRGSEFSGKGDVPNTSL

NSTSQPVTKLATEKDISLTSQTVTELPPHTVEGTSASLNDGSKTVLRSPH

MNLSGTAESLNTVSITEYEEESLLTSFKLDTGAEDSSGSSPATSAIPFIS

ENISQGYIFSSENPETITYDVLIPESARNASEDSTSSGSEESLKDPSMEG

NVWFPSSTDITAQPDVGSGRESFLQTNYTEIRVDESEKTTKSFSAGPVMS

QGPSVTDLEMPHYSTFAYFPTEVTPHAFTPSSRQQDLVSTVNVVYSQTTQ

PVYNGETPLQPSYSSEVFPLVTPLLLDNQILNTTPAASSSDSALHATPVF

PSVDVSFESILSSYDGAPLLPFSSASFSSELFRHLHTVSQILPQVTSATE

SDKVPLHASLPVAGGDLLLEPSLAQYSDVLSTTHAASETLEFGSESGVLY

-continued

KTLMFSQVEPPSSDAMMHARSSGPEPSYALSDNEGSQHIFTVSYSSAIPV

HDSVGVTYQGSLFSGPSHIPIPKSSLITPTASLLQPTHALSGDGEWSGAS

SDSEFLLPDTDGLTALNISSPVSVAEFTYTTSVFGDDNKALSKSEIIYGN

ETELQIPSFNEMVYPSESTVMPNMYDNVNKLNASLQETSVSISSTKGMFP

GSLAHTTTKVFDHEISQVPENNFSVQPTHTVSQASGDTSLKPVLSANSEP

ASSDPASSEMLSPSTQLLFYETSASFSTEVLLQPSFQASDVDTLLKTVLP

AVPSDPILVETPKVDKISSTMLHLIVSNSASSENMLHSTSVPVFDVSPTS

HMHSASLQGLTISYASEKYEPVLLKSESSHQVVPSLYSNDELFQTANLEI

NQAHPPKGRHVFATPVLSIDEPLNTLINKLIHSDEILTSTKSSVTGKVFA

GIPTVASDTFVSTDHSVPIGNGHVAITAVSPHRDGSVTSTKLLFPSKATS

ELSHSAKSDAGLVGGGEDGDTDDDGDDDDDDRGSDGLSIHKCMSCSSYRE

SQEKVMNDSDTHENSLMDQNNPISYSLSENSEEDNRVTSVSSDSQTGMDR

SPGKSPSANGLSQKHNDGKEENDIQTGSALLPLSPESKAWAVLTSDEESG

SGQGTSDSLNENETSTDFSFADTNEKDADGILAAGDSEITPGFPQSPTSS

VTSENSEVFHVSEAEASNSSHESRIGLAEGLESEKKAVIPLVIVSALTFI

CLVVLVGILIYWRKCFQTAHFYLEDSTSPRVISTPPTPIFPISDDVGAIP

IKHFPKHVADLHASSGFTEEFETLKEFYQEVQSCTVDLGITADSSNHPDN

KHKNRYINIVAYDHSRVKLAQLAEKDGKLTDYINANYVDGYNRPKAYIAA

QGPLKSTAEDFWRMIWEHNVEVIVMITNLVEKGRRKCDQYWPADGSEEYG

NFLVTQKSVQVLAYYTVRNFTLRNTKIKKGSQKGRPSGRVVTQYHYTQWP

DMGVPEYSLPVLTFVRKAAYAKRHAVGPVVVHCSAGVGRTGTYIVLDSML

QQIQHEGTVNIFGFLKHIRSQRNYLVQTEEQYVFIHDTLVEAILSKETEV

LDSHIFIAYVNALLIPGPAGKTKLEKQFQLLSQSNIQQSDYSAALKQCNR

EKNRTSSIIPVERSRVGISSLSGEGTDYINASYIMGYYQSNEFIITQHPL

LHTIKDFWRMIWDHNAQLVVMIPDGQNMAEDEFVYWPNKDEPINCESFKV

TLMAEEHKCLSNEEKLIIQDFILEATQDDYVLEVRHFQCPKWPNPDSPIS

KTFELISVIKEEAANRDGPMIVHDEHGGVTAGTFCALTTLMHQLEKENSV

DVYQVAKMINLMRPGVFADIEQYQFLYKVILSLVSTRQEENPSTSLDSNG

AALPDGNIAESLESLV,

PTPRZ1 Isoform 2 having the following amino acid sequence:

(SEQ ID NO: 21)

MRILKRFLACIQLLCVCRLDWANGYYRQQRKLVEEIGWSYTGALNQKNWG

KKYPTCNSPKQSPINIDEDLTQVNVNLKKLKFQGWDKTSLENTFIHNTGK

TVEINLTNDYRVSGGVSEMVFKASKITFHWGKCNMSSDGSEHSLEGQKFP

LEMQIYCFDADRFSSFEEAVKGKGKLRALSILFEVGTEENLDFKAIIDGV

ESVSRFGKQAALDPFILLNLLPNSTDKYYIYNGSLTSPPCTDTVDWIVFK

DTVSISESQLAVFCEVLTMQQSGYVMLMDYLQNNFREQQYKFSRQVFSSY

TGKEEIHEAVCSSEPENVQADPENYTSLLVTWERPRVVYDTMIEKFAVLY

QQLDGEDQTKHEFLTDGYQDLGAILNNLLPNMSYVLQIVAICTNGLYGKY

SDQLIVDMPTDNPELDLFPELIGTEEIIKEEEEGKDIEEGAIVNPGRDSA

-continued

TNQIRKKEPQISTTTHYNRIGTKYNEAKTNRSPTRGSEFSGKGDVPNTSL

NSTSQPVTKLATEKDISLTSQTVTELPPHTVEGTSASLNDGSKTVLRSPH

MNLSGTAESLNTVSITEYEEESLLTSFKLDTGAEDSSGSSPATSAIPFIS

ENISQGYIFSSENPETITYDVLIPESARNASEDSTSSGSEESLKDPSMEG

NVWFPSSTDITAQPDVGSGRESFLQTNYTEIRVDESEKTTKSFSAGPVMS

QGPSVTDLEMPHYSTFAYFPTEVTPHAFTPSSRQQDLVSTVNVVYSQTTQ

PVYNGETPLQPSYSSEVFPLVTPLLLDNQILNTTPAASSSDSALHATPVF

PSVDVSFESILSSYDGAPLLPFSSASFSSELFRHLHTVSQILPQVTSATE

SDKVPLHASLPVAGGDLLLEPSLAQYSDVLSTTHAASETLEFGSESGVLY

KTLMFSQVEPPSSDAMMHARSSGPEPSYALSDNEGSQHIFTVSYSSAIPV

HDSVGVTYQGSLFSGPSHIPIPKSSLITPTASLLQPTHALSGDGEWSGAS

SDSEFLLPDTDGLTALNISSPVSVAEFTYTTSVFGDDNKALSKSEIIYGN

ETELQIPSFNEMVYPSESTVMPNMYDNVNKLNASLQETSVSISSTKGMFP

GSLAHTTTKVFDHEISQVPENNFSVQPTHTVSQASGDTSLKPVLSANSEP

ASSDPASSEMLSPSTQLLFYETSASFSTEVLLQPSFQASDVDTLLKTVLP

AVPSDPILVETPKVDKISSTMLHLIVSNSASSENMLHSTSVPVFDVSPTS

HMHSASLQGLTISYASEKYEPVLLKSESSHQVVPSLYSNDELFQTANLEI

NQAHPPKGRHVFATPVLSIDEPLNTLINKLIHSDEILTSTKSSVTGKVFA

GIPTVASDTFVSTDHSVPIGNGHVAITAVSPHRDGSVTSTKLLFPSKATS

ELSHSAKSDAGLVGGGEDGDTDDDGDDDDDDRGSDGLSIHKCMSCSSYRE

SQEKVMNDSDTHENSLMDQNNPISYSLSENSEEDNRVTSVSSDSQTGMDR

SPGKSPSANGLSQKHNDGKEENDIQTGSALLPLSPESKAWAVLTSDEESG

SGQGTSDSLNENETSTDFSFADTNEKDADGILAAGDSEITPGFPQSPTSS

VTSENSEVFHVSEAEASNSSHESRIGLAEGLESEKKAVIPLVIVSALTFI

CLVVLVGILIYWRKCFQTAHFYLEDSTSPRVISTPPTPIFPISDDVGAIP

IKHFPKHVADLHASSGFTEEFEEVQSCTVDLGITADSSNHPDNKHKNRYI

NIVAYDHSRVKLAQLAEKDGKLTDYINANYVDGYNRPKAYIAAQGPLKST

AEDFWRMIWEHNVEVIVMITNLVEKGRRKCDQYWPADGSEEYGNFLVTQK

SVQVLAYYTVRNFTLRNTKIKKGSQKGRPSGRVVTQYHYTQWPDMGVPEY

SLPVLTFVRKAAYAKRHAVGPVVVHCSAGVGRTGTYIVLDSMLQQIQHEG

TVNIFGFLKHIRSQRNYLVQTEEQYVFIHDTLVEAILSKETEVLDSHIHA

YVNALLIPGPAGKTKLEKQFQLLSQSNIQQSDYSAALKQCNREKNRTSSI

IPVERSRVGISSLSGEGTDYINASYIMGYYQSNEFIITQHPLLHTIKDFW

RMIWDHNAQLVVMIPDGQNMAEDEFVYWPNKDEPINCESFKVTLMAEEHK

CLSNEEKLIIQDFILEATQDDYVLEVRHFQCPKWPNPDSPISKTFELISV

IKEEAANRDGPMIVHDEHGGVTAGTFCALTTLMHQLEKENSVDVYQVAKM

INLMRPGVFADIEQYQFLYKVILSLVSTRQEENPSTSLDSNGAALPDGNI

AESLESLV, and PTPRZ1 Isoform 3 having the following amino acid sequence:

(SEQ ID NO: 22)

MRILKRFLACIQLLCVCRLDWANGYYRQQRKLVEEIGWSYTGALNQKNWG

KKYPTCNSPKQSPINIDEDLTQVNVNLKKLKFQGWDKTSLENTFIHNTGK

TVEINLTNDYRVSGGVSEMVFKASKITFHWGKCNMSSDGSEHSLEGQKFP

LEMQIYCFDADRFSSFEEAVKGKGKLRALSILFEVGTEENLDFKAIIDGV

ESVSRFGKQAALDPFILLNLLPNSTDKYYIYNGSLTSPPCTDTVDWIVFK

DTVSISESQLAVFCEVLTMQQSGYVMLMDYLQNNFREQQYKFSRQVFSSY

TGKEEIHEAVCSSEPENVQADPENYTSLLVTWERPRVVYDTMIEKFAVLY

QQLDGEDQTKHEFLTDGYQDLGAILNNLLPNMSYVLQIVAICTNGLYGKY

SDQLIVDMPTDNPELDLFPELIGTEEIIKEEEEGKDIEEGAIVNPGRDSA

TNQIRKKEPQISTTTHYNRIGTKYNEAKTNRSPTRGSEFSGKGDVPNTSL

NSTSQPVTKLATEKDISLTSQTVTELPPHTVEGTSASLNDGSKTVLRSPH

MNLSGTAESLNTVSITEYEEESLLTSFKLDTGAEDSSGSSPATSAIPFIS

ENISQGYIFSSENPETITYDVLIPESARNASEDSTSSGSEESLKDPSMEG

NVWFPSSTDITAQPDVGSGRESFLQTNYTERVDESEKTTKSFSAGPVMSQ

GPSVTDLEMPHYSTFAYFPTEVTPHAFTPSSRQQDLVSTVNVVYSQTTQP

VYNEASNSSHESRIGLAEGLESEKKAVIPLVIVSALTFICLVVLVGILIY

WRKCFQTAHFYLEDSTSPRVISTPPTPIFPISDDVGAIPIKHFPKHVADL

HASSGFTEEFEEVQSCTVDLGITADSSNHPDNKHKNRYINIVAYDHSRVK

LAQLAEKDGKLTDYINANYVDGYNRPKAYIAAQGPLKSTAEDFWRMIWEH

NVEVIVMITNLVEKGRRKCDQYWPADGSEEYGNFLVTQKSVQVLAYYTVR

NFTLRNTKIKKGSQKGRPSGRVVTQYHYTQWPDMGVPEYSLPVLTFVRKA

AYAKRHAVGPVVVHCSAGVGRTGTYIVLDSMLQQIQHEGTVNIFGFLKHI

RSQRNYLVQTEEQYVFIHDTLVEAILSKETEVLDSHIHAYVNALLIPGPA

GKTKLEKQFQLLSQSNIQQSDYSAALKQCNREKNRTSSIIPVERSRVGIS

SLSGEGTDYINASYIMGYYQSNEFIITQHPLLHTIKDFWRMIWDHNAQLV

VMIPDGQNMAEDEFVYWPNKDEPINCESFKVTLMAEEHKCLSNEEKLIIQ

DFILEATQDDYVLEVRHFQCPKWPNPDSPISKTFELISVIKEEAANRDGP

MIVHDEHGGVTAGTFCALTTLMHQLEKENSVDVYQVAKMINLMRPGVFAD

IEQYQFLYKVILSLVSTRQEENPSTSLDSNGAALPDGNIAESLESLV.

In some instances, the methods described herein may employ a BTTS that specifically binds PTPRZ1, including e.g., human PTPRZ1 Isoform 1, human PTPRZ1 Isoform 2, human PTPRZ1 Isoform 3, or any combination thereof.

In some instances, useful priming antigens may include neuronal cell adhesion molecule (NRCAM). NRCAM is a cell adhesion molecule member of the immunoglobulin superfamily with multiple immunoglobulin-like C2-type domains and fibronectin type-III domains encoded by the neuronal cell adhesion molecule gene, located in humans at 7q31.1, NRCAM protein may be found in at least one isoform in humans, including NRCAM Isoform 1 having the following amino acid sequence:

(SEQ ID NO: 23)

MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISVDELNDTIAA

NLSDTEFYGAKSSRERPPTFLTPEGNASNKEELRGNVLSLECIAEGLPTP

IIYWAKEDGMLPKNRTVYKNFEKTLQIIHVSEADSGNYQCIAKNALGAIH

HTISVRVKAAPYWITAPQNLVLSPGEDGTLICRANGNPKPRISWLTNGVP

IEIAPDDPSRKIDGDTIIFSNVQERSSAVYQCNASNEYGYLLANAFVNVL

AEPPRILTPANTLYQVIANRPALLDCAFFGSPLPTIEWFKGAKGSALHED

IYVLHENGTLEIPVAQKDSTGTYTCVARNKLGMAKNEVHLEIKDPTWIVK

QPEYAVVQRGSMVSFECKVKHDHTLSLTVLWLKDNRELPSDERFTVDKDH

LVVADVSDDDSGTYTCVANTTLDSVSASAVLSVVAPTPTPAPVYDVPNPP

FDLELTDQLDKSVQLSWTPGDDNNSPITKFIIEYEDAMHKPGLWHHQTEV

SGTQTTAQLKLSPYVNYSFRVMAVNSIGKSLPSEASEQYLTKASEPDKNP

TAVEGLGSEPDNLVITWKPLNGFESNGPGLQYKVSWRQKDGDDEWTSVVV

ANVSKYIVSGTPTFVPYLIKVQALNDMGFAPEPAVVMGHSGEDLPMVAPG

NVRVNVVNSTLAEVHWDPVPLKSIRGHLQGYRIYYWKTQSSSKRNRRHIE

KKILTFQGSKTHGMLPGLEPFSHYTLNVRVVNGKGEGPASPDRVFNTPEG

VPSAPSSLKIVNPTLDSLTLEWDPPSHPNGILTEYTLKYQPINSTHELGP

LVDLKIPANKTRWTLKNLNFSTRYKFYFYAQTSAGSGSQITEEAVTTVDE

AGILPPDVGAGKVQAVNPRISNLTAAAAETYANISWEYEGPEHVNFYVEY

GVAGSKEEWRKEIVNGSRSFFGLKGLMPGTAYKVRVGAVGDSGFVSSEDV

FETGPAMASRQVDIATQGWFIGLMCAVALLILILLIVCFIRRNKGGKYPV

KEKEDAHADPEIQPMKEDDGTFGEYSDAEDHKPLKKGSRTPSDRTVKKED

SDDSLVDYGEGVNGQFNEDGSFIGQYSGKKEKEPAEGNESSEAPSPVNAM

NSFV,

NRCAM Isoform 2 having the following amino acid sequence:

(SEQ ID NO: 24)

MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISVDELNDTIAA

NLSDTEFYGAKSSRERPPTFLTPEGNASNKEELRGNVLSLECIAEGLPTP

IIYWAKEDGMLPKNRTVYKNFEKTLQIIHVSEADSGNYQCIAKNALGAIH

HTISVRVKAAPYWITAPQNLVLSPGEDGTLICRANGNPKPRISWLTNGVP

IEIAPDDPSRKIDGDTIIFSNVQERSSAVYQCNASNEYGYLLANAFVNVL

AEPPRILTPANTLYQVIANRPALLDCAFFGSPLPTIEWFKGAKGSALHED

IYVLHENGTLEIPVAQKDSTGTYTCVARNKLGMAKNEVHLEIKDPTWIVK

QPEYAVVQRGSMVSFECKVKHDHTLSLTVLWLKDNRELPSDERFTVDKDH

LVVADVSDDDSGTYTCVANTTLDSVSASAVLSVVAPTPTPAPVYDVPNPP

FDLELTDQLDKSVQLSWTPGDDNNSPITKFIIEYEDAMHKPGLWHHQTEV

SGTQTTAQLKLSPYVNYSFRVMAVNSIGKSLPSEASEQYLTKASEPDKNP

TAVEGLGSEPDNLVITWKPLNGFESNGPGLQYKVSWRQKDGDDEWTSVVV

ANVSKYIVSGTPTFVPYLIKVQALNDMGFAPEPAVVMGHSGEDLPMVAPG

NVRVNVVNSTLAEVHWDPVPLKSIRGHLQGYRIYYWKTQSSSKRNRRHIE

KKILTFQGSKTHGMLPGLEPFSHYTLNVRVVNGKGEGPASPDRVFNTPEG

VPSAPSSLKIVNPTLDSLTLEWDPPSHPNGILTEYTLKYQPINSTHELGP

LVDLKIPANKTRWTLKNLNFSTRYKFYFYAQTSAGSGSQITEEAVTTVDE

AGILPPDVGAGKVQAVNPRISNLTAAAAETYANISWEYEGPEHVNFYVEY

GVAGSKEEWRKEIVNGSRSFFGLKGLMPGTAYKVRVGAVGDSGFVSSEDV

FETGPAMASRQVDIATQGWFIGLMCAVALLILILLIVCFIRRNKGGKYPV

KEKEDAHADPEIQPMKEDDGTFGEYRLFSFVSSASF,

NRCAM Isoform 3 having the following amino acid sequence:

(SEQ ID NO: 25)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISAKSSRERPPT

FLTPEGNASNKEELRGNVLSLECIAEGLPTPIIYWAKEDGMLPKNRTVYK

NFEKTLQIIHVSEADSGNYQCIAKNALGAIHHTISVRVKAAPYWITAPQN

LVLSPGEDGTLICRANGNPKPRISWLTNGVPIEIAPDDPSRKIDGDTIIF

SNVQERSSAVYQCNASNEYGYLLANAFVNVLAEPPRILTPANTLYQVIAN

RPALLDCAFFGSPLPTIEWFKGAKGSALHEDIYVLHENGTLEIPVAQKDS

TGTYTCVARNKLGMAKNEVHLEIKDPTWIVKQPEYAVVQRGSMVSFECKV

KHDHTLSLTVLWLKDNRELPSDERFTVDKDHLVVADVSDDDSGTYTCVAN

TTLDSVSASAVLSVVAPTPTPAPVYDVPNPPFDLELTDQLDKSVQLSWTP

GDDNNSPITKFIIEYEDAMHKPGLWHHQTEVSGTQTTAQLKLSPYVNYSF

RVMAVNSIGKSLPSEASEQYLTKASEPDKNPTAVEGLGSEPDNLVITWKP

LNGFESNGPGLQYKVSWRQKDGDDEWTSVVVANVSKYIVSGTPTFVPYLI

KVQALNDMGFAPEPAVVMGHSGEDLPMVAPGNVRVNVVNSTLAEVHWDPV

PLKSIRGHLQGYRIYYWKTQSSSKRNRRHIEKKILTFQGSKTHGMLPGLE

PFSHYTLNVRVVNGKGEGPASPDRVFNTPEGVPSAPSSLKIVNPTLDSLT

LEWDPPSHPNGILTEYTLKYQPINSTHELGPLVDLKIPANKTRWTLKNLN

FSTRYKFYFYAQTSAGSGSQITEEAVTTVDEAMASRQVDIATQGWFIGLM

CAVALLILILLIVCFIRRNKGGKYPVKEKEDAHADPEIQPMKEDDGTFGE

YSDAEDHKPLKKGSRTPSDRTVKKEDSDDSLVDYGEGVNGQFNEDGSFIG

QYSGKKEKEPAEGNESSEAPSPVNAMNSFV,

NRCAM Isoform 4 having the following amino acid sequence:

(SEQ ID NO: 26)
MQLKIMPKKKRLSAGRVPLILFLCQMISALEVPLDLVQPPTITQQSPKDY

IIDPRENIVIQCEAKGKPPPSFSWTRNGTHFDIDKDPLVTMKPGTGTLII

NIMSEGKAETYEGVYQCTARNERGAAVSNNIVVRPSRSPLWTKEKLEPIT

LQSGQSLVLPCRPPIGLPPPIIFWMDNSFQRLPQSERVSQGLNGDLYFSN

VLPEDTREDYICYARFNHTQTIQQKQPISVKVISVDELNDTIAANLSDTE

FYGAKSSRERPPTFLTPEGNASNKEELRGNVLSLECIAEGLPTPIIYWAK

EDGMLPKNRTVYKNFEKTLQIIHVSEADSGNYQCIAKNALGAIHHTISVR

VKAAPYWITAPQNLVLSPGEDGTLICRANGNPKPRISWLTNGVPIEIAPD

DPSRKIDGDTIIFSNVQERSSAVYQCNASNEYGYLLANAFVNVLAEPPRI

LTPANTLYQVIANRPALLDCAFFGSPLPTIEWFKGAKGSALHEDIYVLHE

NGTLEIPVAQKDSTGTYTCVARNKLGMAKNEVHLEIKDPTWIVKQPEYAV

VQRGSMVSFECKVKHDHTLSLTVLWLKDNRELPSDERFTVDKDHLVVADV

SDDDSGTYTCVANTTLDSVSASAVLSVVDVPNPPFDLELTDQLDKSVQLS

WTPGDDNNSPITKFIIEYEDAMHKPGLWHHQTEVSGTQTTAQLKLSPYVN

YSFRVMAVNSIGKSLPSEASEQYLTKASEPDKNPTAVEGLGSEPDNLVIT

WKPLNGFESNGPGLQYKVSWRQKDGDDEWTSVVVANVSKYIVSGTPTFVP

YLIKVQALNDMGFAPEPAVVMGHSGEDLPMVAPGNVRVNVVNSTLAEVHW

DPVPLKSIRGHLQGYRIYYWKTQSSSKRNRRHIEKKILTFQGSKTHGMLP

GLEPFSHYTLNVRVVNGKGEGPASPDRVFNTPEGVPSAPSSLKIVNPTLD

SLTLEWDPPSHPNGILTEYTLKYQPINSTHELGPLVDLKIPANKTRWTLK

NLNFSTRYKFYFYAQTSAGSGSQITEEAVTTVDEAMASRQVDIATQGWFI

GLMCAVALLILILLIVCFIRRNKGGKYPVKEKEDAHADPEIQPMKEDDGT

FGEYSDAEDHKPLKKGSRTPSDRTVKKEDSDDSLVDYGEGVNGQFNEDGS

FIGQYSGKKEKEPAEGNESSEAPSPVNAMNSFV,

NRCAM Isoform 5 having the following amino acid sequence:

(SEQ ID NO: 27)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISVDELNDTIAA

NLSDTEFYGAKSSRERPPTFLTPEGNASNKEELRGNVLSLECIAEGLPTP

IIYWAKEDGMLPKNRTVYKNFEKTLQIIHVSEADSGNYQCIAKNALGAIH

HTISVRVKAAPYWITAPQNLVLSPGEDGTLICRANGNPKPRISWLTNGVP

-continued

```
IEIAPDDPSRKIDGDTIIFSNVQERSSAVYQCNASNEYGYLLANAFVNVL

AEPPRILTPANTLYQVIANRPALLDCAFFGSPLPTIEWFKGAKGSALHED

IYVLHENGTLEIPVAQKDSTGTYTCVARNKLGMAKNEVHLEIKDPTWIVK

QPEYAVVQRGSMVSFECKVKHDHTLSLTVLWLKDNRELPSDERFTVDKDH

LVVADVSDDDSGTYTCVANTTLDSVSASAVLSVVAPTPTPAPVYDVPNPP

FDLELTDQLDKSVQLSWTPGDDNNSPITKFIIEYEDAMHKPGLWHHQTEV

SGTQTTAQLKLSPYVNYSFRVMAVNSIGKSLPSEASEQYLTKASEPDKNP

TAVEGLGSEPDNLVITWKPLNGFESNGPGLQYKVSWRQKDGDDEWTSVVV

ANVSKYIVSGTPTFVPYLIKVQALNDMGFAPEPAVVMGHSGEDLPMVAPG

NVRVNVVNSTLAEVHWDPVPLKSIRGHLQGYRIYYWKTQSSSKRNRRHIE

KKILTFQGSKTHGMLPGLEPFSHYTLNVRVVNGKGEGPASPDRVFNTPEG

VPSAPSSLKIVNPTLDSLTLEWDPPSHPNGILTEYTLKYQPINSTHELGP

LVDLKIPANKTRWTLKNLNFSTRYKFYFYAQTSAGSGSQITEEAVTTVDE

AGILPPDVGAGKVQAVNPRISNLTAAAAETYANISWEYEGPEHVNFYVEY

GVAGSKEEWRKEIVNGSRSFFGLKGLMPGTAYKVRVGAVGDSGFVSSEDV

FETGPAMASRQVDIATQGWFIGLMCAVALLILILLIVCFIRRNKGGKYPV

KEKEDAHADPEIQPMKEDDGTFGEYRSLESDAEDHKPLKKGSRTPSDRTV

KKEDSDDSLVDYGEGVNGQFNEDGSFIGQYSGKKEKEPAEGNESSEAPSP

VNAMNSFV
``` and NRCAM Isoform 6 having the following amino acid sequence:

```
                                      (SEQ ID NO: 28)
MQLKIMPKKKRLSAGRVPLILFLCQMISALEVPLDPKLLEDLVQPPTITQ

QSPKDYIIDPRENIVIQCEAKGKPPPSFSWTRNGTHFDIDKDPLVTMKPG

TGTLIINIMSEGKAETYEGVYQCTARNERGAAVSNNIVVRPSRSPLWTKE

KLEPITLQSGQSLVLPCRPPIGLPPPIIFWMDNSFQRLPQSERVSQGLNG

DLYFSNVLPEDTREDYICYARFNHTQTIQQKQPISVKVISAKSSRERPPT

FLTPEGNASNKEELRGNVLSLECIAEGLPTPIIYWAKEDGMLPKNRTVYK

NFEKTLQIIHVSEADSGNYQCIAKNALGAIHHTISVRVKAAPYWITAPQN

LVLSPGEDGTLICRANGNPKPRISWLTNGVPIEIAPDDPSRKIDGDTIIF

SNVQERSSAVYQCNASNEYGYLLANAFVNVLAEPPRILTPANTLYQVIAN

RPALLDCAFFGSPLPTIEWFKGAKGSALHEDIYVLHENGTLEIPVAQKDS

TGTYTCVARNKLGMAKNEVHLEIKDPTWIVKQPEYAVVQRGSMVSFECKV

KHDHTLSLTVLWLKDNRELPSDERFTVDKDHLVVADVSDDDSGTYTCVAN

TTLDSVSASAVLSVVAPTPTPAPVYDVPNPPFDLELTDQLDKSVQLSWTP

GDDNNSPITKFIIEYEDAMHKPGLWHHQTEVSGTQTTAQLKLSPYVNYSF

RVMAVNSIGKSLPSEASEQYLTKASEPDKNPTAVEGLGSEPDNLVITWKP

LNGFESNGPGLQYKVSWRQKDGDDEWTSVVVANVSKYIVSGTPTFVPYLI

KVQALNDMGFAPEPAVVMGHSGEDLPMVAPGNVRVNVVNSTLAEVHWDPV

PLKSIRGHLQGYRIYYWKTQSSSKRNRRHIEKKILTFQGSKTHGMLPGLE

PFSHYTLNVRVVNGKGEGPASPDRVFNTPEGVPSAPSSLKIVNPTLDSLT
```

-continued

```
LEWDPPSHPNGILTEYTLKYQPINSTHELGPLVDLKIPANKTRWTLKNLN

FSTRYKFYFYAQTSAGSGSQITEEAVTTVDEAGILPPDVGAGKAMASRQV

DIATQGWFIGLMCAVALLILILLIVCFIRRNKGGKYPVKEKEDAHADPEI

QPMKEDDGTFGEYSDAEDHKPLKKGSRTPSDRTVKKEDSDDSLVDYGEGV

NGQFNEDGSFIGQYSGKKEKEPAEGNESSEAPSPVNAMNSFV.
```

In some instances, the methods described herein may employ a BTTS that specifically binds NRCAM, including e.g., human NRCAM Isoform 1, human NRCAM Isoform 2, human NRCAM Isoform 3, human NRCAM Isoform 4, human NRCAM Isoform 5, human NRCAM Isoform 6, or any combination thereof.

In some instances, useful priming antigens may include Cadherin-10 (CDH10). CDH10 is a calcium-dependent cell adhesion protein predominantly expressed in brain and a type II classical cadherin of the cadherin superfamily encoded by the cadherin 10 gene, located in humans at 5p14.2-p14.1, CDH10 protein may be found in multiple transcript variants due to alternative splicing and at least one isoform is found in humans, including the CDH10 protein having the following amino acid sequence:

```
                                      (SEQ ID NO: 29)
MTIHQFLLLFLFWVCLPHFCSPEIMFRRTPVPQQRILSSRVPRSDGKILH

RQKRGWMWNQFFLLEEYTGSDYQYVGKLHSDQDKGDGSLKYILSGDGAGT

LFIIDEKTGDIHATRRIDREEKAFYTLRAQAINRRTLRPVEPESEFVIKI

HDINDNEPTFPEEIYTASVPEMSVVGTSVVQVTATDADDPSYGNSARVIY

SILQGQPYFSVEPETGIIRTALPNMNRENREQYQVVIQAKDMGGQMGGLS

GTTTVNITLTDVNDNPPRFPQNTIHLRVLESSPVGTAIGSVKATDADTGK

NAEVEYRIIDGDGTDMFDIVTEKDTQEGIITVKKPLDYESRRLYTLKVEA

ENTHVDPRFYYLGPFKDTTIVKISIEDVDEPPVFSRSSYLFEVHEDIEVG

TIIGTVMARDPDSISSPIRFSLDRHTDLDRIFNIHSGNGSLYTSKPLDRE

LSQWHNLTVIAAEINNPKETTRVAVFVRILDVNDNAPQFAVFYDTFVCEN

ARPGQLIQTISAVDKDDPLGGQKFFFSLAAVNPNFTVQDNEDNTARILTR

KNGFNRHEISTYLLPVVISDNDYPIQSSTGTLTIRVCACDSQGNMQSCSA

EALLLPAGLSTGALIAILLCIIILLVIVVLFAALKRQRKKEPLILSKEDI

RDNIVSYNDEGGGEEDTQAFDIGTLRNPAAIEEKKLRRDIIPETLFIPRR

TPTAPDNTDVRDFINERLKEHDLDPTAPPYDSLATYAYEGNDSIAESLSS

LESGTTEGDQNYDYLREWGPRFNKLAEMYGGGESDKDS.
```

In some instances, the methods described herein may employ a BTTS that specifically binds CDH10, including e.g., human CDH10 and the CDH10 amino acid sequence provided above.

In some instances, useful priming antigens may include Protocadherin gamma-C5 (PCDHGC5; also known as PCDH-gamma-C5). PCDHGC5 is a member of the protocadherin gamma gene cluster, has an immunoglobulin-like organization and is a neural cadherin-like cell adhesion protein encoded by the protocadherin gamma subfamily C, 5 gene, located in humans at 5q31.3. PCDHGC5 protein may be found in at least one isoform in humans, including PCDHGC5 Isoform 1 having the following amino acid sequence:

(SEQ ID NO: 30)

MGPKTLPQLAGKWQVLCMLSLCCWGWVSGQLRYSVVEESEPGTLVGNVAQ

DLGLKMTDLLSRRLQLGSEENGRYFSLSLMSGALAVNQKIDRESLCGAST

SCLLPVQVVTEHPLELIRVEVEILDLNDNSPSFATPEREMRISESAASGA

RFPPLDSAQDPDVGTNTVSFYTLSPNSHFSLNVKTLKDGKPFFPELVLEQQL

DREAQARHQLVLTAVDGGTPARSGTTLISVIVLDINDNAPTFQSSVLRVG

IPENAPIGTLLLRLNATDPDEGTNGQLDYSFGDHTSEAVRNLFGLDPSSG

AIHVLGPIDFEESRFYEIHARARDQGQPAMEGHCVIQVDVGDVNDNAPEV

LLASLANPVLESTPVGTVVGLFNVRDRDSGRNGEVSLDISPDLPFQIKPS

ENHYSLLTSQPLDREATSHYIIELLASDAGSPSLHKHLTIRLNISDVNDN

APRFNQQLYTAYILENRPPGSLLCTVAASDPDTGDNARLTYSIVGNQVQG

APASFVYVNPEDGRIFAQRTFDYELLQMLQIVVGVRDSGSPPLHANTSLH

VFVLDENDNAPAVLHPRPDWEHSAPQRLPRSAPPGSLVTKVTAVDADAGH

NAWLSYSLLPQSTAPGLFLVSTHTGEVRTARALLEDDSDTQQVVVLVRDN

GDPSLSSTATVLLVLEDEDPEEMPKSSDFLIHPPERSDLTLYLIVALATV

SLLSLVTFTFLSAKCLQGNADGDGGGGQCCRRQDSPSPDFYKQSSPNLQV

SSDGTLKYMEVTLRPTDSQSHCYRTCFSPASDGSDFTFLRPLSVQQPTAL

ALEPDAIRSRSNTLRERSQQAPPNTDWRFSQAQRPGTSGSQNGDDTGTWP

NNQFDTEMLQAMILASASEAADGSSTLGGGAGTMGLSARYGPQFTLQHVP

DYRQNVYIPGSNATLTNAAGKRDGKAPAGGNGNKKKSGKKEKK, and PCDHGC5 Isoform 2 having the following amino acid sequence:

(SEQ ID NO: 31)

MGPKTLPQLAGKWQVLCMLSLCCWGWVSGQLRYSVVEESEPGTLVGNVAQ

DLGLKMTDLLSRRLQLGSEENGRYFSLSLMSGALAVNQKIDRESLCGAST

SCLLPVQVVTEHPLELIRVEVEILDLNDNSPSFATPEREMRISESAASGA

RFPPLDSAQDPDVGTNTVSFYTLSPNSHFSLNVKTLKDGKPFFPELVLEQQL

DREAQARHQLVLTAVDGGTPARSGTTLISVIVLDINDNAPTFQSSVLRVG

IPENAPIGTLLLRLNATDPDEGTNGQLDYSFGDHTSEAVRNLFGLDPSSG

AIHVLGPIDFEESRFYEIHARARDQGQPAMEGHCVIQVDVGDVNDNAPEV

LLASLANPVLESTPVGTVVGLFNVRDRDSGRNGEVSLDISPDLPFQIKPS

ENHYSLLTSQPLDREATSHYIIELLASDAGSPSLHKHLTIRLNISDVNDN

APRFNQQLYTAYILENRPPGSLLCTVAASDPDTGDNARLTYSIVGNQVQG

APASFVYVNPEDGRIFAQRTFDYELLQMLQIVVGVRDSGSPPLHANTSL

HVFVLDENDNAPAVLHPRPDWEHSAPQRLPRSAPPGSLVTKVTAVDADAG

HNAWLSYSLLPQSTAPGLFLVSTHTGEVRTARALLEDDSDTQQVVVLVRD

NGDPSLSSTATVLLVLEDEDPEEMPKSSDFLIHPPERSDLTLYLIVALAT

VSLLSLVTFTFLSAKCLQGNADGDGGGGQCCRRQDSPSPDFYKQSSPNLQ

VSSDGTLKYMEVTLRPTDSQSHCYRTCFSPASDGSDFTFLRPLSVQQPTA

LALEPDAIRSRSNTLRERSQVRGSAPPRATPGGGTGEAARPHKGLNLHPL

LSGRLGRWLRSTRFSGSLDRLRETRVAD.

In some instances, the methods described herein may employ a BTTS that specifically binds PCDHGC5, including e.g., human PCDHGC5 Isoform 1, human PCDHGC5 Isoform 2, or both.

In some instances, useful priming antigens may include CD70 (Also known as CD27L; LPFS3; CD27-L; CD27LG; TNFSF7; TNLG8A). CD70 is a cytokine that belongs to the tumor necrosis factor (TNF) ligand family and is encoded by the CD70 gene, located in humans at T9p13.3. CD7 is a ligand for TNFRSF27/HCD2 and is a surface antigen on activated, but not on resting, T and B lymphocytes. CD70 protein may be found in at least two isoforms in humans, including CD7V isoform 1 having the following amino acid sequence:

(SEQ ID NO: 32)

MPEEGSGCSVRRRPYGCVLRAALVPLVAGLVICLVVCIQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

CTIASQRLTPLARGDTLCTNLTGTLLPSRNTDETFFGVQWVRP, and isoform 2 having the following sequence:

(SEQ ID NO: 33)

MPEEGSGCSVRRRPYGCVLRAALVPLVAGLVICLVVCIQRFAQAQQQLPL

ESLGWDVAELQLNHTGPQQDPRLYWQGGPALGRSFLHGPELDKGQLRIHR

DGIYMVHIQVTLAICSSTTASRHHPTTLAVGICSPASRSISLLRLSFHQG

LFGFWNWGLKVKCFLRHLIWTAHCHPLTQLVFMQALQSWRNHHCSHFTDE

ENRGVNR.

In some instances, the methods described herein may employ a BTTS that specifically binds CD70, including e.g., human CD70.

In some instances, useful priming antigens may include chondroitin sulfate proteoglycan 5 (CSPG5; also known as NGC, Acidic leucine-rich EGF-like domain-containing brain protein and Neuroglycan C). CSPG5 is a proteoglycan that may function as a neural growth and differentiation factor and is encoded by the CSPG5 gene, located in humans at 3p21.31. CSPG5 may function as a growth and differentiation factor involved in neuritogenesis. CSPG5 protein may be found in at least three isoforms in humans, including CSPG5 isoform 1 having the following amino acid sequence:

(SEQ ID NO: 34)

MGRAGGGGPGRGPPPLLLFLGAALVLASGAVPAREAGSAVEAEELVKGSP

AWEPPANDTREEAGPPAAGEDEASWTAPGGELAGPEEVLQESAAVTGTAW

LEADSPGLGGVTAEAGSGDAQALPATLQAPHEVLGQSIMPPAIPEATEAS

GPPSPTPGDKLSPASELPKESPLEVWLNLGGSTPDPQGPELTYPFQGTLE

PQPASDIIDIDYFEGLDGEGRGADLGSFPGSPGTSENHPDTEGETPSWSL

LDLYDDFTPFDESDFYPTTSFYDDLDEEEEEEEDDKDAVGGGDLEDENEL

LVPTGKPGLGPGTGQPTSRWHAVPPQHTLGSVPGSSIALRPRPGEPGRDL

ASSENGTECRSGFVRHNGSCRSVCDLFPSYCHNGGQCYLVENIGAFCRCN

TQDYIWHKGMRCESIITDFQVMCVAVGSAALVLLLLFMMTVFFAKKLYLL

KTENTKLRRTNKFRTPSELHNDNFSLSTIAEGSHPNVRKLCNTPRTSSPH

ARALAHYDNVICQDDPSAPHKIQEVLKSCLKEEESFNIQNSMSPKLEGGK

GDQADLDVNCLQNNLT;

CSPG5 isoform 2 having the following amino acid sequence:

(SEQ ID NO: 35)
MGRAGGGGPGRGPPPLLLFLGAALVLASGAVPAREAGSAVEAEELVKGSP

AWEPPANDTREEAGPPAAGEDEASWTAPGGELAGPEEVLQESAAVTGTAW

LEADSPGLGGVTAEAGSGDAQALPATLQAPHEVLGQSIMPPAIPEATEAS

GPPSPTPGDKLSPASELPKESPLEVWLNLGGSTPDPQGPELTYPFQGTLE

PQPASDIIDIDYFEGLDGEGRGADLGSFPGSPGTSENHPDTEGETPSWSL

LDLYDDFTPFDESDFYPTTSFYDDLDEEEEEEEDDKDAVGGGDLEDENEL

LVPTGKPGLGPGTGQPTSRWHAVPPQHTLGSVPGSSIALRPRPGEPGRDL

ASSENGTECRSGFVRHNGSCRSVCDLFPSYCHNGGQCYLVENIGAFCRCN

TQDYIWHKGMRCESIITDFQVMCVAVGSAALVLLLLFMMTVFFAKKLYLL

KTENTKLRRTNKFRTPSELHNDNFSLSTIAEGSHPNDDPSAPHKIQEVLK

SCLKEEESFNIQNSMSPKLEGGKGDQADLDVNCLQNNLT;

(SEQ ID NO : 36)
MPPAIPEATEASGPPSPTPGDKLSPASELPKESPLEVWLNLGGSTPDPQG

PELTYPFQGTLEPQPASDIIDIDYFEGLDGEGRGADLGSFPGSPGTSENH

PDTEGETPSWSLLDLYDDFTPFDESDFYPTTSFYDDLDEEEEEEEDDKDA

VGGGDLEDENELLVPTGKPGLGPGTGQPTSRWHAVPPQHTLGSVPGSSIA

LRPRPGEPGRDLASSENGTECRSGFVRHNGSCRSVCDLFPSYCHNGGQCY

LVENIGAFCRCNTQDYIWHKGMRCESIITDFQVMCVAVGSAALVLLLLFM

MTVFFAKKLYLLKTENTKLRRTNKFRTPSELHNDNFSLSTIAEGSHPNDD

PSAPHKIQEVLKSCLKEEESFNIQNSMSPKLEGGKGDQADLDVNCLQNNL

T.

In some instances, the methods described herein may employ a BTTS that specifically binds CSPG5, including e.g., human CSPG5.

In some instances, useful priming antigens may include brevican (BCAN; Also known as Brevican core protein; Chondroitin sulfate proteoglycan 7 (CSPG7); Brain-enriched hyaluronan-binding protein (BEHAB)). BCAN is a member of the lectican family of chondroitin sulfate proteoglycans that is specifically expressed in the central nervous system and is encoded by the BCAN gene, located in humans at 1q23.1. BCAN may play a role in the terminally differentiating and the adult nervous system during postnatal development. BCAN protein may be found in at least two isoforms in humans, including BCAN isoform 1 having the following amino acid sequence:

(SEQ ID NO: 37)
MAQLFLPLLAALVLAQAPAALADVLEGDSSEDRAFRVRIAGDAPLQGVLG

GALTIPCHVHYLRPPPSRRAVLGSPRVKWTFLSRGREAEVLVARGVRVKV

NEAYRFRVALPAYPASLTDVSLALSELRPNDSGIYRCEVQHGIDDSSDAV

EVKVKGVVFLYREGSARYAFSFSGAQEACARIGAHIATPEQLYAAYLGGY

EQCDAGWLSDQTVRYPIQTPREACYGDMDGFPGVRNYGVVDPDDLYDVYC

YAEDLNGELFLGDPPEKLTLEEARAYCQERGAEIATTGQLYAAWDGGLDH

CSPGWLADGSVRYPIVTPSQRCGGGLPGVKTLFLFPNQTGFPNKHSRFNV

YCFRDSAQPSAIPEASNPASNPASDGLEAIVTVTETLEELQLPQEATESE

SRGAIYSIPIMEDGGGGSSTPEDPAEAPRTLLEFETQSMVPPTGFSEEEG

KALEEEEKYEDEEEKEEEEEEEVEDEALWAWPSELSSPGPEASLPTEPA

AQEESLSQAPARAVLQPGASPLPDGESEASRPPRVHGPPTETLPTPRERN

LASPSPSTLVEAREVGEATGGPELSGVPRGESEETGSSEGAPSLLPATRA

PEGTRELEAPSEDNSGRTAPAGTSVQAQPVLPTDSASRGGVAVVPASGDC

VPSPCHNGGTCLEEEEGVRCLCLPGYGGDLCDVGLRFCNPGWDAFQGACY

KHFSTRRSWEEAETQCRMYGAHLASISTPEEQDFINNRYREYQWIGLNDR

TIEGDFLWSDGVPLLYENWNPGQPDSYFLSGENCVVMVWHDQGQWSDVPC

NYHLSYTCKMGLVSCGPPPELPLAQVFGRPRLRYEVDTVLRYRCREGLAQ

RNLPLIRCQENGRWEAPQISCVPRRPARALHPEEDPEGRQGRLLGRWKAL

LIPPSSPMPGP;

and BCAN isoform 2 having the following amino acid sequence:

(SEQ ID NO: 38)
MAQLFLPLLAALVLAQAPAALADVLEGDSEDRAFRVRIAGDAPLQGVLGG

ALTIPCHVHYLRPPPSRRAVLGSPRVKWTFLSRGREAEVLVARGVRVKVN

EAYRFRVALPAYPASLTDVSLALSELRPNDSGIYRCEVQHGIDDSSDAVE

VKVKGVVFLYREGSARYAFSFSGAQEACARIGAHIATPEQLYAAYLGGYE

QCDAGWLSDQTVRYPIQTPREACYGDMDGFPGVRNYGVVDPDDLYDVYCY

AEDLNGELFLGDPPEKLTLEEARAYCQERGAEIATTGQLYAAWDGGLDHC

SPGWLADGSVRYPIVTPSQRCGGGLPGVKTLFLFPNQTGFPNKHSRFNVY

CFRDSAQPSAIPEASNPASNPASDGLEAIVTVTETLEELQLPQEATESES

RGAIYSIPIMEDGGGGSSTPEDPAEAPRTLLEFETQSMVPPTGFSEEEGK

ALEEEEKYEDEEEKEEEEEEEVEDEALWAWPSELSSPGPEASLPTEPAA

QEESLSQAPARAVLQPGASPLPDGESEASRPPRVHGPPTETLPTPRERNL

ASPSPSTLVEAREVGEATGGPELSGVPRGESEETGSSEGAPSLLPATRAP

EGTRELEAPSEDNSGRTAPAGTSVQAQPVLPTDSASRGGVAVVPASGNSA

QGSTALSILLLFFPLQLWVT.

In some instances, the methods described herein may employ a BTTS that specifically binds BCAN, including e.g., human BCAN.

In some instances, useful priming antigens may include glutamate metabotropic receptor 3 (GRM3; Also known as GLUR3, mGlu3; GPRC1C; MGLUR3; Metabotropic glutamate receptor 3). GRM3 is a G-protein coupled receptor for glutamate that is encoded by the GRM3 gene, located in humans at 7q21,11-q21.12, GRM3 ligand binding causes a conformation change that triggers signaling via guanine nucleotide-binding proteins (G proteins) and modulates the activity of down-stream effectors. Signaling inhibits adenylate cyclase activity. GRM3 protein may be found in at least two isoforms in humans, including GRM3 isoform 1 having the following amino acid sequence:

```
                                      (SEQ ID NO: 39)
MKMLTRLQVLTLALFSKGFLLSLGDHNFLRREIKIEGDLVLGGLFPINEK

GTGTEECGRINEDRGIQRLEAMLFAIDEINKDDYLLPGVKLGVHILDTCS

RDTYALEQSLEFVRASLTKVDEAEYMCPDGSYAIQEMPLLIAGVIGGSYS

SVSIQVANLLRLFQIPQISYASTSAKLSDKSRYDYFARTVPPDFYQAKAM

AEILRFFNWTYVSTVASEGDYGETGIEAFEQEARLRNICIATAEKVGRSN

IRKSYDSVIRELLQKPNARVVVLFMRSDDSRELIAAASRANASFTWVASD

GWGAQESIIKGSEHVAYGAITLELASQPVRQFDRYFQSLNPYNNHRNPWF

RDFWEQKFQCSLQNKRNHRRVCDKHLAIDSSNYEQESKIMFVVNAVYAMA

HALHKMQRTLCPNTTKLCDAMKILDGKKLYKDYLLKINFTAPFNPNKDAD

SIVKFDTFGDGMGRYNVFNFQNVGGKYSYLKVGHWAETLSLDVNSIHWSR

NSVPTSQCSDPCAPNEMKNMQPGDVCCWICIPCEPYEYLADEFTCMDCGS

GQWPTADLTGCYDLPEDYIRWEDAWAIGPVTIACLGFMCTCMVVTVFIKH

NNTPLVKASGRELCYILLFGVGLSYCMTFFFIAKPSPVICALRRLGLGSS

FAICYSALLTKTNCIARIFDGVKNGAQRPKFISPSSQVFICLGLILVQIV

MVSVWLILEAPGTRRYTLAEKRETVILKCNVKDSMLISLTYDVILVILCT

VYAFKTRKCPENFNEAKFIGFTMYTTCIIWLAFLPIFYVTSSDYRVQTTT

MCISVSLSGFVVLGCLFAPKVHIILFQPQKNVVTHRLHLNRFSVSGTGTT

YSQSSASTYVPTVCNGREVLDSTTSSL;
``` and GRM3 isoform 2 having the following amino acid sequence:

```
                                      (SEQ ID NO: 40)
MKMLTRLQVLTLALFSKGFLLSLGDHNFLRREIKIEGDLVLGGLFPINEK

GTGTEECGRINEDRGIQRLEAMLFAIDEINKDDYLLPGVKLGVHILDTCS

RDTYALEQSLEFVRASLTKVDEAEYMCPDGSYAIQEMPLLIAGVIGGSYS

SVSIQVANLLRLFQIPQISYASTSAKLSDKSRYDYFARTVPPDFYQAKAM

AEILRFFNWTYVSTVASEGDYGETGIEAFEQEARLRNICIATAEKVGRSN

IRKSYDSVIRELLQKPNARVVVLFMRSDDSRELIAAASRANASFTWVASD

GWGAQESIIKGSEHVAYGAITLELASQPVRQFDRYFQSLNPYNNHRNPWF

RDFWEQKFQCSLQNKRNHRRVCDKHLAIDSNYEQESKIMFVVNAVYAMAH

ALHKMQRTLCPNTTKLCDAMKILDGKKLYKDYLLKINFTGADDNHVHLCQ

PEWLCGLGLFVCTQGSHHPVSTPEECCHTQTAPQQVQCQWNWDHILSVLC

KHVCANGVQWAGSPRLHHLISVIVNCSSVLVFLDC.
```

In some instances, the methods described herein may employ a BTTS that specifically binds GRM3, including e.g., human GRM3.

In some instances, useful priming antigens may include Protein crumbs homolog 1 (CRB1; LCA8; RP 12). CRB1 is similar to the Drosofila crumbs protein and localizes to the inner segment of mammalian photoreceptors and is encoded by the crumbs cell polarity complex component 1 gene, located in humans at 1q31.3, CRB1 may maintain cell polarization and adhesion. CRB1 protein may be found in at least five isoforms in humans, including CRB1 isoform 1 having the following amino acid sequence:

```
                                      (SEQ ID NO: 41)
MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGVNCELEIDECWSQPCLNGATCQDALGAYFCDC

APGFLGDHCELNTDECASQPCLHGGLCVDGENRYSCNCTGSGFTGTHCET

LMPLCWSKPCHNNATCEDSVDNYTCHCWPGYTGAQCEIDLNECNSNPCQS

NGECVELSSEKQYGRITGLPSSFSYHEASGYVCICQPGFTGIHCEEDVNE

CSSNPCQNGGTCENLPGNYTCHCPFDNLSRTFYGGRDCSDILLGCTHQQC

LNNGTCIPHFQDGQHGFSCLCPSGYTGSLCEIATTLSFEGDGFLWVKSGS

VTTKGSVCNIALRFQTVQPMALLLFRSNRDVFVKLELLSGYIHLSIQVNN

QSKVLLFISHNTSDGEWHFVEVIFAEAVTLTLIDDSCKEKCIAKAPTPLE

SDQSICAFQNSFLGGLPVGMTSNGVALLNFYNMPSTPSFVGCLQDIKIDW

NHITLENISSGSSLNVKAGCVRKDWCESQPCQSRGRCINLWLSYQCDCHR

PYEGPNCLREYVAGRFGQDDSTGYVIFTLDESYGDTISLSMFVRTLQPSG

LLLALENSTYQYIRVWLERGRLAMLTPNSPKLVVKFVLNDGNVHLISLKI

KPYKIELYQSSQNLGFISASTWKIEKGDVIYIGGLPDKQETELNGGFFKG

CIQDVRLNNQNLEFFPNPTNNASLNPVLVNVTQGCAGDNSCKSNPCHNGG

VCHSRWDDFSCSCPALTSGKACEEVQWCGFSPCPHGAQCQPVLQGFECIA

NAVFNGQSGQILFRSNGNITRELTNITFGFRTRDANVIILHAEKEPEFLN

ISIQDSRLFFQLQSGNSFYMLSLTSLQSVNDGTWHEVTLSMTDPLSQTSR

WQMEVDNETPFVTSTIATGSLNFLKDNTDIYVGDRAIDNIKGLQGCLSTI

EIGGIYLSYFENVHGFINKPQEEQFLKISTNSVVTGCLQLNVCNSNPCLH

GGNCEDIYSSYHCSCPLGWSGKHCELNIDECFSNPCIFIGNCSDRVAAYH

CTCEPGYTGVNCEVDIDNCQSHQCANGATCISHTNGYSCLCFGNFTGKFC

RQSRLPSTVCGNEKTNLTCYNGGNCTEFQTELKCMCRPGFTGEWCEKDID

ECASDPCVNGGLCQDLLNKFQCLCDVAFAGERCEVDLADDLISDIFTTIG

SVTVALLLILLLAIVASVVTSNKRATQGTYSPSRQEKEGSRVEMWNLMPP

PAMERLI;
```

CRB1 isoform 2 having the following amino acid sequence:

```
                                      (SEQ ID NO: 42)
MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGVNCELEIDECWSQPCLNGATCQDALGAYFCDC

APGFLGDHCELNTDECASQPCLHGGLCVDGENRYSCNCTGSGFTGTHCET

LMPLCWSKPCHNNATCEDSVDNYTCHCWPGYTGAQCEIDLNECNSNPCQS
```

NGECVELSSEKQYGRITGLPSSFSYHEASGYVCICQPGFTGIHCEEDVNE

CSSNPCQNGGTCENLPGNYTCHCPFDNLSRTFYGGRDCSDILLGCTHQQC

LNNGTCIPHFQDGQHGFSCLCPSGYTGSLCEIATTLSFEGDGFLWVKSGS

VTTKGSVCNIALRFQTVQPMALLLFRSNRDVFVKLELLSGYIHLSIQVNN

QSKVLLFISHNTSDGEWHFVEVIFAEAVTLTLIDDSCKEKCIAKAPTPLE

SDQSICAFQNSFLGGLPVGMTSNGVALLNFYNMPSTPSFVGCLQDIKIDW

NHITLENISSGSSLNVKAGCVRKDWCESQPCQSRGRCINLWLSYQCDCHR

PYEGPNCLREYVAGRFGQDDSTGYVIFTLDESYGDTISLSMFVRTLQPSG

LLLALENSTYQYIRVWLERGRLAMLTPNSPKLVVKFVLNDGNVHLISLKI

KPYKIELYQSSQNLGFISASTWKIEKGDVIYIGGLPDKQETELNGGFFKG

CIQDVRLNNQNLEFFPNPTNNASLNPVLVNVTQGCAGDNSCKSNPCHNGG

VCHSRWDDFSCSCPALTSGKACEEVQWCGFSPCPHGAQCQPVLQGFECIA

NAVFNGQSGQILFRSNGNITRELTNITFGFRTRDANVIILHAEKEPEFLN

ISIQDSRLFFQLQSGNSFYMLSLTSLQSVNDGTWHEVTLSMTDPLSQTSR

WQMEVDNETPFVTSTIATGSLNFLKDNTDIYVGDRAIDNIKGLQGCLSTI

EIGGIYLSYFENVHGFINKPQEEQFLKISTNSVVTGCLQLNVCNSNPCLH

GGNCEDIYSSYHCSCPLGWSGKHCELNIDECFSNPCIFIGNCSDRVAAYH

CTCEPGYTGVNCEVDIDNCQSHQCANGATCISHTNGYSCLCFGNFTGKFC

RQSRLPSTVCGNEKTNLTCYNGGNCTEFQTELKCMCRPGFTGEWCEKDID

ECASDPCVNGGLCQDLLNKFQCLCDVAFAGERCEVDVSSLSFYVSLLFWQ

NLFQLLSYLILRMNDEPVVEWGEQEDY;

CRB1 isoform 3 having the following amino acid sequence:

(SEQ ID NO: 43)

MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGYTGAQCEIDLNECNSNPCQSNGECVELSSEKQ

YGRITGLPSSFSYHEASGYVCICQPGFTGIHCEEDVNECSSNPCQNGGTC

ENLPGNYTCHCPFDNLSRTFYGGRDCSDILLGCTHQQCLNNGTCIPHFQD

GQHGFSCLCPSGYTGSLCEIATTLSFEGDGFLWVKSGSVTTKGSVCNIAL

RFQTVQPMALLLFRSNRDVFVKLELLSGYIHLSIQVNNQSKVLLFISHNT

SDGEWHFVEVIFAEAVTLTLIDDSCKEKCIAKAPTPLESDQSICAFQNSF

LGGLPVGMTSNGVALLNFYNMPSTPSFVGCLQDIKIDWNHITLENISSGS

SLNVKAGCVRKDWCESQPCQSRGRCINLWLSYQCDCHRPYEGPNCLREYV

AGRFGQDDSTGYVIFTLDESYGDTISLSMFVRTLQPSGLLLALENSTYQY

IRVWLERGRLAMLTPNSPKLVVKFVLNDGNVHLISLKIKPYKIELYQSSQ

NLGFISASTWKIEKGDVIYIGGLPDKQETELNGGFFKGCIQDVRLNNQNL

EFFPNPTNNASLNPVLVNVTQGCAGDNSCKSNPCHNGGVCHSRWDDFSCS

CPALTSGKACEEVQWCGFSPCPHGAQCQPVLQGFECIANAVFNGQSGQIL

FRSNGNITRELTNITFGFRTRDANVIILHAEKEPEFLNISIQDSRLFFQL

QSGNSFYMLSLTSLQSVNDGTWHEVTLSMTDPLSQTSRWQMEVDNETPFV

TSTIATGSLNFLKDNTDIYVGDRAIDNIKGLQGCLSTIEIGGIYLSYFEN

VHGFINKPQEEQFLKISTNSVVTGCLQLNVCNSNPCLHGGNCEDIYSSYH

CSCPLGWSGKHCELNIDECFSNPCIHGNCSDRVAAYHCTCEPGYTGVNCE

VDIDNCQSHQCANGATCISHTNGYSCLCFGNFTGKFCRQSRLPSTVCGNE

KTNLTCYNGGNCTEFQTELKCMCRPGFTGEWCEKDIDECASDPCVNGGLC

QDLLNKFQCLCDVAFAGERCEVDLADDLISDIFTTIGSVTVALLLILLLA

IVASVVTSNKRATQGTYSPSRQEKEGSRVEMWNLMPPPAMERLI;

CRB1 isoform 4 having the following amino acid sequence; and (SEQ ID NO: 44)

MIRNSLCQPSRCLDEYLFFNRKMFGARTHGFHILMAMLIGIHCEEDVNEC

SSNPCQNGGTCENLPGNYTCHCPFDNLSRTFYGGRDCSDILLGCTHQQCL

NNGTCIPHFQDGQHGFSCLCPSGYTGSLCEIATTLSFEGDGFLWVKSGSV

TTKGSVCNIALRFQTVQPMALLLFRSNRDVFVKLELLSGYIHLSIQVNNQ

SKVLLFISHNTSDGEWHFVEVIFAEAVTLTLIDDSCKEKCIAKAPTPLES

DQSICAFQNSFLGGLPVGMTSNGVALLNFYNMPSTPSFVGCLQDIKIDWN

HITLENISSGSSLNVKAGCVRKDWCESQPCQSRGRCINLWLSYQCDCHRP

YEGPNCLREYVAGRFGQDDSTGYVIFTLDESYGDTISLSMFVRTLQPSGL

LLALENSTYQYIRVWLERGRLAMLTPNSPKLVVKFVLNDGNVHLISLKIK

PYKIELYQSSQNLGFISASTWKIEKGDVIYIGGLPDKQETELNGGFFKGC

IQDVRLNNQNLEFFPNPTNNASLNPVLVNVTQGCAGDNSCKSNPCHNGGV

CHSRWDDFSCSCPALTSGKACEEVQWCGFSPCPHGAQCQPVLQGFECIAN

AVFNGQSGQILFRSNGNITRELTNITFGFRTRDANVIILHAEKEPEFLNI

SIQDSRLFFQLQSGNSFYMLSLTSLQSVNDGTWHEVTLSMTDPLSQTSRW

QMEVDNETPFVTSTIATGSLNFLKDNTDIYVGDRAIDNIKGLQGCLSTIE

IGGIYLSYFENVHGFINKPQEEQFLKISTNSVVTGCLQLNVCNSNPCLHG

GNCEDIYSSYHCSCPLGWSGKHCELNIDECFSNPCIFIGNCSDRVAAYHC

TCEPGYTGVNCEVDIDNCQSHQCANGATCISHTNGYSCLCFGNFTGKFCR

QSRLPSTVCGNEKTNLTCYNGGNCTEFQTELKCMCRPGFTGEW;

and CRB1 isoform 5 having the following amino acid sequence:

(SEQ ID NO: 45)

MALKNINYLLIFYLSFSLLIYIKNSFCNKNNTRCLSNSCQNNSTCKDFSK

DNDCSCSDTANNLDKDCDNMKDPCFSNPCQGSATCVNTPGERSFLCKCPP

GYSGTICETTIGSCGKNSCQHGGICHQDPIYPVCICPAGYAGRFCEIDHD

ECASSPCQNGAVCQDGIDGYSCFCVPGYQGRHCDLEVDECASDPCKNEAT

CLNEIGRYTCICPHNYSGVNCELEIDECWSQPCLNGATCQDALGAYFCDC

APGFLGDHCELNTDECASQPCLHGGLCVDGENRYSCNCTGSGFTGTHCET

LMPLCWSKPCHNNATCEDSVDNYTCHCWPGYTGAQCEIDLNECNSNPCQS

-continued

NGECVELSSEKQYGRITGLPSSFSYHEASGYVCICQPGFTGIHCEEDVNE

CSSNPCQNGGTCENLPGNYTCHCPFDNLSRTFYGGRDCSDILLGCTHQQC

LNNGTCIPHFQDGQHGFSCLCPSGYTGSLCEIATTLSFEGDGFLWVKSGS

VTTKGSVCNIALRFQTVQPMALLLFRSNRDVFVKLELLSGYIHLSIQVNN

QSKVLLFISHNTSDGEWHFVEVIFAEAVTLTLIDDSCKEKCIAKAPTPLE

SDQSICAFQNSFLGGLPVGMTSNGVALLNFYNMPSTPSFVGCLQDIKIDW

NHITLENISSGSSLNVKAGCVRKDWCESQPCQSRGRCINLWLSYQCDCHR

PYEGPNCLRGKFCRQSRLPSTVCGNEKTNLTCYNGGNCTEFQTELKCMCR

PGFTGEWCEKDIDECASDPCVNGGLCQDLLNKFQCLCDVAFAGERCEVDL

ADDLISDIFTTIGSVTVALLLILLLAIVASVVTSNKRATQGTYSPSRQEK

EGSRVEMWNLMPPPAMERLI.

In some instances, the methods described herein may employ a BTTS that specifically binds CRB1, including e.g., human CRB1.

In some instances, useful priming antigens may include Neuromodulin (GAP43; Also known as B-50; PP46; Axonal membrane protein GAP-43; Neural phosphoprotein B-50; pp46). GAP43 has been termed a 'growth' or 'plasticity' protein because it is expressed at high levels in neuronal growth cones during development and axonal regeneration and is encoded by the growth associated protein 43 gene, located in humans at 3q13.31. GAP43 is a major component of the motile "growth cones" that form the tips of elongating axons. GAP43 protein may be found in at least two isoforms in humans, including GAP43 isoform 1 having the following amino acid sequence:

(SEQ ID NO: 46)
MLCCMRRTKQVEKNDDDQKIEQDGIKPEDKAHKAATKIQASFRGHITRKK

LKGEKKDDVQAAEAEANKKDEAPVADGVEKKGEGTTTAEAAPATGSKPDE

PGKAGETPSEEKKGEGDAATEQAAPQAPASSEEKAGSAETESATKASTDN

SPSSKAEDAPAKEEPKQADVPAAVTAAAATTPAAEDAAAKATAQPPTETG

ESSQAEENIEAVDETKPKESARQDEGKEEEPEADQEHA;

and GAP43 isoform 2 having the following amino acid sequence:

(SEQ ID NO: 47)
MTKSCSELCHPALHFLPCLGGLRKNLQRAVRPSPYSLGFLTFWISRVEKN

DDDQKIEQDGIKPEDKAHKAATKIQASFRGHITRKKLKGEKKDDVQAAEA

EANKKDEAPVADGVEKKGEGTTTAEAAPATGSKPDEPGKAGETPSEEKKG

EGDAATEQAAPQAPASSEEKAGSAETESATKASTDNSPSSKAEDAPAKEE

PKQADVPAAVTAAAATTPAAEDAAAKATAQPPTETGESSQAEENIEAVDE

TKPKESARQDEGKEEEPEADQEHA.

In some instances, the methods described herein may employ a BTTS that specifically binds GAP43, including e.g., human GAP43.

In some instances, useful priming antigens may include Sodium/potassium-transporting ATPase subunit beta-2 (ATP1B2; also known as Adhesion molecule in glia. AMOG; Sodium/potassium-dependent ATPase subunit beta- 2). ATP1B2 is the non-catalytic component of the active enzyme, which catalyzes the hydrolysis of ATP coupled with the exchange of Na+ and K+ ions across the plasma membrane and is encoded by the ATPase Na+/K+ transporting subunit beta 2 gene, located in humans at 17p13.1. ATP1B2 belongs to the family of Na+/K+ and H+/K+ ATPases beta chain proteins, and to the subfamily of Na+/K+-ATPases. ATP1B2 protein may be found in at least one isoform in humans, including ATP1B2 having the following amino acid sequence:

(SEQ ID NO: 48)
MVIQKEKKSCGQVVEEWKEFVWNPRTHQFMGRTGTSWAFILLFYLVFYGF

LTAMFTLTMWVMLQTVSDHTPKYQDRLATPGLMIRPKTENLDVIVNVSDT

ESWDQHVQKLNKFLEPYNDSIQAQKNDVCRPGRYYEQPDNGVLNYPKRAC

QFNRTQLGNCSGIGDSTHYGYSTGQPCVFIKMNRVINFYAGANQSMNVTC

AGKRDEDAENLGNFVMFPANGNIDLMYFPYYGKKFHVNYTQPLVAVKFLN

VTPNVEVNVECRINAANIATDDERDKFAGRVAFKLRINKT.

In some instances, the methods described herein may employ a BTTS that specifically binds ATP1B2, including e.g., human ATP1B2.

In some instances, useful priming antigens may include Ran guanine nucleotide release factor MOG1 (MOG1; also known as RANGRF, Ran guanine nucleotide release factor, RanGNRF. Ran-binding protein MOG1. HSPC165; HSPC236). MOG1 is a protein that has been shown to function as a guanine nucleotide release factor in mouse and to regulate the expression and function of the Nav1.5 cardiac sodium channel in humans and is encoded by the RAN guanine nucleotide release factor gene, located in humans at 7p13.1, MOG1 may regulate the intracellular trafficking of RAN, promote guanine nucleotide release from RAN, inhibit binding of new GTP by preventing the binding of the RAN guanine nucleotide exchange factor RCC1, regulate the levels of GTP-bound RAN in the nucleus, and/or enhance the expression of SCN5A at the cell membrane in cardiomyocytes. MOG1 protein may be found in at least four isoforms in humans, including MOG1 isoform 1 having the following amino acid sequence:

(SEQ ID NO: 70)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQVAKDVTLHQALLRLPQYQTDLLLTFNQPPPDNR

SSLGPENLSPAPWSLGDFEQLVTSLTLHDPNIFGPQ;

MOG1 isoform 2 having the following amino acid sequence:

(SEQ ID NO: 71)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQVAKDVTLHQALLRLPQYQTDLLLTFNQPP;

MOG1 isoform 3 having the following amino acid sequence:

(SEQ ID NO: 72)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQVRARECVMSWKGGSGDAEIQVSILTLIPLGSKG

RDTSSGLAEAAPVPD;

and MOG1 isoform 4 having the following amino acid sequence:

(SEQ ID NO: 73)
MEPTRDCPLFGGAFSAILPMGAIDVSDLRPVPDNQEVFCHPVTDQSLIVE

LLELQAHVRGEAAARYHFEDVGGVQGARAVHVESVQPLSLENLALRGRCQ

EAWVLSGKQQIAKENQQP.

In some instances, the methods described herein may employ a BTTS that specifically binds MOG1, including e.g., human MOG11.

In some instances, useful priming antigens may include PTPRZ1-MET. PTPRZ1-MET is a fusion of PTPRZ1, described herein, and Hepatocyte growth factor receptor (MET; also known as HGF receptor, HGFR; AUTS9; RCCP2; c-Met; DFNB97; Proto-oncogene c-Met), which is encoded by the MET proto-oncogene, receptor tyrosine kinase gene, located in humans at 7q31.2. MET is a member of the receptor tyrosine kinase family of proteins and the product of the proto-oncogene MET. MET protein may be found in at least three isoforms in humans, including MET isoform 1 having the following amino acid sequence:

(SEQ ID NO: 49)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISGGSTITGVGKNLNSVSVPRMVINVHEAGRNFTVACQHRSNSEIIC

CTTPSLQQLNLQLPLKTKAFFMLDGILSKYFDLIYVHNPVFKPFEKPVMI

SMGNENVLEIKGNDIDPEAVKGEVLKVGNKSCENIHLHSEAVLCTVPNDL

LKLNSELNIEWKQAISSTVLGKVIVQPDQNFTGLIAGVVSISTALLLLLG

FFLWLKKRKQIKDLGSELVRYDARVHTPHLDRLVSARSVSPTTEMVSNES

VDYRATFPEDQFPNSSQNGSCRQVQYPLTDMSPILTSGDSDISSPLLQNT

VHIDLSALNPELVQAVQHVVIGPSSLIVHFNEVIGRGHFGCVYHGTLLDN

DGKKIHCAVKSLNRITDIGEVSQFLTEGIIMKDFSHPNVLSLLGICLRSE

GSPLVVLPYMKHGDLRNFIRNETHNPTVKDLIGFGLQVAKGMKYLASKKF

VHRDLAARNCMLDEKFTVKVADFGLARDMYDKEYYSVHNKTGAKLPVKWM

ALESLQTQKFTTKSDVWSFGVLLWELMTRGAPPYPDVNTFDITVYLLQGR

RLLQPEYCPDPLYEVMLKCWHPKAEMRPSFSELVSRISAIFSTFIGEHYV

HVNATYVNVKCVAPYPSLLSSEDNADDEVDTRPASFWETS;

MET isoform 2 having the following amino acid sequence:

(SEQ ID NO: 50)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFISTWWKEPLNIVSFLFCFASGGSTITGVGKNLNSVSVPRMVINVHEA

GRNFTVACQHRSNSEIICCTTPSLQQLNLQLPLKTKAFFMLDGILSKYFD

LIYVHNPVFKPFEKPVMISMGNENVLEIKGNDIDPEAVKGEVLKVGNKSC

ENIHLHSEAVLCTVPNDLLKLNSELNIEWKQAISSTVLGKVIVQPDQNFT

GLIAGVVSISTALLLLLGFFLWLKKRKQIKDLGSELVRYDARVHTPHLDR

LVSARSVSPTTEMVSNESVDYRATFPEDQFPNSSQNGSCRQVQYPLTDMS

PILTSGDSDISSPLLQNTVHIDLSALNPELVQAVQHVVIGPSSLIVHFNE

VIGRGHFGCVYHGTLLDNDGKKIHCAVKSLNRITDIGEVSQFLTEGIIMK

DFSHPNVLSLLGICLRSEGSPLVVLPYMKHGDLRNFIRNETHNPTVKDLI

GFGLQVAKGMKYLASKKFVHRDLAARNCMLDEKFTVKVADFGLARDMYDK

EYYSVHNKTGAKLPVKWMALESLQTQKFTTKSDVWSFGVLLWELMTRGAP

PYPDVNTFDITVYLLQGRRLLQPEYCPDPLYEVMLKCWHPKAEMRPSFSE

-continued

```
LVSRISAIFSTFIGEHYVHVNATYVNVKCVAPYPSLLSSEDNADDEVDTR

PASFWETS;
```

MET isoform 3 having the following amino acid sequence:

```
                                          (SEQ ID NO: 51)
MKAPAVLAPGILVLLFTLVQRSNGECKEALAKSEMNVNMKYQLPNFTAET

PIQNVILHEHHIFLGATNYIYVLNEEDLQKVAEYKTGPVLEHPDCFPCQD

CSSKANLSGGVWKDNINMALVVDTYYDDQLISCGSVNRGTCQRHVFPHNH

TADIQSEVHCIFSPQIEEPSQCPDCVVSALGAKVLSSVKDRFINFFVGNT

INSSYFPDHPLHSISVRRLKETKDGFMFLTDQSYIDVLPEFRDSYPIKYV

HAFESNNFIYFLTVQRETLDAQTFHTRIIRFCSINSGLHSYMEMPLECIL

TEKRKKRSTKKEVFNILQAAYVSKPGAQLARQIGASLNDDILFGVFAQSK

PDSAEPMDRSAMCAFPIKYVNDFFNKIVNKNNVRCLQHFYGPNHEHCFNR

TLLRNSSGCEARRDEYRTEFTTALQRVDLFMGQFSEVLLTSISTFIKGDL

TIANLGTSEGRFMQVVVSRSGPSTPHVNFLLDSHPVSPEVIVEHTLNQNG

YTLVITGKKITKIPLNGLGCRHFQSCSQCLSAPPFVQCGWCHDKCVRSEE

CLSGTWTQQICLPAIYKVFPNSAPLEGGTRLTICGWDFGFRRNNKFDLKK

TRVLLGNESCTLTLSESTMNTLKCTVGPAMNKHFNMSIIISNGHGTTQYS

TFSYVDPVITSISPKYGPMAGGTLLTLTGNYLNSGNSRHISIGGKTCTLK

SVSNSILECYTPAQTISTEFAVKLKIDLANRETSIFSYREDPIVYEIHPT

KSFIRHVNIALIQR.
```

In some instances, the methods described herein may employ a BTTS that specifically binds a PTPRZ1-MET, including e.g., a human PTPRZ1-MET fusion. PTPRZ1-MET fusions are described in Hu et al. Cell, 2018 Nov. 29; 175(6):1665-1678; Bao et al. Genome Res. 2014 November; 24(11):1765-73; and Zeng et al. Oncogene. 2017 Sep. 21; 36(38):5369-5381; the disclosures of which are incorporated herein by reference in their entirety.

In some instances, combinations of two or more priming antigens may be employed, including but not limited to e.g., where such combinations include but are not limited to one or more of the above described examples of suitable priming antigens. In some instances, such combinations may find use in an OR gate as described herein. In some instances, a two-headed BTTS may be employed, including but not limited to e.g., where the two-headed BTTS binds to two priming antigens, including but not limited to two of the above described examples of suitable priming antigens.

In some instances, all cells of a heterogeneous GBM may express an employed killing antigen. Such heterogeneous GBMs may be said to be homogeneous for killing antigen expression. In some instances, a heterogeneous GBM may be heterogeneous for priming antigen expression but homogeneous for killing antigen expression. Accordingly, in certain embodiments, certain cells of the heterogeneous GBM may express both the priming antigen and the killing antigen. In such instances, the methods of the present disclosure may be employed where the heterogeneous GBM still includes cells that express the killing antigen but not the priming antigen.

In some instances, a heterogeneous GBM may be heterogeneous for both priming antigen expression and targeting/ killing antigen expression, including where the targeting/killing antigen is expressed by less than 100% of the cells of the heterogeneous GBM. In some instances, the targeting/killing antigen may be expressed in a majority of the cells of the heterogeneous GBM but less than 100% of the cells, including but not limited to e.g., where more than 95%, more than 90%, more than 85%, more than 80%, more than 75%, more than 70%, more than 65%, more than 60%, more than 55%, or more than 50% of the cells of the heterogeneous GBM.

In some instances, multiple antigen-specific therapeutics targeting different targeting/killing antigens may be employed. In some instances, antigen-specific therapeutics targeting multiple different targeting/killing antigens may be employed. In some instances, multiple targeting/killing antigens may be targeted in cases where targeting/killing antigen expression is heterogeneous, including where e.g., one or more of the subject targeting/killing antigens is expressed by a majority of the cells of the GBM, where one or more of the subject targeting/killing antigens is expressed by a minority of the cells of the GBM, and the like. In some instances, the targeting of two or more different targeting/killing antigens results in combination of antigens employed targeting 100% or nearly 100% (e.g., 99% or greater, 98% or greater, 95% or greater, 90% or greater, etc.) of the cells of the GBM.

In some instances, a targeting/killing antigen may be expressed by non-GBM cells in the subject. Put another way, a subject having a EGFRvIII(−) GBM having heterogeneous or homogeneous expression of a targeting/killing antigen may, in some instances, also express the targeting/killing antigen in cells other than the GBM, e.g., away from the GBM. Such cells may, in some instances, be referred to as bystander cells. In some instances, through the use of a circuit described herein, bystander cells at a site other than GBM or outside of the relative proximity of the GBM may not be substantially or unduly affected by immune cells employed in the methods described herein.

Useful antigens that may be employed as targeting antigens include but are not limited to e.g., Ephrin type-A receptor 2 (EphA2), Ephrin type-A receptor 3 (EphA3), Interleukin-13 receptor (IL13R) (e.g., IL13RA1 or IL13RA2). Epidermal growth factor receptor (EGFR), erb-b2 receptor tyrosine kinase 2 (ERBB2) and the like. In some instances, an employed priming antigen may find use as a targeting antigen. For example, in some instances, a priming antigen may be employed as both a priming antigen and a killing antigen, including but not limited to e.g., as in a AND-OR gate where the priming antigen functions as a priming antigen to induce expression of one or more antigen-specific therapeutics specific for the priming antigen as a first targeting/killing antigen and a second targeting/killing antigen. In such instances, the second targeting/killing antigen may, but need not necessarily, be selected from EphA2, EphA3, IL13R (e.g., IL13RA1 or IL13RA2), EGFR, and ERBB2.

In some instances, useful targeting/killing antigens include Ephrin type-A receptor 2 (EphA2). EphA2 is a receptor tyrosine kinase encoded by the EPH receptor A2 gene located at 1p36.13 in humans. EphA2 protein may be found in at least one isoform in humans, including EphA2 Isoform 1 having the following amino acid sequence:

(SEQ ID NO: 52)

MELQAARACFALLWGCALAAAAAAQGKEVVLLDFAAAGGELGWLTHPYGK

GWDLMQNIMNDMPIYMYSVCVMSGDQDNWLRTNWVYRGEAERIFIELKFT

VRDCNSFPGGASSCKETFNLYYAESDLDYGTNFQKRLFTKIDTIAPDEIT

VSSDFEARHVKLNVEERSVGPLTRKGFYLAFQDIGACVALLSVRVYYKKC

PELLQGLAHFPETIAGSDAPSLATVAGTCVDHAVVPPGGEEPRMHCAVDG

EWLVPIGQCLCQAGYEKVEDACQACSPGFFKFEASESPCLECPEHTLPSP

EGATSCECEEGFFRAPQDPASMPCTRPPSAPHYLTAVGMGAKVELRWTPP

QDSGGREDIVYSVTCEQCWPESGECGPCEASVRYSEPPHGLTRTSVTVSD

LEPHMNYTFTVEARNGVSGLVTSRSFRTASVSINQTEPPKVRLEGRSTTS

LSVSWSIPPPQQSRVWKYEVTYRKKGDSNSYNVRRTEGFSVTLDDLAPDT

TYLVQVQALTQEGQGAGSKVHEFQTLSPEGSGNLAVIGGVAVGVVLLLVL

AGVGFFIHRRRKNQRARQSPEDVYFSKSEQLKPLKTYVDPHTYEDPNQAV

LKFTTEIHPSCVTRQKVIGAGEFGEVYKGMLKTSSGKKEVPVAIKTLKAG

YTEKQRVDFLGEAGIMGQFSHHNIIRLEGVISKYKPMMIITEYMENGALD

KFLREKDGEFSVLQLVGMLRGIAAGMKYLANMNYVHRDLAARNILVNSNL

VCKVSDFGLSRVLEDDPEATYTTSGGKIPIRWTAPEAISYRKFTSASDVW

SFGIVMWEVMTYGERPYWELSNHEVMKAINDGFRLPTPMDCPSAIYQLMM

QCWQQERARRPKFADIVSILDKLIRAPDSLKTLADFDPRVSIRLPSTSGS

EGVPFRTVSEWLESIKMQQYTEHFMAAGYTAIEKVVQMTNDDIKRIGVRL

PGHQKRIAYSLLGLKDQVNTVGIPI;

and EphA2 Isoform 2 having the following amino acid sequence:

(SEQ ID NO: 53)

MELQAARACFALLWGCALAAAAAAQGKEVVLLDFAAAGGELGWLTHPYGK

GWDLMQNIMNDMPIYMYSVCNVMSGDQDNWLRTNWVYRGEAERIFIELKF

TVRDCNSFPGGASSCKETFNLYYAESDLDYGTNFQKRLFTKIDTIAPDEI

TVSSDFEARHVKLNVEERSVGPLTRKGFYLAFQDIGACVALLSVRVYYKK

CPELLQGLAHFPETIAGSDAPSLATVAGTCVDHAVVPPGGEEPRMHCAVD

GEWLVPIGQCLCQAGYEKVEDACQACSPGFFKFEASESPCLECPEHTLPS

PEGATSCECEEGFFRAPQDPASMPCTRPPSAPHYLTAVGMGAKVELRWTP

PQDSGGREDIVYSVTCEQCWPESGECGPCEASVRYSEPPHGLTRTSVTVS

DLEPHMNYTFTVEARNGVSGLVTSRSFRTASVSINQTEPPKVRLEGRSTT

SLSVSWSIPPPQQSRVWKYEVTYRKKVTPRGAGLALAGPTAGDRLVT.

In some instances, the methods described herein may employ an antigen-specific therapeutic that specifically binds EphA2, including e.g., human EphA2 Isoform 1, human EphA2 Isoform 2, or both human EphA2 Isoform 1 and human EphA2 Isoform 2.

In some instances, useful EphA2 binding domains may include antibody based EphA2 binding domains, including but not limited to an EphA2 scFv. In some instances, a useful EphA2 scFv may have the following amino acid sequence or a variant thereof:

(SEQ ID NO: 54)

EIVLTQSPGTLSLSPGERATLSCRASQSVSSSNLAWYQQKPGQAPRLLIY

GASSRATGVPDRFSGSGSGTDFTLTISRLEPEDFAVYYCQQSSSYPWTFG

QGTKVEIKRTGGGGSGAGGSGGGGTGGGGSEVDLLESGGGLVQPGGSLRL

SCAASGFTFSRYWMHWVRQAPGKGLEWVSSISPYDGETNYADSVKGRFTI

SRDNSKNTLYLQMNSLRAEDTAVYYCARISEWYNWAVDVFDYWGQGTLVT

VSS;

including e.g., where the useful EphA2 has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, a useful EphA2 scFv may have the following amino acid sequence or a variant thereof:

(SEQ ID NO: 55)

QVQLLESGGGLVQPGGSLRLSCAASGFTFSSYTMSWVRQAPGQALEWMGT

ISSGGTYTYYPDSVKGRFTISRDNAKNSLYLQMNSLRAEDTAVYYCAREA

IFTYWGRGTLVTSSGGGGSGGGGSGGGGSDIQLTQSPSSLSASVGDRVTI

TCKASQDINNYLSWYQQKPGQAPRLLIYRANRLVDGVPDRFSGSGYGTDF

TLTINNIESEDAAYYFCLKYDVFPYTFGQGTKVEIKS;

including e.g., where the useful EphA2 has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful EphA2 binding domains include those described in Goldgur et al., Growth Factors. (2014) 32(6):214-22 and Damschroder et al., Mol Immunol. (2007) 44(11):3049-60; the disclosures of which are incorporated herein by reference in their entirety.

In some instances, useful targeting/killing antigens include Ephrin type-A receptor 3 (EphA3). EphA3 is a receptor tyrosine kinase encoded by the EPH receptor A3 gene located at 3p11.1 in humans. EphA3 protein may be found in at least two isoforms in humans, including EphA3 Isoform 1 having the following amino acid sequence:

(SEQ ID NO: 56)

MDCQLSILLLLSCSVLDSFGELIPQPSNEVNLLDSKTIQGELGWISYPSH

GWEEISGVDEHYTPIRTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDSFSISGESSQVVMIAISAA

-continued

```
VAIILLTVVIYVLIGRFCGYKSKHGADEKRLHFGNGHLKLPGLRTYVDPH

TYEDPTQAVHEFAKELDATNISIDKVVGAGEFGEVCSGRLKLPSKKEISV

AIKTLKVGYTEKQRRDFLGEASIMGQFDHPNIIRLEGVVTKSKPVMIVTE

YMENGSLDSFLRKHDAQFTVIQLVGMLRGIASGMKYLSDMGYVHRDLAAR

NILINSNLVCKVSDFGLSRVLEDDPEAAYTTRGGKIPIRWTSPEAIAYRK

FTSASDVWSYGIVLWEVMSYGERPYWEMSNQDVIKAVDEGYRLPPPMDCP

AALYQLMLDCWQKDRNNRPKFEQIVSILDKLIRNPGSLKIITSAAARPSN

LLLDQSNVDITTFRTTGDWLNGVWTAHCKEIFTGVEYSSCDTIAKISTDD

MKKVGVTVVGPQKKIISSIKALETQSKNGPVPV;
``` and EphA3 Isoform 2 having the following amino acid sequence:

(SEQ ID NO: 57)
```
MDCQLSILLLLSCSVLDSFGELIPQPSNEVNLLDSKTIQGELGWISYPSH

GWEEISGVDEHYTP1RTYQVCNVMDHSQNNWLRTNWVPRNSAQKIYVELK

FTLRDCNSIPLVLGTCKETFNLYYMESDDDHGVKFREHQFTKIDTIAADE

SFTQMDLGDRILKLNTEIREVGPVNKKGFYLAFQDVGACVALVSVRVYFK

KCPFTVKNLAMFPDTVPMDSQSLVEVRGSCVNNSKEEDPPRMYCSTEGEW

LVPIGKCSCNAGYEERGFMCQACRPGFYKALDGNMKCAKCPPHSSTQEDG

SMNCRCENNYFRADKDPPSMACTRPPSSPRNVISNINETSVILDWSWPLD

TGGRKDVTFNIICKKCGWNIKQCEPCSPNVRFLPRQFGLTNTTVTVTDLL

AHTNYTFEIDAVNGVSELSSPPRQFAAVSITTNQAAPSPVLTIKKDRTSR

NSISLSWQEPEHPNGIILDYEVKYYEKQEQETSYTILRARGTNVTISSLK

PDTIYVFQIRARTAAGYGTNSRKFEFETSPDCMYYFNAV.
```

In some instances, the methods described herein may employ an antigen-specific therapeutic that specifically binds EphA3, including e.g., human EphA3 Isoform 1, human EphA3 Isoform 2, or both human EphA3 Isoform 1 and human EphA3 Isoform 2.

In some instances, useful targeting/killing antigens include receptors for Interleukin-13 (IL13), IL13 is an immunoregulatory cytokine encoded by the interleukin 13 gene located at 5q31.1 in humans, which is a ligand for IL13R proteins: interleukin 13 receptor subunit alpha 1 (IL13RA1) and interleukin 13 receptor subunit alpha 2 (IL13RA2). An exemplary amino acid sequence of human IL13 is as follows:

(SEQ ID NO: 58)
```
MHPLLNPLLLALGLMALLLTTVIALTCLGGFASPGPVPPSTALRELIEEL

VNITQNQKAPLCNGSMVWSINLTAGMYCAALESLINVSGCSAIEKTQRML

SGFCPHKVSAGQFSSLHVRDTKIEVAQFVKDLLLHLKKLFREGRFN.
```

In some instances, the methods described herein may employ an antigen-specific therapeutic that specifically binds an IL13R, including IL13RA1 and/or IL13RA2, including e.g., human IL13RA1 Isoform 1, human IL13RA1 Isoform 2, human IL13RA2, or any combination thereof. Representative human amino acid sequences of IL13RA1 and IL13RA2 and isoforms thereof are provided above.

In some instances, useful IL13R binding domains may be derived from IL13, including but not limited to IL13 conjugation products (e.g., wild-type or mutated IL13 conjugated to one or more moieties), derivatives or mutants of IL13, e.g., IL13 muteins, and the like. Useful muteins include but are not limited to e.g., IL13 muteins including one or more amino acid substitutions including E13K and/or K105R.

In some instances, as summarized above, useful IL13R binding domains may include a ligand-based binding domain derived from IL13, including but not limited to an IL13 mutein-based binding domain. In some instances, a useful IL13 mutein-based binding domain may have the following amino acid sequence or a variant thereof:

(SEQ ID NO: 59)
```
LTCLGGFASPGPVPPSTALRKLIEELVNITQNQKAPLCNGSMVWSINLTA

GMYCAALESLINVSGCSAIEKTQRMLSGFCPHKVSAGQFSSLHVRDTKIE

VAQFVKDLLLHLRKLFREGRFN;
``` including e.g., where the useful IL13 mutein-based binding domain has a sequence identity of 100% or less, including e.g., at least 99%, at least 98%, at least 97%, at least 96%, at least 95%, at least 90%, at least 85%, at least 80%, etc., sequence identity with the sequence presented above.

In some instances, useful IL13R (e.g., IL13RA1 or IL13RA2) binding domains include those described in Krebs et al., Cytotherapy. (2014) 16(8):1121-31; the disclosure of which is incorporated herein by reference in its entirety.

In some instances, useful targeting/killing antigens include epidermal growth factor receptor (EGFR, also known as Proto-oncogene c-ErbB-1. Receptor tyrosine-protein kinase erbB-1, ERBB. HER1, mENA, ERBB1, PIG61, and NISBD2). EGFR is a receptor tyrosine kinase encoded by the epidermal growth factor receptor gene, present at 7p11.2 in humans. Known ligands of EGFR include EGF, TGFA/TGF-alpha, amphiregulin, epigen/EPGN, BTC/betacellulin, epiregulin/EREG and HBEGF/heparin-binding EGF. EGFR protein may be found in at least one isoform in humans, including EGFR Isoform 1 having the following amino acid sequence:

(SEQ ID NO: 60)
```
MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGCTGPGLEGCPTNGPKIPSIATGM

VGALLLLLVVALGIGLFMRRRHIVRKRTLRRLLQERELVEPLTPSGEAPN
```

-continued

QALLRILKETEFKKIKVLGSGAFGTVYKGLW1PEGEKVKIPVAIKELREA

TSPKANKEILDEAYVMASVDNPHVCRLLGICLTSTVQLITQLMPFGCLLD

YVREHKDNIGSQYLLNWCVQIAKGMNYLEDRRLVHRDLAARNVLVKTPQH

VKITDFGLAKLLGAEEKEYHAEGGKVPIKWMALESILHRIYTHQSDVWSY

GVTVWELMTFGSKPYDG1PASEISSILEKGERLPQPPICTIDVYMIMVKC

WMIDADSRPKFRELIIEFSKMARDPQRYLVIQGDERMHLPSPTDSNFYRA

LMDEEDMDDVVDADEYLIPQQGFFSSPSTSRTPLLSSLSATSNNSTVACI

DRNGLQSCPIKEDSFLQRYSSDPTGALTEDSIDDTFLPVPEYINQSVPKR

PAGSVQNPVYHNQPLNPAPSRDPHYQDPHSTAVGNPEYLNTVQPTCVNST

FDSPAHWAQKGSHQISLDNPDYQQDFFPKEAKPNGIFKGSTAENAEYLRV

APQSSEFIGA,

EGFR Isoform 2 having the following amino acid sequence:

(SEQ ID NO: 61)

MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGLS,

EGFR Isoform 3 having the following amino acid sequence:

(SEQ ID NO: 62)

MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGQKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGPGNESLKAMLFCLFKLSSCNQSN

DGSVSHQSGSPAAQESCLGWIPSLLPSEFQLGWGGCSHLHAWPSASVIIT

ASSCH, and EGFR Isoform 4 having the following amino acid sequence:

(SEQ ID NO: 63)

MRPSGTAGAALLALLAALCPASRALEEKKVCQGTSNKLTQLGTFEDHFLS

LQRMFNNCEVVLGNLEITYVQRNYDLSFLKTIQEVAGYVLIALNTVERIP

LENLQIIRGNMYYENSYALAVLSNYDANKTGLKELPMRNLQEILHGAVRF

SNNPALCNVESIQWRDIVSSDFLSNMSMDFQNHLGSCQKCDPSCPNGSCW

GAGEENCQKLTKIICAQQCSGRCRGKSPSDCCHNQCAAGCTGPRESDCLV

CRKFRDEATCKDTCPPLMLYNPTTYQMDVNPEGKYSFGATCVKKCPRNYV

VTDHGSCVRACGADSYEMEEDGVRKCKKCEGPCRKVCNGIGIGEFKDSLS

INATNIKHFKNCTSISGDLHILPVAFRGDSFTHTPPLDPQELDILKTVKE

ITGFLLIQAWPENRTDLHAFENLEIIRGRTKQHGQFSLAVVSLNITSLGL

RSLKEISDGDVIISGNKNLCYANTINWKKLFGTSGOKTKIISNRGENSCK

ATGQVCHALCSPEGCWGPEPRDCVSCRNVSRGRECVDKCNLLEGEPREFV

ENSECIQCHPECLPQAMNITCTGRGPDNCIQCAHYIDGPHCVKTCPAGVM

GENNTLVWKYADAGHVCHLCHPNCTYGS.

In some instances, the methods described herein may employ an antigen-specific therapeutic that specifically binds an EGFR, including human EGFR, including e.g., human EGFR Isoform 1, human EGFR Isoform 2, human EGFR Isoform 3, EGFR Isoform 4, or any combination thereof.

In some instances, useful targeting/killing antigens include Erb-b2 receptor tyrosine kinase 2 (ERBB2; also known as Metastatic lymph node gene 19 protein, Proto-oncogene Neu, Proto-oncogene c-ErbB-2, Tyrosine kinase-type cell surface receptor HER2, NEU, NGL, HER2, TKR1, CD340, HER-2, MLN 19, and HER-2/neu). ERBB2 is a protein tyrosine kinase that is encoded by the erb-b2 receptor tyrosine kinase 2 gene, located at 17q12 in humans. ERBB2 protein may be found in at least one isoform in humans, including ERBB2 Isoform 1 having the following amino acid sequence:

(SEQ ID NO: 64)

MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNPQLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFQNLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSCVDLDDKGCPAEQRASP

LTSIISAVVGILLVVVLGVVFGILIKRRQQKIRKYTMRRLLQETELVEPL

TPSGAMPNQAQMRILKETELRKVKVLGSGAFGTVYKGIWIPDGENVKIPV

-continued

AIKVLRENTSPKANKEILDEAYVMAGVGSPYVSRLLGICLTSTVQLVTQL

MPYGCLLDHVRENRGRLGSQDLLNWCMQIAKGMSYLEDVRLVHRDLAARN

VLVKSPNHVKITDFGLARLLDIDETEYHADGGKVPIKWMALESILRRRFT

HQSDVWSYGVTVWELMTFGAKPYDGIPAREIPDLLEKGERLPQPPICTID

VYMIMVKCWMIDSECRPRFRELVSEFSRMARDPQRFVVIQNEDLGPASPL

DSTFYRSLLEDDDMGDLVDAEEYLVPQQGFFCPDPAPGAGGMVHHRHRSS

STRSGGGDLTLGLEPSEEEAPRSPLAPSEGAGSDVFDGDLGMGAAKGLQS

LPTHDPSPLQRYSEDPTVPLPSETDGYVAPLTCSPQPEYVNQPDVRPQPP

SPREGPLPAARPAGATLERPKTLSPGKNGVVKDVFAFGGAVENPEYLTPQ

GGAAPQPHPPPAFSPAFDNLYYWDQDPPERGAPPSTFKGTPTAENPEYLG

LDVPV,

ERBB2 Isoform 2 having the following amino acid sequence:

(SEQ ID NO: 65)

MPIWKFPDEEGACQPCPINCTHSCVDLDDKGCPAEQRASPLTSIISAVVG

ILLVVVLGVVFGILIKRRQQKIRKYTMRRLLQETELVEPLTPSGAMPNQA

QMRILKETELRKVKVLGSGAFGTVYKGIWIPDGENVKIPVAIKVLRENTS

PKANKEILDEAYVMAGVGSPYVSRLLGICLTSTVQLVTQLMPYGCLLDHV

RENRGRLGSQDLLNWCMQIAKGMSYLEDVRLVHRDLAARNVLVKSPNHVK

ITDFGLARLLDIDETEYHADGGKVPIKWMALESILRRRFTHQSDVWSYGV

TVWELMTFGAKPYDGIPAREIPDLLEKGERLPQPPICTIDVYMIMVKCWM

IDSECRPRFRELVSEFSRMARDPQRFVVIQNEDLGPASPLDSTFYRSLLE

DDDMGDLVDAEEYLVPQQGFFCPDPAPGAGGMVHHRHRSSSTRSGGGDLT

LGLEPSEEEAPRSPLAPSEGAGSDVFDGDLGMGAAKGLQSLPTHDPSPLQ

RYSEDPTVPLPSETDGYVAPLTCSPQPEYVNQPDVRPQPPSPREGPLPAA

RPAGATLERPKTLSPGKNGVVKDVFAFGGAVENPEYLTPQGGAAPQPHPP

PAFSPAFDNLYYWDQDPPERGAPPSTFKGTPTAENPEYLGLDVPV,

ERBB2 Isoform 3 having the following amino acid sequence:

(SEQ ID NO: 66)

MRRLLQETELVEPLTPSGAMPNQAQMRILKETELRKVKVLGSGAFGTVYK

GIWIPDGENVKIPVAIKVLRENTSPKANKEILDEAYVMAGVGSPYVSRLL

GICLTSTVQLVTQLMPYGCLLDHVRENRGRLGSQDLLNWCMQIAKGMSYL

EDVRLVHRDLAARNVLVKSPNHVKITDFGLARLLDIDETEYHADGGKVPI

KWMALESILRRRFTHQSDVWSYGVTVWELMTFGAKPYDGIPAREIPDLLE

KGERLPQPPICTIDVYMIMVKCWMIDSECRPRFRELVSEFSRMARDPQRF

VVIQNEDLGPASPLDSTFYRSLLEDDDMGDLVDAEEYLVPQQGFFCPDPA

PGAGGMVHHRHRSDSTRSGGGDLTLGLEPSEEEAPRSPLAPSEGAGSDVF

DGDLGMGAAKGLQSLPTHDPSPLQRYSEDPTVPLPSETDGYVAPLTCSPQ

PEYVNQPDVRPQPPSPREGPLPAARPAGATLERPKTLSPGKNGVVKDVFA

-continued

FGGAVENPEYLTPQGGAAPQPHPPPAFSPAFDNLYYWDQDPPERGAPPST

FKGTPTAENPEYLGLDVPV,

ERBB2 Isoform 4 having the following amino acid sequence:

(SEQ ID NO: 67)

MPRGSWKPQVCTGTDMKLRLPASPETHLDMLRHLYQGCQVVQGNLELTYL

PTNASLSFLQDIQEVQGYVLIAHNQVRQVPLQRLRIVRGTQLFEDNYALA

VLDNGDPLNNTTPVTGASPGGLRELQLRSLTEILKGGVLIQRNPQLCYQD

TILWKDIFHKNNQLALTLIDTNRSRACHPCSPMCKGSRCWGESSEDCQSL

TRTVCAGGCARCKGPLPTDCCHEQCAAGCTGPKHSDCLACLHFNHSGICE

LHCPALVTYNTDTFESMPNPEGRYTFGASCVTACPYNYLSTDVGSCTLVC

PLHNQEVTAEDGTQRCEKCSKPCARVCYGLGMEHLREVRAVTSANIQEFA

GCKKIFGSLAFLPESFDGDPASNTAPLQPEQLQVFETLEEITGYLYISAW

PDSLPDLSVFQNLQVIRGRILHNGAYSLTLQGLGISWLGLRSLRELGSGL

ALIHHNTHLCFVHTVPWDQLFRNPHQALLHTANRPEDECVGEGLACHQLC

ARGHCWGPGPTQCVNCSQFLRGQECVEECRVLQGLPREYVNARHCLPCHP

ECQPQNGSVTCFGPEADQCVACAHYKDPPFCVARCPSGVKPDLSYMPIWK

FPDEEGACQPCPINCTHSCVDLDDKGCPAEQRASPLTSIISAVVGILLVV

VLGVVFGILIKRRQQKIRKYTMRRLLQETELVEPLTPSGAMPNQAQMRIL

KETELRKVKVLGSGAFGTVYKGIWIPDGENVKIPVAIKVLRENTSPKANK

EILDEAYVMAGVGSPYVSRLLGICLTSTVQLVTQLMPYGCLLDHVRENRG

RLGSQDLLNWCMQIAKGMSYLEDVRLVHRDLAARNVLVKSPNHVKITDFG

LARLLDIDETEYHADGGKVPIKWMALESILRRRFTHQSDVWSYGVTVWEL

MTFGAKPYDGIPAREIPDLLEKGERLPQPPICTIDVYMIMVKCWMIDSEC

RPRFRELVSEFSRMARDPQRFVVIQNEDLGPASPLDSTFYRSLLEDDDMG

DLVDAEEYLVPQQGFFCPDPAPGAGGMVHHRHRSSSTRSGGGDLTLGLEP

SEEEAPRSPLAPSEGAGSDVFDGDLGMGAAKGLQSLPTHDPSPLQRYSED

PTVPLPSETDGYVAPLTCSPQPEYVNQPDVRPQPPSPREGPLPAARPAGA

TLERPKTLSPGKNGVVKDVFAFGGAVENPEYLTPQGGAAPQPHPPPAFSP

AFDNLYYWDQDPPERGAPPSTFKGTPTAENPEYLGLDVPV,

ERBB2 Isoform 5 having the following amino acid sequence:

(SEQ ID NO: 68)

MKLRLPASPETHLDMLRHLYQGCQVVQGNLELTYLPTNASLSFLQDIQEV

QGYVLIAHNQVRQVPLQRLRIVRGTQLFEDNYALAVLDNGDPLNNTTPVT

GASPGGLRELQLRSLTEILKGGVLIQRNPQLCYQDTILWKDIFHKNNQLA

LTLIDTNRSRACHPCSPMCKGSRCWGESSEDCQSLTRTVCAGGCARCKGP

LPTDCCHEQCAAGCTGPKHSDCLACLHFNHSGICELHCPALVTYNTDTFE

SMPNPEGRYTFGASCVTACPYNYLSTDVGSCTLVCPLHNQEVTAEDGTQR

CEKCSKPCARVCYGLGMEHLREVRAVTSANIQEFAGCKKIFGSLAFLPES

FDGDPASNTAPLQPEQLQVFETLEEITGYLYISAWPDSLPDLSVFQNLQV

-continued

```
IRGRILHNGAYSLTLQGLGISWLGLRSLRELGSGLALIHHNTHLCFVHTV

PWDQLFRNPHQALLHTANRPEDECVGEGLACHQLCARGHCWGPGPTQCVN

CSQFLRGQECVEECRVLQGLPREYVNARHCLPCHPECQPQNGSVTCFGPE

ADQCVACAHYKDPPFCVARCPSGVKPDLSYMPIWKFPDEEGACQPCPINC

THSCVDLDDKGCPAEQRASPLTSIISAVVGILLVVVLGVVFGILIKRRQQ

KIRKYTMRRLLQETELVEPLTPSGAMPNQAQMRILKETELRKVKVLGSGA

FGTVYKGIWIPDGENVKIPVAIKVLRENTSPKANKEILDEAYVMAGVGSP

YVSRLLGICLTSTVQLVTQLMPYGCLLDHVRENRGRLGSQDLLNWCMQIA

KGMSYLEDVRLVHRDLAARNVLVKSPNHVKITDFGLARLLDIDETEYHAD

GGKVPIKWMALESILRRRFTHQSDVWSYGVTVWELMTFGAKPYDGIPARE

IPDLLEKGERLPQPPICTIDVYMIMVKCWMIDSECRPRFRELVSEFSRMA

RDPQRFVVIQNEDLGPASPLDSTFYRSLLEDDDMGDLVDAEEYLVPQQGF

FCPDPAPGAGGMVHHRHRSSSTRSGGGDLTLGLEPSEEEAPRSPLAPSEG

AGSDVFDGDLGMGAAKGLQSLPTHDPSPLQRYSEDPTVPLPSETDGYVAP

LTCSPQPEYVNQPDVRPQPPSPREGPLPAARPAGATLERPKTLSPGKNGV

VKDVFAFGGAVENPEYLTPQGGAAPQPHPPPAFSPAFDNLYYWDQDPPER

GAPPSTFKGTPTAENPEYLGLDVPV,
``` and ERBB2 Isoform 6 having the following amino acid sequence:

```
                                         (SEQ ID NO: 69)
MELAALCRWGLLLALLPPGAASTQVCTGTDMKLRLPASPETHLDMLRHLY

QGCQVVQGNLELTYLPTNASLSFLODIQEVOGYVLIAHNOVROVPLORLR

IVRGTQLFEDNYALAVLDNGDPLNNTTPVTGASPGGLRELQLRSLTEILK

GGVLIORNPOLCYQDTILWKDIFHKNNQLALTLIDTNRSRACHPCSPMCK

GSRCWGESSEDCQSLTRTVCAGGCARCKGPLPTDCCHEQCAAGCTGPKHS

DCLACLHFNHSGICELHCPALVTYNTDTFESMPNPEGRYTFGASCVTACP

YNYLSTDVGSCTLVCPLHNQEVTAEDGTQRCEKCSKPCARVCYGLGMEHL

REVRAVTSANIQEFAGCKKIFGSLAFLPESFDGDPASNTAPLQPEQLQVF

ETLEEITGYLYISAWPDSLPDLSVFONLQVIRGRILHNGAYSLTLQGLGI

SWLGLRSLRELGSGLALIHHNTHLCFVHTVPWDQLFRNPHQALLHTANRP

EDECVGEGLACHQLCARGHCWGPGPTQCVNCSQFLRGQECVEECRVLQGL

PREYVNARHCLPCHPECQPQNGSVTCFGPEADQCVACAHYKDPPFCVARC

PSGVKPDLSYMPIWKFPDEEGACQPCPINCTHSPLTSIISAVVGILLVVV

LGVVFGILIKRROOKIRKYTMRRLLOETELVEPLTPSGAMPNQAQMRILK

ETELRKVKVLGSGAFGTVYKGIWIPDGENVKIPVAIKVLRENTSPKANKE

ILDETISNLFSNFAPRGPSACCEPTCWCHSGKGQDSLPREEWGRQRRFCL

WGCRGEPRVLDTPGRSCPSAPPSSCLQPSLRQPLLLGPGPTRAGGSTQHL

QRDTYGREPRVPGSGRASVNQKAKSAEALMCPQGAGKA.
```

In some instances, the methods described herein may employ an antigen-specific therapeutic that specifically binds an ERBB2, including human ERBB2, including e.g., human ERBB2 Isoform 1, human ERBB2 Isoform 2, human ERBB2 Isoform 3, human ERBB2 Isoform 4, human ERBB2 Isoform 5, human ERBB2 Isoform 6, or any combination thereof.

In some instances, combinations of two or more targeting antigens may be employed, including but not limited to e.g., where such combinations include EphA2 and EphA3. EphA2 and IL13R (e.g., IL13RA1 or IL13RA2). EphA2 and EGFR. EphA2 and ERBB2, EphA3 and IL13R (e.g., IL13RA1 or IL13RA2). EphA3 and EGFR. EphA3 and ERBB2, IL13R (e.g., IL13RA1 or IL13RA2) and EGFR, IL13R (e.g., IL13RA1 or IL13RA2) and ERBB2, or EGFR and ERBB2. In some instances, such combinations may find use in an OR gate as described herein. In some instances, a two-headed antigen-specific therapeutic may be employed, including but not limited to e.g., where the two-headed antigen-specific therapeutic binds to EphA2 and EphA3, EphA2 and IL13R (e.g., IL13RA1 or IL13RA2), EphA2 and EGFR, EphA2 and ERBB2, EphA3 and IL13R (e.g., IL13RA1 or IL13RA2), EphA3 and EGFR, EphA3 and ERBB2, IL13R (e.g., IL13RA1 or IL13RA2) and EGFR, IL13R (e.g., IL13RA1 or IL13RA2) and ERBB2, or EGFR and ERBB2.

Antigen-Specific Therapeutics

As summarized above, in the present methods a BTTS responsive to a priming antigen may induce the expression of an antigen-specific therapeutic responsive to one or more targeting antigens. Useful antigen-specific therapeutics will vary and may include surfaced expressed and secreted antigen-specific therapeutics. For example, in some instances, an antigen-specific therapeutic used in the methods of the present disclosure may be expressed, in response to the activation of a BTTS, on the surface of an immune cell, i.e., the immune cell genetically modified to encode a priming/targeting circuit as described herein. In some instances, an antigen-specific therapeutic used in the methods of the present disclosure may be secreted, in response to the activation of a BTTS, from an immune cell, i.e., the immune cell genetically modified to encode a priming/targeting circuit as described herein.

In general, except where described otherwise, the antigen-specific therapeutic of a herein described circuit will not be expressed in the absence of the activation of the BTTS that induces its expression. Also, except where described otherwise, an antigen-specific therapeutic of a herein described circuit will not be active in the absence of the antigen to which it binds, i.e., without binding the antigen to which the antigen-specific therapeutic is specific. Binding of its respective antigen, or antigens in the case of multi- or bispecific agents, results in activation of the antigen-specific therapeutic. When expressed by, or otherwise engaged with, an immune cell and bound to antigen(s) the antigen-specific therapeutic may activate the immune cell. Activated immune cells may mediate one or more beneficial effects with respect to a heterogeneous GBM of a subject, including those described herein such as but not limited to e.g., cancer cell killing, cytokine release, and the like.

The term "antigen", with respect to the herein described antigen-specific binding domains, is used in a broad sense to refer to essentially any specific binding partner to which the antigen-specific therapeutic binds. As such, any convenient specific binding pair, i.e., specific binding member and specific binding partner pair, may find use in the antigen-specific therapeutics of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds.

In some instances, the specific binding member may be a receptor and its binding partner may be a ligand to which the receptor specifically binds. In some instances, the specific binding member may be a ligand and its binding partner may be a receptor to which the ligand specifically binds.

In some instances, useful ligand-receptor specific binding pairs may include where the specific binding member is a mutein of a ligand having at least one mutation relative to the wild-type ligand, including but not limited to e.g., one or more mutations, two or more mutations, three or more mutations, four or more mutations, five or more mutations, etc. In some instances, useful muteins will have at least 90% sequence identity with the relevant wild-type amino acid sequence, including but not limited to e.g., at least 95%, at least 96%, at least 97%, at least 98%, at least 99%, etc., sequence identity with the relevant wild-type amino acid sequence. In some instances, a mutein employed in the subject polypeptide may have higher affinity for the receptor as compared to the affinity between the receptor and the wild-type ligand.

Antigen-specific therapeutics useful in the methods of the present disclosure will vary and may include but are not limited to e.g., chimeric antigen receptors (CARs), T cell receptors (TCRs), chimeric bispecific binding members, and the like.

Useful CARs include essentially any CAR useful in the treatment of cancer, including single-chain and multi-chain CARs, directed to one or more targeting antigens. A CAR used in WO 2019/1955% PCT/US2019/025860 the instant methods will generally include, at a minimum, an antigen binding domain, a transmembrane domain and an intracellular signaling domain. An employed CAR may further include one or more costimulatory domains.

Non-limiting examples of CARs that may be employed include those used in commercialized CAR T cell (CART) therapies that are directed to one or more appropriate targeting antigens or have been modified to be directed to one or more appropriate targeting antigens. For example, in some instances, one or more CARs may be employed that target one or more targeting antigens, including but not limited to e.g., EphA2, EphA3, IL13R (e.g., IL13RA1 or IL13RA2), EGFR, and ERBB2.

Useful CARs that may be modified to be directed to one or more appropriate targeting antigens include but are not limited to those CARs directed to CD19 and BCMA, including e.g., the anti-CD19-4-1BB-CD3ζ CAR expressed by lentivirus loaded CTL019 (Tisagenlecleucel-T) CAR-T cells, also referred to as Kymriah™(tisagenlecleucel) as commercialized by Novartis (Basel, Switzerland) and the anti-BCMA-4-1BB-CD3ζCAR expressed by lentivirus loaded CAR-T cells called "bb2121" as commercialized by bluebird bio, Inc. (Cambridge, MA) and Celgene Corporation (Summit. NJ).

Useful CARs, e.g., that may be modified to be directed to an appropriate targeting antigen, or useful domains thereof, e.g., that may be employed in a CAR directed to an appropriate targeting antigens, in some instances may include those described in U.S. Pat. Nos. 9,914,909; 9,821, 012; 9,815,901; 9,777,061; 9,662,405; 9,657,105; 9,629, 877; 9,624,276; 9,598,489; 9,587,020; 9,574,014; 9,573, 988; 9,499,629; 9,446,105; 9,394,368; 9,328,156; 9,233, 125; 9,175,308 and 8,822,647; the disclosures of which are incorporated herein by reference in their entirety. In some instances, useful CARs may include or exclude heterodimeric, also referred to as dimerizable or switchable, CARs and/or include or exclude one or more of the domains thereof. Useful heterodimeric CARs and/or useful domains thereof may, in some instances, include those described in U.S. Pat. Nos. 9,587,020 and 9,821,012 as well as U.S. Pub. Nos. US20170081411 A1, US20160311901A1, US20160311907A1, US20150266973A1 and PCT Pub. Nos. WO2014127261 A1, WO2015142661A1, WO2015090229A1 and WO2015017214A1; the disclosures of which are incorporated herein by reference in their entirety.

As summarized above, in some instances, the antigen binding domain of a CAR, such but not limited to e.g., those described in any one of the documents referenced above, may be substituted or amended with an alternative or additional antigen binding domain directed to a different antigen, such as but not limited to one or more of the antigens described herein, for use in the herein described methods. In such instances, the intracellular portions (i.e., the intracellular signaling domain or the one or more costimulatory domains) of the antigen-domain-substituted CAR may or may not be modified.

Useful CARs and/or useful domains thereof may, in some instances, include those that have been or are currently being investigated in one or more clinical trials, including but not limited to the CARs directed to the following antigens (listed with an exemplary corresponding clinical trial number, further information pertaining to which may be retrieved by visiting www(dot)clinicaltrials(dot)gov): AFP, e.g., in NCT03349255; BCMA, e.g., in NCT03288493; CD10, e.g., in NCT03291444; CD117, e.g., in NCT03291444; CD123, e.g., in NCT03114670; CD133, e.g., in NCT02541370; CD138, e.g., in NCT01886976; CD171, e.g., in NCT02311621; CD19, e.g., in NCT02813252: CD20, e.g., in NCT03277729; CD22, e.g., in NCT03244306; CD30, e.g., in NCT02917083; CD33, e.g., in NCT03126864; CD34, e.g., in NCT03291444; CD38, e.g., in NCT03291444; CD5, e.g., in NCT03081910; CD56, e.g., in NCT03291444; CD7, e.g., in NCT02742727; CD70, e.g., in NCT02830724; CD80, e.g., in NCT03356808; CD86, e.g., in NCT03356808; CEA, e.g., in NCT02850536; CLD18, e.g., in NCT03159819; CLL-1, e.g., in NCT03312205; cMet, e.g., in NCT01837602; EGFR, e.g., in NCT03182816; EGFRvIII, e.g., in NCT02664363; EpCAM, e.g., in NCT03013712; EphA2, e.g., in NCT02575261; GD-2, e.g., in NCT01822652; Glypican 3, e.g., in NCT02905188; GPC3, e.g., in NCT02723942; HER-2, e.g., in NCT02547961; kappa immunoglobulin, e.g., in NCT00881920; LeY, e.g., in NCT02958384: LMP1, e.g., in NCT02980315; mesothelin, e.g., in NCT02930993; MG7, e.g., in NCT02862704; MUC1, e.g., in NCT02587689; NKG2D-ligands. e.g., in NCT02203825; PD-L1, e.g., in NCT03330834; PSCA, e.g., in NCT02744287; PSMA, e.g., in NCT03356795; ROR1, e.g., in NCT02706392; ROR1R, e.g., in NCT02194374; TACI. e.g., in NCT03287804; and VEGFR2, e.g., in NCT01218867.

Useful TCRs include essentially any TCR useful in the treatment of cancer, including single-chain and multi-chain TCRs, directed to a targeting antigen. A TCR used in the instant methods will generally include, at a minimum, an antigen binding domain and a modified or unmodified TCR chain, or portion thereof, including but not limited to e.g., a modified or unmodified α-chain, a modified or unmodified β-chain, etc. An employed TCR may further include one or more costimulatory domains. In some instances, a TCR employed herein will include an alpha chain and a beta chain and recognize antigen when presented by a major histocompatibility complex.

Essentially any TCR can be induced by a BTFS using a method of the present disclosure including e.g., TCRs that are specific for any of a variety of epitopes, including, e.g., an epitope expressed on the surface of a cancer cell, a peptide-MHC complex on the surface of cancer cell, and the like. In some cases, the TCR is an engineered TCR.

Non-limiting examples of engineered TCRs, including those having immune cell activation function and that may be modified to include an antigen-binding domain specific for a suitable targeting antigen, useful in the methods described herein include, e.g., antigen-specific TCRs, Monoclonal TCRs (MTCRs), Single chain MTCRs. High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685. WO 2004/044004, WO 2005/114215, WO 2006/000830, WO 2008/038002, WO 2008/039818. WO 2004/074322, WO 2005/113595, WO 2006/125962; Strommes et al. Immunol Rev. 2014; 257(1):145-64; Schmitt et al. Blood. 2013; 122(3):348-56; Chapuls et al. Sci Transl Med. 2013; 5(174):174ra27; Thaxton et al. Hum Vaccin Immunother. 2014; 10(11):3313-21 (PMID: 25483644); Gschweng et al. Immunol Rev. 2014; 257(1): 237-49 (PMID:24329801); Hinrichs et al. Immunol Rev. 2014; 257(1):56-71 (PMID:24329789); Zoete et al. Front Immunol. 2013; 4:268 (PMID:24062738); Marr et al. Clin Exp Immunol. 2012; 167(2):216-25 (PMID:22235997); Zhang et al. Adv Drug Deliv Rev. 2012; 64(8):756-62 (PMID:22178904); Chhabra et al. Scientific World Journal. 2011; 11:121-9 (PMID:21218269); Boulter et al. Clin Exp Immunol. 2005; 142(3):454-60 (PMID:16297157); Sami et al. Protein Eng Des Sel. 2007; 20(8):397-403; Boulter et al. Protein Eng. 2003; 16(9):707-11; Ashfield et al. IDrugs. 2006; 9(8):554-9; Li et al. Nat Biotechnol. 2005; 23(3):349-54; Dunn et al. Protein Sci. 2006; 15(4):710-21; Liddy et al. Mol Biotechnol. 2010; 45(2); Liddy et al. Nat Med. 2012; 18(6):980-7; Oates, et al. Oncoimmunology. 2013; 2(2): e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of which are incorporated herein by reference in their entirety.

Useful TCRs include those having wild-type affinity for their respective antigen as well as those having enhanced affinity for their respective antigen. TCRs having enhanced affinity for their respective antigen may be referred to as "affinity enhanced" or "enhanced affinity" TCRs. The affinity of a TCR may be enhanced by any convenient means, including but not limited to binding-site engineering (i.e., rational design), screening (e.g., TCR display), or the like. Non-limiting examples of affinity enhanced TCRs and methods of generating enhanced affinity TCRs include but are not limited to e.g., those described in PCT Pub. Nos. 20150118208, 2013256159, 20160083449; 20140349855, 20100113300, 20140371085, 20060127377, 20080292549, 20160280756, 20140065111, 20130058908, 20110038842, 20110014169, 2003276403 and the like; the disclosures of which are incorporated herein by reference in their entirety. Further engineered TCRs, modified to be directed to an appropriate targeting antigen, that may be expressed in response to release of an intracellular domain of a BTTS of the present disclosure include e.g., those described in PCT Application No. US2017/048040; the disclosure of which is incorporated herein by reference in its entirety.

Useful TCRs, which may be modified to be directed to an appropriate targeting antigen, may, in some instances, also include those described in U.S. Pat. Nos. 9,889,161; 9,889,160; 9,868,765; 9,862,755; 9,717,758; 9,676,867; 9,409,969; 9,115,372; 8,951,510; 8,906,383; 8,889,141; 8,722,048; 8,697,854; 8,603,810; 8,383,401; 8,361,794; 8,283,446; 8,143,376; 8,003,770; 7,998,926; 7,666,604; 7,456,263; 7,446,191; 7,446,179; 7,329,731; 7,265,209; and 6,770,749; the disclosures of which are incorporated herein by reference in their entirety.

As described above, in some instances, the antigen binding domain of a TCR, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., the transmembrane domain, any intracellular signaling domains, etc.) of the antigen-domain-substituted TCR may or may not be modified.

As summarized above, in some instances, useful antigen-specific therapeutics may include those that, upon induction by an activated BTTS, are expressed and secreted from the producing cell, including e.g., where the secreting cell is an immune cell. For example, upon binding of a BTTS expressed by an immune cell, the BTTS may induce expression and secretion of an encoded antigen-specific therapeutic specific for a targeting antigen. The secreted antigen-specific therapeutic may target a target antigen expressing cancer cell in trans, thereby mediating killing of the target cell. As described herein, in some instances, a secreted antigen-specific therapeutic may increase the zone of targeting or the zone of killing of a subject circuit as compared to a similar circuit encoding a non-secreted (e.g., membrane expressed) antigen-specific therapeutic.

Useful secreted antigen-specific therapeutics will vary and in some instances may include but are not limited to e.g., chimeric bispecific binding members. In some instances, useful chimeric bispecific binding members may include those that target a protein expressed on the surface of an immune cell, including but not limited to e.g., a component of the T cell receptor (TCR), e.g., one or more T cell co-receptors. Chimeric bispecific binding members that bind to a component of the TCR may be referred to herein as a TCR-targeted bispecific binding agent. Chimeric bispecific binding members useful in the instant methods will generally be specific for a targeting antigen and may, in some instances, be specific for a targeting antigen and a protein expressed on the surface of an immune cell (e.g., a component of a TCR such as e.g., a CD3 co-receptor).

Non-limiting examples of useful chimeric bispecific binding members include those that bind Ephrin type-A receptor 2 (EphA2). Ephrin type-A receptor 3 (EphA3), Interleukin-13 receptor (IL13R) (e.g., IL13RA1 or IL13RA2), Epidermal growth factor receptor (EGFR) or erb-b2 receptor tyrosine kinase 2 (ERBB2). Non-limiting examples of useful chimeric bispecific binding members also include those that have been modified to bind EphA2, EphA3, IL13R (e.g., IL13RA1 or IL13RA2). EGFR or ERBB2.

In some instances, useful chimeric bispecific binding members may include a bispecific T cell engager (BiTE). A BiTE is generally made by fusing a specific binding member (e.g., a scFv) that binds an immune cell antigen to a specific binding member (e.g., a scFv) that binds a cancer antigen (e.g., a tumor associated antigen, a tumor specific antigen, etc.). For example, an exemplary BiTE includes an anti-CD3 scFv fused to an anti-tumor associated antigen (e.g., EpCAM, CD19, etc.) scFv via a short peptide linker (e.g., a five amino acid linker, e.g., GGGGS).

In some instances, a BiTE, suitable for use in the herein described methods may include e.g., an anti-CD3 x anti-CD19 BiTE (e.g., Blinatumomab) that has been modified to bind a suitable targeting antigen (including but not limited to e.g., EphA2, EphA3, IL13R (e.g., IL13RA1 or IL13RA2), EGFR or ERBB2), an anti-EpCAM x anti-CD3 BiTE (e.g., MT110) that has been modified to bind a suitable targeting antigen (including but not limited to e.g., EphA2, EphA3, IL13R (e.g., IL13RA1 or IL13RA2), EGFR or ERBB2), an anti-CEA x anti-CD3 BiTE (e.g., MT111/MEDI-565) that has been modified to bind a suitable targeting antigen (including but not limited to e.g., EphA2, EphA3, IL13R (e.g., IL13RA1 or IL13RA2), EGFR or ERBB2), an anti-CD33 x anti-CD3 BiTE that has been modified to bind a suitable targeting antigen (including but not limited to e.g., EphA2, EphA3, IL13R (e.g., IL13RA1 or IL13RA2). EGFR or ERBB2), an anti-HER2 BiTE that has been modified to bind a suitable targeting antigen (including but not limited to e.g., EphA2, EphA3, IL13R (e.g., IL13RA1 or IL13RA2), EGFR or ERBB2), an anti-EGFR BiTE, an anti-IgE BiTE that has been modified to bind a suitable targeting antigen (including but not limited to e.g., EphA2, EphA3, IL13R (e.g., IL13RA1 or IL13RA2). EGFR or ERBB2), and the like.

As summarized above, in some instances, the antigen binding domain of a chimeric bispecific binding member, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., linker domain, any immune cell targeting domains, etc.) of the antigen-domain-substituted chimeric bispecific binding member may or may not be modified.

In some instances, a payload induced by binding of a BTTS to its respective priming antigen in a herein described method may include a secreted bio-orthogonal adapter molecule. Such bio-orthogonal adapter molecules may, in some instances, be configured to target and bind a targeting antigen and also bind or be bound by a heterologous polypeptide expressed by an immune cell.

For example, in some instances, a subject circuit employed in the herein described methods may encode, within an immune cell: a BTTS responsive to a priming antigen; a bio-orthogonal adapter molecule specific for a targeting antigen; and a therapeutic, or portion thereof, which binds the bio-orthogonal adapter molecule. In such a circuit, expression and secretion of the bio-orthogonal adapter molecule is induced upon binding of the BTTS to the priming antigen (including but not limited to e.g., IL13RA2, IL13RA1, Neuroligin, NRXN1, PTPRZ1, NRCAM, CDH10, PCDHGC5, CD70, CSPG5, BCAN, GRM3, CRB1, GAP43, ATP1B2, MOG1, and PTPRZ1-MET). Then, in the presence of both (1) a cancer cell expressing the targeting antigen and (2) the therapeutic that binds the bio-orthogonal adapter molecule, the therapeutic binds the bio-orthogonal adapter molecule which then binds the targeting antigen, thereby activating the therapeutic. The activated therapeutic may then mediate a therapeutic effect (e.g., a cytotoxic effect) on the cancer cell expressing the targeting antigen, including where the targeting antigen is expressed in trans with respect to the priming antigen. As described herein, in some instances, a secreted bio-orthogonal adapter molecule may increase the zone of targeting or the zone of killing of a subject circuit as compared to a similar circuit encoding a non-secreted (e.g., membrane expressed) antigen-specific therapeutic.

Bio-orthogonal adapter molecules may be employed in various contexts within the herein described methods. For example, in some instances, a bio-orthogonal adapter molecule may be employed that includes a diffusible antigen binding portion of an antigen-specific therapeutic, such as e.g., a diffusible antigen binding portion of a CAR, a diffusible antigen binding portion of a TCR, or the like. In some instances, such diffusible antigen binding portion of antigen-specific therapeutics may be referred to a "diffusible head", including e.g., a "diffusible CAR head", a "diffusible TCR head", and the like. In some instances, a diffusible antigen binding portion may be specific for one or more of EphA2, EphA3, IL13R (e.g., IL13RA1 or IL13RA2). EGFR and/or ERBB2.

In some instances, the therapeutic may bind directly to the bio-orthogonal adapter molecule. Strategies for direct binding of the therapeutic to the bio-orthogonal adapter molecule may vary. For example, in some instances, the therapeutic may include a binding domain (e.g., such as an orthogonal antibody or fragment thereof) that binds a binding moiety (e.g., an orthogonal epitope to which an antibody may be directed) covalently attached to the bio-orthogonal adapter. As a non-limiting example, a therapeutic may include a binding domain to a non-naturally occurring epitope, e.g., an anti-fluorescein antibody or a fragment thereof, and the bio-orthogonal adapter molecule may include the epitope, e.g., a fluorescein, covalently attached thereto. In some instances, the configuration of the bio-orthogonal adapter molecule and therapeutic interaction may be reversed as compared to that previously described, including e.g., where the therapeutic includes a covalently attached epitope and the bio-orthogonal adapter molecule includes a binding domain to the epitope. Useful epitopes will vary and may include but are not limited to e.g., small molecule-based epitopes, peptide-based epitopes (e.g., peptide neo-epitopes), oligonucleotide-based epitopes, and the like. The epitope-binding domains will vary correspondingly and may include but are not limited to e.g., small molecule binding domains, peptide binding domains, oligonucleotide binding domains, and the like.

Non-limiting examples of useful bio-orthogonal adapter molecules, and the domains that bind thereto, include but are not limited to e.g., the peptide neo-epitopes and the antibody binding domains that bind thereto as used in switchable CAR (sCAR) T cells, including but not limited to e.g., those described in Rodgers et al. Proc Natl Acad Sci USA. (2016) 113(4):E459-68 and Cao et al., Angew Chem Int Ed Engl. 2016 Jun. 20; 55(26):7520-4 as well as PCT Pub. No. WO2016168773; the disclosures of which are incorporated herein by reference in their entirety.

In some instances, the therapeutic may bind indirectly to the bio-orthogonal adapter molecule, including e.g., where binding is mediated by a diffusible dimerizing agent. Non-limiting examples of suitable dimerizing agents, and the dimerizing domains that bind thereto, include protein dimerizers.

Protein dimerizers generally include polypeptide pairs that dimerize, e.g., in the presence of or when exposed to a dimerizing agent. The dimerizing polypeptide pairs of a protein dimerizer may homo-dimerize or hetero-dimerize (i.e., the dimerizing polypeptide pairs may include two of the same polypeptide that form a homodimer or two different polypeptides that form a heterodimer). Non-limiting pairs of protein dimerizers (with the relevant dimerizing agent in parentheses) include but are not limited to e.g., FK506 binding protein (FKBP) and FKBP (rapamycin); FKBP and calcineurin catalytic subunit A (CnA) (rapamycin); FKBP and cyclophilin (rapamycin); FKBP and FKBP-rapamycin associated protein (FRB) (rapamycin); gyrase B (GyrB) and GyrB (coumermycin); dihydrofolate reductase (DHFR) and DHFR (methotrexate); DmrB and DmrB (AP20187); PYL and ABI (abscisic acid); Cry2 and CIB1 (blue light); GAI and GID1 (gibberellin); and the like. Further description, including the amino acid sequences, of such protein dimerizers is provided in U.S. Patent Application Publication No. US 2015-0368342 A1; the disclosure of which is incorporated herein by reference in its entirety.

Useful protein dimerizers also include those nuclear hormone receptor derived protein dimerizers that dimerize in the presence of a dimerizing agent described in PCT Pub. No. WO 2017/120546 and U.S. Patent Pub. No. US 2017/0306303 A1; the disclosures of which are incorporated by reference herein in their entirety, and the like. Such nuclear hormone receptor derived dimerizers will generally include a first member of the dimerization pair that is a co-regulator of a nuclear hormone receptor and a second member of the dimerization pair comprises an LBD of the nuclear hormone receptor.

Where a bio-orthogonal adapter molecule is employed in a subject circuit, the expression of the therapeutic, which binds the bio-orthogonal adapter molecule to mediate targeting antigen recognition, may or may not be controlled by the circuit. Put another way, the expression of the therapeutic may or may not be tied to the activation of the BTTS (e.g., the binding of the BTTS to priming antigen or another antigen) of the circuit. In some instances, the circuit may be configured such that binding of a BTTS to its antigen induces expression of a therapeutic which binds a bio-orthogonal adapter molecule. In some instances, the BTTS that induces expression of the therapeutic is the same BTTS that induces expression of the bio-orthogonal adapter molecule. In some instance, the therapeutic is induced by a BTTS that is different (i.e., separate) from the BTTS that induces expression of the bio-orthogonal adapter molecule.

In some instances, expression of a therapeutic which binds a bio-orthogonal adapter molecule may not be induced by a BTTS. For example, in some instances, rather than being induced by a BTTS, such a therapeutic is expressed under the control of a separate regulatory element or sequence, including but not limited to e.g., where the expression of the therapeutic is constitutive, inducible, conditional, tissue specific, cell type specific, or the like. In some instances, for example, independent expression (e.g., constitutive expression, inducible expression, etc.) of the therapeutic by introduced immune cells allows for a diffusible bio-orthogonal adapter molecule to mediate the activation of the therapeutic in immune cells that are distant from the site of priming.

In some instances, expression of a bio-orthogonal adapter molecule, bound by a therapeutic, may not be induced by a BTTS, including where the corresponding therapeutic is induced by a BTTS. For example, in some instances, rather than being induced by a BTTS, such a bio-orthogonal adapter molecule is expressed under the control of a separate regulatory element or sequence, including but not limited to e.g., where the expression of the bio-orthogonal adapter molecule is constitutive, inducible, conditional, tissue specific, cell type specific, or the like. In some instances, the bio-orthogonal adapter molecule may be externally provided.

In some instances, an antigen-specific therapeutic may have an extracellular domain that includes a first member of a specific binding pair that binds a second member of the specific binding pair, wherein the extracellular domain does not include any additional first or second member of a second specific binding pair. For example, in some instances, an antigen-specific therapeutic may have an extracellular domain that includes a first antigen-binding domain that binds an antigen, wherein the extracellular domain does not include any additional antigen-binding domains and does not bind any other antigens. A subject antigen-specific therapeutic may, in some instances, include only a single extracellular domain. Accordingly, an employed antigen-specific therapeutic may be specific for a single antigen and only specific for the single antigen. Such, antigen-specific therapeutics may be referred to as a "single antigen antigen-specific therapeutic".

In some instances, an antigen-specific therapeutic may have an extracellular domain that includes the first or second members of two or more specific binding pairs. For example, in some instances, an antigen-specific therapeutic may have an extracellular domain that includes a first antigen-binding domain and a second antigen-binding domain that are different such that the extracellular domain is specific for two different antigens. In some instances, an antigen-specific therapeutic may have two or more extracellular domains that each includes the first or second members of two different specific binding pairs. For example, in some instances, an antigen-specific therapeutic may have a first extracellular domain that includes a first antigen-binding domain and a second extracellular domain that includes a second antigen-binding domain where the two different antigen binding domains are each specific for a different antigen. As such, the antigen-specific therapeutic may be specific for two different antigens.

An antigen-specific therapeutic specific for two or more different antigens, containing either two extracellular domains or one extracellular domain specific for two different antigens, may be configured such that the binding of either antigen to the antigen-specific therapeutic is sufficient to active the antigen-specific therapeutic. Such an antigen-specific therapeutic, capable of being activated by any of two or more antigens, may find use in the described circuits as a component of a logic gate containing OR functionality. In some instances, an antigen-specific therapeutic specific for two different antigens may be referred to as a "two-headed antigen-specific therapeutic". Antigen-specific therapeutics specific for multiple antigens will not be limited to only two antigens and may, e.g., be specific for and/or activated by more than two antigens, including e.g., three or more, four or more, five or more, etc.

For example, an antigen-specific therapeutic specific for two or more different antigens may bind, and/or be activated by, EphA2 or EphA3, EphA2 or IL13RA1, EphA2 or IL13RA2, EphA2 or EGFR, EphA2 or ERBB2, EphA3 or IL13RA1, EphA3 or IL13RA2, EphA3 or EGFR, EphA3 or ERBB2, IL13RA1 or IL13RA2, IL13RA1 or EGFR, IL13RA1 or ERBB2, IL13RA2 or EGFR, IL13RA2 or ERBB2, or EGFR or ERBB2.

An example of an antigen-specific therapeutic specific for two or more different antigens is a tandem CAR (also referred to as "tan CAR" or "tanCAR"). A "tandem CAR" is a bispecific CAR that includes two or more non-identical antigen recognition domains. Non-limiting examples of tandem CARs include those described in U.S. Pat. Nos. 9,447,194; 10,155,038; 10,189,903; and 10,239,948; U.S. Patent Application Pub. No. 20130280220 and PCT Application Pub. No. WO/2013/123061; the disclosures of which are incorporated herein by reference in their entirety. Tandem CARs may be configured to bind a variety of different antigens, including but not limited to e.g., two or more or the antigens described herein and/or two or more of the antigens described in U.S. Pat. Nos. 9,447,194; 10,155,038; 10,189, 903; and 10,239,948; U.S. Patent Application Pub. No. 20130280220 and PCT Application Pub. No. WO/2013/123061.

Binding Triggered Transcriptional Switches (BTTS)

The methods of the instant disclosure include the use of circuits employing a BTTS to induce expression of an encoded antigen-specific therapeutic. As used herein, a "binding-triggered transcriptional switch" or BTTS generally refers to a synthetic modular polypeptide or system of interacting polypeptides having an extracellular domain that includes a first member of a specific binding pair, a binding-transducer and an intracellular domain. Upon binding of the second member of the specific binding pair to the BTTS the binding signal is transduced to the intracellular domain such that the intracellular domain becomes activated and performs some function within the cell that it does not perform in the absence of the binding signal. Binding triggered transcriptional switches are described in e.g., PCT Pub. No. WO 2016/138034 as well as U.S. Pat. Nos. 9,670,281 and 9,834,608; the disclosures of which are incorporated herein by reference in their entirety.

The specific binding member of the extracellular domain generally determines the specificity of the BTTS. In some instances, a BTTS may be referred according to its specificity as determined based on its specific binding member. For example, a specific binding member having binding partner "X" may be referred to as an X-BTTS or an anti-X BTTS.

Any convenient specific binding pair, i.e., specific binding member and specific binding partner pair, may find use in the BTTS of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a scaffold protein and its binding partner may be a protein to which the scaffold protein specifically binds. Useful specific binding pairs include those specific for priming antigen and/or one or more targeting/killing antigens, including those described herein.

In some cases, the specific binding member is an antibody. The antibody can be any antigen-binding antibody-based polypeptide, a wide variety of which are known in the art. In some instances, the specific binding member is or includes a monoclonal antibody, a single chain Fv (scFv), a Fab, etc. Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

Where the specific binding member of a BTTS is an antibody-based binding member, the BTTS can be activated in the presence of a binding partner to the antibody-based binding member, including e.g., an antigen specifically bound by the antibody-based binding member. In some instances, antibody-based binding member may be defined, as is commonly done in the relevant art, based on the antigen bound by the antibody-based binding member, including e.g., where the antibody-based binding member is described as an "anti-" antigen antibody, e.g., an anti-priming antigen antibody (e.g., an anti-IL13RA2 antibody, anti-IL13RA1 antibody, anti-Neuroligin antibody, anti-NRXN1 antibody, anti-PTPRZ1 antibody, anti-NRCAM antibody, anti-CDH10 antibody, anti-PCDHGC5 antibody, anti-CD70 antibody anti-CSPG5 antibody, anti-BCAN antibody, anti-GRM3 antibody, anti-CRB1 antibody, anti-GAP43 antibody, anti-ATP1B2 antibody, anti-PTPRZ1-MET fusion antibody, etc.). Accordingly, antibody-based binding members suitable for inclusion in a BTTS or an antigen-specific therapeutic of the present methods can have a variety of antigen-binding specificities.

The components of BTTSs, employed in the described methods, and the arrangement of the components of the switch relative to one another will vary depending on many factors including but not limited to e.g., the desired binding trigger, the activity of the intracellular domain, the overall function of the BTTS, the broader arrangement of a molecular circuit comprising the BTTS, etc. The first binding member may include but is not limited to e.g., those agents that bind an antigen described herein. The intracellular domain may include but is not limited e.g., those intracellular domains that activate or repress transcription at a regulatory sequence, e.g., to induce or inhibit expression of a downstream component of a particular circuit.

The binding transducer of BTTSs will also vary depending on the desired method of transduction of the binding signal. Generally, binding transducers may include those polypeptides and/or domains of polypeptides that transduce an extracellular signal to intracellular signaling e.g., as performed by the receptors of various signal transduction pathways. Transduction of a binding signal may be achieved through various mechanisms including but not limited to e.g., binding-induced proteolytic cleavage, binding-induced phosphorylation, binding-induced conformational change, etc. In some instances, a binding-transducer may contain a ligand-inducible proteolytic cleavage site such that upon binding the binding-signal is transduced by cleavage of the BTTS, e.g., to liberate an intracellular domain. For example, in some instances, a BTTS may include a Notch derived cleavable binding transducer, such as, e.g., a chimeric notch receptor polypeptide as described herein.

In other instances, the binding signal may be transduced in the absence of inducible proteolytic cleavage. Any signal transduction component or components of a signaling transduction pathway may find use in a BTTS whether or not proteolytic cleavage is necessary for signal propagation. For example, in some instances, a phosphorylation-based binding transducer, including but not limited to e.g., one or more signal transduction components of the Jak-Stat pathway, may find use in a non-proteolytic BTTS.

For simplicity. BTTSs, including but not limited to chimeric notch receptor polypeptides, are described primarily as single polypeptide chains. However, BTTSs, including chimeric notch receptor polypeptides, may be divided or split across two or more separate polypeptide chains where the joining of the two or more polypeptide chains to form a functional BTTS, e.g., a chimeric notch receptor polypeptide, may be constitutive or conditionally controlled. For example, constitutive joining of two portions of a split BTTS may be achieved by inserting a constitutive heterodimerization domain between the first and second portions of the split polypeptide such that upon heterodimerization the split portions are functionally joined.

Useful BTTSs that may be employed in the subject methods include, but are not limited to modular extracellular sensor architecture (MESA) polypeptides. A MESA polypeptide comprises: a) a ligand binding domain; b) a transmembrane domain; c) a protease cleavage site; and d) a functional domain. The functional domain can be a transcription regulator (e.g., a transcription activator, a transcription repressor). In some cases, a MESA receptor comprises two polypeptide chains. In some cases, a MESA receptor comprises a single polypeptide chain. Non-limiting examples of MESA polypeptides are described in, e.g., U.S. Patent Publication No. 2014/0234851; the disclosure of which is incorporated herein by reference in its entirety.

Useful BTTSs that may be employed in the subject methods include, but are not limited to polypeptides employed in the TANGO assay. The subject TANGO assay employs a TANGO polypeptide that is a heterodimer in which a first polypeptide comprises a tobacco etch virus (Tev) protease and a second polypeptide comprises a Tev proteolytic cleavage site (PCS) fused to a transcription factor. When the two polypeptides are in proximity to one another, which proximity is mediated by a native protein-protein interaction, Tev cleaves the PCS to release the transcription factor. Non-limiting examples of TANGO polypeptides are described in, e.g., Barnea et al. (Proc Natl Acad Sci USA. 2008 Jan. 8; 105(1):64-9); the disclosure of which is incorporated herein by reference in its entirety.

Useful BTTSs that may be employed in the subject methods include, but are not limited to von Willebrand Factor (vWF) cleavage domain-based BTTSs, such as but not limited to e.g., those containing a unmodified or modified vWF A2 domain. A subject vWF cleavage domain-based BTTS will generally include: an extracellular domain comprising a first member of a binding pair, a von Willebrand Factor (vWF) cleavage domain comprising a proteolytic cleavage site; a cleavable transmembrane domain and an intracellular domain. Non-limiting examples of vWF cleavage domains and vWF cleavage domain-based BTTSs are described in Langridge & Struhl (Cell (2017) 171(6): 1383-1396); the disclosure of which is incorporated herein by reference in its entirety.

Useful BTTSs that may be employed in the subject methods include, but are not limited to chimeric Notch receptor polypeptides, such as but not limited to e.g., synNotch polypeptides, non-limiting examples of which are described in PCT Pub. No. WO 2016/138034. U.S. Pat. Nos. 9,670,281, 9,834,608, Roybal et al. Cell (2016) 167(2):419-432, Roybal et al. Cell (2016) 164(4):770-9, and Morsut et al. Cell (2016) 164(4):780-91; the disclosures of which are incorporated herein by reference in their entirety.

SynNotch polypeptides are generally proteolytically cleavable chimeric polypeptides that generally include: a) an extracellular domain comprising a specific binding member; b) a proteolytically cleavable Notch receptor polypeptide comprising one or more proteolytic cleavage sites; and c) an intracellular domain. Binding of the specific binding member by its binding partner generally induces cleavage of the synNotch at the one or more proteolytic cleavage sites, thereby releasing the intracellular domain. In some instances, the instant methods may include where release of the intracellular domain triggers (i.e., induces) the production of an encoded payload, the encoding nucleic acid sequence of which is contained within the cell. Depending on the particular context, the produced payload is then generally expressed on the cell surface or secreted. Syn- Notch polypeptides generally include at least one sequence that is heterologous to the Notch receptor polypeptide (i.e., is not derived from a Notch receptor), including e.g., where the extracellular domain is heterologous, where the intracellular domain is heterologous, where both the extracellular domain and the intracellular domain are heterologous to the Notch receptor, etc.

Useful synNotch BTTSs will vary in the domains employed and the architecture of such domains. SynNotch polypeptides will generally include a Notch receptor polypeptide that includes one or more ligand-inducible proteolytic cleavage sites. The length of Notch receptor polypeptides will vary and may range in length from about 50 amino acids or less to about 1000 amino acids or more.

In some cases, the Notch receptor polypeptide present in a synNotch polypeptide has a length of from 50 amino acids (aa) to 1000 aa, e.g., from 50 aa to 75 aa, from 75 aa to 100 aa, from 100 aa to 150 aa, from 150 aa to 200 aa, from 200 aa to 250 aa, from 250 a to 300 aa, from 300 aa to 350 aa, from 350 aa to 400 aa, from 400 aa to 450 aa, from 450 aa to 500 aa, from 500 aa to 550 aa, from 550 aa to 600 aa, from 600 aa to 650 aa, from 650 aa to 700 aa, from 700 aa to 750 aa, from 750 aa to 800 aa, from 800 aa to 850 aa, from 850 aa to 900 aa, from 900 aa to 950 aa, or from 950 aa to 1000 aa. In some cases, the Notch receptor polypeptide present in a synNotch polypeptide has a length of from 300 aa to 400 aa, from 300 aa to 350 aa, from 300 aa to 325 aa, from 350 aa to 400 aa, from 750 aa to 850 aa, from 50 aa to 75 aa. In some cases, the Notch receptor polypeptide has a length of from 310 aa to 320 aa, e.g., 310 aa, 311 aa, 312 aa, 313 aa, 314 aa, 315 aa, 316 aa, 317 aa, 318 aa, 319 aa, or 320 aa. In some cases, the Notch receptor polypeptide has a length of 315 aa. In some cases, the Notch receptor polypeptide has a length of from 360 aa to 370 aa, e.g., 360 aa, 361 aa, 362 aa, 363 aa 364 aa, 365 aa, 366 aa, 367 aa, 368 aa, 369 aa, or 370 aa. In some cases, the Notch receptor polypeptide has a length of 367 aa.

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence.

Subject Notch regulatory regions may include or exclude various components (e.g., domains, cleavage sites, etc.) thereof. Examples of such components of Notch regulatory regions that may be present or absent in whole or in part, as appropriate, include e.g., one or more EGF-like repeat domains, one or more Lin12/Notch repeat domains, one or more heterodimerization domains (e.g., HD-N or HD-C), a transmembrane domain, one or more proteolytic cleavage sites (e.g., a furin-like protease site (e.g., an S1 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta-binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

Non-limiting examples of particular synNotch BTTSs, the domains thereof, and suitable domain arrangements are described in PCT Pub. Nos. WO 2016/138034, WO 2017/193059, WO 2018/039247 and U.S. Pat. Nos. 9,670,281 and 9,834,608; the disclosures of which are incorporated herein by reference in their entirety.

Domains of a useful BTTS, e.g., the extracellular domain, the binding-transducer domain, the intracellular domain, etc., may be joined directly, i.e., with no intervening amino acid residues or may include a peptide linker that joins two domains. Peptide linkers may be synthetic or naturally derived including e.g., a fragment of a naturally occurring polypeptide.

A peptide linker can vary in length of from about 3 amino acids (aa) or less to about 200 aa or more, including but not limited to e.g., from 3 aa to 10 aa, from 5 aa to 15 aa, from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa, A peptide linker can have a length of from 3 aa to 30 aa, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 aa, A peptide linker can have a length of from 5 aa to 50 aa, e.g., from 5 aa to 40 aa, from 5 aa to 35 aa, from 5 aa to 30 aa, from 5 aa to 25 aa, from 5 aa to 20 aa, from 5 aa to 15 aa or from 5 aa to 10 aa.

In some instances, a BTTS may have an extracellular domain that includes a first member of a specific binding pair that binds a second member of the specific binding pair, wherein the extracellular domain does not include any additional first or second member of a second specific binding pair. For example, in some instances, a BTTS may have an extracellular domain that includes a first antigen-binding domain that binds an antigen, wherein the extracellular domain does not include any additional antigen-binding domains and does not bind any other antigens. A subject BTTS may, in some instances, include only a single extracellular domain. Accordingly, an employed BTTS may be specific for a single antigen and only specific for the single antigen. Such, BTTSs may be referred to as a "single antigen BTTS". In some instances, a "dual antigen BTTS" may be employed.

In some instances, a BTTS may have an extracellular domain that includes the first or second members of two or more specific binding pairs. For example, in some instances, a BTTS may have an extracellular domain that includes a first antigen-binding domain and a second antigen-binding domain that are different such that the extracellular domain is specific for two different antigens. In some instances, a BTTS may have two or more extracellular domains that each includes the first or second members of two different specific binding pairs. For example, in some instances, a BTTS may have a first extracellular domain that includes a first antigen-binding domain and a second extracellular domain that includes a second antigen-binding domain where the two different antigen binding domains are each specific for a different antigen. As such, the BTTS may be specific for two different antigens.

For example, a BTTS that is specific for two or more different antigens may bind, and/or be activated by, IL13RA2 or IL13RA1, IL13RA2 or Neuroligin, IL13RA2 or NRXN1, IL13RA2 or PTPRZ1, IL13RA2 or NRCAM, IL13RA2 or CDH10, IL13RA2 or PCDHGC5, IL13RA2 or CD70, IL13RA2 or CSPG5, IL13RA2 or BCAN, IL13RA2 or GRM3, IL13RA2 or CRB1, IL13RA2 or GAP43, IL13RA2 or ATP1B2, IL13RA2 or MOG1, IL13RA2 or PTPRZ1-MET, IL13RA1 or Neuroligin, IL13RA1 or NRXN1, IL13RA1 or PTPRZ1, IL13RA1 or NRCAM, IL13RA1 or CDH10, IL13RA1 or PCDHGC5, IL13RA1 or CD70, IL13RA1 or CSPG5, IL13RA1 or BCAN, IL13RA1 or GRM3, IL13RA1 or CRB1, IL13RA1 or GAP43, IL13RA1 or ATP1B2, IL13RA1 or MOG1, IL13RA1 or PTPRZ1-MET, Neuroligin or NRXN1, Neuroligin or PTPRZ1. Neuroligin or NRCAM, Neuroligin or CDH10, Neuroligin or PCDHGC5, Neuroligin or CD70, Neuroligin or CSPG5. Neuroligin or BCAN. Neuroligin or GRM3, Neuroligin or CRB1, Neuroligin or GAP43, Neuroligin or ATP1B2, Neuroligin or MOG1, Neuroligin or PTPRZ1-MET, NRXN1 or PTPRZ1, NRXN1 or NRCAM, NRXN1 or CDH10, NRXN1 or PCDHGC5, NRXN1 or CD70, NRXN1 or CSPG5, NRXN1 or BCAN, NRXN1 or GRM3, NRXN1 or CRB1, NRXN1 or GAP43, NRXN1 or ATP1B2, NRXN1 or MOG1, NRXN1 or PTPRZ1-MET, PTPRZ1 or NRCAM, PTPRZ1 or CDH10, PTPRZ1 or PCDHGC5, PTPRZ1 or CD70, PTPRZ1 or CSPG5, PTPRZ1 or BCAN, PTPRZ1 or GRM3, PTPRZ1 or CRB1, PTPRZ1 or GAP43, PTPRZ1 or ATP1B2, PTPRZ1 or MOG1, PTPRZ1 or PTPRZ1-MET, NRCAM or CDH10, NRCAM or PCDHGC5, NRCAM or CD70, NRCAM or CSPG5, NRCAM or BCAN, NRCAM or GRM3, NRCAM or CRB1, NRCAM or GAP43, NRCAM or ATP1B2, NRCAM or MOG1, NRCAM or PTPRZ1-MET, CDH10 or PCDHGC5, CDH10 or CD70, CDH10 or CSPG5, CDH10 or BCAN, CDH10 or GRM3, CDH10 or CRB1, CDH10 or GAP43, CDH10 or ATP1B2, CDH10 or MOG1, CDH10 or PTPRZ1-MET, PCDHGC5 or CD70, PCDHGC5 or CSPG5, PCDHGC5 or BCAN, PCDHGC5 or GRM3, PCDHGC5 or CRB1, PCDHGC5 or GAP43, PCDHGC5 or ATP1B2, PCDHGC5 or MOG1, PCDHGC5 or PTPRZ1-MET, CD70 or CSPG5, CD70 or BCAN, CD70 or GRM3, CD70 or CRB1, CD70 or GAP43, CD70 or ATP1B2, CD70 or MOG1, CD70 or PTPRZ1-MET, CSPG5 or BCAN, CSPG5 or GRM3, CSPG5 or CRB1, CSPG5 or GAP43, CSPG5 or ATP1B2, CSPG5 or MOG1. CSPG5 or PTPRZ1-MET, BCAN or GRM3, BCAN or CRB1, BCAN or GAP43, BCAN or ATP1B2, BCAN or MOG1, BCAN or PTPRZ1-MET, GRM3 or CRB1, GRM3 or GAP43, GRM3 or ATP1B2, GRM3 or MOG1, GRM3 or PTPRZ1-MET, CRB1 or GAP43, CRB1 or ATP1B2, CRB1 or MOG1, CRB1 or PTPRZ1-MET, GAP43 or ATP1B2, GAP43 or MOG1, GAP43 or PTPRZ1-MET, ATP1B2 or MOG1, ATP1B2 or PTPRZ1-MET, or MOG1 or PTPRZ1-MET.

A BTTS specific for two or more different antigens, containing either two extracellular domains or one extracellular domain specific for two different antigens, may be configured such that the binding of either antigen to the BTTS is sufficient to trigger activation of the BTTS, e.g., proteolytic cleavage of a cleavage domain of the BTTS, e.g., releasing an intracellular domain of the BTTS. Such a BTTS, capable of being triggered by any of two or more antigens, may find use in the described circuits as a component of a logic gate containing OR functionality. In some instances, a BTTS specific for two different antigens may be referred to as a "two-headed BTTS" or a tandem BTTS (or tanBTTS). For example, in some instances, a synNotch BTTS configured to bind two or more different antigens may be referred to as a tandem SynNotch or tanSynNotch. BTTS specific for multiple antigens will not be limited to only two antigens and may, e.g., be specific for and/or triggered by more than two antigens, including e.g., three or more, four or more, five or more, etc.

Methods of Making

The present disclosure further includes methods of making the nucleic acids, circuits, and cells employed in the herein described methods. In making the subject nucleic acids and circuits, and components thereof, any convenient methods of nucleic acid manipulation, modification and amplification (e.g., collectively referred to as "cloning") may be employed. In making the subject cells, containing the nucleic acids encoding the described circuits, convenient methods of transfection, transduction, culture, etc., may be employed.

A nucleotide sequence encoding all or a portion of the components of a circuit of the present disclosure can be present in an expression vector and/or a cloning vector. Where a subject circuit or component thereof is split between two or more separate polypeptides, nucleotide sequences encoding the two or more polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adenoassociated virus (see, e.g., Ali et al., Hum Gene Ther 9:81 86, 1998. Flannery et al., PNAS 94:6916 6921, 1997; Bennett et al., Invest Opthalmol Vis Sci 38:2857 2863, 1997; Jomary et al., Gene Ther 4:683 690, 1997. Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding a circuit or component thereof of the present disclosure will in some embodiments be DNA or RNA, e.g., in vitro synthesized DNA, recombinant DNA, in vitro synthesized RNA, recombinant RNA, etc. Methods for in vitro synthesis of DNA/RNA are known in the art; any known method can be used to synthesize DNA/RNA comprising a desired sequence. Methods for introducing DNA/RNA into a host cell are known in the art. Introducing DNA/RNA into a host cell can be carried out in vitro or ex vivo or in vivo. For example, a host cell (e.g., an NK cell, a cytotoxic T lymphocyte, etc.) can be transduced, transfected or electroporated in vitro or ex vivo with DNA/RNA comprising a nucleotide sequence encoding all or a portion of a circuit of the present disclosure.

Methods of the instant disclosure may further include culturing a cell genetically modified to encode a circuit of the instant disclosure including but not limited to e.g., culturing the cell prior to administration, culturing the cell in vitro or ex vivo (e.g., the presence or absence of one or more antigens), etc. Any convenient method of cell culture may be employed whereas such methods will vary based on various factors including but not limited to e.g., the type of cell being cultured, the intended use of the cell (e.g., whether the cell is cultured for research or therapeutic purposes), etc. In some instances, methods of the instant disclosure may further include common processes of cell culture including but not limited to e.g., seeding cell cultures, feeding cell cultures, passaging cell cultures, splitting cell cultures, analyzing cell cultures, treating cell cultures with a drug, harvesting cell cultures, etc.

Methods of the instant disclosure may, in some instances, further include receiving and/or collecting cells that are used in the subject methods. In some instances, cells are collected from a subject. Collecting cells from a subject may include obtaining a tissue sample from the subject and enriching, isolating and/or propagating the cells from the tissue sample. Isolation and/or enrichment of cells may be performed using any convenient method including e.g., isolation/enrichment by culture (e.g., adherent culture, suspension culture, etc.), cell sorting (e.g., FACS, microfluidics, etc.), and the like. Cells may be collected from any convenient cellular tissue sample including but not limited to e.g., blood (including e.g., peripheral blood, cord blood, etc.), bone marrow, a biopsy, a skin sample, a cheek swab, etc. In some instances, cells are received from a source including e.g., a blood bank, tissue bank, etc. Received cells may have been previously isolated or may be received as part of a tissue sample thus isolation/enrichment may be performed after receiving the cells and prior to use. In certain instances, received cells may be non-primary cells including e.g., cells of a cultured cell line. Suitable cells for use in the herein described methods are further detailed herein.

Nucleic Acids

As summarized above, the present disclosure provides nucleic acids encoding a circuit for treating a subject for a heterogeneous EGFRvIII(−) GBM and components thereof. The subject nucleic acids may include, e.g., a sequence encoding a BTTS specific for a priming antigen, including e.g., a priming antigen specific-BTTS specific for one or more of IL13RA2, IL13RA1, Neuroligin, NRXN1, PTPRZ1, NRCAM, CDH10, PCDHGC5, CD70, CSPG5, BCAN, GRM3, CRB1, GAP43, ATP1B2, MOG1, and/or PTPRZ1-MET, and a sequence encoding a targeting antigen-specific therapeutic, including e.g., a targeting antigen-specific therapeutic specific for one or more of EphA2, EphA3, IL13R (e.g., IL13RA1 or IL13RA2), EGFR and/or ERBB2.

Such nucleic acids may be configured such that the sequence encoding the targeting antigen-specific therapeutic is operably linked to a regulatory sequence responsive to activation of the BTTS. Provided are nucleic acids encoding essentially any circuit employing trans-targeting utilizing recognition of a priming antigen expressed on a first EGFRvIII(−) GBM cell to target a second EGFRvIII(−) GBM cell expressing a targeting antigen, including but not limited to those circuits specifically described herein. Encompassed are isolated nucleic acids encoding the subject circuits as well as various configurations containing such nucleic acids, such as vectors, e.g., expression cassettes, recombinant expression vectors, viral vectors, and the like.

Recombinant expression vectors of the present disclosure include those comprising one or more of the described nucleic acids. A nucleic acid comprising a nucleotide sequence encoding all or a portion of the components of a circuit of the present disclosure will in some embodiments be DNA, including, e.g., a recombinant expression vector. A nucleic acid comprising a nucleotide sequence encoding all or a portion of the components of a circuit of the present disclosure will in some embodiments be RNA, e.g., in vitro synthesized RNA.

As summarized above, in some instances, the subject circuits may make use of an encoding nucleic acid (e.g., a nucleic acid encoding a BTTS or an antigen-specific therapeutic) that is operably linked to a regulatory sequence such as a transcriptional control element (e.g., a promoter; an enhancer, etc.). In some cases, the transcriptional control element is inducible. In some cases, the transcriptional control element is constitutive. In some cases, the promoters are functional in eukaryotic cells. In some cases, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter, herpes simplex virus thymidine kinase promoter; early and late SV40 promoters; promoter present in long terminal repeats from a retrovirus; mouse metallothionein-I promoter, and various art-known tissue specific promoters.

In some instances, a transcriptional control element of a herein described nucleic acid may include a cis-acting regulatory sequence. Any suitable cis-acting regulatory sequence may find use in the herein described nucleic acids. For example, in some instances a cis-acting regulatory sequence may be or include an upstream activating sequence or upstream activation sequence (UAS). In some instances, a UAS of a herein described nucleic acid may be a Gal4 responsive UAS.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is an immune cell promoter such as a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Nal. Acad. Sci. USA* 90: 7739; and Marodon et al. (2003) Blood 101:3416. As another example, a CD8 gene promoter can be used. NK cell-specific expression can be achieved by use of an *Ncrl* (p46) promoter; see, e.g., Eckelhart et al. (2011) *Blood* 117:1565.

In some instances, an immune cell specific promoter of a nucleic acid of the present disclosure may be a promoter of a B29 gene promoter, a CD14 gene promoter, a CD43 gene promoter, a CD45 gene promoter, a CD68 gene promoter, a IFN-β gene promoter, a WASP gene promoter, a T-cell receptor β-chain gene promoter, a V9 γ (TRGV9) gene promoter, a V2 δ (TRDV2) gene promoter, and the like.

In some cases, a nucleic acid comprising a nucleotide sequence encoding a circuit of the present disclosure, or one or more components thereof, is a recombinant expression vector or is included in a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding a circuit of the present disclosure, or one or more components thereof, is a recombinant lentivirus vector. In some cases, a nucleic acid comprising a nucleotide sequence encoding a circuit of the present disclosure, or one or more components thereof, is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson. PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239. Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

In some instances, nucleic acids of the present disclosure may have a single sequence encoding two or more polypeptides where expression of the two or more polypeptides is made possible by the presence of a sequence element between the individual coding regions that facilitates separate expression of the individual polypeptides. Such sequence elements, may be referred to herein as bicistronic-facilitating sequences, where the presence of a bicistronic-facilitating sequence between two coding regions makes possible the expression of a separate polypeptide from each coding region present in a single nucleic acid sequence. In some instances, a nucleic acid may contain two coding regions encoding two polypeptides present in a single nucleic acid with a bicistronic-facilitating sequence between the coding regions. Any suitable method for separate expression of multiple individual polypeptides from a single nucleic acid sequence may be employed and, similarly, any suitable method of bicistronic expression may be employed.

In some instances, a bicistronic-facilitating sequence may allow for the expression of two polypeptides from a single nucleic acid sequence that are temporarily joined by a cleavable linking polypeptide. In such instances, a bicistronic-facilitating sequence may include one or more encoded peptide cleavage sites. Suitable peptide cleavage sites include those of self-cleaving peptides as well as those cleaved by a separate enzyme. In some instances, a peptide cleavage site of a bicistronic-facilitating sequence may include a furin cleavage site (i.e., the bicistronic-facilitating sequence may encode a furin cleavage site).

In some instances, the bicistronic-facilitating sequence may encode a self-cleaving peptide sequence. Useful self-cleaving peptide sequences include but are not limited to e.g., peptide 2A sequences, including but not limited to e.g., the T2A sequence.

In some instances, a bicistronic-facilitating sequence may include one or more spacer encoding sequences. Spacer encoding sequences generally encode an amino acid spacer, also referred to in some instances as a peptide tag. Useful spacer encoding sequences include but are not limited to e.g., V5 peptide encoding sequences, including those sequences encoding a V5 peptide tag.

Multi- or bicistronic expression of multiple coding sequences from a single nucleic acid sequence may make use of but is not limited to those methods employing furin cleavage, T2A, and V5 peptide tag sequences. For example, in some instances, an internal ribosome entry site (IRES) based system may be employed. Any suitable method of bicistronic expression may be employed including but not limited to e.g., those described in Yang et al. (2008) Gene Therapy. 15(21):1411-1423; Martin et al. (2006) BMC Biotechnology. 6:4; the disclosures of which are incorporated herein by reference in their entirety.

Cells

As summarized above, the present disclosure also provides immune cells. Immune cells of the present disclosure include those that contain one or more of the described nucleic acids, expression vectors, etc., encoding a described circuit. Immune cells of the present disclosure include mammalian immune cells including e.g., those that are genetically modified to produce the components of a circuit of the present disclosure or to which a nucleic acid, as described above, has been otherwise introduced. In some instances, the subject immune cells have been transduced with one or more nucleic acids and/or expression vectors to express one or more components of a circuit of the present disclosure.

Suitable mammalian immune cells include primary cells and immortalized cell lines. Suitable mammalian cell lines include human cell lines, non-human primate cell lines, rodent (e.g., mouse, rat) cell lines, and the like. In some instances, the cell is not an immortalized cell line, but is instead a cell (e.g., a primary cell) obtained from an individual. For example, in some cases, the cell is an immune cell, immune cell progenitor or immune stem cell obtained from an individual. As an example, the cell is a lymphoid cell, e.g., a lymphocyte, or progenitor thereof, obtained from an individual. As another example, the cell is a cytotoxic cell, or progenitor thereof, obtained from an individual. As another example, the cell is a stem cell or progenitor cell obtained from an individual.

As used herein, the term "immune cells" generally includes white blood cells (leukocytes) which are derived from hematopoietic stem cells (HSC) produced in the bone marrow. "Immune cells" includes, e.g., lymphoid cells, i.e., lymphocytes (T cells, B cells, natural killer (NK) cells), and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses. "B cell" includes mature and immature cells of the B cell lineage including e.g., cells that express CD19 such as Pre B cells, Immature B cells, Mature B cells, Memory B cells and plasmablasts. Immune cells also include B cell progenitors such as Pro B cells and B cell lineage derivatives such as plasma cells.

Immune cells encoding a circuit of the present disclosure may be generated by any convenient method. Nucleic acids encoding one or more components of a subject circuit may be stably or transiently introduced into the subject immune cell, including where the subject nucleic acids are present only temporarily, maintained extrachromosomally, or integrated into the host genome. Introduction of the subject nucleic acids and/or genetic modification of the subject immune cell can be carried out in vivo, in vitro, or ex vivo.

In some cases, the introduction of the subject nucleic acids and/or genetic modification is carried out ex vivo. For example, a T lymphocyte, a stem cell, or an NK cell is obtained from an individual; and the cell obtained from the individual is modified to express components of a circuit of the present disclosure. The modified cell can thus be redirected to one or more antigens of choice, as defined by the one or more antigen binding domains present on the introduced components of the circuit. In some cases, the modified cell is modulated ex vivo. In other cases, the cell is introduced into (e.g., the individual from whom the cell was obtained) and/or already present in an individual; and the cell is modulated in vivo, e.g., by administering a nucleic acid or vector to the individual in vivo.

Circuits

As summarized above, the present disclosure also provides circuits encoded by nucleic acid sequences, also referred to in some instances as molecular circuits. Such circuits may, in some instances, be present and/or configured in expression vectors and/or expression cassettes. The subject nucleic acids of the present circuits may, in some instances, be contained within a vector, including e.g., viral and non-viral vectors. Such circuits may, in some instances, be present in cells, such as immune cells, or may be introduced into cells by various means, including e.g., through the use of a viral vector. Cells may, in some instances, be genetically modified to encode a subject circuit, where such modification may be effectively permanent (e.g., integrated) or transient as desired.

Encoded components of the circuits of the present disclosure will generally include at a minimum at least one encoded BTTS and at least one encoded antigen-specific therapeutic. Circuits of the present disclosure integrate multiple inputs, where such inputs include antigens, such as one or more priming antigens (e.g., IL13RA2, IL13RA1, Neuroligin, NRXN1, PTPRZ1, NRCAM, CDH10, PCDHGC5, CD70, CSPG5. BCAN, GRM3, CRB1, GAP43, ATP1B2, MOG1, PTPRZ1-MET and/or combinations thereof), one or more targeting antigens (e.g., EphA2. EphA3, IL13R (e.g., IL13RA1 or IL13RA2), EGFR, ERBB2 and/or combinations thereof) and the like. The expression of a component of a circuit of the present disclosure may be dependent upon the state (i.e., active/inactive state) of another component of the circuit. For example, the expression of an antigen-specific therapeutic may be dependent upon the activation of a BTTS, where the BTTS is activated by binding to an antigen for which the BTTS is specific. In some instances, dependency of one component of the circuit on another may be mediated by a regulatory sequence. For example, a sequence encoding a second component of a circuit may be operably linked to a regulatory sequence that is responsive to the activation of a first component of the circuit, thus linking the expression of the second component to the activation of the first.

The use of a BTTS in a circuit of the present disclosure facilitates the linking of expression and/or activity to molecular binding events. Systems involving binding-triggered transcriptional switches, and components thereof, have been described in PCT Publication No. WO 2016/138034, US Patent Application Pub. No. US 2016-0264665 A1 and issued U.S. Pat. Nos. 9,670,281 and 9,834.608; the disclosures of which are incorporated by reference herein in their entirety.

Circuits of the present disclosure may be configured in various ways. In some instances, the independent activities and/or induced expression of two or more polypeptides or domains of a single polypeptide may generate a logic gated circuit. Such logic gated circuits may include but are not limited to e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates). In some instances, useful circuits may further include IF/THEN gates.

"AND" gates include where two or more inputs are required for propagation of a signal. For example, in some instances, an AND gate allows signaling through a first input of a first polypeptide or a first polypeptide domain and a second input dependent upon the output of the first input. In an AND gate two inputs, e.g., two antigens, are required for signaling through the circuit.

"OR" gates include where either of two or more inputs may allow for the propagation of a signal. For example, in some instances, an OR gate allows signaling through binding of either of two different antigens. In an OR gate any one input, e.g., either of two antigens, may induce the signaling output of the circuit. In one embodiment, an OR gate may be achieved through the use of two separate molecules or constructs. In another embodiment, an OR gate may be achieved through the use of a single construct that recognizes two antigens, including e.g., a BTTS or an antigen-specific therapeutic (e.g., a CAR or TCR) having two different antigen binding domains that each bind a different antigen and each binding event can independently propagate the signal (e.g., induce expression of a downstream component of the circuit, activate an immune cell, etc.).

"NOT" gates include where an input is capable of preventing the propagation of a signal. For example, in some instances, a NOT gate inhibits signaling through a circuit of the instant disclosure. In one embodiment, a NOT gate may prevent the expression of a component of a circuit, or activation of a particular component of the circuit, e.g., a CAR or a TCR.

"IF/THEN" gates include where the output of the gate depends upon a first input. For example, in some instances. IF a first input is present THEN signaling may proceed through a second input, and where the first input is absent signaling may not proceed. A non-limiting example of a circuit that includes an IF/THEN gate is a circuit having at least two receptors where the first receptor, in response to an input, induces expression of the second receptor, which has some output in response to a second input. As such, IF the first input of the first receptor is present, THEN the second receptor is expressed and signaling can proceed through the second receptor via the second input to produce the output. IF/THEN gates may or may not include an OR component (e.g., a receptor with OR functionality).

Figure 4:
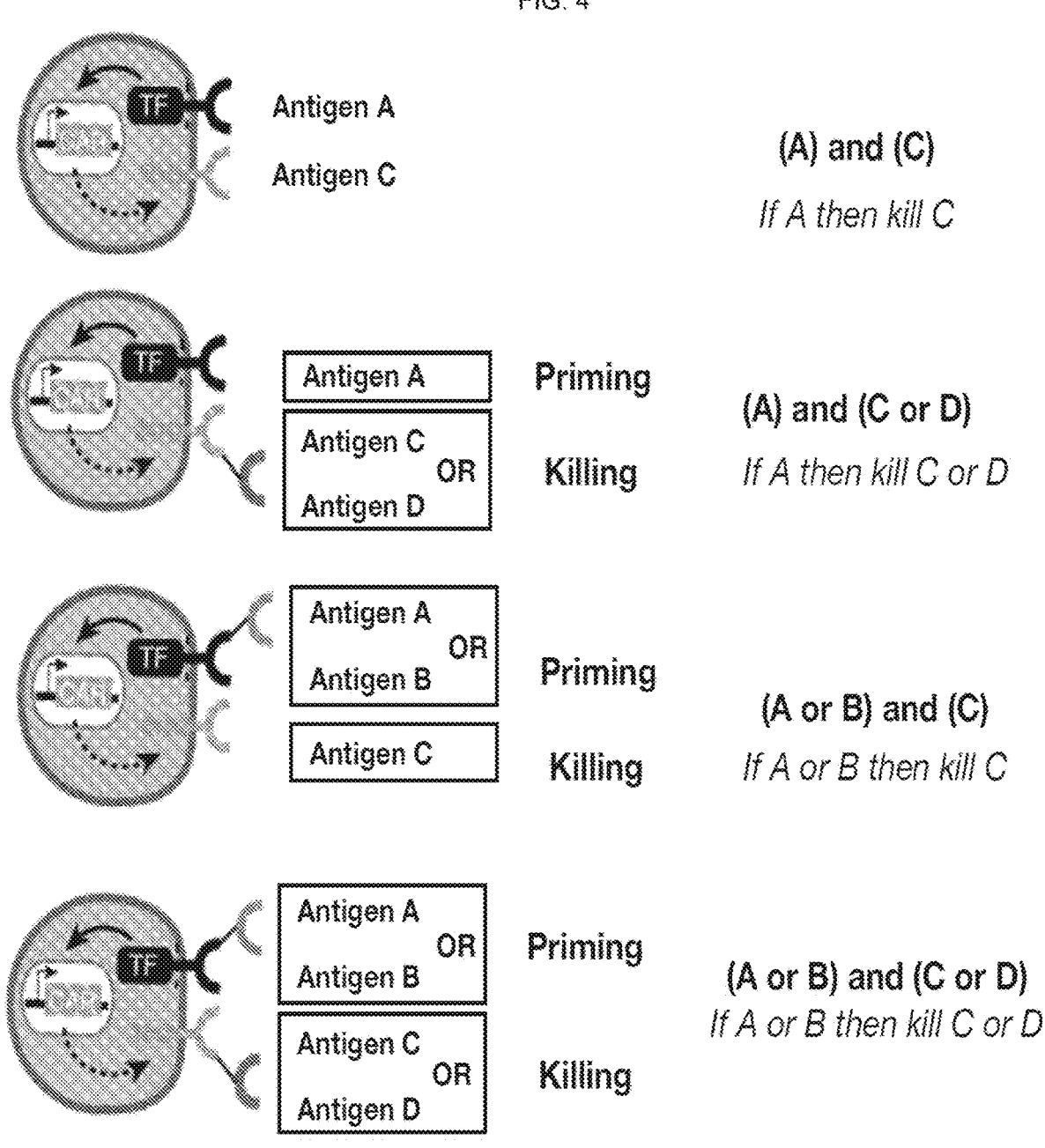
FIG. 4 depicts cells that contain IF/THEN circuits with and without OR gate functionality at the relevant binding triggered transcriptional switch, the antigen-specific therapeutic, or both.

Non-limiting examples of IF/THEN gates, including examples with OR functionality, are depicted in FIG. 4. The circuit depicted in the first (top) cell of FIG. 4 includes a BTTS responsive to antigen "A" and an antigen-specific therapeutic that binds antigen "C". Note that although the antigen-specific therapeutic is depicted as a CAR, the disclosure is not so limited and other antigen-specific therapeutics may be readily substituted. In the first (top) circuit, IF antigen A is present THEN cell killing is induced based on the presence of antigen C.

In various embodiments, OR functionality may be employed, including where one or more components of a subject circuit include an OR functionality. As shown in the second, third and fourth cells depicted in FIG. 4. OR functionality may be provided by a BTTS, an antigen-specific therapeutic, or both having specificity for, and being triggered or activated by, two or more antigens.

For example, in the second (from the top) cell depicted in FIG. 4, a circuit is employed that includes a BTTS responsive to antigen "A" and an antigen-specific therapeutic that binds to, and is activated by, antigen "C" or antigen "D". In such a circuit. IF antigen A is present THEN cell killing is induced based on the presence of antigen C OR antigen D. Note that killing of cells expressing antigen C and antigen D may also be induced, as well as killing of cells that express antigen C alone or antigen D alone.

In the third (from the top) cell depicted in FIG. 4, a circuit is employed that includes a BTTS responsive to antigen "A" or antigen "B" and an antigen-specific therapeutic that binds to, and is activated by, antigen "C". In such a circuit, IF antigen A OR antigen B is present THEN cell killing is induced based on the presence of antigen C. Note that the immune cells encoding the subject circuit may be primed to kill by a cell expressing only antigen A, only antigen B, or both antigens A and B.

In the fourth (bottom) cell depicted in FIG. 4, a circuit is employed that includes a BTTS responsive to antigen "A" or antigen "B" and an antigen-specific therapeutic that binds to, and is activated by, antigen "C" or antigen "D". In such a circuit, IF antigen A OR antigen B is present THEN cell killing is induced based on the presence of antigen C or antigen D. Note that the immune cells encoding the subject circuit may be primed to kill by a cell expressing only antigen A, only antigen B, or both antigens A and B. Also note that killing of cells expressing antigen C and antigen D may also be induced, as well as killing of cells that express antigen C alone or antigen D alone.

In some instances, the use of OR functionality may have certain advantages. For example, the above described circuits having OR gate functionality (i.e., the second, third and fourth cells of FIG. 4) and variations thereof provide resistance to escape and improved efficacy for heterogeneous cancers because, without being bound by theory, to escape a cancer (or tumor) would need to contain, or evolve/produce, a cell that does not express either of the two priming and/or killing antigens.

In some instances, multiple antigen binding domains present on a BTTS or antigen-specific therapeutic may provide an OR gate capability to the herein described molecular circuits. For example, in some instances, a BTTS having two different antigen binding domains may be responsive to a first antigen (e.g., a first priming antigen) OR a second antigen (e.g., a second priming antigen). In some instances, an antigen-specific therapeutic (e.g., a CAR, a TCR, etc.) having two different antigen binding domains may be responsive to a first antigen (e.g., a first targeting antigen) OR a second antigen (e.g., a second targeting antigen).

In some instances, such OR gates may be combined with other gates, including an AND gate. For example, a nucleic acid encoding an OR-gate antigen-specific therapeutic having two different antigen binding domains may be operably linked to a promoter that is responsive to a BTTS which is responsive to a priming antigen. As such, upon binding the priming antigen, the BTTS drives expression of the antigen-specific therapeutic which is responsive to two different antigens, resulting in an AND-OR gate.

In some instances, OR gates may find use in the circuits of the present disclosure to produce an OR gate for two or more targeting antigens (or two or more killing antigens). For example, in some instances, the circuit may be configured such that the cell genetically modified with the circuit contains a nucleic acid sequence encoding an antigen-specific therapeutic that binds to a first targeting/killing antigen or a second targeting/killing antigen expressed by a targeted cancer cell (or expressed by two different targeted cancer cells), thereby producing a cell that is activated, e.g., activated for cell killing, by either the first targeting/killing antigen or the second targeting/killing antigen. In some instances, a circuit of the present disclosure may include nucleic acid sequence encoding a first antigen-specific therapeutic and second antigen-specific therapeutic that each bind to a different targeting/killing antigen. Useful antigens in such dual antigen-specific therapeutic OR gates include but are not limited to e.g., EphA2. EphA3, IL13R (e.g., IL13RA1 or IL13RA2), EGFR and ERBB2.

In some instances, an OR gate may be employed to allow for simultaneous targeting of cells both in trans and in cis. For example, in some instances, a second killing antigen to which an OR gate is directed may be expressed by the priming cell. In some instances, an OR gate for targeting may be employed to target two antigens that that are not mutually exclusively expressed within cells of the EGFRvIII (–) GBM (i.e., GBM cells with overlapping, but not completely coincident, expression of two antigens). For example, in some instances, the second killing antigen to which an OR gate is targeted may be expressed by a subpopulation of GBM cells that also expresses the first killing antigen. However, the cancer may further include a subpopulation of cells that express the second killing antigen but not the first killing antigen. In some instances, the first and second killing antigens employed in an OR gate will not have overlapping expression in the cells of the heterogeneous cancer. As such, in some instances, the second killing antigen may be expressed by a cell of the heterogeneous EGFRvIII(–) GBM other than the priming cell and/or the GBM cell that expresses the first killing antigen.

Kits

The present disclosure provides a kit for carrying out a method as described herein and/or constructing one or more circuits, components thereof, nucleic acids encoding a circuit or a component thereof, etc. In some cases, a subject kit comprises a vector, e.g., an expression vector or a delivery vector, comprising a nucleotide sequence encoding a circuit of the present disclosure or one or more portions thereof. Delivery vectors may be provided in a delivery device or may be provided separately, e.g., as a kit that includes the delivery vector and the delivery device as separate components of the kit.

In some cases, a subject kit comprises a cell, e.g., a host cell or host cell line, that is or is to be genetically modified with a nucleic acid comprising nucleotide sequence encoding a circuit of the present disclosure or a portion thereof. In some cases, a subject kit comprises a cell, e.g., a host cell, that is or is to be genetically modified with a recombinant expression vector comprising a nucleotide sequence encoding a circuit of the present disclosure. Kit components can be in the same container, or in separate containers.

Any of the above-described kits can further include one or more additional reagents, where such additional reagents can be selected from: a dilution buffer, a reconstitution solution; a wash buffer, a control reagent; a control expression vector, a nucleic acid encoding a negative control (e.g., a circuit that lacks the one or more critical elements); a nucleic acid encoding a positive control polypeptide; and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of treating a subject for an epidermal growth factor receptor variant 111 (EGFRvIII) negative glioblastoma, the method comprising:

administering to the subject an immune cell genetically modified with:

(a) a nucleic acid sequence encoding a binding triggered transcriptional switch (BTTS) that binds to a priming antigen expressed by the EGFRvIII negative glioblastoma;

(b) a nucleic acid sequence encoding an antigen-specific therapeutic that binds to a killing antigen expressed by the EGFRvIII negative glioblastoma; and (c) a regulatory sequence operably linked to (b) that is responsive to the BTTS;

wherein binding of the BTTS to the priming antigen activates expression of the antigen-specific therapeutic which binds the killing antigen thereby inducing killing of glioblastoma cells expressing the killing antigen.

2a. The method according to aspect 1, wherein the priming antigen is selected from the group consisting of: Interleukin-13 receptor subunit alpha-2 (IL13RA2). Interleukin-13 receptor subunit alpha-1 (IL13RA1), Neuroligin, Neurexin-1-beta (NRXN1), Receptor-type tyrosine-protein phosphatase zeta (PTPRZ1), Neuronal cell adhesion molecule (NRCAM). Cadherin-10 (CDH10) and Protocadherin gamma-C5 (PCDHGC5).

2b. The method according to aspect 1, wherein the priming antigen is selected from the group consisting of: CD70 antigen (CD70), Chondroitin sulfate proteoglycan 5 (CSPG5), Brevican core protein (BCAN), Metabotropic glutamate receptor 3 (GRM3), Protein crumbs homolog 1 (CRB1), Neuromodulin (GAP43), Sodium/potassium-transporting ATPase subunit beta-2 (ATP1B2), Ran-binding protein MOG1 (MOG1), and a Receptor-type tyrosine-protein phosphatase zeta-Hepatocyte growth factor receptor fusion (PTPRZ1-MET).

3a. The method according to any of the preceding aspects, wherein less than 95% of the cells of the EGFRvIII negative glioblastoma express the priming antigen.

3b. The method according to any of the preceding aspects, wherein less than 90% of the cells of the EGFRvIII negative glioblastoma express the priming antigen.

4. The method according to any of the preceding aspects, wherein less than 50% of the cells of the EGFRvIII negative glioblastoma express the priming antigen.

5. The method according to any of the preceding aspects, wherein the killing antigen is expressed by all cells of the glioblastoma.

6. The method according to any of the preceding aspects, wherein the killing antigen is expressed by non-glioblastoma cells in the subject.

7. The method according to any of the preceding aspects, wherein the killing antigen is selected from the group consisting of: Ephrin type-A receptor 2 (EphA2). Ephrin type-A receptor 3 (EphA3), Interleukin-13 receptor subunit alpha-1 (IL13RA1), Interleukin-13 receptor subunit alpha-2 (IL13RA2). Epidermal growth factor receptor (EGFR) and erb-b2 receptor tyrosine kinase 2 (ERBB2).

8. The method according to any of the preceding aspects, wherein the antigen-specific therapeutic, when expressed, is expressed on the surface of the immune cell.

9. The method according to aspect 8, wherein the antigen-specific therapeutic is a chimeric antigen receptor (CAR) or a T cell receptor (TCR).

10. The method according to any of aspects 1 to 7, wherein the antigen-specific therapeutic, when expressed, is secreted by the immune cell.

11. The method according to aspect 10, wherein the antigen-specific therapeutic is a chimeric bispecific binding member.

12. The method according to aspect 11, wherein the chimeric bispecific binding member is a TCR-targeted bispecific binding agent.

13. The method according to aspect 11 or aspect 12, wherein the chimeric bispecific binding member is specific for the killing antigen and a protein expressed on the surface of an immune cell.

14. The method according to any of the preceding aspects, wherein the antigen-specific therapeutic comprises a bio-orthogonal adapter molecule.

15. The method according to aspect 14, wherein the bio-orthogonal adapter molecule is bound by an extracellular domain of a switchable CAR.

16. The method according to aspect 14 or aspect 15, wherein the bio-orthogonal adapter molecule binds an antigen selected from the group consisting of: EphA2. EphA3, IL13RA1. IL12RA2, EGFR and ERBB2.

17. The method according to any of the preceding aspects, wherein the antigen-specific therapeutic binds two different killing antigens expressed by the glioblastoma.

18. The method according to aspect 17, wherein the two different killing antigens are expressed by glioblastoma cells expressing the priming antigen.

19. The method according to aspect 17, wherein the two different killing antigens are expressed by glioblastoma cells not expressing the priming antigen.

20. The method according to aspect 17, wherein the two different killing antigens are expressed in the same glioblastoma cells.

21. The method according to aspect 17, wherein the two different killing antigens are expressed in different glioblastoma cells.

22. The method according to any of aspects 17 to 21, wherein the two different killing antigens are selected from the group consisting of: EphA2, EphA3, IL13RA1, IL12RA2, EGFR and ERBB2.

23. The method according to any of the preceding aspects, wherein the BTTS binds two different priming antigens.

24. The method according to aspect 23, wherein the two different priming antigens are selected from the group consisting of: IL13RA2, IL13RA1. Neuroligin, NRXN1, PTPRZ1, NRCAM, CDH10, PCDHGC5, CD70, CSPG5, BCAN, GRM3, CRB1, GAP43, ATP1B2, MOG1, and PTPRZ1-MET.

25. The method according to any of the preceding aspects, wherein the immune cell is further genetically modified with a nucleic acid sequence encoding a second antigen-specific therapeutic that binds to a second killing antigen expressed by the glioblastoma.

26. The method according to aspect 25, wherein the second killing antigen is expressed by glioblastoma cells expressing the priming antigen.

27. The method according to aspect 25, wherein the second killing antigen is expressed by glioblastoma cells not expressing the priming antigen.

28. The method according to any of aspects 25 to 27, wherein the second killing antigen is expressed by glioblastoma cells expressing the first killing antigen.

29. The method according to any of aspects 25 to 28, wherein the second killing antigen is selected from the group consisting of: EphA2. EphA3, IL13R, EGFR and ERBB2.

30. The method according to any of aspects 25 to 29, wherein the second killing antigen is expressed by all cells of the glioblastoma.

31. The method according to any of aspects 25 to 30, wherein the second killing antigen is expressed by non-glioblastoma cells in the subject.

32. The method according to any of the preceding aspects, wherein the BTTS is a SynNotch polypeptide.

33. The method according to any of the preceding aspects, wherein the immune cell is a myeloid cell.

34. The method according to any of aspects 1 to 32, wherein the immune cell is a lymphoid cell.

35. The method according to aspect 34, wherein the lymphoid cell is selected from the group consisting of: a T lymphocyte, a B lymphocyte and a Natural Killer cell.

36. The method according to any of the preceding aspects, wherein the method further comprises identifying that the glioblastoma is EGFRvIII negative.

37. The method according to any of the preceding aspects, wherein the method further comprises identifying that the glioblastoma comprises cells that express the killing antigen.

38. The method according to aspect 36 or aspect 37, wherein the identifying comprises assaying cellular expression of EGFRvIII, the killing antigen or both in a sample of the glioblastoma obtained from the subject.

39. The method according to aspect 38, wherein the sample is a biopsy.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g, amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min. minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Treatment of EGFRvIII(−)
Glioblastoma Using Prime/Kill Circuit

Amplification of the epidermal growth factor receptor (EGFR) gene is the most frequent genetic change associated with glioblastoma (GBM), which results in overexpression of the transmembrane tyrosine kinase receptor, EGFR. GBM showing amplified EGFR frequently overexpresses the receptor variant III (EGFRvIII). Certain forms of GBM, however, do not display EGFRvIII expression. Despite a lack of EGFRvIII expression, at the cellular level EGFRvIII (−) GBM tumors are nonetheless frequently heterogeneous.

No known single antigen, which could potentially be targeted in GBM, is absolutely specific and homogeneously present in all GBM tumor cells. Also, many antigens that could potentially be targeted in GBM are also expressed in other normal tissues. Thus, even combining two or more independently targeted antigens in EGFRvIII(−) GBM would either still not be expected to be completely effective (i.e., not all cells of the GBM would be targeted) or be expected to yield toxic cross-reactivity (i.e., non-cancerous bystander cells/tissues would also be targeted).

In this example, a novel approach to use the targeting specificity of two or more antigens in EGFRvIII(−) tumors was developed. The method employs a priming antigen expressed by the GBM to prime the expression of a second molecule that targets and kills tumor cells based on a second antigen (or combination of antigens). This approach is effective even if the second antigen(s) are not perfectly tumor-specific. Without being bound by theory, in essence this approach harnesses two or more imperfect antigens to develop a combinatorial T cell that shows both high selectivity and is insensitive to antigen expression heterogeneity.

Circuits were designed in which a therapeutic cell is primed based on a priming antigen, inducing expression of a killing agent (e.g., a CAR, a BiTE, etc.) that then kills based on a homogenous antigen (see FIG. 1A). In other words, in this example, the circuit is primed based on a cancer-specific but heterogeneous antigen, but is then activated to kill in a "killing zone" around the priming antigen cells by targeting a homogeneously expressed antigen (see FIG. 1B). The killing zone size is tunable based on a variety of factors such as, but not limited to, killing receptor (e.g., CAR) stability or the use of extracellular diffusible agents as killing payload (e.g. bispecific adapters) (see FIG. 1C and FIG. 1D).

As depicted in FIG. 1A-1D, priming of therapeutic cells, such as a cell engineered with a circuit as depicted in FIG. 1A, creates a killing zone around the therapeutic cell such that tumor cells expressing the killing antigen are targeted even when such tumor cells do not express the priming antigen. An example of this scenario is schematized in FIG. 1B, which shows a therapeutic cell, shown as a T cell, primed by a tumor heterogeneously expressing the priming antigen. The primed therapeutic cell targets and kills tumor cells in its proximity, including those expressing the killing antigen but not the priming antigen. In this way, cells in the proximity of the tumor prime the therapeutic cells to create a killing zone around the primed cell, leading to effective clearance of all tumor cells.

The size of the killing zone may be widened or tuned as desired, e.g., through the use of a diffusible payload, stability of the therapeutic employed (e.g., CAR stability). For example, FIG. 1C depicts a circuit that includes a synNotch binding-triggered transcriptional switch configured to bind a priming antigen (circle) which induces expression of a diffusible CAR head. The diffusible CAR head is specific for a killing antigen (triangle) and is bound by a portion of a CAR, referred to in FIG. 1C as a "split CAR", that includes the intracellular signaling components necessary for T cell activation upon antigen binding. Accordingly, by diffusing away from the primed cell, the diffusible CAR head serves to mediate antigen recognition and target cell killing in more distant T cells that express the split CAR, but do not necessarily express the diffusible CAR head.

As depicted in the left panel of FIG. 1D, by using a circuit that includes a synNotch driving expression of a traditional CAR (i.e., a single continuous chain having an antigen recognition domain and the intracellular signaling components), the killing radius of non-priming cancer cells that express the killing antigen is kept relatively short. In comparison, as depicted in the right panel of FIG. 1D, by using a circuit that includes a diffusible orthogonal bispecific adapter, such as a diffusible CAR head, the killing radius of non-priming cancer cells that express the killing antigen is widened. Accordingly, the desired killing radius may be controlled as desired. In some instances, e.g., a short killing radius may be desired where a killing antigen is expressed in non-cancerous tissues (i.e., bystander tissues). In other instances, a wide killing radius may be desired where, e.g., relatively few cells expressing the priming antigen are present diffusely throughout a cancerous area of a subject.

Example 2: Testing SynNotch Receptor Antigen Targets for Glioblastoma

In this example, circuits employing synNotch receptors to various target antigens were tested in T cells for targeting of GBM. Specifically, human primary CD8+ T cells were engineered with a selection of synNotch receptor antigen targets for Glioblastoma, namely EGFRvIII, NRCAM, EphA2, EphA3, IL13Ra2, Her2, EGFR, and PTRZ1, and the corresponding response elements controlling expression of a reporter (eGFP). These CD8+ synNotch AND-gate T cells are configured to first sense the respective surface GBM antigen via the synNotch receptor, and then, if detected, express the eGFP reporter. Primary CD8+ synNotch AND-gate T cells were cultured alone ("T cell only") or co-cultured with GBM cells ("T cell+GBM6). The GMB cells employed were GBM6 cells, a human patient-derived xeno-graft (PDX) adult glioblastoma cell line. FIG. 2A provides histograms of reporter (eGFP) expression levels, showing synNotch receptor activation for the various antigens.

FIG. 2B provides quantification related to FIG. 2A. Specifically, quantification of CD8+ synNotch AND-gate primary T cell activation minus the basal leakage of GFP expression that is independent of synNotch receptor binding to its target antigen. These data show the various levels of activation of the construct tested with the particular GBM6 cell line, demonstrating that various antigens may be targeted, e.g., depending on the desired level of activation sensitivity and/or the presence and/or level of the particular antigen in target cell populations.

Circuits employing IL13Ra2 and EphA2 antigen targeting were further evaluated. Specifically, human primary CD8+ T cells were engineered with the anti-IL13Ra2 synNotch receptor or anti-EphA2 synNotch receptor with the corresponding response elements controlling expression of the anti-IL13Ra2/EphA2-4-1BBz CAR GFP receptor. These CD8+ synNotch AND-gate T cells first sense surface EphA2 or IL13Ra2, respectively, via the synNotch receptor, and then the cells express the anti-IL13Ra2/EphA2 CAR and are primed for activation in response to CAR antigen binding. FIG. 3A provides forward (FSC) and side scatter (SSC) flow cytometry plots after 24 hr co-culture of CD8+ synNotch AND-gate primary T cells with a primary GBM cell line (SF11411). The target SF11411 are indicated in the circular gates. As shown by a reduction of cells in the SF11411 gate in the IL13Ra2 synNotch and EphA2 synNotch panels as compared to the untransduced controls, the synNotch AND-gate T cells targeting either antigen resulted in killing of the targeted SF11411 GBM cells.

Expression of the CAR, as measured via the GFP reporter, was assessed in the presence ("T cell+SF11411") and absence ("T cell only") of target SF11411 GBM cells. FIG. 3B provides histograms of a-IL13Ra2/EphA2 CAR GFP receptor expression level in these contexts, showing that the CAR is expressed, and/or expression is increased, when the engineered T cells are co-cultured with SF11411 as compared to when the engineered T cells are cultured alone.

Figure 3C:
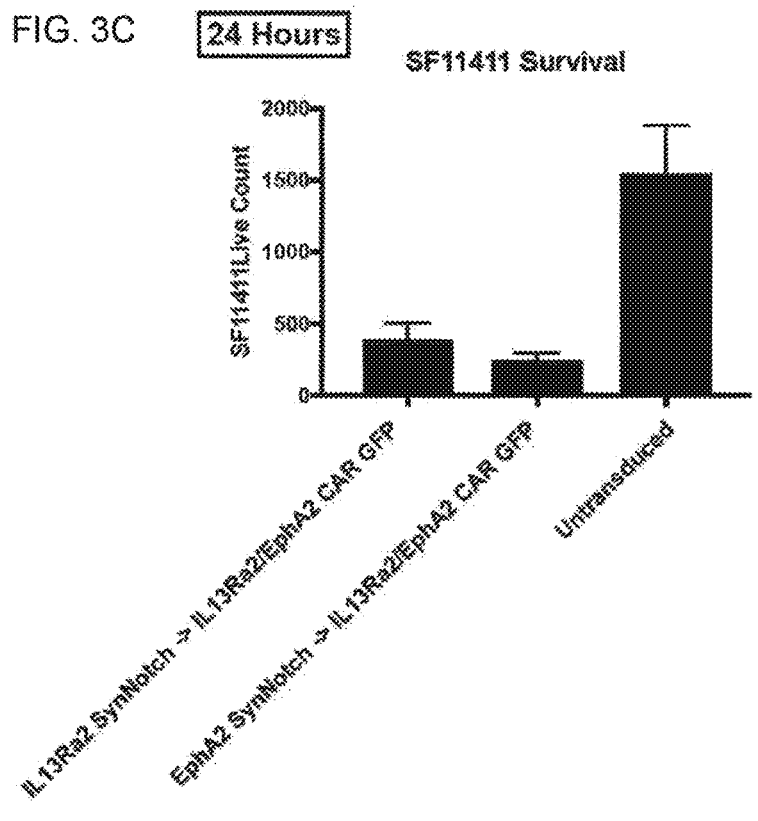
Figure 3D:
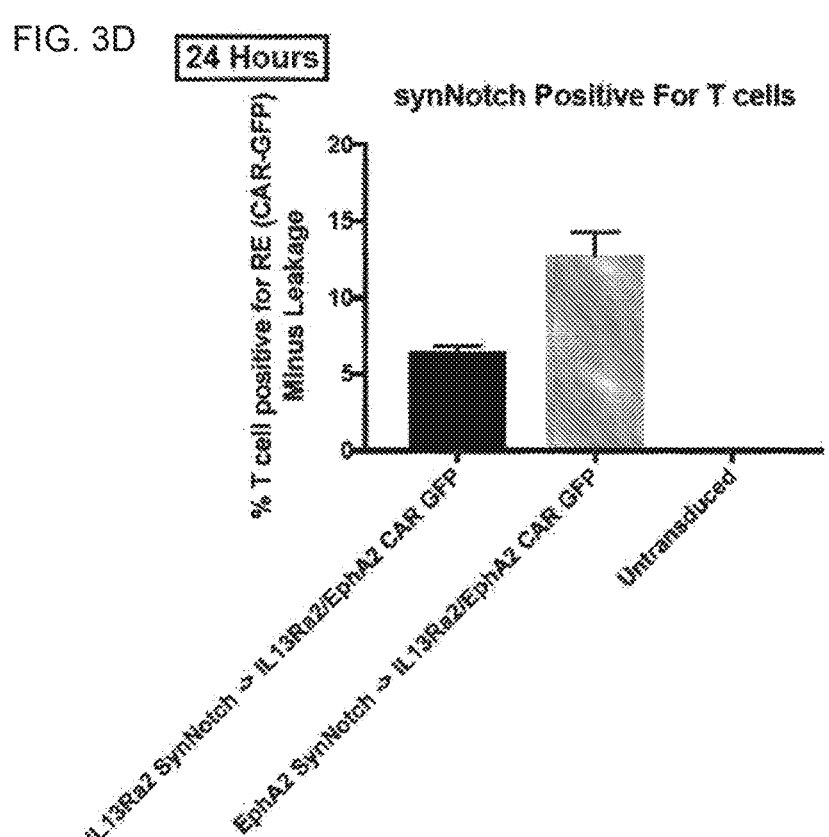

FIG. 3C provides quantification related to FIG. 3A, specifically showing quantification of replicate CD8+ synNotch AND-gate primary T cell cytotoxicity induced by the IL13Ra2 synNotch and EphA2 synNotch circuits. FIG. 3D provides quantification related to FIG. 3B, specifically showing quantification of CD8+ synNotch AND-gate primary T cell activation minus the basal leakage of GFP expression that is independent of synNotch receptor binding to its target antigen. As can be seen in the data, expression of the encoded CAR is induced in the presence of GBM target cells (SF11411).

Collectively, these data demonstrate that various antigens may be employed in the subject circuits to drive expression of an antigen-specific therapeutic, such as a CAR, in the presence of target GBM cells. In addition, the target therapeutic is essentially not expressed in the absence of the target GBM cells due to the absence of the antigen which induces expression of the therapeutic. Correspondingly, these data demonstrate targeted and effective killing of GBM cells the circuits described herein.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A method of treating a subject for a glioblastoma, the method comprising:
administering to the subject an immune cell genetically modified with:
(a) a nucleic acid sequence encoding a binding triggered transcriptional switch (BTTS) that binds to a priming antigen that is tissue-specifically expressed in the central nervous system;
(b) a nucleic acid sequence encoding a tandem chimeric antigen receptor (CAR) or T cell receptor (TCR) that has a first binding domain that recognizes Ephrin type-A receptor 2 (EphA2) and a second binding domain that recognizes Interleukin-13 receptor subunit alpha-2 (IL13RA2); and
(c) a regulatory sequence operably linked to (b) that is responsive to the BTTS;
wherein binding of the BTTS to the priming antigen activates expression of the tandem CAR or TCR, which binds EphA2 and/or IL13RA2 in the glioblastoma and induces killing of glioblastoma cells.

2. The method of claim 1, wherein the glioblastoma is an epidermal growth factor receptor variant III (EGFRvIII) negative glioblastoma.

3. The method of claim 1, wherein the glioblastoma is an epidermal growth factor receptor variant III (EGFRvIII) positive glioblastoma.

4. The method of claim 1, wherein the priming antigen is CDH10, NRCAM, PTPRZ1, or BCAN.

5. The method of claim 1, wherein the nucleic acid sequence of (b) encodes the tandem CAR.

6. The method of claim 1, wherein the immune cell is a cytotoxic T cell.

7. The method of claim 1, wherein the subject is a human subject.

8. The method of claim 1, wherein the BTTS comprises:
an extracellular domain that comprises a binding domain that recognizes the priming antigen;
a transmembrane domain;
one or more protease cleavage domains; and
a transcriptional activator,
wherein binding of the extracellular domain to the priming antigen results in cleavage of the BTTS at the one or more protease cleavage domains to release the transcriptional activator, and wherein the released transcriptional activator binds to the regulatory sequence of (c) and activates expression of the tandem chimeric antigen receptor (CAR) or T cell receptor (TCR).

* * * * *

SEQUENCE LISTING

```
Sequence total quantity: 73
SEQ ID NO: 1              moltype = AA   length = 943
FEATURE                  Location/Qualifiers
source                   1..943
                         mol_type = protein
                         organism = Homo sapiens
SEQUENCE: 1
MRPSGTAGAA FLALLAALCP ASRALEEKKG NYVVTDHGSC VRACGADSYE MEEDGVRKCK   60
KCEGPCRKVC NGIGIGEFKD SLSINATNIK HFKNCTSISG DLHILPVAFR GDSFTHTPPL  120
DPQELDILKT VKEITGFLLI QAWPENRTDL HAFENLEIIR GRTKQHGQFS LAVVSLNITS  180
LGLRSLKEIS DGDVIISGNK NLCYANTINW KKLFGTSGQK TKIISNRGEN SCKATGQVCH  240
ALCSPEGCWG PEPRDCVSCR NVSRGRECVD KCNLLEGEPR EFVENSECIQ CHPCLPQAM   300
NITCTGRGPD NYIQCAHYID GPHCVKTCPA GVMGENNTLV WKYADAGHVC HLCHPNCTYG  360
CTGPGLEGCP TNGPKIPSIA TGMVGALLLL LVVALGIGLF MRRRHIVRKR TLRRLLQERE  420
LVEPLTPSGE APNQALLRIL KETEFKKIKV LGSGAFGTVY KGLWIPEGEK VKIPVAIKEL  480
REATSPKANK EILDEAYVMA SVDNPHVCRL LGICLTSTVQ LITQLMPFGC LLDYVREHKD  540
NIGSQYLLNW CVQIAKGMNY LEDRRLVHRD LAARNVLVKT PQHVKITDFG LAKLLGAEEK  600
EYHAEGGKVP IKWMALESIL HRIYTHQSDV WSYGVTVWEL MTFGSKPYDG IPASEISSIL  660
EKGERLPQPP ICTIDVYMIM VKCWMIDADS RPKFRELIIE FSKMARDPQR YLVIQGDERM  720
HLPSPTDSNF YRALMDEEDM DDVVDADEYL IPQQGFFSSP STSRTPLLSS LSATSNNSTV  780
ACIDRNGLQS CPIKEDSFLQ RYSSDPTGAL TEDSIDDTFL PVPEYINQSV PKRPAGSVQN  840
PVYHNQPLNP APSRDPHYQD PHSTAVGNPE YLNTVQPTCV NSTFDSPAHW AQKGSHQISL  900
DNPDYQQDFF PKEAKPNGIF KGSTAENAEY LRVAPQSSEF IGA                    943

SEQ ID NO: 2              moltype = AA   length = 380
FEATURE                  Location/Qualifiers
source                   1..380
                         mol_type = protein
                         organism = Homo sapiens
SEQUENCE: 2
MAFVCLAIGC LYTFLISTTF GCTSSSDTEI KVNPPQDFEI VDPGYLGYLY LQWQPPLSLD   60
HFKECTVEYE LKYRNIGSET WKTIITKNLH YKDGFDLNKG IEAKIHTLLP WQCTNGSEVQ  120
SSWAETTYWI SPQGIPETKV QDMDCVYYNW QYLLCSWKPG IGVLLDTNYN LFYWYEGLDH  180
ALQCVDYIKA DGQNIGCRFP YLEASDYKDF YICVNGSSEN KPIRSSYFTF QLQNIVKPLP  240
PVYLTFTRES SCEIKLKWSI PLGPIPARCF DYEIEIREDD TTLVTATVEN ETYTLKTTNE  300
TRQLCFVVRS KVNIYCSDDG IWSEWSDKQC WEGEDLSKKT LLRFWLPFGF ILILVIFVTG  360
LLLRKPNTYP KMIPEFFCDT                                              380

SEQ ID NO: 3              moltype = AA   length = 427
FEATURE                  Location/Qualifiers
source                   1..427
                         mol_type = protein
                         organism = Homo sapiens
SEQUENCE: 3
MEWPARLCGL WALLLCAGGG GGGGGAAPTE TQPPVTNLSV SVENLCTVIW TWNPPEGASS   60
NCSLWYFSHF GDKQDKKIAP ETRRSIEVPL NERICLQVGS QCSTNESEKP SILVEKCISP  120
PEGDPESAVT ELQCIWHNLS YMKCSWLPGR NTSPDTNYTL YYWHRSLEKI HQCENIFREG  180
QYFGCSFDLT KVKDSSFEQH SVQIMVKDNA GKIKPSFNIV PLTSRVKPDP PHIKNLSFHN  240
DDLYVQWENP QNFISRCLFY EVEVNNSQTE THNVFYVQEA KCENPEFERN VENTSCFMVP  300
GVLPDTLNTV RIRVKTNKLC YEDDKLWSNW SQEMSIGKKR NSTLYITMLL IVPVIVAGAI  360
IVLLLYLKRL KIIIFPPIPD PGKIFKEMFG DQNDDTLHWK KYDIYEKQTK EETDSVVLIE  420
NLKKASQ                                                            427

SEQ ID NO: 4              moltype = AA   length = 279
FEATURE                  Location/Qualifiers
source                   1..279
                         mol_type = protein
                         organism = Homo sapiens
```

```
SEQUENCE: 4
MEWPARLCGL WALLLCAGGG GGGGGAAPTE TQPPVTNLSV SVENLCTVIW TWNPPEGASS  60
NCSLWYFSHF GDKQDKKIAP ETRRSIEVPL NERICLQVGS QCSTNESEKP SILVEKCISP  120
PEGDPESAVT ELQCIWHNLS YMKCSWLPGR NTSPDTNYTL YYWHRSLEKI HQCENIFREG  180
QYFGCSFDLT KVKDSSFEQH SVQIMVKDNA GKIKPSFNIV PLTSRVKPDP PHIKNLSFHN  240
DDLYVQWENP QNFISRCLFY EVEVNNSQTE THNVFYVRF                         279

SEQ ID NO: 5             moltype = AA  length = 816
FEATURE                  Location/Qualifiers
source                   1..816
                         mol_type = protein
                         organism = Homo sapiens
SEQUENCE: 5
MSRPQGLLWL PLLFTPVCVM LNSNVLLWLT ALAIKFTLID SQAQYPVVNT NYGKIRGLRT  60
PLPNEILGPV EQYLGVPYAS PPTGERRFQP PEPPSSWTGI RNTTQFAAVC PQHLDERSLL  120
HDMLPIWFTA NLDTLMTYVQ DQNEDCLYLN IYVPTEDDIH DQNSKKPVMV YIHGGSYMEG  180
TGNMIDGSIL ASYGNVIVIT INYRLGILGF LSTGDQAAKG NYGLLDQIQA LRWIEENVGA  240
FGGDPKRVTI FGSGAGASCV SLLTLSHYSE GLFQKAIIQS GTALSSWAVN YQPAKYTRIL  300
ADKVGCNMLD TTDMVECLRN KNYKELIQQT ITPATYHIAF GPVIDGDVIP DDPQILMEQG  360
EFLNYDIMLG VNQGEGLKFV DGIVDNEDGV TPNDFDFSVS NFVDNLYGYP EGKDTLRETI  420
KFMYTDWADK ENPETRRKTL VALFTDHQWV APAVATADLH AQYGSPTYFY AFYHHCQSEM  480
KPSWADSAHG DEVPYVFGIP MIGPTELFSC NFSKNDVMLS AVVMTYWTNF AKTGDPNQPV  540
PQDTKFIHTK PNRFEEVAWS KYNPKDQLYL HIGLKPRVRD HYRATKVAFW LELVPHLHNL  600
NEIFQYVSTT TKVPPPDMTS FPYGTRRSPA KIWPTTKRPA ITPANNPKHS KDPHKTGPED  660
TTVLIETKRD YSTELSVTIA VGASLLFLNI LAFAALYYKK DKRRHETHRR PSPQRNTTND  720
IAHIQNEEIM SLQMKQLEHD HECESLQAHD TLRLTCPPDY TLTLRRSPDD IPLMTPNTIT  780
MIPNTLTGMQ PLHTFNTFSG GQNSTNLPHG HSTTRV                           816

SEQ ID NO: 6             moltype = AA  length = 836
FEATURE                  Location/Qualifiers
source                   1..836
                         mol_type = protein
                         organism = Homo sapiens
SEQUENCE: 6
MSRPQGLLWL PLLFTPVCVM LNSNVLLWLT ALAIKFTLID SQAQYPVVNT NYGKIRGLRT  60
PLPNEILGPV EQYLGVPYAS PPTGERRFQP PEPPSSWTGI RNTTQFAAVC PQHLDERSLL  120
HDMLPIWFTA NLDTLMTYVQ DQNEDCLYLN IYVPTEDGAN TKKNADDITS NDRGEDEDIH  180
DQNSKKPVMV YIHGGSYMEG TGNMIDGSIL ASYGNVIVIT INYRLGILGF LSTGDQAAKG  240
NYGLLDQIQA LRWIEENVGA FGGDPKRVTI FGSGAGASCV SLLTLSHYSE GLFQKAIIQS  300
GTALSSWAVN YQPAKYTRIL ADKVGCNMLD TTDMVECLRN KNYKELIQQT ITPATYHIAF  360
GPVIDGDVIP DDPQILMEQG EFLNYDIMLG VNQGEGLKFV DGIVDNEDGV TPNDFDFSVS  420
NFVDNLYGYP EGKDTLRETI KFMYTDWADK ENPETRRKTL VALFTDHQWV APAVATADLH  480
AQYGSPTYFY AFYHHCQSEM KPSWADSAHG DEVPYVFGIP MIGPTELFSC NFSKNDVMLS  540
AVVMTYWTNF AKTGDPNQPV PQDTKFIHTK PNRFEEVAWS KYNPKDQLYL HIGLKPRVRD  600
HYRATKVAFW LELVPHLHNL NEIFQYVSTT TKVPPPDMTS FPYGTRRSPA KIWPTTKRPA  660
ITPANNPKHS KDPHKTGPED TTVLIETKRD YSTELSVTIA VGASLLFLNI LAFAALYYKK  720
DKRRHETHRR PSPQRNTTND IAHIQNEEIM SLQMKQLEHD HECESLQAHD TLRLTCPPDY  780
TLTLRRSPDD IPLMTPNTIT MIPNTLTGMQ PLHTFNTFSG GQNSTNLPHG HSTTRV      836

SEQ ID NO: 7             moltype = AA  length = 816
FEATURE                  Location/Qualifiers
source                   1..816
                         mol_type = protein
                         organism = Homo sapiens
SEQUENCE: 7
MLRPQGLLWL PLLFTSVCVM LNSNVLLWIT ALAIKFTLID SQAQYPVVNT NYGKIQGLRT  60
PLPSEILGPV EQYLGVPYAS PPTGERRFQP PESPSSWTGI RNATQFSAVC PQHLDERFLL  120
HDMLPIWFTT SLDTLMTYVQ DQNEDCLYLN IYVPMEDDIH EQNSKKPVMV YIHGGSYMEG  180
TGNMIDGSIL ASYGNVIVIT INYRLGILGF LSTGDQAAKG NYGLLDQIQA LRWIEENVGA  240
FGGDPKRVTI FGSGAGASCV SLLTLSHYSE GLFQKAIIQS GTALSSWAVN YQPAKYTRIL  300
ADKVGCNMLD TTDMVECLKN KNYKELIQQT ITPATYHIAF GPVIDGDVIP DDPQILMEQG  360
EFLNYDIMLG VNQGEGLKFV DGIVDNEDGV TPNDFDFSVS NFVDNLYGYP EGKDTLRETI  420
KFMYTDWADK ENPETRRKTL VALFTDHQWV APAVATADLH AQYGSPTYFY AFYHHCQSEM  480
KPSWADSAHG DEVPYVFGIP MIGPTELFSC NFSKNDVMLS AVVMTYWTNF AKTGDPNQPV  540
PQDTKFIHTK PNRFEEVAWS KYNPKDQLYL HIGLKPRVRD HYRATKVAFW LELVPHLHNL  600
NEIFQYVSTT TKVPPPDMTS FPYGTRRSPA KIWPTTKRPA ITPANNPKHS KDPHKTGPED  660
TTVLIETKRD YSTELSVTIA VGASLLFLNI LAFAALYYKK DKRRHETHRH PSPQRNTTND  720
ITHIQNEEIM SLQMKQLEHD HECESLQAHD TLRLTCPPDY TLTLRRSPDD IPFMTPNTIT  780
MIPNTLMGMQ PLHTFKTFSG GQNSTNLPHG HSTTRV                           816

SEQ ID NO: 8             moltype = AA  length = 648
FEATURE                  Location/Qualifiers
source                   1..648
                         mol_type = protein
                         organism = Homo sapiens
SEQUENCE: 8
MVYIHGGSYM EGTGNMIDGS ILASYGNVIV ITINYRLGIL GFLSTGDQAA KGNYGLLDQI  60
QALRWIEENV GAFGGDPKRV TIFGSGAGAS CVSLLTLSHY SEGLFQKAII QSGTALSSWA  120
VNYQPAKYTR ILADKVGCNM LDTTDMVECL KNKNYKELIQ QTITPATYHI AFGPVIDGDV  180
```

```
IPDDPQILME QGEFLNYDIM LGVNQGEGLK FVDGIVDNED GVTPNDFDFS VSNFVDNLYG      240
YPEGKDTLRE TIKFMYTDWA DKENPETRRK TLVALFTDHQ WVAPAVATAD LHAQYGSPTY      300
FYAFYHHCQS EMKPSWADSA HGDEVPYVFG IPMIGPTELF SCNFSKNDVM LSAVVMTYWT      360
NFAKTGDPNQ PVPQDTKFIH TKPNRFEEVA WSKYNPKDQL YLHIGLKPRV RDHYRATKVA      420
FWLELVPHLH NLNEIFQYVS TTTKVPPPDM TSFPYGTRRS PAKIWPTTKR PAITPANNPK      480
HSKDPHKTGP EDTTVLIETK RDYSTELSVT IAVGASLLFL NILAFAALYY KKDKRRHETH      540
RHPSPQRNTT NDITHIQNEE IMSLQMKQLE HDHECESLQA HDTLRLTCPP DYTLTLRRSP      600
DDIPFMTPNT ITMIPNTLMG MQPLHTFKTF SGGQNSTNLP HGHSTTRV                   648

SEQ ID NO: 9               moltype = AA  length = 134
FEATURE                    Location/Qualifiers
source                     1..134
                           mol_type = protein
                           organism = Homo sapiens
SEQUENCE: 9
MLPIWFTTSL DTLMTYVQDQ NEDCLYLNIY VPMEDGTNIK RNADDITSND HGEDKDIHEQ      60
NSKKPVMVYI HGGSYMEGTG NMIDGSILAS YGNVIVITIN YRLGILGMQE ARLCGSSKMF      120
NYFKSPFTNL INFF                                                       134

SEQ ID NO: 10              moltype = AA  length = 256
FEATURE                    Location/Qualifiers
source                     1..256
                           mol_type = protein
                           organism = Homo sapiens
SEQUENCE: 10
MLRPQGLLWL PLLFTSVCVM LNSNVLLWIT ALAIKFTLID SQAQYPVVNT NYGKIQGLRT      60
PLPSEILGPV EQYLGVPYAS PPTGERRFQP PESPSSWTGI RNATQFSAVC PQHLDERFLL      120
HDMLPIWFTT SLDTLMTYVQ DQNEDCLYLN IYVPMEDGTN IKRNADDITS NDHGEDKDIH      180
EQNSKKPVMV YIHGGSYMEG TGNMIDGSIL ASYGNVIVIT INYRLGILGM QEARLCGSSK      240
MFNYFKSPFT NLINFF                                                     256

SEQ ID NO: 11              moltype = AA  length = 848
FEATURE                    Location/Qualifiers
source                     1..848
                           mol_type = protein
                           organism = Homo sapiens
SEQUENCE: 11
MWLRLGPPSL SLSPKPTVGR SLCLTLWFLS LALRASTQAP APTVNTHFGK LRGARVPLPS      60
EILGPVDQYL GVPYAAPPIG EKRFLPPEPP PSWSGIRNAT HFPPVCPQNI HTAVPEVMLP      120
VWFTANLDIV ATYIQEPNED CLYLNVYVPT EDVKRISKEC ARKPNKKICR KGGSGAKKQG      180
EDLADNDGDE DEDIRDSGAK PVMVYIHGGS YMEGTGNMID GSILASYGNV IVITLNYRVG      240
VLGFLSTGDQ AAKGNYGLLD QIQALRWVSE NIAFFGGDPR RITVFGSGIG ASCVSLLTLS      300
HHSEGLFQRA IIQSGSALSS WAVNYQPVKY TSLLADKVGC NVLDTVDMVD CLRQKSAKEL      360
VEQDIQPARY HVAFGPVIDG DVIPDDPEIL MEQGEFLNYD IMLGVNQGEG LKFVEGVVDP      420
EDGVSGTDFD YSVSNFVDNL YGYPEGKDTL RETIKFMYTD WADRDNPETR RKTLVALFTD      480
HQWVEPSVVT ADLHARYGSP TYFYAFYHHC QSLMKPAWSD AAHGDEVPYV FGVPMVGPTD      540
LFPCNFSKND VMLSAVVMTY WTNFAKTGDP NKPVPQDTKF IHTKANRFEE VAWSKYNPRD      600
QLYLHIGLKP RVRDHYRATK VAFWKHLVPH LYNLHDMFHY TSTTTKVPPP DTTHSSHITR      660
RPNGKTWSTK RPAISPAYSN ENAQGSWNGD QDAGPLLVEN PRDYSTELSV TIAVGASLLF      720
LNVLAFAALY RKDKRRQEP LRQPSPQRGA GAPELGAAPE EELAALQLGP THHECEAGPP      780
HDTLRLTALP DYTLTLRRSP DDIPLMTPNT ITMIPNSLVG LQTLHPYNTF AAGFNSTGLP      840
HSHSTTRV                                                              848

SEQ ID NO: 12              moltype = AA  length = 828
FEATURE                    Location/Qualifiers
source                     1..828
                           mol_type = protein
                           organism = Homo sapiens
SEQUENCE: 12
MWLRLGPPSL SLSPKPTVGR SLCLTLWFLS LALRASTQAP APTVNTHFGK LRGARVPLPS      60
EILGPVDQYL GVPYAAPPIG EKRFLPPEPP PSWSGIRNAT HFPPVCPQNI HTAVPEVMLP      120
VWFTANLDIV ATYIQEPNED CLYLNVYVPT EDGSGAKKQG EDLADNDGDE DEDIRDSGAK      180
PVMVYIHGGS YMEGTGNMID GSILASYGNV IVITLNYRVG VLGFLSTGDQ AAKGNYGLLD      240
QIQALRWVSE NIAFFGGDPR RITVFGSGIG ASCVSLLTLS HHSEGLFQRA IIQSGSALSS      300
WAVNYQPVKY TSLLADKVGC NVLDTVDMVD CLRQKSAKEL VEQDIQPARY HVAFGPVIDG      360
DVIPDDPEIL MEQGEFLNYD IMLGVNQGEG LKFVEGVVDP EDGVSGTDFD YSVSNFVDNL      420
YGYPEGKDTL RETIKFMYTD WADRDNPETR RKTLVALFTD HQWVEPSVVT ADLHARYGSP      480
TYFYAFYHHC QSLMKPAWSD AAHGDEVPYV FGVPMVGPTD LFPCNFSKND VMLSAVVMTY      540
WTNFAKTGDP NKPVPQDTKF IHTKANRFEE VAWSKYNPRD QLYLHIGLKP RVRDHYRATK      600
VAFWKHLVPH LYNLHDMFHY TSTTTKVPPP DTTHSSHITR RPNGKTWSTK RPAISPAYSN      660
ENAQGSWNGD QDAGPLLVEN PRDYSTELSV TIAVGASLLF LNVLAFAALY RKDKRRQEP      720
LRQPSPQRGA GAPELGAAPE EELAALQLGP THHECEAGPP HDTLRLTALP DYTLTLRRSP      780
DDIPLMTPNT ITMIPNSLVG LQTLHPYNTF AAGFNSTGLP HSHSTTRV                   828

SEQ ID NO: 13              moltype = AA  length = 808
FEATURE                    Location/Qualifiers
source                     1..808
                           mol_type = protein
                           organism = Homo sapiens
```

```
SEQUENCE: 13
MWLRLGPPSL SLSPKPTVGR SLCLTLWFLS LALRASTQAP APTVNTHFGK LRGARVPLPS   60
EILGPVDQYL GVPYAAPPIG EKRFLPPEPP PSWSGIRNAT HFPPVCPQNI HTAVPEVMLP  120
VWFTANLDIV ATYIQEPNED CLYLNVYVPT EDDIRDSGAK PVMVYIHGGS YMEGTGNMID  180
GSILASYGNV IVITLNYRVG VLGFLSTGDQ AAKGNYGLLD QIQALRWVSE NIAFFGGDPR  240
RITVFGSGIG ASCVSLLTLS HHSEGLFQRA IIQSGSALSS WAVNYQPVKY TSLLADKVGC  300
NVLDTVDMVD CLRQKSAKEL VEQDIQPARY HVAFGPVIDG DVIPDDPEIL MEQGEFLNYD  360
IMLGVNQGEG LKFVEGVVDP EDGVSGTDFD YSVSNFVDNL YGYPEGKDTL RETIKFMYTD  420
WADRDNPETR RKTLVALFTD HQWVEPSVVT ADLHARYGSP TYFYAFYHHC QSLMKPAWSD  480
AAHGDEVPYV FGVPMVGPTD LFPCNFSKND VMLSAVVMTY WTNFAKTGDP NKPVPQDTKF  540
IHTKANRFEE VAWSKYNPRD QLYLHIGLKP RVRDHYRATK VAFWKHLVPH LYNLHDMFHY  600
TSTTTKVPPP DTTHSSHITR RPNGKTWSTK RPAISPAYSN ENAQGSWNGD QDAGPLLVEN  660
PRDYSTELSV TIAVGASLLF LNVLAFAALY YRKDKRRQEP LRQPSPQRGA GAPELGAAPE  720
EELAALQLGP THHECEAGPP HDTLRLTALP DYTLTLRRSP DDIPLMTPNT ITMIPNSLVG  780
LQTLHPYNTF AAGFNSTGLP HSHSTTRV                                     808

SEQ ID NO: 14        moltype = AA  length = 472
FEATURE              Location/Qualifiers
source               1..472
                     mol_type = protein
                     organism = Homo sapiens
SEQUENCE: 14
MYQRMLRCGA ELGSPGGGGG GGGGGGAGGR LALLWIVPLT LSGLLGVAWG ASSLGAHHIH   60
HFHGSSKHHS VPIAIYRSPA SLRGGHAGTT YIFSKGGGQI TYKWPPNDRP STRADRLAIG  120
FSTVQKEAVL VRVDSSSGLG DYLELHIHQG KIGVKFNVGT DDIAIEESNA IINDGKYHVV  180
RFTRSGGNAT LQVDSWPVIE RYPAGNNDNE RLAIARQRIP YLGRVVDNL LLDKGRQLTI  240
FNSQATIIIG GKEQGQPFQG QLSGLYYNGL KVLNMAAEND ANIAIVGNVR LVGEVPSSMT  300
TESTATAMQS EMSTSIMETT TTLATSTARR GKPPTKEPIS QTTDDILVAS AECPSDDEDI  360
DPCEPSSGGL ANPTRAGGRE PYPGSAEVIR ESSSTTGMVV GIVAAAALCI LILLYAMYKY  420
RNRDEGSYHV DESRNYISNS AQSNGAVVKE KQPSSAKSSN KNKKNKDKEY YV           472

SEQ ID NO: 15        moltype = AA  length = 442
FEATURE              Location/Qualifiers
source               1..442
                     mol_type = protein
                     organism = Homo sapiens
SEQUENCE: 15
MYQRMLRCGA ELGSPGGGGG GGGGGGAGGR LALLWIVPLT LSGLLGVAWG ASSLGAHHIH   60
HFHGSSKHHS VPIAIYRSPA SLRGGHAGTT YIFSKGGGQI TYKWPPNDRP STRADRLAIG  120
FSTVQKEAVL VRVDSSSGLG DYLELHIHQG KIGVKFNVGT DDIAIEESNA IINDGKYHVV  180
RFTRSGGNAT LQVDSWPVIE RYPAGRQLTI FNSQATIIIG GKEQGQPFQG QLSGLYYNGL  240
KVLNMAAEND ANIAIVGNVR LVGEVPSSMT TESTATAMQS EMSTSIMETT TTLATSTARR  300
GKPPTKEPIS QTTDDILVAS AECPSDDEDI DPCEPSSGGL ANPTRAGGRE PYPGSAEVIR  360
ESSSTTGMVV GIVAAAALCI LILLYAMYKY RNRDEGSYHV DESRNYISNS AQSNGAVVKE  420
KQPSSAKSSN KNKKNKDKEY YV                                           442

SEQ ID NO: 16        moltype = AA  length = 1477
FEATURE              Location/Qualifiers
source               1..1477
                     mol_type = protein
                     organism = Homo sapiens
SEQUENCE: 16
MGTALLQRGG CFLLCLSLLL LGCWAELGSG LEFPGAEGQW TRFPKWNACC ESEMSFQLKT   60
RSARGLVLYF DDEGFCDFLE LILTRGGRLQ LSFSIFCAEP ATLLADTPVN DGAWHSVRIR  120
RQFRNTTLFI DQVEAKWVEV KSKRRDMTVF SGLFVGGLPP ELRAAALKLT LASVREREPF  180
KGWIRDVRVN SSQVLPVDSG EVKLDDEPPN SGGGSPCEAG EEGEGGVCLN GGVCSVVDDQ  240
AVCDCSRTGF RGKDCSQEDN NVEGLAHLMM GDQGKSKGKE EYIATFKGSE YFCYDLSQNP  300
IQSSSDEITL SFKTLQRNGL MLHTGKSADY VNLALKNGAV SLVINLGSGA FEALVEPVNG  360
KFNDNAWHDV KVTRNLRQHS GIGHAMVTIS VDGILTTTGY TQEDYTMLGS DDFFYVGGSP  420
STADLPGSPV SNNFMGCLKE VVYKNNDVRL ELSRLAKQGD PKMKIHGVVA FKCENVATLD  480
PITFETPESF ISLPKWNAKK TGSISFDFRT TEPNGLILFS HGKPRHQKDA KHPQMIKVDF  540
FAIEMLDGHL YLLLDMGSGT IKIKALLKKV NDGEWYHVDF QRDGRSGTIS VNTLRTPYTA  600
PGESEILDLD DELYLGGLPE NKAGLVFPTE VWTALLNYGY VGCIRDLFID GQSKDIRQMA  660
EVQSTAGVKP SCSKETAKPC LSNPCKNNGM CRDGWNRYVC DCSGTGYLGR SCEREATVLS  720
YDGSMFMKIQ LPVVMHTEAE DVSLRFRSQR AYGILMATTS RDSADTLRLE LDAGRVKLTV  780
NLDCIRINCN SSKGPETLFA GYNLNDNEWH TVRVVRRGKS LKLTVDDQQA MTGQMAGDHT  840
RLEFHNIETG IITERRYLSS VPSNFIGHLQ SLTFNGMAYI DLCKNGDIDY CELNARFGFR  900
NIIADPVTFK TKSSYVALAT LQAYTSMHLF FQFKTTSLDG LILYNSGDGN DFIVVELVKG  960
YLHYVFDLGN GANLIKGSSN KPLNDNQWHN VMISRDTSNL HTVKIDTKIT TQITAGARNL 1020
DLKSDLYIGG VAKETYKSLP KLVHAKEGFQ GCLASVDLNG RLPDLISDAL FCNGQIERGC 1080
EGPSTTCQED SCSNQGVCLQ QWDGFSCDCS MTSFSGPLCN DPGTTYIFSK GGGQITYKWP 1140
PNDRPSTRAD RLAIGFSTVQ KEAVLVRVDS SSGLGDYLEL HIHQGKIGVK FNVGTDDIAI 1200
EESNAIINDG KYHVVRFTRS GGNATLQVDS WPVIERYPAG RQLTIFNSQA TIIIGGKEQG 1260
QPFQGQLSGL YYNGLKVLNM AAENDANIAI VGNVRLVGEV PSSMTTESTA TAMQSEMSTS 1320
IMETTTTLAT STARRGKPPT KEPISQTTDD ILVASAECPS DDEDIDPCEP SSGGLANPTR 1380
AGGREPYPGS AEVIRESSST TGMVVGIVAA AALCILILLY AMYKYRNRDE GSYHVDESRN 1440
YISNSAQSNG AVVKEKQPSS AKSSNKNKKN KDKEYYV                          1477

SEQ ID NO: 17        moltype = AA  length = 1496
```

```
FEATURE              Location/Qualifiers
source               1..1496
                     mol_type = protein
                     organism = Homo sapiens
SEQUENCE: 17
MGTALLQRGG CFLLCLSLLL LGCWAELGSG LEFPGAEGQW TRFPKWNACC ESEMSFQLKT    60
RSARGLVLYF DDEGFCDFLE LILTRGGRLQ LSFSIFCAEP ATLLADTPVN DGAWHSVRIR   120
RQFRNTTLFI DQVEAKWVEV KSKRRDMTVF SGLFVGGLPP ELRAAALKLT LASVREREPF   180
KGWIRDVRVN SSQVLPVDSG EVKLDDEPPN SGGGSPCEAG EEGEGGVCLN GGVCSVVDDQ   240
AVCDCSRTGF RGKDCSQEDN NVEGLAHLMM GDQGKSKGKE EYIATFKGSE YFCYDLSQNP   300
IQSSSDEITL SFKTLQRNGL MLHTGKSADY VNLALKNGAV SLVINLGSGA FEALVEPVNG   360
KFNDNAWHDV KVTRNLRQVT ISVDGILTTT GYTQEDYTML GSDDFFYVGG SPSTADLPGS   420
PVSNNFMGCL KEVVYKNNDV RLELSRLAKQ GDPKMKIHGV VAFKCENVAT LDPITFETPE   480
SFISLPKWNA KKTGSISFDF RTTEPNGLIL FSHGKPRHQK DAKHPQMIKV DFFAIEMLDG   540
HLYLLLDMGS GTIKIKALLK KVNDGEWYHV DFQRDGRSGT ISVNTLRTPY TAPGESEILD   600
LDDELYLGGL PENKAGLVFP TEVWTALLNY GYVGCIRDLF IDGQSKDIRQ MAEVQSTAGV   660
KPSCSKETAK PCLSNPCKNN GMCRDGWNRY VCDCSGTGYL GRSCEREATV LSYDGSMFMK   720
IQLPVVMHTE AEDVSLRFRS QRAYGILMAT TSRDSADTLR LELDAGRVKL TVNLDCIRIN   780
CNSSKGPETL FAGYNLNDNE WHTVRVVRRG KSLKLTVDDQ QAMTGQMAGD HTRLEFHNIE   840
TGIITERRYL SSVPSNFIGH LQSLTFNGMA YIDLCKNGDI DYCELNARFG FRNIIADPVT   900
FKTKSSYVAL ATLQAYTSMH LFFQFKTTSL DGLILYNSGD GNDFIVVELV KGYLHYVFDL   960
GNGANLIKGS SNKPLNDNQW HNVMISRDTS NLHTVKIDTK ITTQITAGAR NLDLKSDLYI  1020
GGVAKETYKS LPKLVHAKEG FQGCLASVDL NGRLPDLISD ALFCNGQIER GCEGPSTTCQ  1080
EDSCSNQGVC LQQWDGFSCD CSMTSFSGPL CNDPGTTYIF SKGGGQITYK WPPNDRPSTR  1140
ADRLAIGFST VQKEAVLVRV DSSSGLGDYL ELHIHQGKIG VKFNVGTDDI AIEESNAIIN  1200
DGKYHVVRFT RSGGNATLQV DSWPVIERYP AGNNDNERLA IARQRIPYRL GRVVDEWLLD  1260
KGRQLTIFNS QATIIIGGKE QGQPFQGQLS GLYYNGLKVL NMAAENDANI AIVGNVRLVG  1320
EVPSSMTTES TATAMQSEMS TSIMETTTTL ATSTARRGKP PTKEPISQTT DDILVASAEC  1380
PSDDEDIDPC EPSSANPTRA GGREPYPGSA EVIRESSSTT GMVVGIVAAA ALCILILLYA  1440
MYKYRNRDEG SYHVDESRNY ISNSAQSNGA VVKEKQPSSA KSSNKNKKNK DKEYYV      1496

SEQ ID NO: 18       moltype = AA  length = 1547
FEATURE              Location/Qualifiers
source               1..1547
                     mol_type = protein
                     organism = Homo sapiens
SEQUENCE: 18
MGTALLQRGG CFLLCLSLLL LGCWAELGSG LEFPGAEGQW TRFPKWNACC ESEMSFQLKT    60
RSARGLVLYF DDEGFCDFLE LILTRGGRLQ LSFSIFCAEP ATLLADTPVN DGAWHSVRIR   120
RQFRNTTLFI DQVEAKWVEV KSKRRDMTVF SGLFVGGLPP ELRAAALKLT LASVREREPF   180
KGWIRDVRVN SSQVLPVDSG EVKLDDEPPN SGGGSPCEAG EEGEGGVCLN GGVCSVVDDQ   240
AVCDCSRTGF RGKDCSQEIK FGLQCVLPVL LHDNDQGKYC CINTAKPLTE KDNNVEGLAH   300
LMMGDQGKSK GKEEYIATFK GSEYFCYDLS QNPIQSSSDE ITLSFKTLQR NGLMLHTGKS   360
ADYVNLALKN GAVSLVINLG SGAFEALVEP VNGKFNDNAW HDVKVTRNLR QHSGIGHAMV   420
NKLHCSVTIS VDGILTTTGY TQEDYTMLGS DDFFYVGGSP STADLPGSPV SNNFMGCLKE   480
VVYKNNDVRL ELSRLAKQGD PKMKIHGVVA FKCENVATLD PITFETPESF ISLPKWNAKK   540
TGSISFDFRT TEPNGLILFS HGKPRHQKDA KHPQMIKVDF FAIEMLDGHL YLLLDMGSGT   600
IKIKALLKKV NDGEWYHVDF QRDGRSGTIS VNTLRTPYTA PGESEILDLD DELYLGGLPE   660
NKAGLVFPTE VWTALLNYGY VGCIRDLFID GQSKDIRQMA EVQSTAGVKP SCSKETAKPC   720
LSNPCKNNGM CRDGWNRYVC DCSGTGYLGR SCEREATVLS YDGSMFMKIQ LPVVMHTEAE   780
DVSLRFRSQR AYGILMATTS RDSADTLRLE LDAGRVKLTV NLDCIRINCN SSKGPETLFA   840
GYNLNDNEWH TVRVVRRGKS LKLTVDDQQA MTGQMAGDHT RLEFHNIETG IITERRYLSS   900
VPSNFIGHLQ SLTFNGMAYI DLCKNGDIDY CELNARFGFR NIIADPVTFK TKSSYVALAT   960
LQAYTSMHLF FQFKTTSLDG LILYNSGDGN DFIVVELVKG YLHYVFDLGN GANLIKGSSN  1020
KPLNDNQWHN VMISRDTSNL HTVKIDTKIT TQITAGARNL DLKSDLYIGG VAKETYKSLP  1080
KLVHAKEGFQ GCLASVDLNG RLPDLISDAL FCNGQIERGC EGPSTTCQED SCSNQGVCLQ  1140
QWDGFSCDCS MTSFSGPLCN DPGTTYIFSK GGGQITYKWP PNDRPSTRAD RLAIGFSTVQ  1200
KEAVLVRVDS SSGLGDYLEL HIHQGKIGVK FNVGTDDIAI EESNAIINDG KYHVVRFTRS  1260
GGNATLQVDS WPVIERYPAG NNDNERLAIA RQRIPYRLGR VVDEWLLDKG RQLTIFNSQA  1320
TIIIGGKEQG QPFQGQLSGL YYNGLKVLNM AAENDANIAI VGNVRLVGEV PSSMTTESTA  1380
TAMQSEMSTS IMETTTTLAT STARRGKPPT KEPISQTTDD ILVASAECPS DDEDIDPCEP  1440
SSGGLANPTR AGGREPYPGS AEVIRESSST TGMVVGIVAA AALCILILLY AMYKYRNRDE  1500
GSYHVDESRN YISNSAQSNG AVVKEKQPSS AKSSNKNKKN KDKEYYV               1547

SEQ ID NO: 19       moltype = AA  length = 139
FEATURE              Location/Qualifiers
source               1..139
                     mol_type = protein
                     organism = Homo sapiens
SEQUENCE: 19
MDMRWHCENS QTTDDILVAS AECPSDDEDI DPCEPSSANP TRAGGREPYP GSAEVIRESS    60
STTGMVVGIV AAAALCILIL LYAMYKYRNR DEGSYHVDES RNYISNSAQS NGAVVKEKQP   120
SSAKSSNKNK KNKDKEYYV                                                139

SEQ ID NO: 20       moltype = AA  length = 2315
FEATURE              Location/Qualifiers
source               1..2315
                     mol_type = protein
                     organism = Homo sapiens
```

```
SEQUENCE: 20
MRILKRFLAC IQLLCVCRLD WANGYYRQQR KLVEEIGWSY TGALNQKNWG KKYPTCNSPK   60
QSPINIDEDL TQVNVNLKKL KFQGWDKTSL ENTFIHNTGK TVEINLTNDY RVSGGVSEMV  120
FKASKITFHW GKCNMSSDGS EHSLEGQKFP LEMQIYCFDA DRFSSFEEAV KGKGKLRALS  180
ILFEVGTEEN LDFKAIIDGV ESVSRFGKQA ALDPFILLNL LPNSTDKYYI YNGSLTSPPC  240
TDTVDWIVFK DTVSISESQL AVFCEVLTMQ QSGYVMLMDY LQNNFREQQY KFSRQVFSSY  300
TGKEEIHEAV CSSEPENVQA DPENYTSLLV TWERPRVVYD TMIEKFAVLY QQLDGEDQTK  360
HEFLTDGYQD LGAILNNLLP NMSYVLQIVA ICTNGLYGKY SDQLIVDMPT DNPELDLFPE  420
LIGTEEIIKE EEEGKDIEEG AIVNPGRDSA TNQIRKKEPQ ISTTTHYNRI GTKYNEAKTN  480
RSPTRGSEFS GKGDVPNTSL NSTSQPVTKL ATEKDISLTS QTVTELPPHT VEGTSASLND  540
GSKTVLRSPH MNLSGTAESL NTVSITEYEE ESLLTSFKLD TGAEDSSGSS PATSAIPFIS  600
ENISQGYIFS SENPETITYD VLIPESARNA SEDSTSSGSE ESLKDPSMEG NVWFPSSTDI  660
TAQPDVGSGR ESFLQTNYTE IRVDESEKTT KSFSAGPVMS QGPSVTDLEM PHYSTFAYFP  720
TEVTPHAFTP SSRQQDLVST VNVVYSQTTQ PVYNGETPLQ PSYSSEVFPL VTPLLLDNQI  780
LNTTPAASSS DSALHATPVF PSVDVSFESI LSSYDGAPLL PFSSASFSSE LFRHLHTVSQ  840
ILPQVTSATE SDKVPLHASL PVAGGDLLLE PSLAQYSDVL STTHAASETL EFGSESGVLY  900
KTLMFSQVEP PSSDAMMHAR SSGPEPSYAL SDNEGSQHIF TVSYSSAIPV HDSVGVTYQG  960
SLFSGPSHIP IPKSSLITPT ASLLQPTHAL SGDGEWSGAS SDSEFLLPDT DGLTALNISS 1020
PVSVAEFTYT TSVFGDDNKA LSKSEIIYGN ETELQIPSFN EMVYPSESTV MPNMYDNVNK 1080
LNASLQETSV SISSTKGMFP GSLAHTTTKV FDHEISQVPE NNFSVQPTHT VSQASGDTSL 1140
KPVLSANSEP ASSDPASSEM LSPSTQLLFY ETSASFSTEV LLQPSFQASD VDTLLKTVLP 1200
AVPSDPILVE TPKVDKISST MLHLIVSNSA SSENMLHSTS VPVFDVSPTS HMHSASLQGL 1260
TISYASEKYE PVLLKSESSH QVVPSLYSND ELFQTANLEI NQAHPPKGRH VFATPVLSID 1320
EPLNTLINKL IHSDEILTST KSSVTGKVFA GIPTVASDTF VSTDHSVPIG NGHVAITAVS 1380
PHRDGSVTST KLLFPSKATS ELSHSAKSDA GLVGGGEDGD TDDDGDDDDD DRGSDGLSIH 1440
KCMSCSSYRE SQEKVMNDSD THENSLMDQN NPISYSLSEN SEEDNRVTSV SSDSQTGMDR 1500
SPGKSPSANG LSQKHNDGKE ENDIQTGSAL LPLSPESKAW AVLTSDEESG SGQGTSDSLN 1560
ENETSTDFSF ADTNEKDADG ILAAGDSEIT PGFPQSPTSS VTSENSEVFH VSEAEASNSS 1620
HESRIGLAEG LESEKKAVIP LVIVSALTFI CLVVLVGILI YWRKCFQTAH FYLEDSTSPR 1680
VISTPPTPIF PISDDVGAIP IKHFPKHVAD LHASSGFTEE FETLKEFYQE VQSCTVDLGI 1740
TADSSNHPDN KHKNRYINIV AYDHSRVKLA QLAEKDGKLT DYINANYVDG YNRPKAYIAA 1800
QGPLKSTAED FWRMIWEHNV EVIVMITNLV EKGRRKCDQY WPADGSEEYG NFLVTQKSVQ 1860
VLAYYTVRNF TLRNTKIKKG SQKGRPSGRV VTQYHYTQWP DMGVPEYSLP VLTFVRKAAY 1920
AKRHAVGPVV VHCSAGVGRT GTYIVLDSML QQIQHEGTVN IFGFLKHIRS QRNYLVQTEE 1980
QYVFIHDTLV EAILSKETEV LDSHIHAYVN ALLIPGPAGK TKLEKQFQLL SQSNIQQSDY 2040
SAALKQCNRE KNRTSSIIPV ERSRVGISSL SGEGTDYINA SYIMGYYQSN EFIITQHPLL 2100
HTIKDFWRMI WDHNAQLVVM IPDGQNMAED EFVYWPNKDE PINCESFKVT LMAEEHKCLS 2160
NEEKLIIQDF ILEATQDDYV LEVRHFQCPK WPNPDSPISK TFELISVIKE EAANRDGPMI 2220
VHDEHGGVTA GTFCALTTLM HQLEKENSVD VYQVAKMINL MRPGVFADIE QYQFLYKVIL 2280
SLVSTRQEEN PSTSLDSNGA ALPDGNIAES LESLV                           2315

SEQ ID NO: 21                moltype = AA  length = 2308
FEATURE                      Location/Qualifiers
source                       1..2308
                             mol_type = protein
                             organism = Homo sapiens
SEQUENCE: 21
MRILKRFLAC IQLLCVCRLD WANGYYRQQR KLVEEIGWSY TGALNQKNWG KKYPTCNSPK   60
QSPINIDEDL TQVNVNLKKL KFQGWDKTSL ENTFIHNTGK TVEINLTNDY RVSGGVSEMV  120
FKASKITFHW GKCNMSSDGS EHSLEGQKFP LEMQIYCFDA DRFSSFEEAV KGKGKLRALS  180
ILFEVGTEEN LDFKAIIDGV ESVSRFGKQA ALDPFILLNL LPNSTDKYYI YNGSLTSPPC  240
TDTVDWIVFK DTVSISESQL AVFCEVLTMQ QSGYVMLMDY LQNNFREQQY KFSRQVFSSY  300
TGKEEIHEAV CSSEPENVQA DPENYTSLLV TWERPRVVYD TMIEKFAVLY QQLDGEDQTK  360
HEFLTDGYQD LGAILNNLLP NMSYVLQIVA ICTNGLYGKY SDQLIVDMPT DNPELDLFPE  420
LIGTEEIIKE EEEGKDIEEG AIVNPGRDSA TNQIRKKEPQ ISTTTHYNRI GTKYNEAKTN  480
RSPTRGSEFS GKGDVPNTSL NSTSQPVTKL ATEKDISLTS QTVTELPPHT VEGTSASLND  540
GSKTVLRSPH MNLSGTAESL NTVSITEYEE ESLLTSFKLD TGAEDSSGSS PATSAIPFIS  600
ENISQGYIFS SENPETITYD VLIPESARNA SEDSTSSGSE ESLKDPSMEG NVWFPSSTDI  660
TAQPDVGSGR ESFLQTNYTE IRVDESEKTT KSFSAGPVMS QGPSVTDLEM PHYSTFAYFP  720
TEVTPHAFTP SSRQQDLVST VNVVYSQTTQ PVYNGETPLQ PSYSSEVFPL VTPLLLDNQI  780
LNTTPAASSS DSALHATPVF PSVDVSFESI LSSYDGAPLL PFSSASFSSE LFRHLHTVSQ  840
ILPQVTSATE SDKVPLHASL PVAGGDLLLE PSLAQYSDVL STTHAASETL EFGSESGVLY  900
KTLMFSQVEP PSSDAMMHAR SSGPEPSYAL SDNEGSQHIF TVSYSSAIPV HDSVGVTYQG  960
SLFSGPSHIP IPKSSLITPT ASLLQPTHAL SGDGEWSGAS SDSEFLLPDT DGLTALNISS 1020
PVSVAEFTYT TSVFGDDNKA LSKSEIIYGN ETELQIPSFN EMVYPSESTV MPNMYDNVNK 1080
LNASLQETSV SISSTKGMFP GSLAHTTTKV FDHEISQVPE NNFSVQPTHT VSQASGDTSL 1140
KPVLSANSEP ASSDPASSEM LSPSTQLLFY ETSASFSTEV LLQPSFQASD VDTLLKTVLP 1200
AVPSDPILVE TPKVDKISST MLHLIVSNSA SSENMLHSTS VPVFDVSPTS HMHSASLQGL 1260
TISYASEKYE PVLLKSESSH QVVPSLYSND ELFQTANLEI NQAHPPKGRH VFATPVLSID 1320
EPLNTLINKL IHSDEILTST KSSVTGKVFA GIPTVASDTF VSTDHSVPIG NGHVAITAVS 1380
PHRDGSVTST KLLFPSKATS ELSHSAKSDA GLVGGGEDGD TDDDGDDDDD DRGSDGLSIH 1440
KCMSCSSYRE SQEKVMNDSD THENSLMDQN NPISYSLSEN SEEDNRVTSV SSDSQTGMDR 1500
SPGKSPSANG LSQKHNDGKE ENDIQTGSAL LPLSPESKAW AVLTSDEESG SGQGTSDSLN 1560
ENETSTDFSF ADTNEKDADG ILAAGDSEIT PGFPQSPTSS VTSENSEVFH VSEAEASNSS 1620
HESRIGLAEG LESEKKAVIP LVIVSALTFI CLVVLVGILI YWRKCFQTAH FYLEDSTSPR 1680
VISTPPTPIF PISDDVGAIP IKHFPKHVAD LHASSGFTEE FEEVQSCTVD LGITADSSNH 1740
PDNKHKNRYI NIVAYDHSRV KLAQLAEKDG KLTDYINANY VDGYNRPKAY IAAQGPLKST 1800
AEDFWRMIWE HNVEVIVMIT NLVEKGRRKC DQYWPADGSE EYGNFLVTQK SVQVLAYYTV 1860
RNFTLRNTKI KKGSQKGRPS GRVVTQYHYT QWPDMGVPEY SLPVLTFVRK AAYAKRHAVG 1920
```

```
PVVVHCSAGV GRTGTYIVLD SMLQQIQHEG TVNIFGFLKH IRSQRNYLVQ TEEQYVFIHD   1980
TLVEAILSKE TEVLDSHIHA YVNALLIPGP AGKTKLEKQF QLLSQSNIQQ SDYSAALKQC   2040
NREKNRTSSI IPVERSRVGI SSLSGEGTDY INASYIMGYY QSNEFIITQH PLLHTIKDFW   2100
RMIWDHNAQL VVMIPDGQNM AEDEFVYWPN KDEPINCESF KVTLMAEEHK CLSNEEKLII   2160
QDFILEATQD DYVLEVRHFQ CPKWPNPDSP ISKTFELISV IKEEAANRDG PMIVHDEHGG   2220
VTAGTFCALT TLMHQLEKEN SVDVYQVAKM INLMRPGVFA DIEQYQFLYK VILSLVSTRQ   2280
EENPSTSLDS NGAALPDGNI AESLESLV                                     2308

SEQ ID NO: 22            moltype = AA  length = 1448
FEATURE                  Location/Qualifiers
source                   1..1448
                         mol_type = protein
                         organism = Homo sapiens
SEQUENCE: 22
MRILKRFLAC IQLLCVCRLD WANGYYRQQR KLVEEIGWSY TGALNQKNWG KKYPTCNSPK   60
QSPINIDEDL TQVNVNLKKL KFQGWDKTSL ENTFIHNTGK TVEINLTNDY RVSGGVSEMV   120
FKASKITFHW GKCNMSSDGS EHSLEGQKFP LEMQIYCFDA DRFSSFEEAV KGKGKLRALS   180
ILFEVGTEEN LDFKAIIDGV ESVSRFGKQA ALDPFILLNL LPNSTDKYYI YNGSLTSPPC   240
TDTVDWIVFK DTVSISESQL AVFCEVLTMQ QSGYVMLMDY LQNNFREQQY KFSRQVFSSY   300
TGKEEIHEAV CSSEPENVQA DPENYTSLLV TWERPRVVYD TMIEKFAVLY QQLDGEDQTK   360
HEFLTDGYQD LGAILNNLLP NMSYVLQIVA ICTNGLYGKY SDQLIVDMPT DNPELDLFPE   420
LIGTEEIIKE EEEGKDIEEG AIVNPGRDSA TNQIRKKEPQ ISTTTHYNRI GTKYNEAKTN   480
RSPTRGSEFS GKGDVPNTSL NSTSQPVTKL ATEKDISLTS QTVTELPPHT VEGTSASLND   540
GSKTVLRSPH MNLSGTAESL NTVSITEYEE ESLLTSFKLD TGAEDSSGSS PATSAIPFIS   600
ENISQGYIFS SENPETITYD VLIPESARNA SEDSTSSGSE ESLKDPSMEG NVWFPSSTDI   660
TAQPDVGSGR ESFLQTNYTE IRVDESEKTT KSFSAGPVMS QGPSVTDLEM PHYSTFAYFP   720
TEVTPHAFTP SSRQQDLVST VNVVYSQTTQ PVYNEASNSS HESRIGLAEG LESEKKAVIP   780
LVIVSALTFI CLVVLVGILI YWRKCFQTAH FYLEDSTSPR VISTPPTPIF PISDDVGAIP   840
IKHFPKHVAD LHASSGFTEE FEEVQSCTVD LGITADSSNH PDNKHKNRYI NIVAYDHSRV   900
KLAQLAEKDG KLTDYINANY VDGYNRPKAY IAAQGPLKST AEDFWRMIWE HNVEVIVMIT   960
NLVEKGRRKC DQYWPADGSE EYGNFLVTQK SVQVLAYYTV RNFTLRNTKI KKGSQKGRPS   1020
GRVVTQYHYT QWPDMGVPEY SLPVLTFVRK AAYAKRHAVG PVVVHCSAGV GRTGTYIVLD   1080
SMLQQIQHEG TVNIFGFLKH IRSQRNYLVQ TEEQYVFIHD TLVEAILSKE TEVLDSHIHA   1140
YVNALLIPGP AGKTKLEKQF QLLSQSNIQQ SDYSAALKQC NREKNRTSSI IPVERSRVGI   1200
SSLSGEGTDY INASYIMGYY QSNEFIITQH PLLHTIKDFW RMIWDHNAQL VVMIPDGQNM   1260
AEDEFVYWPN KDEPINCESF KVTLMAEEHK CLSNEEKLII QDFILEATQD DYVLEVRHFQ   1320
CPKWPNPDSP ISKTFELISV IKEEAANRDG PMIVHDEHGG VTAGTFCALT TLMHQLEKEN   1380
SVDVYQVAKM INLMRPGVFA DIEQYQFLYK VILSLVSTRQ EENPSTSLDS NGAALPDGNI   1440
AESLESLV                                                          1448

SEQ ID NO: 23            moltype = AA  length = 1304
FEATURE                  Location/Qualifiers
source                   1..1304
                         mol_type = protein
                         organism = Homo sapiens
SEQUENCE: 23
MQLKIMPKKK RLSAGRVPLI LFLCQMISAL EVPLDPKLLE DLVQPPTITQ QSPKDYIIDP   60
RENIVIQCEA KGKPPPSFSW TRNGTHFDID KDPLVTMKPG TGTLIINIMS EGKAETYEGV   120
YQCTARNERG AAVSNNIVVR PSRSPLWTKE KLEPITLQSG QSLVLPCRPP IGLPPPIIFW   180
MDNSFQRLPQ SERVSQGLNG DLYFSNVLPE DTREDYICYA RFNHTQTIQQ KQPISVKVIS   240
VDELNDTIAA NLSDTEFYGA KSSRERPPTF LTPEGNASNK EELRGNVLSL ECIAEGLPTP   300
IIYWAKEDGM LPKNRTVYKN FEKTLQIIHV SEADSGNYQC IAKNALGAIH HTISVRVKAA   360
PYWITAPQNL VLSPGEDGTL ICRANGNPKP RISWLTNGVP IEIAPDDPSR KIDGDTIIFS   420
NVQERSSAVY QCNASNEYGY LLANAFVNVL AEPPRILTPA NTLYQVIANR PALLDCAFFG   480
SPLPTIEWFK GAKGSALHED IYVLHENGTL EIPVAQKDST GTYTCVARNK LGMAKNEVHL   540
EIKDPTWIVK QPEYAVVQRG SMVSFECKVK HDHTLSLTVL WLKDNRELPS DERFTVDKDH   600
LVVADVSDDD SGTYTCVANT TLDSVSASAV LSVVAPTPTP APVYDVPNPP FDLELTDQLD   660
KSVQLSWTPG DDNNSPITKF IIEYEDAMHK PGLWHHQTEV SGTQTTAQLK LSPYVNYSFR   720
VMAVNSIGKS LPSEASEQYL TKASEPDKNP TAVEGLGSEP DNLVITWKPL NGFESNGPGL   780
QYKVSWRQKD GDDEWTSVVV ANVSKYIVSG TPTFVPYLIK VQALNDMGFA PEPAVVMGHS   840
GEDLPMVAPG NVRVNVVNST LAEVHWDPVP LKSIRGHLQG YRIYYWKTQS SSKRNRRHIE   900
KKILTFQGSK THGMLPGLEP FSHYTLNVRV VNGKGEGPAS PDRVFNTPEG VPSAPSSLKI   960
VNPTLDSLTL EWDPPSHPNG ILTEYTLKYQ PINSTHELGP LVDLKIPANK TRWTLKNLNP   1020
STRYKFYFYA QTSAGSGSQI TEEAVTTVDE AGILPPDVGA GKVQAVNPRI SNLTAAAAET   1080
YANISWEYEG PEHVNFYVEY GVAGSKEEWR KEIVNGSRSF FGLKGLMPGT AYKVRVGAVG   1140
DSGFVSSEDV FETGPAMASR QVDIATQGWF IGLMCAVALL ILILLIVCFI RRNKGGKYPV   1200
KEKEDAHADP EIQPMKEDDG TFGEYSDAED HKPLKKGSRT PSDRTVKKED SDDSLVDYGE   1260
GVNGQFNEDG SFIGQYSGKK EKEPAEGNES SEAPSPVNAM NSFV                   1304

SEQ ID NO: 24            moltype = AA  length = 1236
FEATURE                  Location/Qualifiers
source                   1..1236
                         mol_type = protein
                         organism = Homo sapiens
SEQUENCE: 24
MQLKIMPKKK RLSAGRVPLI LFLCQMISAL EVPLDPKLLE DLVQPPTITQ QSPKDYIIDP   60
RENIVIQCEA KGKPPPSFSW TRNGTHFDID KDPLVTMKPG TGTLIINIMS EGKAETYEGV   120
YQCTARNERG AAVSNNIVVR PSRSPLWTKE KLEPITLQSG QSLVLPCRPP IGLPPPIIFW   180
MDNSFQRLPQ SERVSQGLNG DLYFSNVLPE DTREDYICYA RFNHTQTIQQ KQPISVKVIS   240
```

```
VDELNDTIAA NLSDTEFYGA KSSRERPPTF LTPEGNASNK EELRGNVLSL ECIAEGLPTP   300
IIYWAKEDGM LPKNRTVYKN FEKTLQIIHV SEADSGNYQC IAKNALGAIH HTISVRVKAA   360
PYWITAPQNL VLSPGEDGTL ICRANGNPKP RISWLTNGVP IEIAPDDPSR KIDGDTIIFS   420
NVQERSSAVY QCNASNEYGY LLANAFVNVL AEPPRILTPA NTLYQVIANR PALLDCAFFG   480
SPLPTIEWFK GAKGSALHED IYVLHENGTL EIPVAQKDST GTYTCVARNK LGMAKNEVHL   540
EIKDPTWIVK QPEYAVVQRG SMVSFECKVK HDHTLSLTVL WLKDNRELPS DERFTVDKDH   600
LVVADVSDDD SGTYTCVANT TLDSVSASAV LSVVAPTPTP APVYDVPNPP FDLELTDQLD   660
KSVQLSWTPG DDNNSPITKF IIEYEDAMHK PGLWHHQTEV SGTQTTAQLK LSPYVNYSFR   720
VMAVNSIGKS LPSEASEQYL TKASEPDKNP TAVEGLGSEP DNLVITWKPL NGFESNGPGL   780
QYKVSWRQKD GDDEWTSVVV ANVSKYIVSG TPTFVPYLIK VQALNDMGFA PEPAVVMGHS   840
GEDLPMVAPG NVRVNVVNST LAEVHWDPVP LKSIRGHLQG YRIYYWKTQS SSKRNRRHIE   900
KKILTFQGSK THGMLPGLEP FSHYTLNVRV VNGKGEGPAS PDRVFNTPEG VPSAPSSLKI   960
VNPTLDSLTL EWDPPSHPNG ILTEYTLKYQ PINSTHELGP LVDLKIPANK TRWTLKNLNF   1020
STRYKFYFYA QTSAGSGSQI TEEAVTTVDE AGILPPDVGA GKVQAVNPRI SNLTAAAAET   1080
YANISWEYEG PEHVNFYVEY GVAGSKEEWR KEIVNGSRSF FGLKGLMPGT AYKVRVGAVG   1140
DSGFVSSEDV FETGPAMASR QVDIATQGWF IGLMCAVALL ILILLIVCFI RRNKGGKYPV   1200
KEKEDAHADP EIQPMKEDDG TFGEYRLFSF VSSASF                             1236

SEQ ID NO: 25              moltype = AA  length = 1180
FEATURE                    Location/Qualifiers
source                     1..1180
                           mol_type = protein
                           organism = Homo sapiens
SEQUENCE: 25
MQLKIMPKKK RLSAGRVPLI LFLCQMISAL EVPLDPKLLE DLVQPPTITQ QSPKDYIIDP   60
RENIVIQCEA KGKPPPSFSW TRNGTHFDID KDPLVTMKPG TGTLIINIMS EGKAETYEGV   120
YQCTARNERG AAVSNNIVVR PSRSPLWTKE KLEPITLQSG QSLVLPCRPP IGLPPPIIFW   180
MDNSFQRLPQ SERVSQGLNG DLYFSNVLPE DTREDYICYA RFNHTQTIQQ KQPISVKVIS   240
AKSSRERPPT FLTPEGNASN KEELRGNVLS LECIAEGLPT PIIYWAKEDG MLPKNRTVYK   300
NFEKTLQIIH VSEADSGNYQ CIAKNALGAI HHTISVRVKA APYWITAPQN LVLSPGEDGT   360
LICRANGNPK PRISWLTNGV PIEIAPDDPS RKIDGDTIIF SNVQERSSAV YQCNASNEYG   420
YLLANAFVNV LAEPPRILTP ANTLYQVIAN RPALLDCAFF GSPLPTIEWF KGAKGSALHE   480
DIYVLHENGT LEIPVAQKDS TGTYTCVARN KLGMAKNEVH LEIKDPTWIV KQPEYAVVQR   540
GSMVSFECKV KHDHTLSLTV LWLKDNRELP SDERFTVDKD HLVVADVSDD DSGTYTCVAN   600
TTLDSVSASA VLSVVAPTPT PAPVYDVPNP PFDLELTDQL DKSVQLSWTP GDDNNSPITK   660
FIIEYEDAMH KPGLWHHQTE VSGTQTTAQL KLSPYVNYSF RVMAVNSIGK SLPSEASEQY   720
LTKASEPDKN PTAVEGLGSE PDNLVITWKP LNGFESNGPG LQYKVSWRQK DGDDEWTSVV   780
VANVSKYIVS GTPTFVPYLI KVQALNDMGF APEPAVVMGH SGEDLPMVAP GNVRVNVVNS   840
TLAEVHWDPV PLKSIRGHLQ GYRIYYWKTQ SSSKRNRRHI EKKILTFQGS KTHGMLPGLE   900
PFSHYTLNVR VVNGKGEGPA SPDRVFNTPE GVPSAPSSLK IVNPTLDSLT LEWDPPSHPN   960
GILTEYTLKY QPINSTHELG PLVDLKIPAN KTRWTLKNLN FSTRYKFYFY AQTSAGSGSQ   1020
ITEEAVTTVD EAMASRQVDI ATQGWFIGLM CAVALLILIL LIVCFIRRNK GGKYPVKEKE   1080
DAHADPEIQP MKEDDGTFGE YSDAEDHKPL KKGSRTPSDR TVKKEDSDDS LVDYGEGVNG   1140
QFNEDGSFIG QYSGKKEKEP AEGNESSEAP SPVNAMNSFV                         1180

SEQ ID NO: 26              moltype = AA  length = 1183
FEATURE                    Location/Qualifiers
source                     1..1183
                           mol_type = protein
                           organism = Homo sapiens
SEQUENCE: 26
MQLKIMPKKK RLSAGRVPLI LFLCQMISAL EVPLDLVQPP TITQQSPKDY IIDPRENIVI   60
QCEAKGKPPP SFSWTRNGTH FDIDKDPLVT MKPGTGTLII NIMSEGKAET YEGVYQCTAR   120
NERGAAVSNN IVVRPSRSPL WTKEKLEPIT LQSGQSLVLP CRPPIGLPPP IIFWMDNSFQ   180
RLPQSERVSQ GLNGDLYFSN VLPEDTREDY ICYARFNHTQ TIQQKQPISV KVISVDELND   240
TIAANLSDTE FYGAKSSRER PPTFLTPEGN ASNKEELRGN VLSLECIAEG LPTPIIYWAK   300
EDGMLPKNRT VYKNFEKTLQ IIHVSEADSG NYQCIAKNAL GAIHHTISVR VKAAPYWITA   360
PQNLVLSPGE DGTLICRANG NPKPRISWLT NGVPIEIAPD DPSRKIDGDT IIFSNVQERS   420
SAVYQCNASN EYGYLLANAF VNVLAEPPRI LTPANTLYQV IANRPALLDC AFFGSPLPTI   480
EWFKGAKGSA LHEDIYVLHE NGTLEIPVAQ KDSTGTYTCV ARNKLGMAKN EVHLEIKDPT   540
WIVKQPEYAV VQRGSMVSFE CKVKHDHTLS LTVLWLKDNR ELPSDERFTV DKDHLVVADV   600
SDDDSGTYTC VANTTLDSVS ASAVLSVVDV PNPPFDLELT DQLDKSVQLS WTPGDDNNSP   660
ITKFIIEYED AMHKPGLWHH QTEVSGTQTT AQLKLSPYVN YSFRVMAVNS IGKSLPSEAS   720
EQYLTKASEP DKNPTAVEGL GSEPDNLVIT WKPLNGFESN GPGLQYKVSW RQKDGDDEWT   780
SVVVANVSKY IVSGTPTFVP YLIKVQALND MGFAPEPAVV MGHSGEDLPM VAPGNVRVNV   840
VNSTLAEVHW DPVPLKSIRG HLQGYRIYYW KTQSSSKRNR RHIEKKILTF QGSKTHGMLP   900
GLEPFSHYTL NVRVVNGKGE GPASPDRVFN TPEGVPSAPS SLKIVNPTLD SLTLEWDPPS   960
HPNGILTEYT LKYQPINSTH ELGPLVDLKI PANKTRWTLN LNFSTRYKFY FYAQTSAGS    1020
GSQITEEAVT TVDEAMASRQ VDIATQGWFI GLMCAVALLI LILLIVCFIR RNKGGKYPVK   1080
EKEDAHADPE IQPMKEDDGT FGEYSDAEDH KPLKKGSRTP SDRTVKKEDS DDSLVDYGEG   1140
VNGQFNEDGS FIGQYSGKKE KEPAEGNESS EAPSPVNAMN SFV                     1183

SEQ ID NO: 27              moltype = AA  length = 1308
FEATURE                    Location/Qualifiers
source                     1..1308
                           mol_type = protein
                           organism = Homo sapiens
SEQUENCE: 27
MQLKIMPKKK RLSAGRVPLI LFLCQMISAL EVPLDPKLLE DLVQPPTITQ QSPKDYIIDP   60
```

-continued

```
RENIVIQCEA KGKPPPSFSW TRNGTHFDID KDPLVTMKPG TGTLIINIMS EGKAETYEGV   120
YQCTARNERG AAVSNNIVVR PSRSPLWTKE KLEPITLQSG QSLVLPCRPP IGLPPPIIFW   180
MDNSFQRLPQ SERVSQGLNG DLYFSNVLPE DTREDYICYA RFNHTQTIQQ KQPISVKVIS   240
VDELNDTIAA NLSDTEFYGA KSSRERPPTF LTPEGNASNK EELRGNVLSL ECIAEGLPTP   300
IIYWAKEDGM LPKNRTVYKN FEKTLQIIHV SEADSGNYQ IAKNALGAIH HTISVRVKAA    360
PYWITAPQNL VLSPGEDGTL ICRANGNPKP RISWLTNGVP IEIAPDDPSR KIDGDTIIFS   420
NVQERSSAVY QCNASNEYGY LLANAFVNVL AEPPRILTPA NTLYQVIANR PALLDCAFFG   480
SPLPTIEWFK GAKGSALHED IYVLHENGTL EIPVAQKDST GTYTCVARNK LGMAKNEVHL   540
EIKDPTWIVK QPEYAVVQRG SMVSFECKVK HDHTLSLTVL WLKDNRELPS DERFTVDKDH   600
LVVADVSDDD SGTYTCVANT TLDSVSASAV LSVVAPTPTP APVYDVPNPP FDLELTDQLD   660
KSVQLSWTPG DDNNSPITKF IIEYEDAMHK PGLWHHQTEV SGTQTTAQLK LSPYVNYSFR   720
VMAVNSIGKS LPSEASEQYL TKASEPDKNP TAVEGLGSEP DNLVITWKPL NGFESNGPGL   780
QYKVSWRQKD GDDEWTSVVV ANVSKYIVSG TPTFVPYLIK VQALNDMGFA PEPAVVMGHS   840
GEDLPMVAPG NVRVNVVNST LAEVHWDPVP LKSIRGHLQG YRIYYWKTQS SSKRNRRHIE   900
KKILTFQGSK THGMLPGLEP FSHYTLNVRV VNGKGEGPAS PDRVFNTPEG VPSAPSSLKI   960
VNPTLDSLTL EWDPPSHPNG ILTEYTLKYQ PINSTHELGP LVDLKIPANK TRWTLKNLNF   1020
STRYKFYFYA QTSAGSGSQI TEEAVTTVDE AGILPPDVGA GKVQAVNPRI SNLTAAAAET   1080
YANISWEYEG PEHVNFYVEY GVAGSKEEWR KEIVNGSRSF FGLKGLMPGT AYKVRVGAVG   1140
DSGFVSSEDV FETGPAMASR QVDIATQGWF IGLMCAVALL ILILLIVCFI RRNKGGKYPV   1200
KEKEDAHADP EIQPMKEDDG TFGEYRSLES DAEDHKPLKK GSRTPSDRTV KKEDSDDSLV   1260
DYGEGVNGQF NEDGSFIGQY SGKKEKEPAE GNESSEAPSP VNAMNSFV                1308
```

```
SEQ ID NO: 28              moltype = AA  length = 1192
FEATURE                    Location/Qualifiers
source                     1..1192
                           mol_type = protein
                           organism = Homo sapiens
SEQUENCE: 28
MQLKIMPKKK RLSAGRVPLI LFLCQMISAL EVPLDPKLLE DLVQPPTITQ QSPKDYIIDP    60
RENIVIQCEA KGKPPPSFSW TRNGTHFDID KDPLVTMKPG TGTLIINIMS EGKAETYEGV   120
YQCTARNERG AAVSNNIVVR PSRSPLWTKE KLEPITLQSG QSLVLPCRPP IGLPPPIIFW   180
MDNSFQRLPQ SERVSQGLNG DLYFSNVLPE DTREDYICYA RFNHTQTIQQ KQPISVKVIS   240
AKSSRERPPT FLTPEGNASN KEELRGNVLS LECIAEGLPT PIIYWAKEDG MLPKNRTVYK   300
NFEKTLQIIH VSEADSGNYQ CIAKNALGAI HHTISVRVKA APYWITAPQN LVLSPGEDGT   360
LICRANGNPK PRISWLTNGV PIEIAPDDPS RKIDGDTIIF SNVQERSSAV YQCNASNEYG   420
YLLANAFVNV LAEPPRILTP ANTLYQVIAN RPALLDCAFF GSPLPTIEWF KGAKGSALHE   480
DIYVLHENGT LEIPVAQKDS TGTYTCVARN KLGMAKNEVH LEIKDPTWIV KQPEYAVVQR   540
GSMVSFECKV KHDHTLSLTV LWLKDNRELP SDERFTVDKD HLVVADVSDD DSGTYTCVAN   600
TTLDSVSASA VLSVVAPTPT PAPVYDVPNP PFDLELTDQL DKSVQLSWTP GDDNNSPITK   660
FIIEYEDAMH KPGLWHHQTE VSGTQTTAQL KLSPYVNYSF RVMAVNSIGK SLPSEASEQY   720
LTKASEPDKN PTAVEGLGSE PDNLVITWKP LNGFESNGPG LQYKVSWRQK DGDDEWTSVV   780
VANVSKYIVS GTPTFVPYLI KVQALNDMGF APEPAVVMGH SGEDLPMVAP GNVRVNVVNS   840
TLAEVHWDPV PLKSIRGHLQ GYRIYYWKTQ SSSKRNRRHI EKKILTFQGS KTHGMLPGLE   900
PFSHYTLNVR VVNGKGEGPA SPDRVFNTPE GVPSAPSSLK IVNPTLDSLT LEWDPPSHPN   960
GILTEYTLKY QPINSTHELG PLVDLKIPAN KTRWTLKNLN FSTRYKFYFY AQTSAGSGSQ   1020
ITEEAVTTVD EAGILPPDVG AGKAMASRQV DIATQGWFIG LMCAVALLIL ILLIVCFIRR   1080
NKGGKYPVKE KEDAHADPEI QPMKEDDGTF GEYSDAEDHK PLKKGSRTPS DRTVKKEDSD   1140
DSLVDYGEGV NGQFNEDGSF IGQYSGKKEK EPAEGNESSE APSPVNAMNS FV            1192
```

```
SEQ ID NO: 29              moltype = AA  length = 788
FEATURE                    Location/Qualifiers
source                     1..788
                           mol_type = protein
                           organism = Homo sapiens
SEQUENCE: 29
MTIHQFLLLF LFWVCLPHFC SPEIMFRRTP VPQQRILSSR VPRSDGKILH RQKRGWMWNQ    60
FFLLEEYTGS DYQYVGKLHS DQDKGDGSLK YILSGDGAGT LFIIDEKTGD IHATRRIDRE   120
EKAFYTLRAQ AINRRTLRPV EPESEFVIKI HDINDNEPTF PEEIYTASVP EMSVVGTSVV   180
QVTATDADDP SYGNSARVIY SILQGQPYFS VEPETGIIRT ALPNMNRENR EQYQVVIQAK   240
DMGGQMGGLS GTTTVNITLT DVNDNPPRFP QNTIHLRVLE SSPVGTAIGS VKATDADTGK   300
NAEVEYRIID GDGTDMFDIV TEKDTQEGII TVKKPLDYES RRLYTLKVEA ENTHVDPRFY   360
YLGPFKDTTI VKISIEDVDE PPVFSRSSYL FEVHEDIEVG TIIGTVMARD PDSISSPIRF   420
SLDRHTDLDR IFNIHSGNGS LYTSKPLDRE LSQWHNLTVI AAEINNPKET TRVAVFVRIL   480
DVNDNAPQFA VFYDTFVCEN ARPGQLIQTI SAVDKDDPLG GQKFFFSLAA VNPNFTVQDN   540
EDNTARILTR KNGFNRHEIS TYLLPVVISD NDYPIQSSTG TLTIRVCACD SQGNMQSCSA   600
EALLLPAGLS TGALIAILLC IIILLVIVVL FAALKRQRKK EPLILSKEDI RDNIVSYNDE   660
GGGEEDTQAF DIGTLRNPAA IEEKKLRRDI IPETLFIPRR TPTAPDNTDV RDFINERLKE   720
HDLDPTAPPY DSLATYAYEG NDSIAESLSS LESGTTEGDQ NYDYLREWGP RFNKLAEMYG   780
GGESDKDS                                                           788
```

```
SEQ ID NO: 30              moltype = AA  length = 944
FEATURE                    Location/Qualifiers
source                     1..944
                           mol_type = protein
                           organism = Homo sapiens
SEQUENCE: 30
MGPKTLPQLA GKWQVLCMLS LCCWGWVSGQ LRYSVVEESE PGTLVGNVAQ DLGLKMTDLL    60
SRRLQLGSEE NGRYFSLSLM SGALAVNQKI DRESLCGAST SCLLPVQVVT EHPLELIRVE   120
VEILDLNDNS PSFATPEREM RISESAASGA RFPLDSAQDP DVGTNTVSFY TLSPNSHFSL   180
```

```
NVKTLKDGKP FPELVLEQQL DREAQARHQL VLTAVDGGTP ARSGTTLISV IVLDINDNAP  240
TFQSSVLRVG IPENAPIGTL LLRLNATDPD EGTNGQLDYS FGDHTSEAVR NLFGLDPSSG  300
AIHVLGPIDF EESRFYEIHA RARDQGQPAM EGHCVIQVDV GDVNDNAPEV LLASLANPVL  360
ESTPVGTVVG LFNVRDRDSG RNGEVSLDIS PDLPFQIKPS ENHYSLLTSQ PLDREATSHY  420
IIELLASDAG SPSLHKHLTI RLNISDVNDN APRFNQQLYT AYILENRPPG SLLCTVAASD  480
PDTGDNARLT YSIVGNQVQG APASSFVYVN PEDGRIFAQR TFDYELLQML QIVVGVRDSG  540
SPPLHANTSL HVFVLDENDN APAVLHPRPD WEHSAPQRLP RSAPPGSLVT KVTAVDADAG  600
HNAWLSYSLL PQSTAPGLFL VSTHTGEVRT ARALLEDDSD TQQVVVLVRD NGDPSLSSTA  660
TVLLVLEDED PEEMPKSSDF LIHPPERSDL TLYLIVALAT VSLLSLVTFT FLSAKCLQGN  720
ADGDGGGGQC CRRQDSPSPD FYKQSSPNLQ VSSDGTLKYM EVTLRPTDSQ SHCYRTCFSP  780
ASDGSDFTFL RPLSVQQPTA LALEPDAIRS RSNTLRERSQ QAPPNTDWRF SQAQRPGTSG  840
SQNGDDTGTW PNNQFDTEML QAMILASASE AADGSSTLGG GAGTMGLSAR YGPQFTLQHV  900
PDYRQNVYIP GSNATLTNAA GKRDGKAPAG GNGNKKKSGK KEKK                   944
```

SEQ ID NO: 31          moltype = AA   length = 878
FEATURE                Location/Qualifiers
source                 1..878
                       mol_type = protein
                       organism = Homo sapiens
SEQUENCE: 31

```
MGPKTLPQLA GKWQVLCMLS LCCWGWVSGQ LRYSVVEESE PGTLVGNVAQ DLGLKMTDLL  60
SRRLQLGSEE NGRYFSLSLM SGALAVNQKI DRESLCGAST SCLLPVQVVT EHPLELIRVE  120
VEILDLNDNS PSFATPEREM RISESAASGA RFPLDSAQDP DVGTNTVSFY TLSPNSHFSL  180
NVKTLKDGKP FPELVLEQQL DREAQARHQL VLTAVDGGTP ARSGTTLISV IVLDINDNAP  240
TFQSSVLRVG IPENAPIGTL LLRLNATDPD EGTNGQLDYS FGDHTSEAVR NLFGLDPSSG  300
AIHVLGPIDF EESRFYEIHA RARDQGQPAM EGHCVIQVDV GDVNDNAPEV LLASLANPVL  360
ESTPVGTVVG LFNVRDRDSG RNGEVSLDIS PDLPFQIKPS ENHYSLLTSQ PLDREATSHY  420
IIELLASDAG SPSLHKHLTI RLNISDVNDN APRFNQQLYT AYILENRPPG SLLCTVAASD  480
PDTGDNARLT YSIVGNQVQG APASSFVYVN PEDGRIFAQR TFDYELLQML QIVVGVRDSG  540
SPPLHANTSL HVFVLDENDN APAVLHPRPD WEHSAPQRLP RSAPPGSLVT KVTAVDADAG  600
HNAWLSYSLL PQSTAPGLFL VSTHTGEVRT ARALLEDDSD TQQVVVLVRD NGDPSLSSTA  660
TVLLVLEDED PEEMPKSSDF LIHPPERSDL TLYLIVALAT VSLLSLVTFT FLSAKCLQGN  720
ADGDGGGGQC CRRQDSPSPD FYKQSSPNLQ VSSDGTLKYM EVTLRPTDSQ SHCYRTCFSP  780
ASDGSDFTFL RPLSVQQPTA LALEPDAIRS RSNTLRERSQ VRGSAPPRAT PGGGTGEAAR  840
PHKGLNLHPL LSGRLGRWLR STRFSGSLDR LRETRVAD                          878
```

SEQ ID NO: 32          moltype = AA   length = 193
FEATURE                Location/Qualifiers
source                 1..193
                       mol_type = protein
                       organism = Homo sapiens
SEQUENCE: 32

```
MPEEGSGCSV RRRPYGCVLR AALVPLVAGL VICLVVCIQR FAQAQQQLPL ESLGWDVAEL  60
QLNHTGPQQD PRLYWQGGPA LGRSFLHGPE LDKGQLRIHR DGIYMVHIQV TLAICSSTTA  120
SRHHPTTLAV GICSPASRSI SLLRLSFHQG CTIASQRLTP LARGDTLCTN LTGTLLPSRN  180
TDETFFGVQW VRP                                                     193
```

SEQ ID NO: 33          moltype = AA   length = 208
FEATURE                Location/Qualifiers
source                 1..208
                       mol_type = protein
                       organism = Homo sapiens
SEQUENCE: 33

```
MPEEGSGCSV RRRPYGCVLR AALVPLVAGL VICLVVCIQR FAQAQQQLPL ESLGWDVAEL  60
QLNHTGPQQD PRLYWQGGPA LGRSFLHGPE LDKGQLRIHR DGIYMVHIQV TLAICSSTTA  120
SRHHPTTLAV GICSPASRSI SLLRLSFHQG LFGFWNWGLK VKCFLRHLIW TAHCFIPLTQ  180
LVFMQALQSW RNHHCSHFTD EENRGVNR                                     208
```

SEQ ID NO: 34          moltype = AA   length = 566
FEATURE                Location/Qualifiers
source                 1..566
                       mol_type = protein
                       organism = Homo sapiens
SEQUENCE: 34

```
MGRAGGGGPG RGPPPLLLFL GAALVLASGA VPAREAGSAV EAEELVKGSP AWEPPANDTR  60
EEAGPPAAGE DEASWTAPGG ELAGPEEVLQ ESAAVTGTAW LEADSPGLGG VTAEAGSGDA  120
QALPATLQAP HEVLGQSIMP PAIPEATEAS GPPSPTPGDK LSPASELPKE SPLEVWLNLG  180
GSTPDPQGPE LTYPFQGTLE PQPASDIIDI DYFEGLDGAG RGADLGSFPG SPGTSENHPD  240
TEGETPSWSL LDLYDDFTPF DESDFYPTTS FYDDLDEEEE EEEDDKDAVG GGDLEDENEL  300
LVPTGKPGLG PGTGQPTSRW HAVPPQHTLG SVPGSSIALR PRPGEPGRDL ASSENGTECR  360
SGFVRHNGSC RSVCDLFPSY CHNGGQCYLV ENIGAFCRCN TQDYIWHKGM RCESIITDFQ  420
VMCVAVGSAA LVLLLLFMMT VFFAKKLYLL KTENTKLRRT NKFRTPSELH NDNFSLSTIA  480
EGSHPNVRKL CNTPRTSSPH ARALAHYDNV ICQDDPSAPH KIQEVLKSCL KEEESFNIQN  540
SMSPKLEGGK GDQADLDVNC LQNNLT                                       566
```

SEQ ID NO: 35          moltype = AA   length = 539
FEATURE                Location/Qualifiers
source                 1..539
                       mol_type = protein -continued

```
                   organism = Homo sapiens
SEQUENCE: 35
MGRAGGGGPG RGPPPLLLFL GAALVLASGA VPAREAGSAV EAEELVKGSP AWEPPANDTR   60
EEAGPPAAGE DEASWTAPGG ELAGPEEVLQ ESAAVTGTAW LEADSPGLGG VTAEAGSGDA  120
QALPATLQAP HEVLGQSIMP PAIPEATEAS GPPSPTPGDK LSPASELPKE SPLEVWLNLG  180
GSTPDPQGPE LTYPFQGTLE PQPASDIIDI DYFEGLDGEG RGADLGSFPG SPGTSENHPD  240
TEGETPSWSL LDLYDDFTPF DESDFYPTTS FYDDLDEEEE EEEDDKDAVG GGDLEDENEL  300
LVPTGKPGLG PGTGQPTSRW HAVPPQHTLG SVPGSSIALR PRPGEPGRDL ASSENGTECR  360
SGFVRHNGSC RSVCDLFPSY CHNGGQCYLV ENIGAFCRCN TQDYIWHKGM RCESIITDFQ  420
VMCVAVGSAA LVLLLLFMMT VFFAKKLYLL KTENTKLRRT NKFRTPSELH NDNFSLSTIA  480
EGSHPNDDPS APHKIQEVLK SCLKEEESFN IQNSMSPKLE GGKGDQADLD VNCLQNNLT   539

SEQ ID NO: 36              moltype = AA   length = 401
FEATURE                    Location/Qualifiers
source                     1..401
                           mol_type = protein
                           organism = Homo sapiens
SEQUENCE: 36
MPPAIPEATE ASGPPSPTPG DKLSPASELP KESPLEVWLN LGGSTPDPQG PELTYPFQGT   60
LEPQPASDII DIDYFEGLDG EGRGADLGSF PGSPGTSENH PDTEGETPSW SLLDLYDDFT  120
PFDESDFYPT TSFYDDLDEE EEEEDDKDA VGGGDLEDEN ELLVPTGKPG LGPGTGQPTS  180
RWHAVPPQHT LGSVPGSSIA LRPRPGEPGR DLASSENGTE CRSGFVRHNG SCRSVCDLFP  240
SYCHNGGQCY LVENIGAFCR CNTQDYIWHK GMRCESIITD FQVMCVAVGS AALVLLLLFM  300
MTVFFAKKLY LLKTENTKLR RTNKFRTPSE LHNDNFSLST IAEGSHPNDD PSAPHKIQEV  360
LKSCLKEEES FNIQNSMSPK LEGGKGDQAD LDVNCLQNNL T                      401

SEQ ID NO: 37              moltype = AA   length = 911
FEATURE                    Location/Qualifiers
source                     1..911
                           mol_type = protein
                           organism = Homo sapiens
SEQUENCE: 37
MAQLFLPLLA ALVLAQAPAA LADVLEGDSS EDRAFRVRIA GDAPLQGVLG GALTIPCHVH   60
YLRPPPSRRA VLGSPRVKWT FLSRGREAEV LVARGVRVAL NEAYRFRVAL PAYPASLTDV  120
SLALSELRPN DSGIYRCEVQ HGIDDSSDAV EVKVKGVVFL YREGSARYAF SFSGAQEACA  180
RIGAHIATPE QLYAAYLGGY EQCDAGWLSD QTVRYPIQTP REACYGDMDG FPGVRNYGVV  240
DPDDLYDVYC YAEDLNGELF LGDPPEKLTL EEARAYCQER GAEIATTGQL YAAWDGGLDH  300
CSPGWLADGS VRYPIVTPSQ RCGGGLPGVK TLFLFPNQTG FPNKHSRFNV YCFRDSAQPS  360
AIPEASNPAS NPASDGLEAI VTVTETLEEL QLPQEATESE SRGAIYSIPI MEDGGGGSST  420
PEDPAEAPRT LLEFETQSMV PPTGFSEEEG KALEEEEKYE DEEEKEEEEE EEEVEDEALW  480
AWPSELSSPG PEASLPTEPA AQEESLSQAP ARAVLQPGAS PLPDGESEAS RPPRVHGPPT  540
ETLPTPRERN LASPSPSTLV EAREVGEATG GPELSGVPRG ESEETGSSEG APSLLPATRA  600
PEGTRELEAP SEDNSGRTAP AGTSVQAQPV LPTDSASRGG VAVVPASGDC VPSPCHNGGT  660
CLEEEEGVRC LCLPGYGGDL CDVGLRFCNP GWDAFQGACY KHFSTRRSWE EAETQCRMYG  720
AHLASISTPE EQDFINNRYR EYQWIGLNDR TIEGDFLWSD GVPLLYENWN PGQPDSYFLS  780
GENCVVMVWH DQGQWSDVPC NYHLSYTCKM GLVSCGPPPE LPLAQVFGRP RLRYEVDTVL  840
RYRCREGLAQ RNLPLIRCQE NGRWEAPQIS CVPRRPARAL HPEEDPEGRQ GRLLGRWKAL  900
LIPPSSPMPG P                                                       911

SEQ ID NO: 38              moltype = AA   length = 671
FEATURE                    Location/Qualifiers
source                     1..671
                           mol_type = protein
                           organism = Homo sapiens
SEQUENCE: 38
MAQLFLPLLA ALVLAQAPAA LADVLEGDSS EDRAFRVRIA GDAPLQGVLG GALTIPCHVH   60
YLRPPPSRRA VLGSPRVKWT FLSRGREAEV LVARGVRVKV NEAYRFRVAL PAYPASLTDV  120
SLALSELRPN DSGIYRCEVQ HGIDDSSDAV EVKVKGVVFL YREGSARYAF SFSGAQEACA  180
RIGAHIATPE QLYAAYLGGY EQCDAGWLSD QTVRYPIQTP REACYGDMDG FPGVRNYGVV  240
DPDDLYDVYC YAEDLNGELF LGDPPEKLTL EEARAYCQER GAEIATTGQL YAAWDGGLDH  300
CSPGWLADGS VRYPIVTPSQ RCGGGLPGVK TLFLFPNQTG FPNKHSRFNV YCFRDSAQPS  360
AIPEASNPAS NPASDGLEAI VTVTETLEEL QLPQEATESE SRGAIYSIPI MEDGGGGSST  420
PEDPAEAPRT LLEFETQSMV PPTGFSEEEG KALEEEEKYE DEEEKEEEEE EEEVEDEALW  480
AWPSELSSPG PEASLPTEPA AQEESLSQAP ARAVLQPGAS PLPDGESEAS RPPRVHGPPT  540
ETLPTPRERN LASPSPSTLV EAREVGEATG GPELSGVPRG ESEETGSSEG APSLLPATRA  600
PEGTRELEAP SEDNSGRTAP AGTSVQAQPV LPTDSASRGG VAVVPASGNS AQGSTALSIL  660
LLFFPLQLWV T                                                       671

SEQ ID NO: 39              moltype = AA   length = 879
FEATURE                    Location/Qualifiers
source                     1..879
                           mol_type = protein
                           organism = Homo sapiens
SEQUENCE: 39
MKMLTRLQVL TLALFSKGFL LSLGDHNFLR REIKIEGDLV LGGGLFPINEK GTGTEECGRI   60
NEDRGIQRLE AMLFAIDEIN KDDYLLPGVK LGVHILDTCS RDTYALEQSL EFVRASLTKV  120
DEAEYMCPDG SYAIQENIPL LIAGVIGGSY SSVSIQVANL LRLFQIPQIS YASTSAKLSD  180
KSRYDYFART VPPDFYQAKA MAEILRFFNW TYVSTVASEG DYGETGIEAF EQEARLRNIC  240
IATAEKVGRS NIRKSYDSVI RELLQKPNAR VVVLFMRSDD SRELIAAASR ANASFTWVAS  300
```

```
DGWGAQESII KGSEHVAYGA ITLELASQPV RQFDRYFQSL NPYNNHRNPW FRDFWEQKFQ  360
CSLQNKRNHR RVCDKHLAID SSNYEQESKI MFVVNAVYAM AHALHKMQRT LCPNTTKLCD  420
AMKILDGKKL YKDYLLKINF TAPFNPNKDA DSIVKFDTFG DGMGRYNVFN FQNVGGKYSY  480
LKVGHWAETL SLDVNSIHWS RNSVPTSQCS DPCAPNEMKN MQPGDVCCWI CIPCEPYEYL  540
ADEFTCMDCG SGQWPTADLT GCYDLPEDYI RWEDAWAIGP VTIACLGFMC TCMVVTVFIK  600
HNNTPLVKAS GRELCYILLF GVGLSYCMTF FFIAKPSPVI CALRRLGLGS SFAICYSALL  660
TKTNCIARIF DGVKNGAQRP KFISPSSQVF ICLGLILVQI VMVSVWLILE APGTRRYTLA  720
EKRETVILKC NVKDSSMLIS LTYDVILVIL CTVYAFKTRK CPENFNEAKF IGFTMYTTCI  780
IWLAFLPIFY VTSSDYRVQT TTMCISVSLS GFVVLGCLFA PKVHIILFQP QKNVVTHRLH  840
LNRFSVSGTG TTYSQSSAST YVPTVCNGRE VLDSTTSSL                         879
```

SEQ ID NO: 40          moltype = AA  length = 537
FEATURE                Location/Qualifiers
source                 1..537
                       mol_type = protein
                       organism = Homo sapiens
SEQUENCE: 40

```
MKMLTRLQVL TLALFSKGFL LSLGDHNFLR REIKIEGDLV LGGLFPINEK GTGTEECGRI  60
NEDRGIQRLE AMLFAIDEIN KDDYLLPGVK LGVHILDTCS RDTYALEQSL EFVRASLTKV  120
DEAEYMCPDG SYAIQENIPL LIAGVIGGSY SSVSIQVANL LRLFQIPQIS YASTSAKLSD  180
KSRYDYFART VPPDFYQAKA MAEILRFFNW TYVSTVASEG DYGETGIEAF EQEARLRNIC  240
IATAEKVGRS NIRKSYDSVI RELLQKPNAR VVVLFMRSDD SRELIAAASR ANASFTWVAS  300
DGWGAQESII KGSEHVAYGA ITLELASQPV RQFDRYFQSL NPYNNHRNPW FRDFWEQKFQ  360
CSLQNKRNHR RVCDKHLAID SSNYEQESKI MFVVNAVYAM AHALHKMQRT LCPNTTKLCD  420
AMKILDGKKL YKDYLLKINF TGADDNHVHL CQPEWLCGLG LFVCTQGSHH PVSTPEECCH  480
TQTAPQQVQC QWNWDHILSV LCKHVCANGV QWAGSPRLHH LISIVINCSS VLVFLDC     537
```

SEQ ID NO: 41          moltype = AA  length = 1406
FEATURE                Location/Qualifiers
source                 1..1406
                       mol_type = protein
                       organism = Homo sapiens
SEQUENCE: 41

```
MALKNINYLL IFYLSFSLLI YIKNSFCNKN NTRCLSNSCQ NNSTCKDFSK DNDCSCSDTA  60
NNLDKDCDNM KDPCFSNPCQ GSATCVNTPG ERSFLCKCPP GYSGTICETT IGSCGKNSCQ  120
HGGICHQDPI YPVCICPAGY AGRFCEIDHD ECASSPCQNG AVCQDGIDGY SCFCVPGYQG  180
RHCDLEVDEC ASDPCKNEAT CLNEIGRYTC ICPHNYSGVN CELEIDECWS QPCLNGATCQ  240
DALGAYFCDC APGFLGDHCE LNTDECASQP CLHGGLCVDG ENRYSCNCTG SGFTGTHCET  300
LMPLCWSKPC HNNATCEDSV DNYTCHCWPG YTGAQCEIDL NECNSNPCQS NGECVELSSE  360
KQYGRITGLP SSFSYHEASG YVCICQPGFT GIHCEEDVNE CSSNPCQNGG TCENLPGNYT  420
CHCPFDNLSR TFYGGRDCSD ILLGCTHQQC LNNGTCIPHF QDGQHGFSCL CPSGYTGSLC  480
EIATTLSFEG DGFLWVKSGS VTTKGSVCNI ALRFQTVQPM ALLLFRSNRD VFVKLELLSG  540
YIHLSIQVNN QSKVLLFISH NTSDGEWHFV EVIFAEAVTL TLIDDSCKEK CIAKAPTPLE  600
SDQSICAFQN SFLGGLPVGM TSNGVALLNF YNMPSTPSFV GCLQDIKIDW NHITLENISS  660
GSSLNVKAGC VRKDWCESQP CQSRGRCINL WLSYQCDCHR PYEGPNCLRE YVAGRFGQDD  720
STGYVIFTLD ESYGDTISLS MFVRTLQPSG LLLALENSTY QYIRVWLERG RLAMLTPNSP  780
KLVVKFVLND GNVHLISLKI KPYKIELYQS SQNLGFISAS TWKIEKGDVI YIGGLPDKQE  840
TELNGGFFKG CIQDVRLNNQ NLEFFPNPTN NASLNPVLVN VTQGCAGDNS CKSNPCHNGG  900
VCHSRWDDFS CSCPALTSGK ACEEVQWCGF SPCPHGAQCQ PVLQGFECIA NAVFNGQSGQ  960
ILFRSNGNIT RELTNITFGF RTRDANVIIL HAEKEPEFLN ISIQDSRLFF QLQSGNSFYM  1020
LSLTSLQSVN DGTWHEVTLS MTDPLSQTSR WQMEVDNETP FVTSTIATGS LNFLKDNTDI  1080
YVGDRAIDNI KGLQGCLSTI EIGGIYLSYF ENVHGFINKP QEEQFLKIST NSVVTGCLQL  1140
NVCNSNPCLH GGNCEDIYSS YHCSCPLGWS GKHCELNIDE CFSNPCIHGN CSDRVAAYHC  1200
TCEPGYTGVN CEVDIDNCQS HQCANGATCI SHTNGYSCLC FGNFTGKFCR QSRLPSTVCG  1260
NEKTNLTCYN GGNCTEFQTE LKCMCRPGFT GEWCEKDIDE CASDPCVNGG LCQDLLNKFQ  1320
CLCDVAFAGE RCEVDLADDL ISDIFTTIGS VTVALLLILL LAIVASVVTS NKRATQGTYS  1380
PSRQEKEGSR VEMWNLMPPP AMERLI                                      1406
```

SEQ ID NO: 42          moltype = AA  length = 1376
FEATURE                Location/Qualifiers
source                 1..1376
                       mol_type = protein
                       organism = Homo sapiens
SEQUENCE: 42

```
MALKNINYLL IFYLSFSLLI YIKNSFCNKN NTRCLSNSCQ NNSTCKDFSK DNDCSCSDTA  60
NNLDKDCDNM KDPCFSNPCQ GSATCVNTPG ERSFLCKCPP GYSGTICETT IGSCGKNSCQ  120
HGGICHQDPI YPVCICPAGY AGRFCEIDHD ECASSPCQNG AVCQDGIDGY SCFCVPGYQG  180
RHCDLEVDEC ASDPCKNEAT CLNEIGRYTC ICPHNYSGVN CELEIDECWS QPCLNGATCQ  240
DALGAYFCDC APGFLGDHCE LNTDECASQP CLHGGLCVDG ENRYSCNCTG SGFTGTHCET  300
LMPLCWSKPC HNNATCEDSV DNYTCHCWPG YTGAQCEIDL NECNSNPCQS NGECVELSSE  360
KQYGRITGLP SSFSYHEASG YVCICQPGFT GIHCEEDVNE CSSNPCQNGG TCENLPGNYT  420
CHCPFDNLSR TFYGGRDCSD ILLGCTHQQC LNNGTCIPHF QDGQHGFSCL CPSGYTGSLC  480
EIATTLSFEG DGFLWVKSGS VTTKGSVCNI ALRFQTVQPM ALLLFRSNRD VFVKLELLSG  540
YIHLSIQVNN QSKVLLFISH NTSDGEWHFV EVIFAEAVTL TLIDDSCKEK CIAKAPTPLE  600
SDQSICAFQN SFLGGLPVGM TSNGVALLNF YNMPSTPSFV GCLQDIKIDW NHITLENISS  660
GSSLNVKAGC VRKDWCESQP CQSRGRCINL WLSYQCDCHR PYEGPNCLRE YVAGRFGQDD  720
STGYVIFTLD ESYGDTISLS MFVRTLQPSG LLLALENSTY QYIRVWLERG RLAMLTPNSP  780
KLVVKFVLND GNVHLISLKI KPYKIELYQS SQNLGFISAS TWKIEKGDVI YIGGLPDKQE  840
TELNGGFFKG CIQDVRLNNQ NLEFFPNPTN NASLNPVLVN VTQGCAGDNS CKSNPCHNGG  900
```

```
VCHSRWDDFS CSCPALTSGK ACEEVQWCGF SPCPHGAQCQ PVLQGFECIA NAVFNGQSGQ    960
ILFRSNGNIT RELTNITFGF RTRDANVIIL HAEKEPEFLN ISIQDSRLFF QLQSGNSFYM   1020
LSLTSLQSVN DGTWHEVTLS MTDPLSQTSR WQMEVDNETP FVTSTIATGS LNFLKDNTDI   1080
YVGDRAIDNI KGLQGCLSTI EIGGIYLSYF ENVHGFINKP QEEQFLKIST NSVVTGCLQL   1140
NVCNSNPCLH GGNCEDIYSS YHCSCPLGWS GKHCELNIDE CFSNPCIHGN CSDRVAAYHC   1200
TCEPGYTGVN CEVDIDNCQS HQCANGATCI SHTNGYSCLC FGNFTGKFCR QSRLPSTVCG   1260
NEKTNLTCYN GGNCTEFQTE LKCMCRPGFT GEWCEKDIDE CASDPCVNGG LCQDLLNKFQ   1320
CLCDVAFAGE RCEVDVSSLS FYVSLLFWQN LFQLLSYLIL RMNDEPVVEW GEQEDY       1376

SEQ ID NO: 43            moltype = AA  length = 1294
FEATURE                  Location/Qualifiers
source                   1..1294
                         mol_type = protein
                         organism = Homo sapiens
SEQUENCE: 43
MALKNINYLL IFYLSFSLLI YIKNSFCNKN NTRCLSNSCQ NNSTCKDFSK DNDCSCSDTA    60
NNLDKDCDNM KDPCFSNPCQ GSATCVNTPG ERSFLCKCPP GYSGTICETT IGSCGKNSCQ   120
HGGICHQDPI YPVCICPAGY AGRFCEIDHD ECASSPCQNG AVCQDGIDGY SCFCVPGYQG   180
RHCDLEVDEC ASDPCKNEAT CLNEIGRYTC ICPHNYSGYT GAQCEIDLNE CNSNPCQSNG   240
ECVELSSEKQ YGRITGLPSS FSYHEASGYV CICQPGFTGI HCEEDVNECS SNPCQNGGTC   300
ENLPGNYTCH CPFDNLSRTF YGGRDCSDIL LGCTHQQCLN NGTCIPHFQD GQHGFSCLCP   360
SGYTGSLCEI ATTLSFEGDG FLWVKSGSVT TKGSVCNIAL RFQTVQPMAL LLFRSNRDVF   420
VKLELLSGYI HLSIQVNNQS KVLLFISHNT SDGEWHFVEV IFAEAVTLTL IDDSCKEKCI   480
AKAPTPLESD QSICAFQNSF LGGLPVGMTS NGVALLNFYN MPSTPSFVGC LQDIKIDWNH   540
ITLENISSGS SLNVKAGCVR KDWCESQPCQ SRGRCINLWL SYQCDCHRPY EGPNCLREYV   600
AGRFGQDDST GYVIFTLDES YGDTISLSMF VRTLQPSGLL LALENSTYQ IRVWLERGRL   660
AMLTPNSPKL VVKFVLNDGN VHLISLKIKP YKIELYQSSQ NLGFISASTW KIEKGDVIYI   720
GGLPDKQETE LNGGFFKGCI QDVRLNNQNL EFFPNPTNNA SLNPVLVNVT QGCAGDNSCK   780
SNPCHNGGVC HSRWDDFSCS CPALTSGKAC EEVQWCGFSP CPHGAQCQPV LQGFECIANA   840
VFNGQSGQIL FRSNGNITRE LTNITFGFRT RDANVIILHA EKEPEFLNIS IQDSRLFFQL   900
QSGNSFYMLS LTSLQSVNDG TWHEVTLSMT DPLSQTSRWQ MEVDNETPFV TSTIATGSLN   960
FLKDNTDIYV GDRAIDNIKG LQGCLSTIEI GGIYLSYFEN VHGFINKPQE EQFLKISTNS   1020
VVTGCLQLNV CNSNPCLHGG NCEDIYSSYH CSCPLGWSGK HCELNIDECF SNPCIHGNCS   1080
DRVAAYHCTC EPGYTGVNCE VDIDNCQSHQ CANGATCISH TNGYSCLCFG NFTGKFCRQS   1140
RLPSTVCGNE KTNLTCYNGG NCTEFQTELK CMCRPGFTGE WCEKDIDECA SDPCVNGGLC   1200
QDLLNKFQCL CDVAFAGERC EVDLADDLIS DIFTTIGSVT VALLLILLLA IVASVVTSNK   1260
RATQGTYSPS RQEKEGSRVE MWNLMPPPAM ERLI                              1294

SEQ ID NO: 44            moltype = AA  length = 942
FEATURE                  Location/Qualifiers
source                   1..942
                         mol_type = protein
                         organism = Homo sapiens
SEQUENCE: 44
MIRNSLCQPS RCLDEYLFFN RKMFGARTHG FHILMAMLIG IHCEEDVNEC SSNPCQNGGT    60
CENLPGNYTC HCPFDNLSRT FYGGRDCSDI LLGCTHQQCL NNGTCIPHFQ DGQHGFSCLC   120
PSGYTGSLCE IATTLSFEGD GFLWVKSGSV TTKGSVCNIA LRFQTVQPMA LLLFRSNRDV   180
FVKLELLSGY IHLSIQVNNQ SKVLLFISHN TSDGEWHFVE VIFAEAVTLT LIDDSCKEKC   240
IAKAPTPLES DQSICAFQNS FLGGLPVGMT SNGVALLNFY NMPSTPSFVG CLQDIKIDWN   300
HITLENISSG SSLNVKAGCV RKDWCESQPC QSRGRCINLW LSYQCDCHRP YEGPNCLREY   360
VAGRFGQDDS TGYVIFTLDE SYGDTISLSM FVRTLQPSGL LLALENSTYQ YIRVWLERGR   420
LAMLTPNSPK LVVKFVLNDG NVHLISLKIK PYKIELYQSS QNLGFISAST WKIEKGDVIY   480
IGGLPDKQET ELNGGFFKGC IQDVRLNNQN LEFFPNPTNN ASLNPVLVNV TQGCAGDNSC   540
KSNPCHNGGV CHSRWDDFSC SCPALTSGKA CEEVQWCGFS PCPHGAQCQP VLQGFECIAN   600
AVFNGQSGQI LFRSNGNITR ELTNITFGFR TRDANVIILHA AEKEPEFLNI SIQDSRLFFQ   660
LQSGNSFYML SLTSLQSVND GTWHEVTLSM TDPLSQTSRW QMEVDNETPF VTSTIATGSL   720
NFLKDNTDIY VGDRAIDNIK GLQGCLSTIE IGGIYLSYFE NVHGFINKPQ EEQFLKISTN   780
SVVTGCLQLN VCNSNPCLHG GNCEDIYSSY HCSCPLGWSG KHCELNIDEC FSNPCIHGNC   840
SDRVAAYHCT CEPGYTGVNC EVDIDNCQSH QCANGATCIS HTNGYSCLCF GNFTGKFCRQ   900
SRLPSTVCGN EKTNLTCYNG GNCTEFQTEL KCMCRPGFTG EW                     942

SEQ ID NO: 45            moltype = AA  length = 870
FEATURE                  Location/Qualifiers
source                   1..870
                         mol_type = protein
                         organism = Homo sapiens
SEQUENCE: 45
MALKNINYLL IFYLSFSLLI YIKNSFCNKN NTRCLSNSCQ NNSTCKDFSK DNDCSCSDTA    60
NNLDKDCDNM KDPCFSNPCQ GSATCVNTPG ERSFLCKCPP GYSGTICETT IGSCGKNSCQ   120
HGGICHQDPI YPVCICPAGY AGRFCEIDHD ECASSPCQNG AVCQDGIDGY SCFCVPGYQG   180
RHCDLEVDEC ASDPCKNEAT CLNEIGRYTC ICPHNYSGVN CELEIDECWS QPCLNGATCQ   240
DALGAYFCDC APGFLGDHCE LNTDECASQP CLHGGLCVDG ENRYSCNCTG SGFTGTHCET   300
LMPLCWSKPC HNNATCEDSV DNYTCHCWPG YTGAQCEIDL NECNSNPCQS NGECVELSSE   360
KQYGRITGLP SSFSYHEASG YVCICQPGFT GIHCEEDVNE CSSNPCQNGG TCENLPGNYT   420
CHCPFDNLSR TFYGGRDCSD ILLGCTHQQC LNNGTCIPHF QDGQHGFSCL CPSGYTGSLC   480
EIATTLSFEG DGFLWVKSGS VTTKGSVCNI ALRFQTVQPM ALLLFRSNRD VFVKLELLSG   540
YIHLSIQVNN QSKVLLFISH NTSDGEWHFV EVIFAEAVTL TLIDDSCKEK CIAKAPTPLE   600
SDQSICAFQN SFLGGLPVGM TSNGVALLNF YNMPSTPSFV GCLQDIKIDW NHITLENISS   660
GSSLNVKAGC VRKDWCESQP CQSRGRCINL WLSYQCDCHR PYEGPNCLRG KFCRQSRLPS   720
```

```
TVCGNEKTNL TCYNGGNCTE FQTELKCMCR PGFTGEWCEK DIDECASDPC VNGGLCQDLL  780
NKFQCLCDVA FAGERCEVDL ADDLISDIFT TIGSVTVALL LILLLAIVAS VVTSNKRATQ  840
GTYSPSRQEK EGSRVEMWNL MPPPAMERLI                                    870

SEQ ID NO: 46                  moltype = AA  length = 238
FEATURE                        Location/Qualifiers
source                         1..238
                               mol_type = protein
                               organism = Homo sapiens
SEQUENCE: 46
MLCCMRRTKQ VEKNDDDQKI EQDGIKPEDK AHKAATKIQA SFRGHITRKK LKGEKKDDVQ  60
AAEAEANKKD EAPVADGVEK KGEGTTTAEA APATGSKPDE PGKAGETPSE EKKGEGDAAT  120
EQAAPQAPAS SEEKAGSAET ESATKASTDN SPSSKAEDAP AKEEPKQADV PAAVTAAAAT  180
TPAAEDAAAK ATAQPPTETG ESSQAEENIE AVDETKPKES ARQDEGKEEE PEADQEHA    238

SEQ ID NO: 47                  moltype = AA  length = 274
FEATURE                        Location/Qualifiers
source                         1..274
                               mol_type = protein
                               organism = Homo sapiens
SEQUENCE: 47
MTKSCSELCH PALHFLPCLG GLRKNLQRAV RPSPYSLGFL TFWISRVEKN DDDQKIEQDG  60
IKPEDKAHKA ATKIQASFRG HITRKKLKGE KKDDVQAAEA EANKKDEAPV ADGVEKKGEG  120
TTTAEAAPAT GSKPDEPGKA GETPSEEKKG EGDAATEQAA PQAPASSEEK AGSAETESAT  180
KASTDNSPSS KAEDAPAKEE PKQADVPAAV TAAAATTPAA EDAAAKATAQ PPTETGESSQ  240
AEENIEAVDE TKPKESARQD EGKEEEPEAD QEHA                               274

SEQ ID NO: 48                  moltype = AA  length = 290
FEATURE                        Location/Qualifiers
source                         1..290
                               mol_type = protein
                               organism = Homo sapiens
SEQUENCE: 48
MVIQKEKKSC GQVVEEWKEF VWNPRTHQFM GRTGTSWAFI LLFYLVFYGF LTAMFTLTMW  60
VMLQTVSDHT PKYQDRLATP GLMIRPKTEN LDVIVNVSDT ESWDQHVQKL NKFLEPYNDS  120
IQAQKNDVCR PGRYYEQPDN GVLNYPKRAC QFNRTQLGNC SGIGDSTHYG YSTGQPCVFI  180
KMNRVINFYA GANQSMNVTC AGKRDEDAEN LGNFVMFPAN GNIDLMYFPY YGKKFHVNYT  240
QPLVAVKFLN VTPNVEVNVE CRINAANIAT DDERDKFAGR VAFKLRINKT             290

SEQ ID NO: 49                  moltype = AA  length = 1390
FEATURE                        Location/Qualifiers
source                         1..1390
                               mol_type = protein
                               organism = Homo sapiens
SEQUENCE: 49
MKAPAVLAPG ILVLLFTLVQ RSNGECKEAL AKSEMNVNMK YQLPNFTAET PIQNVILHEH  60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
GAKVLSSVKD RFINFFVGNT INSSYFPDHP LHSISVRRLK ETKDGFMFLT DQSYIDVLPE  240
FRDSYPIKYV HAFESNNFIY FLTVQRETLD AQTFHTRIIR FCSINSGLHS YMEMPLECIL  300
TEKRKKRSTK KEVFNILQAA YVSKPGAQLA RQIGASLNDD LLFGVFAQSK PDSAEPMDRS  360
AMCAFPIKYV NDFFNKIVNK NNVRCLQHFY GPNHEHCFNR TLLRNSSGCE ARRDEYRTEF  420
TTALQRVDLF MGQFSEVLLT SISTFIKGDL TIANLGTSEG RFMQVVVSRS GPSTPHVNFL  480
LDSHPVSPEV IVEHTLNQNG YTLVITGKKI TKIPLNGLGC RHFQSCSQCL SAPPFVQCGW  540
CHDKCVRSEE CLSGTWTQQI CLPAIYKVFP NSAPLEGGTR LTICGWDFGF RRNNKFDLKK  600
TRVLLGNESC TLTLSESTMN TLKCTVGPAM NKHFNMSIII SNGHGTTQYS TFSYVDPVIT  660
SISPKYGPMA GGTLLTLTGN YLNSGNSRHI SIGGKTCTLK SVSNSILECY TPAQTISTEF  720
AVKLKIDLAN RETSIFSYRE DPIVYEIHPT KSFISGGSTI TGVGKNLNSV SVPRMVINVH  780
EAGRNFTVAC QHRSNSEIIC CTTPSLQQLN LQLPLKTKAF FMLDGILSKY FDLIYVHNPV  840
FKPFEKPVMI SMGNENVLEI KGNDIDPEAV KGEVLKVGNK SCENIHLHSE AVLCTVPNDL  900
LKLNSELNIE WKQAISSTVL GKVIVQPDQN FTGLIAGVVS ISTALLLLLG FFLWLKKRKQ  960
IKDLGSELVR YDARVHTPHL DRLVSARSVS PTTEMVSNES VDYRATFPED QFPNSSQNGS  1020
CRQVQYPLTD MSPILTSGDS DISSPLLQNT VHIDLSALNP ELVQAVQHVV IGPSSLIVHF  1080
NEVIGRGHFG CVYHGTLLDN DGKKIHCAVK SLNRITDIGE VSQFLTEGII MKDFSHPNVL  1140
SLLGICLRSE GSPLVVLPYM KHGDLRNFIR NETHNPTVKD LIGFGLQVAK GMKYLASKKF  1200
VHRDLAARNC MLDEKFTVKV ADFGLARDMY DKEYYSVHNK TGAKLPVKWM ALESLQTQKF  1260
TTKSDVWSFG VLLWELMTRG APPYPDVNTF DITVYLLQGR RLLQPEYCPD PLYEVMLKCW  1320
HPKAEMRPSF SELVSRISAI FSTFIGEHYV HVNATYVNVK CVAPYPSLLS SEDNADDEVD  1380
TRPASFWETS                                                          1390

SEQ ID NO: 50                  moltype = AA  length = 1408
FEATURE                        Location/Qualifiers
source                         1..1408
                               mol_type = protein
                               organism = Homo sapiens
SEQUENCE: 50
MKAPAVLAPG ILVLLFTLVQ RSNGECKEAL AKSEMNVNMK YQLPNFTAET PIQNVILHEH  60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
```

-continued

```
GAKVLSSVKD RFINFFVGNT INSSYFPDHP LHSISVRRLK ETKDGFMFLT DQSYIDVLPE   240
FRDSYPIKYV HAFESNNFIY FLTVQRETLD AQTFHTRIIR FCSINSGLHS YMEMPLECIL   300
TEKRKKRSTK KEVFNILQAA YVSKPGAQLA RQIGASLNDD ILFGVFAQSK PDSAEPMDRS   360
AMCAFPIKYV NDFFNKIVNK NNVRCLQHFY GPNHEHCFNR TLLRNSSGCE ARRDEYRTEF   420
TTALQRVDLF MGQFSEVLLT SISTFIKGDL TIANLGTSEG RFMQVVVSRS GPSTPHVNFL   480
LDSHPVSPEV IVEHTLNQNG YTLVITGKKI TKIPLNGLGC RHFQSCSQCL SAPPFVQCGW   540
CHDKCVRSEE CLSGTWTQQI CLPAIYKVFP NSAPLEGGTR LTICGWDFGF RRNNKFDLKK   600
TRVLLGNESC TLTLSESTMN TLKCTVGPAM NKHFNMSIII SNGHGTTQYS TFSYVDPVIT   660
SISPKYGPMA GGTLLTLTGN YLNSGNSRHI SIGGKTCTLK SVSNSILECY TPAQTISTEF   720
AVKLKIDLAN RETSIFSYRE DPIVYEIHPT KSFISTWWKE PLNIVSFLFC FASGGSTITG   780
VGKNLNSVSV PRMVINVHEA GRNFTVACQH RSNSEIICCT TPSLQQLNLQ LPLKTKAFFM   840
LDGILSKYFD LIYVHNPVFK PFEKPVMISM GNENVLEIKG NDIDPEAVKG EVLKVGNKSC   900
ENIHLHSEAV LCTVPNDLLK LNSELNIEWK QAISSTVLGK VIVQPDQNFT GLIAGVVSIS   960
TALLLLLGFF LWLKKRKQIK DLGSELVRYD ARVHTPHLDR LVSARSVSPT TEMVSNESVD  1020
YRATFPEDQF PNSSQNGSCR QVQYPLTDMS PILTSGDSDI SSPLLQNTVH IDLSALNPEL  1080
VQAVQHVVIG PSSLIVHFNE VIGRGHFGCV YHGTLLDNDG KKIHCAVKSL NRITDIGEVS  1140
QFLTEGIIMK DFSHPNVLSL LGICLRSEGS PLVVLPYMKH GDLRNFIRNE THNPTVKDLI  1200
GFGLQVAKGM KYLASKKFVH RDLAARNCML DEKFTVKVAD FGLARDMYDK EYYSVHNKTG  1260
AKLPVKWMAL ESLQTQKFTT KSDVWSFGVL LWELMTRGAP PYPDVNTFDI TVYLLQGRRL  1320
LQPEYCPDPL YEVMLKCWHP KAEMRPSFSE LVSRISAIFS TFIGEHYVHV NATYVNVKCV  1380
APYPSLLSSE DNADDEVDTR PASFWETS                                    1408

SEQ ID NO: 51          moltype = AA   length = 764
FEATURE                Location/Qualifiers
source                 1..764
                       mol_type = protein
                       organism = Homo sapiens
SEQUENCE: 51
MKAPAVLAPG ILVLLFTLVQ RSNGECKEAL AKSEMNVNMK YQLPNFTAET PIQNVILHEH   60
HIFLGATNYI YVLNEEDLQK VAEYKTGPVL EHPDCFPCQD CSSKANLSGG VWKDNINMAL  120
VVDTYYDDQL ISCGSVNRGT CQRHVFPHNH TADIQSEVHC IFSPQIEEPS QCPDCVVSAL  180
GAKVLSSVKD RFINFFVGNT INSSYFPDHP LHSISVRRLK ETKDGFMFLT DQSYIDVLPE  240
FRDSYPIKYV HAFESNNFIY FLTVQRETLD AQTFHTRIIR FCSINSGLHS YMEMPLECIL  300
TEKRKKRSTK KEVFNILQAA YVSKPGAQLA RQIGASLNDD ILFGVFAQSK PDSAEPMDRS  360
AMCAFPIKYV NDFFNKIVNK NNVRCLQHFY GPNHEHCFNR TLLRNSSGCE ARRDEYRTEF  420
TTALQRVDLF MGQFSEVLLT SISTFIKGDL TIANLGTSEG RFMQVVVSRS GPSTPHVNFL  480
LDSHPVSPEV IVEHTLNQNG YTLVITGKKI TKIPLNGLGC RHFQSCSQCL SAPPFVQCGW  540
CHDKCVRSEE CLSGTWTQQI CLPAIYKVFP NSAPLEGGTR LTICGWDFGF RRNNKFDLKK  600
TRVLLGNESC TLTLSESTMN TLKCTVGPAM NKHFNMSIII SNGHGTTQYS TFSYVDPVIT  660
SISPKYGPMA GGTLLTLTGN YLNSGNSRHI SIGGKTCTLK SVSNSILECY TPAQTISTEF  720
AVKLKIDLAN RETSIFSYRE DPIVYEIHPT KSFIRHVNIA LIQR                   764

SEQ ID NO: 52          moltype = AA   length = 976
FEATURE                Location/Qualifiers
source                 1..976
                       mol_type = protein
                       organism = Homo sapiens
SEQUENCE: 52
MELQAARACF ALLWGCALAA AAAAQGKEVV LLDFAAAGGE LGWLTHPYGK GWDLMQNIMN   60
DMPIYMYSVC NVMSGDQDNW LRTNWVYRGE AERIFIELKF TVRDCNSFPG GASSCKETFN  120
LYYAESDLDY GTNFQKRLFT KIDTIAPDEI TVSSDFEARH VKLNVEERSV GPLTRKGFYL  180
AFQDIGACVA LLSVRVYYKK CPELLQGLAH FPETIAGSDA PSLATVAGTC VDHAVVPPGG  240
EEPRMHCAVD GEWLVPIGQC LCQAGYEKVE DACQACSPGF FKFEASESPC LECPEHTLPS  300
PEGATSCECE EGFFRAPQDP ASMPCTRPPS APHYLTAVGM GAKVELRWTP PQDSGGREDI  360
VYSVTCEQCW PESGECGPCE ASVRYSEPPH GLTRTSVTVS DLEPHMNYTF TVEARNGVSG  420
LVTSRSFRTA SVSINQTEPP KVRLEGRSTT SLSVSWSIPP PQQSRVWKYE VTYRKKGDSN  480
SYNVRRTEGF SVTLDDLAPD TTYLVQVQAL TQEGQGAGSK VHEFQTLSPE GSGNLAVIGG  540
VAVGVVLLLV LAGVGFFIHR RRKNQRARQS PEDVYFSKSE QLKPLKTYVD PHTYEDPNQA  600
VLKFTTEIHP SCVTRQKVIG AGEFGEVYKG MLKTSSGKKE VPVAIKTLKA GYTEKQRVDF  660
LGEAGIMGQF SHHNIIRLEG VISKYKPMMI ITEYMENGAL DKFLREKDGE FSVLQLVGML  720
RGIAAGMKYL ANMNYVHRDL AARNILVNSN LVCKVSDFGL SRVLEDDPEA TYTTSGGKIP  780
IRWTAPEAIS YRKFTSASDV WSFGIVMWEV MTYGERPYWE LSNHEVMKAI NDGFRLPTPM  840
DCPSAIYQLM MQCWQQERAR RPKFADIVSI LDKLIRAPDS LKTLADFDPR VSIRLPSTSG  900
SEGVPFRTVS EWLESIKMQQ YTEHFMAAGY TAIEKVVQMT NDDIKRIGVR LPGHQKRIAY  960
SLLGLKDQVN TVGIPI                                                 976

SEQ ID NO: 53          moltype = AA   length = 497
FEATURE                Location/Qualifiers
source                 1..497
                       mol_type = protein
                       organism = Homo sapiens
SEQUENCE: 53
MELQAARACF ALLWGCALAA AAAAQGKEVV LLDFAAAGGE LGWLTHPYGK GWDLMQNIMN   60
DMPIYMYSVC NVMSGDQDNW LRTNWVYRGE AERIFIELKF TVRDCNSFPG GASSCKETFN  120
LYYAESDLDY GTNFQKRLFT KIDTIAPDEI TVSSDFEARH VKLNVEERSV GPLTRKGFYL  180
AFQDIGACVA LLSVRVYYKK CPELLQGLAH FPETIAGSDA PSLATVAGTC VDHAVVPPGG  240
EEPRMHCAVD GEWLVPIGQC LCQAGYEKVE DACQACSPGF FKFEASESPC LECPEHTLPS  300
PEGATSCECE EGFFRAPQDP ASMPCTRPPS APHYLTAVGM GAKVELRWTP PQDSGGREDI  360
VYSVTCEQCW PESGECGPCE ASVRYSEPPH GLTRTSVTVS DLEPHMNYTF TVEARNGVSG  420
```

```
LVTSRSFRTA SVSINQTEPP KVRLEGRSTT SLSVSWSIPP PQQSRVWKYE VTYRKKVTPR    480
GAGLALAGPT AGDRLVT                                                   497

SEQ ID NO: 54          moltype = AA  length = 253
FEATURE                Location/Qualifiers
source                 1..253
                       mol_type = protein
                       organism = Homo sapiens
SEQUENCE: 54
EIVLTQSPGT LSLSPGERAT LSCRASQSVS SSNLAWYQQK PGQAPRLLIY GASSRATGVP    60
DRFSGSGSGT DFTLTISRLE PEDFAVYYCQ QSSSYPWTFG QGTKVEIKRT GGGGSGAGGS   120
GGGGTGGGGS EVDLLESGGG LVQPGGSLRL SCAASGFTFS RYWMHWVRQA PGKGLEWVSS   180
ISPYDGETNY ADSVKGRFTI SRDNSKNTLY LQMNSLRAED TAVYYCARIS EWYNWAVDVF   240
DYWGQGTLVT VSS                                                      253

SEQ ID NO: 55          moltype = AA  length = 237
FEATURE                Location/Qualifiers
source                 1..237
                       mol_type = protein
                       organism = Homo sapiens
SEQUENCE: 55
QVQLLESGGG LVQPGGSLRL SCAASGFTFS SYTMSWVRQA PGQALEWMGT ISSGGTYTYY    60
PDSVKGRFTI SRDNAKNSLY LQMNSLRAED TAVYYCAREA IFTYWGRGTL VTSSGGGGSG   120
GGGSGGGGSD IQLTQSPSSL SASVGDRVTI TCKASQDINN YLSWYQQKPG QAPRLLIYRA   180
NRLVDGVPDR FSGSGYGTDF TLTINNIESE DAAYYFCLKY DVFPYTFGQG TKVEIKS      237

SEQ ID NO: 56          moltype = AA  length = 983
FEATURE                Location/Qualifiers
source                 1..983
                       mol_type = protein
                       organism = Homo sapiens
SEQUENCE: 56
MDCQLSILLL LSCSVLDSFG ELIPQPSNEV NLLDSKTIQG ELGWISYPSH GWEEISGVDE    60
HYTPIRTYQV CNVMDHSQNN WLRTNWVPRN SAQKIYVELK FTLRDCNSIP LVLGTCKETF   120
NLYYMESDDD HGVKFREHQF TKIDTIAADE SFTQMDLGDR ILKLNTEIRE VGPVNKKGFY   180
LAFQDVGACV ALVSVRVYFK KCPFTVKNLA MFPDTVPMDS QSLVEVRGSC VNNSKEEDPP   240
RMYCSTEGEW LVPIGKCSCN AGYEERGFMC QACRPGFYKA LDGNMKCAKC PPHSSTQEDG   300
SMNCRCENNY FRADKDPPSM ACTRPPSSPR NVISNINETS VILDWSWPLD TGGRKDVTFN   360
IICKKCGWNI KQCEPCSPNV RFLPRQFGLT NTTVTVTDLL AHTNYTFEID AVNGVSELSS   420
PPRQFAAVSI TTNQAAPSPV LTIKKDRTSR NSISLSWQEP EHPNGIILDY EVKYYEKQEQ   480
ETSYTILRAR GTNVTISSLK PDTIYVFQIR ARTAAGYGTN SRKFEFETSP DSFSISGESS   540
QVVMIAISAA VAIILLTVVI YVLIGRFCGY KSKHGADEKR LHFGNGHLKL PGLRTYVDPH   600
TYEDPTQAVH EFAKELDATN ISIDKVVGAG EFGEVCSGRL KLPSKKEISV AIKTLKVGYT   660
EKQRRDFLGE ASIMGQFDHP NIIRLEGVVT KSKPVMIVTE YMENGSLDSF LRKHDAQFTV   720
IQLVGMLRGI ASGMKYLSDM GYVHRDLAAR NILINSNLVC KVSDFGLSRV LEDDPEAAYT   780
TRGGKIPIRW TSPEAIAYRK FTSASDVWSY GIVLWEVMSY GERPYWEMSN QDVIKAVDEG   840
YRLPPPMDCP AALYQLMLDC WQKDRNNRPK FEQIVSILDK LIRNPGSLKI ITSAAARPSN   900
LLLLDQSNVDI TTFRTTGDWL NGVWTAHCKE IFTGVEYSSC DTIAKISTDD MKKVGVTVVG   960
PQKKIISSIK ALETQSKNGP VPV                                           983

SEQ ID NO: 57          moltype = AA  length = 539
FEATURE                Location/Qualifiers
source                 1..539
                       mol_type = protein
                       organism = Homo sapiens
SEQUENCE: 57
MDCQLSILLL LSCSVLDSFG ELIPQPSNEV NLLDSKTIQG ELGWISYPSH GWEEISGVDE    60
HYTPIRTYQV CNVMDHSQNN WLRTNWVPRN SAQKIYVELK FTLRDCNSIP LVLGTCKETF   120
NLYYMESDDD HGVKFREHQF TKIDTIAADE SFTQMDLGDR ILKLNTEIRE VGPVNKKGFY   180
LAFQDVGACV ALVSVRVYFK KCPFTVKNLA MFPDTVPMDS QSLVEVRGSC VNNSKEEDPP   240
RMYCSTEGEW LVPIGKCSCN AGYEERGFMC QACRPGFYKA LDGNMKCAKC PPHSSTQEDG   300
SMNCRCENNY FRADKDPPSM ACTRPPSSPR NVISNINETS VILDWSWPLD TGGRKDVTFN   360
IICKKCGWNI KQCEPCSPNV RFLPRQFGLT NTTVTVTDLL AHTNYTFEID AVNGVSELSS   420
PPRQFAAVSI TTNQAAPSPV LTIKKDRTSR NSISLSWQEP EHPNGIILDY EVKYYEKQEQ   480
ETSYTILRAR GTNVTISSLK PDTIYVFQIR ARTAAGYGTN SRKFEFETSP DCMYYFNAV    539

SEQ ID NO: 58          moltype = AA  length = 146
FEATURE                Location/Qualifiers
source                 1..146
                       mol_type = protein
                       organism = Homo sapiens
SEQUENCE: 58
MHPLLNPLLL ALGLMALLLT TVIALTCLGG FASPGPVPPS TALRELIEEL VNITQNQKAP    60
LCNGSMVWSI NLTAGMYCAA LESLINVSGC SAIEKTQRML SGFCPHKVSA GQFSSLHVRD   120
TKIEVAQFVK DLLLHLKKLF REGRFN                                        146

SEQ ID NO: 59          moltype = AA  length = 122
FEATURE                Location/Qualifiers
REGION                 1..122
```

-continued

```
                              note = synthetic polypeptide sequence
source                        1..122
                              mol_type = protein
                              organism = synthetic construct
SEQUENCE: 59
LTCLGGFASP GPVPPSTALR KLIEELVNIT QNQKAPLCNG SMVWSINLTA GMYCAALESL    60
INVSGCSAIE KTQRMLSGFC PHKVSAGQFS SLHVRDTKIE VAQFVKDLLL HLRKLFREGR   120
FN                                                                  122

SEQ ID NO: 60        moltype = AA  length = 1210
FEATURE              Location/Qualifiers
source               1..1210
                     mol_type = protein
                     organism = Homo sapiens
SEQUENCE: 60
MRPSGTAGAA LLALLAALCP ASRALEEKKV CQGTSNKLTQ LGTFEDHFLS LQRMFNNCEV    60
VLGNLEITYV QRNYDLSFLK TIQEVAGYVL IALNTVERIP LENLQIIRGN MYYENSYALA   120
VLSNYDANKT GLKELPMRNL QEILHGAVRF SNNPALCNVE SIQWRDIVSS NMSMDF       180
QNHLGSCQKC DPSCPNGSCW GAGEENCQKL TKIICAQQCS GRCRGKSPSD CCHNQCAAGC   240
TGPRESDCLV CRKFRDEATC KDTCPPLMLY NPTTYQMDVN PEGKYSFGAT CVKKCPRNYV   300
VTDHGSCVRA CGADSYEMEE DGVRKCKKCE GPCRKVCNGI GIGEFKDSLS INATNIKHFK   360
NCTSISGDLH ILPVAFRGDS FTHTPPLDPQ ELDILKTVKE ITGFLLIQAW PENRTDLHAF   420
ENLEIIRGRT KQHGQFSLAV VSLNITSLGL RSLKEISDGD VIISGNKNLC YANTINWKKL   480
FGTSGQKTKI ISNRGENSCK ATGQVCHALC SPEGCWGPEP RDCVSCRNVS RGRECVDKCN   540
LLEGEPREFV ENSECIQCHP ECLPQAMNIT CTGRGPDNCI QCAHYIDGPH CVKTCPAGVM   600
GENNTLVWKY ADAGHVCHLC HPNCTYGCTG PGLEGCPTNG PKIPSIATGM VGALLLLLVV   660
ALGIGLFMRR RHIVRKRTLR RLLQERELVE PLTPSGEAPN QALLRILKET EFKKIKVLGS   720
GAFGTVYKGL WIPEGEKVKI PVAIKELREA TSPKANKEIL DEAYVMASVD NPHVCRLLGI   780
CLTSTVQLIT QLMPFGCLLD YVREHKDNIG SQYLLNWCVQ IAKGMNYLED RRLVHRDLAA   840
RNVLVKTPQH VKITDFGLAK LLGAEEKEYH AEGGKVPIKW MALESILHRI YTHQSDVWSY   900
GVTVWELMTF GSKPYDGIPA SEISSILEKG ERLPQPPICT IDVYMIMVKC WMIDADSRPK   960
FRELIIEFSK MARDPQRYLV IQGDERMHLP SPTDSNFYRA LMDEEDMDDV VDADEYLIPQ  1020
QGFFSSPSTS RTPLLSSLSA TSNNSTVACI DRNGLQSCPI KEDSFLQRYS SDPTGALTED  1080
SIDDTFLPVP EYINQSVPKR PAGSVQNPVY HNQPLNPAPS RDPHYQDPHS TAVGNPEYLN  1140
TVQPTCVNST FDSPAHWAQK GSHQISLDNP DYQQDFFPKE AKPNGIFKGS TAENAEYLRV  1200
APQSSEFIGA                                                        1210

SEQ ID NO: 61        moltype = AA  length = 405
FEATURE              Location/Qualifiers
source               1..405
                     mol_type = protein
                     organism = Homo sapiens
SEQUENCE: 61
MRPSGTAGAA LLALLAALCP ASRALEEKKV CQGTSNKLTQ LGTFEDHFLS LQRMFNNCEV    60
VLGNLEITYV QRNYDLSFLK TIQEVAGYVL IALNTVERIP LENLQIIRGN MYYENSYALA   120
VLSNYDANKT GLKELPMRNL QEILHGAVRF SNNPALCNVE SIQWRDIVSS DFLSNMSMDF   180
QNHLGSCQKC DPSCPNGSCW GAGEENCQKL TKIICAQQCS GRCRGKSPSD CCHNQCAAGC   240
TGPRESDCLV CRKFRDEATC KDTCPPLMLY NPTTYQMDVN PEGKYSFGAT CVKKCPRNYV   300
VTDHGSCVRA CGADSYEMEE DGVRKCKKCE GPCRKVCNGI GIGEFKDSLS INATNIKHFK   360
NCTSISGDLH ILPVAFRGDS FTHTPPLDPQ ELDILKTVKE ITGLS                  405

SEQ ID NO: 62        moltype = AA  length = 705
FEATURE              Location/Qualifiers
source               1..705
                     mol_type = protein
                     organism = Homo sapiens
SEQUENCE: 62
MRPSGTAGAA LLALLAALCP ASRALEEKKV CQGTSNKLTQ LGTFEDHFLS LQRMFNNCEV    60
VLGNLEITYV QRNYDLSFLK TIQEVAGYVL IALNTVERIP LENLQIIRGN MYYENSYALA   120
VLSNYDANKT GLKELPMRNL QEILHGAVRF SNNPALCNVE SIQWRDIVSS DFLSNMSMDF   180
QNHLGSCQKC DPSCPNGSCW GAGEENCQKL TKIICAQQCS GRCRGKSPSD CCHNQCAAGC   240
TGPRESDCLV CRKFRDEATC KDTCPPLMLY NPTTYQMDVN PEGKYSFGAT CVKKCPRNYV   300
VTDHGSCVRA CGADSYEMEE DGVRKCKKCE GPCRKVCNGI GIGEFKDSLS INATNIKHFK   360
NCTSISGDLH ILPVAFRGDS FTHTPPLDPQ ELDILKTVKE ITGFLLIQAW PENRTDLHAF   420
ENLEIIRGRT KQHGQFSLAV VSLNITSLGL RSLKEISDGD VIISGNKNLC YANTINWKKL   480
FGTSGQKTKI ISNRGENSCK ATGQVCHALC SPEGCWGPEP RDCVSCRNVS RGRECVDKCN   540
LLEGEPREFV ENSECIQCHP ECLPQAMNIT CTGRGPDNCI QCAHYIDGPH CVKTCPAGVM   600
GENNTLVWKY ADAGHVCHLC HPNCTYGPGN ESLKAMLFCL FKLSSCQSN DGSVSHQSGS   660
PAAQESCLGW IPSLLPSEFQ LGWGGCSHLH AWPSASVIIT ASSCH                  705

SEQ ID NO: 63        moltype = AA  length = 628
FEATURE              Location/Qualifiers
source               1..628
                     mol_type = protein
                     organism = Homo sapiens
SEQUENCE: 63
MRPSGTAGAA LLALLAALCP ASRALEEKKV CQGTSNKLTQ LGTFEDHFLS LQRMFNNCEV    60
VLGNLEITYV QRNYDLSFLK TIQEVAGYVL IALNTVERIP LENLQIIRGN MYYENSYALA   120
VLSNYDANKT GLKELPMRNL QEILHGAVRF SNNPALCNVE SIQWRDIVSS DFLSNMSMDF   180
```

```
QNHLGSCQKC DPSCPNGSCW GAGEENCQKL TKIICAQQCS GRCRGKSPSD CCHNQCAAGC  240
TGPRESDCLV CRKFRDEATC KDTCPPLMLY NPTTYQMDVN PEGKYSFGAT CVKKCPRNYV  300
VTDHGSCVRA CGADSYEMEE DGVRKCKKCE GPCRKVCNGI GIGEFKDSLS INATNIKHFK  360
NCTSISGDLH ILPVAFRGDS FTHTPPLDPQ ELDILKTVKE ITGFLLIQAW PENRTDLHAF  420
ENLEIIRGRT KQHGQFSLAV VSLNITSLGL RSLKEISDGD VIISGNKNLC YANTINWKKL  480
FGTSGQKTKI ISNRGENSCK ATGQVCHALC SPEGCWGPEP RDCVSCRNVS RGRECVDKCN  540
LLEGEPREFV ENSECIQCHP ECLPQAMNIT CTGRGPDNCI QCAHYIDGPH CVKTCPAGVM  600
GENNTLVWKY ADAGHVCHLC HPNCTYGS                                    628

SEQ ID NO: 64               moltype = AA  length = 1255
FEATURE                     Location/Qualifiers
source                      1..1255
                            mol_type = protein
                            organism = Homo sapiens
SEQUENCE: 64
MELAALCRWG LLLALLPPGA ASTQVCTGTD MKLRLPASPE THLDMLRHLY QGCQVVQGNL  60
ELTYLPTNAS LSFLQDIQEV QGYVLIAHNQ VRQVPLQRLR IVRGTQLFED NYALAVLDNG  120
DPLNNTTPVT GASPGGLREL QLRSLTEILK GGVLIQRNPQ LCYQDTILWK DIFHKNNQLA  180
LTLIDTNRSR ACHPCSPMCK GSRCWGESSE DCQSLTRTVC AGGCARCKGP LPTDCCHEQC  240
AAGCTGPKHS DCLACLHFNH SGICELHCPA LVTYNTDTFE SMPNPEGRYT FGASCVTACP  300
YNYLSTDVGS CTLVCPLHNQ EVTAEDGTQR CEKCSKPCAR VCYGLGMEHL REVRAVTSAN  360
IQEFAGCKKI FGSLAFLPES FDGDPASNTA PLQPEQLQVF ETLEEITGYL YISAWPDSLP  420
DLSVFQNLQV IRGRILHNGA YSLTLQGLGI SWLGLRSLRE LGSGLALIHH NTHLCFVHTV  480
PWDQLFRNPH QALLHTANRP EDECVGEGLA CHQLCARGHC WGPGPTQCVN CSQFLRGQEC  540
VEECRVLQGL PREYVNARHC LPCHPECQPQ NGSVTCFGPE ADQCVACAHY KDPPFCVARC  600
PSGVKPDLSY MPIWKFPDEE GACQPCPINC THSCVDLDDK GCPAEQRASP LTSIISAVVG  660
ILLVVVLGVV FGILIKRRQQ KIRKYTMRRL LQETELVEPL TPSGAMPNQA QMRILKETEL  720
RKVKVLGSGA FGTVYKGIWI PDGENVKIPV AIKVLRENTS PKANKEILDE AYVMAGVGSP  780
YVSRLLGICL TSTVQLVTQL MPYGCLLDHV RENRGRLGSQ DLLNWCMQIA KGMSYLEDVR  840
LVHRDLAARN VLVKSPNHVK ITDFGLARLL DIDETEYHAD GGKVPIKWMA LESILRRRFT  900
HQSDVWSYGV TVWELMTFGA KPYDGIPARE IPDLLEKGER LPQPPICTID VYMIMVKCWM  960
IDSECRPRFR ELVSEFSRMA RDPQRFVVIQ NEDLGPASPL DSTFYRSLLE DDDMGDLVDA  1020
EEYLVPQQGF FCPDPAPGAG GMVHHRHRSS STRSGGGDLT LGLEPSEEEA PRSPLAPSEG  1080
AGSDVFDGDL GMGAAKGLQS LPTHDPSPLQ RYSEDPTVPL PSETDGYVAP LTCSPQPEYV  1140
NQPDVRPQPP SPREGPLPAA RPAGATLERP KTLSPGKNGV VKDVFAFGGA VENPEYLTPQ  1200
GGAAPQPHPP PAFSPAFDNL YYWDQDPPER GAPPSTFKGT PTAENPEYLG LDVPV       1255

SEQ ID NO: 65               moltype = AA  length = 645
FEATURE                     Location/Qualifiers
source                      1..645
                            mol_type = protein
                            organism = Homo sapiens
SEQUENCE: 65
MPIWKFPDEE GACQPCPINC THSCVDLDDK GCPAEQRASP LTSIISAVVG ILLVVVLGVV  60
FGILIKRRQQ KIRKYTMRRL LQETELVEPL TPSGAMPNQA QMRILKETEL RKVKVLGSGA  120
FGTVYKGIWI PDGENVKIPV AIKVLRENTS PKANKEILDE AYVMAGVGSP YVSRLLGICL  180
TSTVQLVTQL MPYGCLLDHV RENRGRLGSQ DLLNWCMQIA KGMSYLEDVR LVHRDLAARN  240
VLVKSPNHVK ITDFGLARLL DIDETEYHAD GGKVPIKWMA LESILRRRFT HQSDVWSYGV  300
TVWELMTFGA KPYDGIPARE IPDLLEKGER LPQPPICTID VYMIMVKCWM IDSECRPRFR  360
ELVSEFSRMA RDPQRFVVIQ NEDLGPASPL DSTFYRSLLE DDDMGDLVDA EEYLVPQQGF  420
FCPDPAPGAG GMVHHRHRSS STRSGGGDLT LGLEPSEEEA PRSPLAPSEG AGSDVFDGDL  480
GMGAAKGLQS LPTHDPSPLQ RYSEDPTVPL PSETDGYVAP LTCSPQPEYV NQPDVRPQPP  540
SPREGPLPAA RPAGATLERP KTLSPGKNGV VKDVFAFGGA VENPEYLTPQ GGAAPQPHPP  600
PAFSPAFDNL YYWDQDPPER GAPPSTFKGT PTAENPEYLG LDVPV                  645

SEQ ID NO: 66               moltype = AA  length = 569
FEATURE                     Location/Qualifiers
source                      1..569
                            mol_type = protein
                            organism = Homo sapiens
SEQUENCE: 66
MRRLLQETEL VEPLTPSGAM PNQAQMRILK ETELRKVKVL GSGAFGTVYK GIWIPDGENV  60
KIPVAIKVLR ENTSPKANKE ILDEAYVMAG VGSPYVSRLL GICLTSTVQL VTQLMPYGCL  120
LDHVRENRGR LGSQDLLNWC MQIAKGMSYL EDVRLVHRDL AARNVLVKSP NHVKITDFGL  180
ARLLDIDETE YHADGGKVPI KWMALESILR RRFTHQSDVW SYGVTVWELM TFGAKPYDGI  240
PAREIPDLLE KGERLPQPPI CTIDVYMIMV KCWMIDSECR PRFRELVSEF SRMARDPQRF  300
VVIQNEDLGP ASPLDSTFYR SLLEDDDMGD LVDAEEYLVP QQGFFCPDPA PGAGGMVHHR  360
HRSSSTRSGG GDLTLGLEPS EEEAPRSPLA PSEGAGSDVF DGDLGMGAAK GLQSLPTHDP  420
SPLQRYSEDP TVPLPSETDG YVAPLTCSPQ PEYVNQPDVR PQPPSPREG PLPAARPAGAT  480
LERPKTLSPG KNGVVKDVFA FGGAVENPEY LTPQGGAAPQ PHPPPAFSPA FDNLYYWDQD  540
PPERGAPPST FKGTPTAENP EYLGLDVPV                                   569

SEQ ID NO: 67               moltype = AA  length = 1240
FEATURE                     Location/Qualifiers
source                      1..1240
                            mol_type = protein
                            organism = Homo sapiens
SEQUENCE: 67
MPRGSWKPQV CTGTDMKLRL PASPETHLDM LRHLYQGCQV VQGNLELTYL PTNASLSFLQ  60
```

```
DIQEVQGYVL IAHNQVRQVP LQRLRIVRGT QLFEDNYALA VLDNGDPLNN TTPVTGASPG     120
GLRELQLRSL TEILKGGVLI QRNPQLCYQD TILWKDIFHK NNQLALTLID TNRSRACHPC     180
SPMCKGSRCW GESSEDCQSL TRTVCAGGCA RCKGPLPTDC CHEQCAAGCT GPKHSDCLAC     240
LHFNHSGICE LHCPALVTYN TDTFESMPNP EGRYTFGASC VTACPYNYLS TDVGSCTLVC     300
PLHNQEVTAE DGTQRCEKCS KPCARVCYGL GMEHLREVRA VTSANIQEFA GCKKIFGSLA     360
FLPESFDGDP ASNTAPLQPE QLQVFETLEE ITGYLYISAW PDSLPDLSVF QNLQVIRGRI     420
LHNGAYSLTL QGLGISWLGL RSLRELGSGL ALIHHNTHLC FVHTVPWDQL FRNPHQALLH     480
TANRPEDECV GEGLACHQLC ARGHCWGPGP TQCVNCSQFL RGQECVEECR VLQGLPREYV     540
NARHCLPCHP ECQPQNGSVT CFGPEADQCV ACAHYKDPPF CVARCPSGVK PDLSYMPIWK     600
FPDEEGACQP CPINCTHSCV DLDDKGCPAE QRASPLTSII SAVVGILLVV VLGVVFGILI     660
KRRQQKIRKY TMRRLLQETE LVEPLTPSGA MPNQAQMRIL KETELRKVKV LGSGAFGTVY     720
KGIWIPDGEN VKIPVAIKVL RENTSPKANK EILDEAYVMA GVGSPYVSRL LGICLTSTVQ     780
LVTQLMPYGC LLDHVRENRG RLGSQDLLNW CMQIAKGMSY LEDVRLVHRD LAARNVLVKS     840
PNHVKITDFG LARLLDIDET EYHADGGKVP IKWMALESIL RRRFTHQSDV WSYGVTVWEL     900
MTFGAKPYDG IPAREIPDLL EKGERLPQPP ICTIDVYMIM VKCWMIDSEC RPRFRELVSE     960
FSRMARDPQR FVVIQNEDLG PASPLDSTFY RSLLEDDDMG DLVDAEEYLV PQQGFFCPDP    1020
APGAGGMVHH RHRSSSTRSG GGDLTLGLEP SEEEAPRSPL APSEGAGSDV FDGDLGMGAA    1080
KGLQSLPTHD PSPLQRYSED PTVPLPSETD GYVAPLTCSP QPEYVNQPDV RPQPPSPREG    1140
PLPAARPAGA TLERPKTLSP GKNGVVKDVF AFGGAVENPE YLTPQGGAAP QPHPPPAFSP    1200
AFDNLYYWDQ DPPERGAPPS TFKGTPTAEN PEYLGLDVPV                         1240
```

```
SEQ ID NO: 68             moltype = AA  length = 1225
FEATURE                   Location/Qualifiers
source                    1..1225
                          mol_type = protein
                          organism = Homo sapiens
SEQUENCE: 68
MKLRLPASPE THLDMLRHLY QGCQVVQGNL ELTYLPTNAS LSFLQDIQEV QGYVLIAHNQ      60
VRQVPLQRLR IVRGTQLFED NYALAVLDNG DPLNNTTPVT GASPGGLREL QLRSLTEILK     120
GGVLIQRNPQ LCYQDTILWK DIFHKNNQLA LTLIDTNRSR ACHPCSPMCK GSRCWGESSE     180
DCQSLTRTVC AGGCARCKGP LPTDCCHEQC AAGCTGPKHS DCLACLHFNH SGICELHCPA     240
LVTYNTDTFE SMPNPEGRYT FGASCVTACP YNYLSTDVGS CTLVCPLHNQ EVTAEDGTQR     300
CEKCSKPCAR VCYGLGMEHL REVRAVTSAN IQEFAGCKKI FGSLAFLPES FDGDPASNTA     360
PLQPEQLQVF ETLEEITGYL YISAWPDSLP DLSVFQNLQV IRGRILHNGA YSLTLQGLGI     420
SWLGLRSLRE LGSGLALIHH NTHLCFVHTV PWDQLFRNPH QALLHTANRP EDECVGEGLA     480
CHQLCARGHC WGPGPTQCVN CSQFLRGQEC VEECRVLQGL PREYVNARHC LPCHPECQPQ     540
NGSVTCFGPE ADQCVACAHY KDPPFCVARC PSGVKPDLSY MPIWKFPDEE GACQPCPINC     600
THSCVDLDDK GCPAEQRASP LTSIISAVVG ILLVVVLGVV FGILIKRRQQ KIRKYTMRRL     660
LQETELVEPL TPSGAMPNQA QMRILKETEL RKVKVLGSGA FGTVYKGIWI PDGENVKIPV     720
AIKVLRENTS PKANKEILDE AYVMAGVGSP YVSRLLGICL TSTVQLVTQL MPYGCLLDHV     780
RENRGRLGSQ DLLNWCMQIA KGMSYLEDVR LVHRDLAARN VLVKSPNHVK ITDFGLARLL     840
DIDETEYHAD GGKVPIKWMA LESILRRRFT HQSDVWSYGV TVWELMTFGA KPYDGIPARE     900
IPDLLEKGER LPQPPICTID VYMIMVKCWM IDSECRPRFR ELVSEFSRMA RDPQRFVVIQ     960
NEDLGPASPL DSTFYRSLLE DDDMGDLVDA EEYLVPQQGF FCPDPAPGAG GMVHHRHRSS    1020
STRSGGGDLT LGLEPSEEEA PRSPLAPSEG AGSDVFDGDL GMGAAKGLQS LPTHDPSPLQ    1080
RYSEDPTVPL PSETDGYVAP LTCSPQPEYV NQPDVRPQPP SPREGPLPAA RPAGATLERP    1140
KTLSPGKNGV VKDVFAFGGA VENPEYLTPQ GGAAPQPHPP PAFSPAFDNL YYWDQDPPER    1200
GAPPSTFKGT PTAENPEYLG LDVPV                                         1225
```

```
SEQ ID NO: 69             moltype = AA  length = 888
FEATURE                   Location/Qualifiers
source                    1..888
                          mol_type = protein
                          organism = Homo sapiens
SEQUENCE: 69
MELAALCRWG LLLALLPPGA ASTQVCTGTD MKLRLPASPE THLDMLRHLY QGCQVVQGNL      60
ELTYLPTNAS LSFLQDIQEV QGYVLIAHNQ VRQVPLQRLR IVRGTQLFED NYALAVLDNG     120
DPLNNTTPVT GASPGGLREL QLRSLTEILK GGVLIQRNPQ LCYQDTILWK DIFHKNNQLA     180
LTLIDTNRSR ACHPCSPMCK GSRCWGESSE DCQSLTRTVC AGGCARCKGP LPTDCCHEQC     240
AAGCTGPKHS DCLACLHFNH SGICELHCPA LVTYNTDTFE SMPNPEGRYT FGASCVTACP     300
YNYLSTDVGS CTLVCPLHNQ EVTAEDGTQR CEKCSKPCAR VCYGLGMEHL REVRAVTSAN     360
IQEFAGCKKI FGSLAFLPES FDGDPASNTA PLQPEQLQVF ETLEEITGYL YISAWPDSLP     420
DLSVFQNLQV IRGRILHNGA YSLTLQGLGI SWLGLRSLRE LGSGLALIHH NTHLCFVHTV     480
PWDQLFRNPH QALLHTANRP EDECVGEGLA CHQLCARGHC WGPGPTQCVN CSQFLRGQEC     540
VEECRVLQGL PREYVNARHC LPCHPECQPQ NGSVTCFGPE ADQCVACAHY KDPPFCVARC     600
PSGVKPDLSY MPIWKFPDEE GACQPCPINC THSPLTSIIS AVVGILLVVV LGVVFGILIK     660
RRQQKIRKYT MRRLLQETEL VEPLTPSGAM PNQAQMRILK ETELRKVKVL GSGAFGTVYK     720
GIWIPDGENV KIPVAIKVLR ENTSPKANKE ILDETISNLF SNPAPRGPSA CCEPTCWCHS     780
GKGQDSLPRE EWGRQRRFCL WGCRGEPRVL DTPGRSCPSA PPSSCLQPSL RQPLLLGPGP     840
TRAGGSTQHL QRDTYGREPR VPGSGRASVN QKAKSAEALM CPQGAGKA                  888
```

```
SEQ ID NO: 70             moltype = AA  length = 186
FEATURE                   Location/Qualifiers
source                    1..186
                          mol_type = protein
                          organism = Homo sapiens
SEQUENCE: 70
MEPTRDCPLF GGAFSAILPM GAIDVSDLRP VPDNQEVFCH PVTDQSLIVE LLELQAHVRG      60
EAAARYHFED VGGVQGARAV HVESVQPLSL ENLALRGRCQ EAWVLSGKQQ IAKENQQVAK     120
```

-continued

```
DVTLHQALLR LPQYQTDLLL TFNQPPPDNR SSLGPENLSP APWSLGDFEQ LVTSLTLHDP  180
NIFGPQ                                                              186

SEQ ID NO: 71          moltype = AA  length = 146
FEATURE                Location/Qualifiers
source                 1..146
                       mol_type = protein
                       organism = Homo sapiens
SEQUENCE: 71
MEPTRDCPLF GGAFSAILPM GAIDVSDLRP VPDNQEVFCH PVTDQSLIVE LLELQAHVRG  60
EAAARYHFED VGGVQGARAV HVESVQPLSL ENLALRGRCQ EAWVLSGKQQ IAKENQQVAK  120
DVTLHQALLR LPQYQTDLLL TFNQPP                                        146

SEQ ID NO: 72          moltype = AA  length = 165
FEATURE                Location/Qualifiers
source                 1..165
                       mol_type = protein
                       organism = Homo sapiens
SEQUENCE: 72
MEPTRDCPLF GGAFSAILPM GAIDVSDLRP VPDNQEVFCH PVTDQSLIVE LLELQAHVRG  60
EAAARYHFED VGGVQGARAV HVESVQPLSL ENLALRGRCQ EAWVLSGKQQ IAKENQQVRA  120
RECVMSWKGG SGDAEIQVSI LTLIPLGSKG RDTSSGLAEA APVPD                  165

SEQ ID NO: 73          moltype = AA  length = 118
FEATURE                Location/Qualifiers
source                 1..118
                       mol_type = protein
                       organism = Homo sapiens
SEQUENCE: 73
MEPTRDCPLF GGAFSAILPM GAIDVSDLRP VPDNQEVFCH PVTDQSLIVE LLELQAHVRG  60
EAAARYHFED VGGVQGARAV HVESVQPLSL ENLALRGRCQ EAWVLSGKQQ IAKENQQP    118
```